United States Patent
Yamamoto et al.

(10) Patent No.: US 9,156,837 B2
(45) Date of Patent: Oct. 13, 2015

(54) HETEROCYCLIC COMPOUND

(75) Inventors: Satoshi Yamamoto, Kanagawa (JP); Junya Shirai, Kanagawa (JP); Atsuko Ochida, Kanagawa (JP); Yoshiyuki Fukase, Kanagawa (JP); Yoshihide Tomata, Kanagawa (JP); Ayumu Sato, Kanagawa (JP); Shotaro Miura, Kanagawa (JP); Kazuko Yonemori, Kanagawa (JP); Ryokichi Koyama, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/235,992

(22) PCT Filed: Jul. 27, 2012

(86) PCT No.: PCT/JP2012/069138
§ 371 (c)(1),
(2), (4) Date: Jan. 29, 2014

(87) PCT Pub. No.: WO2013/018695
PCT Pub. Date: Feb. 7, 2013

(65) Prior Publication Data
US 2014/0163001 A1    Jun. 12, 2014

(30) Foreign Application Priority Data
Jul. 29, 2011   (JP) .................. 2011-167693

(51) Int. Cl.
| | |
|---|---|
| C07D 277/30 | (2006.01) |
| C07D 277/56 | (2006.01) |
| C07D 211/90 | (2006.01) |
| C07D 417/12 | (2006.01) |
| C07D 471/04 | (2006.01) |
| C07D 401/12 | (2006.01) |
| C07D 277/24 | (2006.01) |
| C07D 401/04 | (2006.01) |
| C07D 417/04 | (2006.01) |
| C07D 417/14 | (2006.01) |
| C07D 491/107 | (2006.01) |

(52) U.S. Cl.
CPC ............ *C07D 471/04* (2013.01); *C07D 417/04* (2013.01); *C07D 417/14* (2013.01); *C07D 491/107* (2013.01)

(58) Field of Classification Search
None
See application file for complete search history.

(56) References Cited

U.S. PATENT DOCUMENTS

| | | | |
|---|---|---|---|
| 5,348,969 A | 9/1994 | Romine et al. | |
| 6,413,997 B1 | 7/2002 | Tisdell et al. | |
| 6,777,421 B2 | 8/2004 | Jordan et al. | |
| 7,053,101 B2 | 5/2006 | Jordan et al. | |
| 7,214,802 B2 | 5/2007 | Cogan et al. | |
| 7,429,665 B2 | 9/2008 | Verhoest et al. | |
| 7,514,458 B2 | 4/2009 | Cogan et al. | |
| 7,825,254 B2 | 11/2010 | Verhoest et al. | |
| 8,198,308 B2 | 6/2012 | Steurer et al. | |
| 8,354,436 B2 | 1/2013 | Leban et al. | |
| 8,389,509 B2 | 3/2013 | Dyckmann et al. | |
| 8,592,456 B2 | 11/2013 | Leban et al. | |

(Continued)

FOREIGN PATENT DOCUMENTS

| | | |
|---|---|---|
| DE | 294 256 | 9/1991 |
| JP | 2000-095778 | 4/2000 |

(Continued)

OTHER PUBLICATIONS

Khimiya Geterotsiklicheskikh Soedinenii (1982) 3 321-327.

(Continued)

*Primary Examiner* — Nyeemah A Grazier
(74) *Attorney, Agent, or Firm* — Hamre, Schumann, Mueller & Larson, P.C.

(57) ABSTRACT

A heterocyclic compound having an RORγt inhibitory activity, which is a compound of formula (I) or a salt thereof is provided. The compound has ring A, which is an optionally (I)

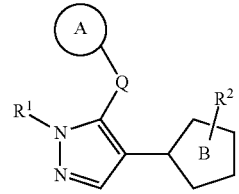

substituted cyclic group and is bound to a pyrazole ring though Q. Q is a bond, optionally substituted $C_{1-10}$ alkylene, optionally substituted $C_{2-10}$ alkenylene, or optionally substituted $C_{2-10}$ alkynylene. $R^1$ is a substituent. Ring B is a thiazole ring, an isothiazole ring or a dihydrothiazole ring, each of which is optionally further substituted by a substituent in addition to $R^2$. $R^2$ is an optionally substituted cyclyl-carbonyl-$C_{1-6}$ alkyl group, an optionally substituted aminocarbonyl-$C_{1-6}$ alkyl group, an optionally substituted cyclyl-$C_{1-6}$ alkyl group, an optionally substituted cyclyl-$C_{1-6}$ alkylamino-carbonyl group, an optionally substituted aminocarbonyl-$C_{2-6}$ alkenyl group, an optionally substituted $C_{1-6}$ alkylcarbonylamino-$C_{1-6}$ alkyl group, an optionally substituted cyclyl-aminocarbonyl group, an optionally substituted cyclyl-carbonyl group or an optionally substituted non-aromatic heterocyclic group.

12 Claims, No Drawings

(56) References Cited

U.S. PATENT DOCUMENTS

| | | |
|---|---|---|
| 2003/0109539 A1 | 6/2003 | Jordan et al. |
| 2005/0004154 A1 | 1/2005 | Jordan et al. |
| 2006/0079519 A1 | 4/2006 | Cogan et al. |
| 2006/0154931 A1 | 7/2006 | Verhoest et al. |
| 2006/0252807 A1 | 11/2006 | Severance et al. |
| 2007/0060589 A1 | 3/2007 | Purandare et al. |
| 2007/0142371 A1 | 6/2007 | Cogan et al. |
| 2008/0182837 A1 | 7/2008 | Steurer et al. |
| 2008/0214607 A1 | 9/2008 | Verhoest et al. |
| 2009/0163545 A1 | 6/2009 | Goldfarb |
| 2010/0240657 A1 | 9/2010 | Sapountizis et al. |
| 2011/0059938 A1 | 3/2011 | Steurer et al. |
| 2011/0183952 A1 | 7/2011 | Sapountizis et al. |
| 2011/0263046 A1 | 10/2011 | Deuschle et al. |
| 2011/0275610 A1 | 11/2011 | Dyckmann et al. |
| 2012/0071460 A1 | 3/2012 | Quattropani et al. |
| 2012/0196861 A1 | 8/2012 | Leban et al. |
| 2012/0196862 A1 | 8/2012 | Leban et al. |

FOREIGN PATENT DOCUMENTS

| | | |
|---|---|---|
| WO | 92/13451 | 8/1992 |
| WO | 00/24739 | 5/2000 |
| WO | 02/059097 | 8/2002 |
| WO | 02/083673 | 10/2002 |
| WO | 03/062206 | 7/2003 |
| WO | 2005/090333 | 9/2005 |
| WO | 2006/069155 | 6/2006 |
| WO | 2006/072828 | 7/2006 |
| WO | 2006/116355 | 11/2006 |
| WO | 2008/003770 | 1/2008 |
| WO | 2009/003998 | 1/2009 |
| WO | 2009/003999 | 1/2009 |
| WO | 2010/049144 | 5/2010 |
| WO | 2010/085584 | 7/2010 |
| WO | 2010/142628 | 12/2010 |
| WO | 2012/101261 | 8/2012 |
| WO | 2012/101263 | 8/2012 |

OTHER PUBLICATIONS

Khimiko-Farmatsevticheskii Zhurnal (1981) 15(11) 40-45.
Ivanov, et al. "The Orphan Nuclear Receptor RORγt Directs the Differentiation Program of Proinflammatory IL-17+ T Helper Cells", Cell, 12, (2006), 1121-1133.
Manel, et al., "The differentiation of human $T_H$-17 cells requires transforming growth factor-β and induction of the nuclear receptor RORγt", Nature Immunology vol. 9, No. 6, (2008), 641-649.
Solt, et al., "Suppression of $T_H$17 differentiation and autoimmunity by a synthetic ROR ligand", Nature, vol. 472, (2011), 491-494.
Kumar, et al., "The Benzenesulfoamide T0901317 [N-(2,2,2-Trifluoroethyl)-*n*-[4-[2,2,2-trifluoro-1-hydroxy-1-(trifluoromethy)ethyl]phenyl]-benzenesulfonamide] is a Novel Retinoic Acid Receptor-Related Orphan Receptor-α/γ Inverse Agonist", Mol. Pharmacol, vol. 77, No. 2, (2010), 228-236.
Huh, et al., "Digoxin and its derivatives suppress $T_H$17 cell differentiation by antagonizing RORγt activity", Nature, vol. 472, (2011), 486.
Wang, et al., "Identification of SR1078, a Synthetic Agonist for the Orphan Nuclear Receptors RORα and RORγ", ACS Chem. Biol., vol. 5, No. 11, (2010), 1029-1034.
Xu, et al., "Ursolic Acid Suppresses Interleukin-17 (IL-17) Production by Selectively Antagonizing the Function of RORγt Protein", J. Bio. Chem., vol. 286, (2011), 22707-22710.
Wang, et al., "Modulation of Retinoic Acid Receptor-related Orphan Receptor α and γ Activity by 7-Oxygenated Sterol Ligands", J. Biol. Chem., vol. 285, (2010), 5013-5025.
Wang, et al., "A second class of nuclear receptors for oxysterols: Regulation of RORα and RORγ activity by 24S-hydroxycholesterol (cerebrosterol)", Biochimica et Biophysica Acta, 1801 (2010) 917-923.
Jin, et al., "Structural Basis for Hydroxycholesterols as Natural Ligands of Orphan Nuclear Receptor RORγ" Mol. Endocrinol., vol. 24, No. 5, (2010), 923-929.
Ukrainskii Khimicheskii Zhurnal (Russian Edition) (1982) 48(7) 765-768.
Dopovidi Akademii Nauk Ukrains'koi RSR, Seriya B Geologichni, Khimichnita Biologichni Nauki (1981) (5) 58-61.
Martins, et al., "Highly Regioselective Synthesis of Novel 1, 4'-Bipyrazoles", J. Braz. Chem. Soc., vol. 21, No. 2, (2010), 240-247.
Prakash, et al., "The chemistry of α,β-ditosyloxyketones: new and convenient route for the synthesis of 1,4,5-trisubstituted pyrazoles from α,β-chalcone ditosylates", Tetrahedron, vol. 65 (2009), 10175-10181.
Huynh, et al., Optimization of pyrazole inhibitors of Coactivator Associated Arginine Methyltransferase 1 (CARM1), Bioorganic & Medicinal Chemistry Letters, vol. 19, (2009), 2924-2927.
Shokol, et al., 5-Phenyl-2-(Pyrazol-4-yl)-1,3,4-Thiadiazoles, Chemistry of Heterocyclic Compounds, vol. 41, No. 5, (2005), 673-678.
Farghaly, et al., "Synthesis Reactions and Antimicrobial Activity of Some new 1,3,4-Oxadiazoles, 1,2,4-Triazoles and 1,3,4-Thiadiazines Derived from Pyrazole", Heterocyclic Communications, vol. 11, No. 3-4, (2005), 255-262.
Mayoral, et al., "A Novel Series of Complexones with Bis- or Biazole Structure as Mixed Ligands of Paramagnetic Contrast Agents for MRI", Bioorganic & Medicinal Chemistry, No. 11, (2003), 5555-5567.
Abdel-Megid, et al., "Studies of 1-Functionally Substituted Alkyl Azoles: Novel Synthesis of Functionally Substituted Azolylbenzimidazoles and functionally Substituted Azolyl-1,2,4-Triazoles", J. Heterocyclic Chem., vol. 39, No. 1, (2002), 105-108.
Fischer, et al., "Neuartig verknüpfte Pyrazolyl- und Isoxazolyl-tetrazole aus Enaminoketon-Vorstufen", Journal fuer Praktische Chemie Chemiker-Zeitung, vol. 336, nol. 1, (1994), 79-82.
Meanwell, et al., "Nonprostanoid Prostacyclin Mimetics. 5. Structure-Activity Relationships Associated with [3-[4-(4,5-Diphenyl-2-oxazolyl)-5-oxazolyl]phenoxy]acetic Acid", J. Med. Chem., vol. 36, (1993), 3884-3903.
Nagarajan, et al., "Nitroimidazoles, Part XXIII—Activity of satranidazole series against anaerobic infections", Indian Journal of Experimental Biology, vol. 30, No. 3, (1992), 193-200.
Nagarajan, et al., "Nitroimidazoles: Part XIX—Structure-activity Relationships", Indian Journal of Chemistry, vol. 23B, No. 4, (1984), 342-362.
Search Results, ZCAPLUS, (2011)—2 pages.

HETEROCYCLIC COMPOUND

TECHNICAL FIELD

The present invention relates to a heterocyclic compound having an RORγt inhibitory activity, a medicament containing the compound, and the like.

BACKGROUND OF THE INVENTION

Various autoimmune diseases such as inflammatory bowel disease (IBD), rheumatoid arthritis, multiple sclerosis and psoriasis cause a decrease in QOL as a severe etiology cell and factor accompanying enhancement of a systemic new immune response. However, the existing therapeutic drugs show only limited effects, and therefore, the earliest possible development of a novel therapeutic drug has been desired.

Involvement of T cells, inter alia, Th17 cell and inflammatory cytokines (IL-17A, IL-17F and the like) produced thereby, in the pathology of these immune diseases has been drawing attention in recent years.

Moreover, it has been recently clarified that a Retinoid-related Orphan Receptor (ROR) γt, which is one of the orphan nuclear receptors, plays an important role in the differentiation of Th17 cells and production of IL-17A/IL-17F. That is, it has been reported that RORγt is mainly expressed in Th17 cells and functions as a transcription factor of IL-17A and IL-17F, as well as a master regulator of Th17 cell differentiation (non-patent documents 1 and 2).

Therefore, a medicament that inhibits the action of RORγt is expected to show a treatment effect on various immune diseases by suppressing differentiation and activation of Th17 cells.

As a compound that regulates RORγ activity, patent document 1 describes a compound represented by the formula:

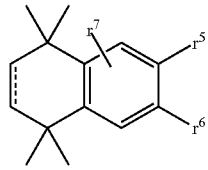

wherein r5 and r6 may together form

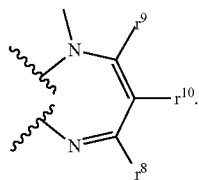

As a compound having an RORα and RORγ inverse agonist activity, non-patent document 3 describes a compound represented by the formula:

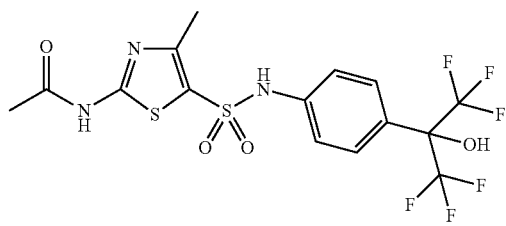 [SMILES: CC(=O)Nc1nc(C)c(S(=O)(=O)Nc2ccc(C(O)(C(F)(F)F)C(F)(F)F)cc2)s1]

(SR1001)
and non-patent document 4 describes a compound represented by the formula:

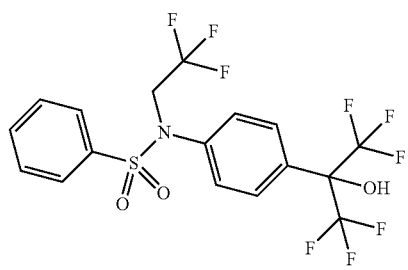 [SMILES: O=S(=O)(c1ccccc1)N(CC(F)(F)F)c1ccc(C(O)(C(F)(F)F)C(F)(F)F)cc1]

(T0901317).
As a compound that antagonizes an RORγt activity, non-patent document 5 describes a compound represented by the formula:

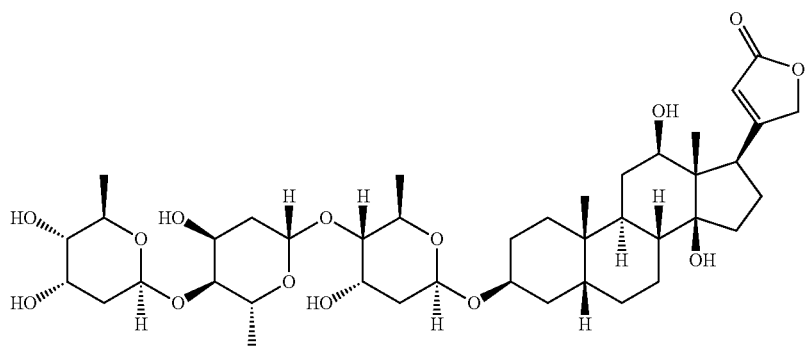

(Digoxin).

As a compound having RORα and RORγ agonist activities, non-patent document 6 describes a compound represented by the formula:

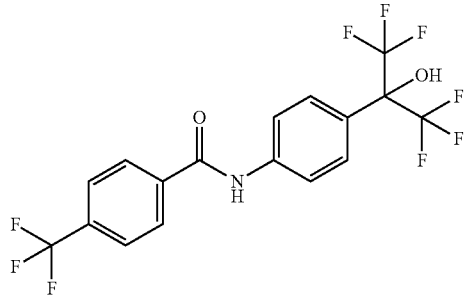 [SMILES: O=C(Nc1ccc(C(O)(C(F)(F)F)C(F)(F)F)cc1)c1ccc(C(F)(F)F)cc1]

(SR1078).

As a compound that regulates RORα and RORγ activities, non-patent document 7 describes a compound represented by the formula:

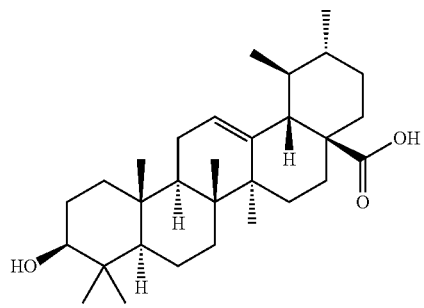

(Ursolic Acid).

As a compound that regulates RORα and RORγ activities, non-patent document 8 describes compounds represented by the formulas:

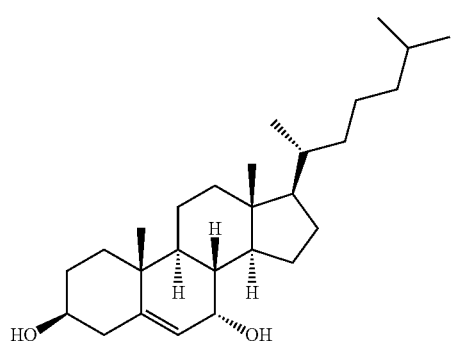

(7α-hydroxycholesterol)

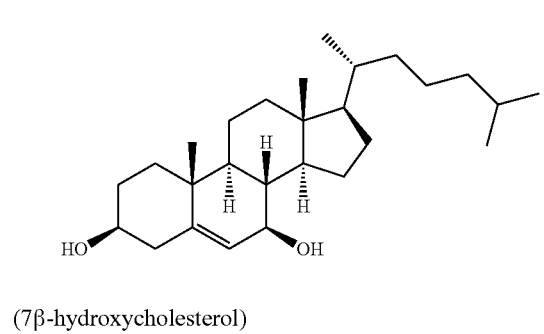

(7β-hydroxycholesterol)

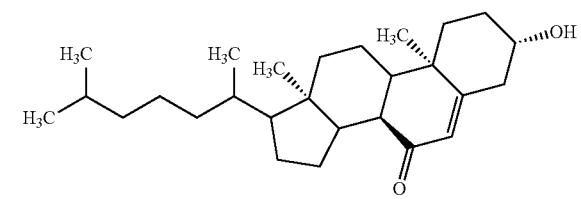

(24-ketocholesterol), and non-patent document 9 describes a compound represented by the formula:

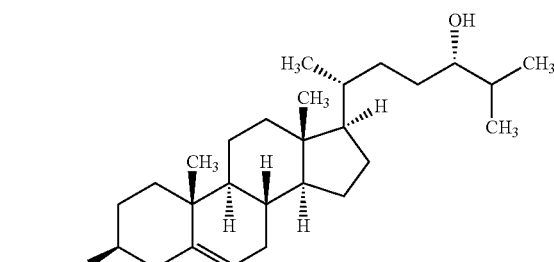

(24S-hydroxycholesterol).

As a ligand of RORγ, non-patent document 10 describes compounds represented by the formulas:

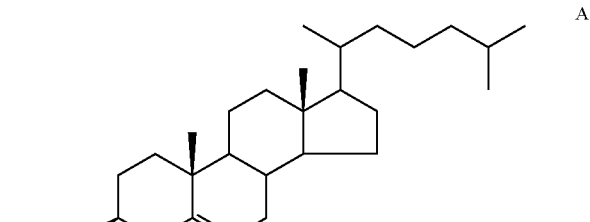

Cholesterol

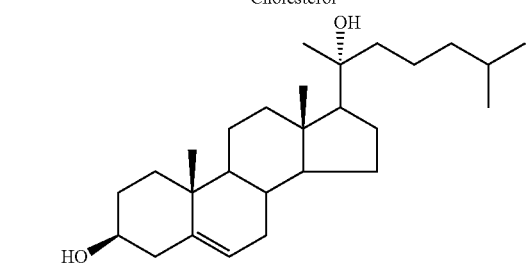

20α-Hydroxycholesterol

-continued

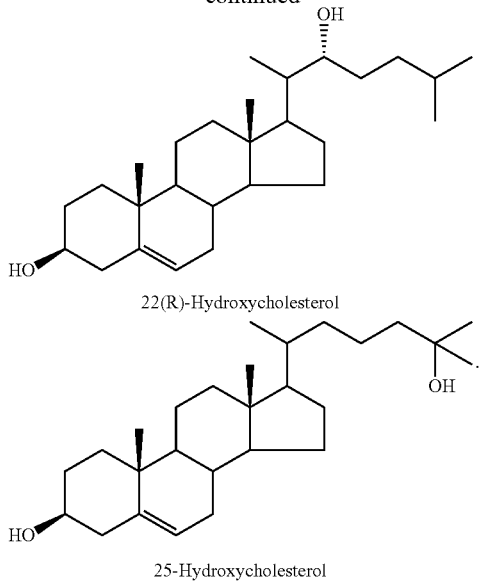

22(R)-Hydroxycholesterol

25-Hydroxycholesterol

DOCUMENT LIST

Patent Document patent document 1: WO 2010/049144

Non-Patent Documents non-patent document 1: Cell 126, 1121-1133 (2006)
non-patent document 2: Nat. Immunol. 9, 641-649 (2008)
non-patent document 3: Nature, 2011, 472, 491
non-patent document 4: Mol. Pharmacol., 2010, 77(2): 228
non-patent document 5: Nature, 2011, 472, 486
non-patent document 6: ACS Chem. Biol. 2010, 5(11), 1029
non-patent document 7: The Journal of Biological Chemistry, 2011, 286, 22707
non-patent document 8: The Journal of Biological Chemistry, 2010, 285, 5013
non-patent document 9: Biochimica et Biophysica Acta, 1801 (2010), 917
non-patent document 10: Mol. Endocrinol, May 2010, 24(5), 923 Nat. Immunol. 9, 641-649 (2008)

SUMMARY OF THE INVENTION

Problems to be Solved by the Invention

The present invention aims to provide a compound having a superior RORγt receptor inhibitory action, and useful as an agent for the prophylaxis or treatment of inflammatory bowel disease (IBD), ulcerative colitis (UC), Crohn's disease (CD), rheumatoid arthritis, multiple sclerosis, psoriasis and the like.

Means of Solving the Problems

The present inventor have found that a compound represented by the following formula (I) or a salt thereof has a superior RORγt receptor inhibitory action based on the specific chemical structure thereof and affords superior efficacy as an agent for the prophylaxis or treatment of inflammatory bowel disease (IBD), ulcerative colitis (UC), Crohn's disease (CD), rheumatoid arthritis, multiple sclerosis, psoriasis and the like. The present inventors have conducted intensive studies based on the finding and completed the present invention.

Accordingly, the present invention relates to
[1] a compound represented by the formula (I):

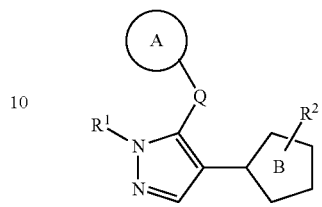

wherein
ring A is an optionally substituted cyclic group,
Q is a bond, optionally substituted $C_{1-10}$ alkylene, optionally substituted $C_{2-10}$ alkenylene, or optionally substituted $C_{2-10}$ alkynylene,
$R^1$ is a substituent,
ring B is a thiazole ring, an isothiazole ring or a dihydrothiazole ring, each of which is optionally further substituted by a substituent in addition to $R^2$, and
$R^2$ is an optionally substituted cyclyl-carbonyl-$C_{1-6}$ alkyl group, an optionally substituted aminocarbonyl-$C_{1-6}$ alkyl group, an optionally substituted cyclyl-$C_{1-6}$ alkyl group, an optionally substituted cyclyl-$C_{1-6}$ alkylamino-carbonyl group, an optionally substituted aminocarbonyl-$C_{2-6}$ alkenyl group, an optionally substituted $C_{1-6}$ alkylcarbonylamino-$C_{1-6}$ alkyl group, an optionally substituted cyclyl-aminocarbonyl group, an optionally substituted cyclyl-carbonyl group or an optionally substituted non-aromatic heterocyclic group, or a salt thereof (hereinafter sometimes to be abbreviated as compound (I));
[2] the compound of [1], wherein $R^1$ is a group selected from the following:
(1) an optionally substituted $C_{1-10}$ alkyl group;
(2) an optionally substituted $C_{2-10}$ alkenyl group;
(3) an optionally substituted $C_{2-10}$ alkynyl group;
(4) an optionally substituted $C_{3-12}$ cycloalkyl group;
(5) an optionally substituted $C_{10-14}$ aryl group;
(6) a phenyl group optionally substituted by the same or different 1 to 5 substituents selected from (a) a halogen atom, (b) a hydroxy group, (c) a nitro group, (d) a cyano group, (e) an optionally substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group;
(7) an optionally substituted $C_{7-16}$ aralkyl group;
(8) an optionally substituted heterocyclic group;
(9) a formyl group;
(10) a carboxy group;
(11) an optionally substituted $C_{1-10}$ alkyl-carbonyl group;
(12) an optionally substituted $C_{3-7}$ cycloalkyl-carbonyl group;
(13) an optionally substituted $C_{6-14}$ aryl-carbonyl group;
(14) an optionally substituted $C_{7-16}$ aralkyl-carbonyl group;
(15) an optionally substituted heterocyclyl-carbonyl group;
(16) an optionally substituted $C_{1-10}$ alkylsulfonyl group;
(17) an optionally substituted $C_{3-7}$ cycloalkylsulfonyl group;
(18) an optionally substituted $C_{6-14}$ arylsulfonyl group;
(19) an optionally substituted heterocyclyl-sulfonyl group;
(20) an optionally substituted $C_{1-10}$ alkylsulfinyl group;
(21) an optionally substituted $C_{3-7}$ cycloalkylsulfinyl group;
(22) an optionally substituted $C_{6-14}$ arylsulfinyl group;
(23) an optionally substituted heterocyclyl-sulfinyl group;
(24) a sulfamoyl group;
(25) a sulfinamoyl group;
(26) a sulfinamoyl group;
(27) a thiocarbamoyl group;
(28) an optionally substituted carbamoyl group;
(29) an optionally substituted $C_{1-10}$ alkoxy-carbonyl group;
(30) an optionally substituted $C_{6-14}$ aryloxy-carbonyl group; and
(31) an optionally substituted $C_{7-16}$ aralkyloxy-carbonyl group, or a salt thereof;
[3] the compound of [1], wherein $R^1$ is (1) a $C_{3-12}$ cycloalkyl group optionally substituted by substituent(s) selected from a hydrocarbon group and a halogen atom, or (2) a tert-butyl group optionally substituted by substituent(s) selected from a hydrocarbon group and a halogen atom, or a salt thereof;
[4] the compound of [1], wherein the partial structure:

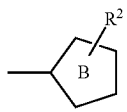

is

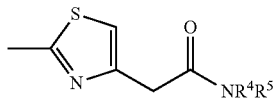

wherein one of $R^4$ and $R^5$ is a hydrogen atom or a $C_{1-3}$ alkyl group, and the other is an optionally substituted cyclyl-$C_{1-6}$ alkyl group,
or a salt thereof;
[5] 2-{2-[1-tert-butyl-5-(4-methoxyphenyl)-1H-pyrazol-4-yl]-1,3-thiazol-4-yl}-N-(tetrahydro-2H-pyran-4-ylmethyl)acetamide or a salt thereof;
[6] 2-{2-[1-cyclohexyl-5-(4-fluorophenyl)-1H-pyrazol-4-yl]-1,3-thiazol-4-yl}-N-(tetrahydro-2H-pyran-4-ylmethyl)acetamide or a salt thereof;
[7] 2-{2-[1-tert-butyl-5-(4-fluorophenyl)-1H-pyrazol-4-yl]-1,3-thiazol-4-yl}-N-[4-(1H-imidazol-1-yl)benzyl]acetamide or a salt thereof;

[8] a medicament comprising the compound of [1] or a salt thereof;
[9] the medicament of [8], which is an RORγt inhibitor;
[10] the medicament of [9], which is a prophylactic or therapeutic drug for an inflammatory disease or autoimmune disease;
[11] the medicament of [9], which is a prophylactic or therapeutic drug for inflammatory bowel disease (IBD), ulcerative colitis (UC), Crohn's disease (CD), rheumatoid arthritis, multiple sclerosis or psoriasis;
[12] a method of inhibiting RORγt, comprising administering an effective amount of the compound of [1] or a salt thereof to a mammal;
[13] a prophylactic or therapeutic method for an inflammatory disease or autoimmune disease, comprising administering an effective amount of the compound of [1] or a salt thereof to a mammal;
[14] a prophylactic or therapeutic method for inflammatory bowel disease (IBD), ulcerative colitis (UC), Crohn's disease (CD), rheumatoid arthritis, multiple sclerosis or psoriasis, comprising administering an effective amount of the compound of [1] or a salt thereof to a mammal;
[15] use of the compound of [1] or a salt thereof for the production of an agent for the prophylaxis or treatment of an inflammatory disease or autoimmune disease;
[16] use of the compound of [1] or a salt thereof for the production of an agent for the prophylaxis or treatment of inflammatory bowel disease (IBD), ulcerative colitis (UC), Crohn's disease (CD), rheumatoid arthritis, multiple sclerosis or psoriasis;
[17] the compound of [1] or a salt thereof for use in the prophylaxis or treatment of an inflammatory disease or autoimmune disease;
[18] the compound of [1] or a salt thereof for use in the prophylaxis or treatment of inflammatory bowel disease (IBD), ulcerative colitis (UC), Crohn's disease (CD), rheumatoid arthritis, multiple sclerosis or psoriasis; and the like.
In addition, the present invention relates to
[1A] a compound represented by the formula (I):

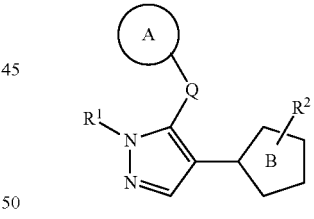

wherein
ring A is an optionally substituted cyclic group,
Q is a bond, optionally substituted $C_{1-10}$ alkylene, optionally substituted $C_{2-10}$ alkenylene, or optionally substituted $C_{2-10}$ alkynylene,
$R^1$ is a substituent,
ring B is a thiazole ring or an isothiazole ring, each of which is optionally further substituted by a substituent in addition to $R^2$, and
$R^2$ is an optionally substituted cyclyl-carbonyl-$C_{1-6}$ alkyl group, an optionally substituted aminocarbonyl-$C_{1-6}$ alkyl group, an optionally substituted cyclyl-$C_{1-6}$ alkyl group, an optionally substituted cyclyl-$C_{1-6}$ alkylamino-carbonyl group, an optionally substituted $C_{1-6}$ alkyl-carbonylamino group, or an optionally substituted non-aromatic heterocyclic group, or a salt thereof (hereinafter sometimes to be abbreviated as compound (I));

[2A] compound [1A] wherein $R^1$ is a group selected from the following:
(1) an optionally substituted $C_{1-10}$ alkyl group;
(2) an optionally substituted $C_{2-10}$ alkenyl group;
(3) an optionally substituted $C_{2-10}$ alkynyl group;
(4) an optionally substituted $C_{3-7}$ cycloalkyl group;
(5) an optionally substituted $C_{10-14}$ aryl group;
(6) a phenyl group optionally substituted by the same or different 1 to 5 substituents selected from (a) a halogen atom, (b) a hydroxy group, (c) a nitro group, (d) a cyano group, (e) an optionally, substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group;
(7) an optionally substituted $C_{7-16}$ aralkyl group;
(8) an optionally substituted heterocyclic group;
(9) a formyl group;
(10) a carboxy group;
(11) an optionally substituted $C_{1-10}$ alkyl-carbonyl group;
(12) an optionally substituted $C_{3-7}$ cycloalkyl-carbonyl group;
(13) an optionally substituted $C_{6-14}$ aryl-carbonyl group;
(14) an optionally substituted $C_{7-16}$ aralkyl-carbonyl group;
(15) an optionally substituted heterocyclyl-carbonyl group;
(16) an optionally substituted $C_{1-10}$ alkylsulfonyl group;
(17) an optionally substituted $C_{3-7}$ cycloalkylsulfonyl group;
(18) an optionally substituted $C_{6-14}$ arylsulfonyl group;
(19) an optionally substituted heterocyclyl-sulfonyl group
(20) an optionally substituted $C_{1-10}$ alkylsulfinyl group;
(21) an optionally substituted $C_{3-7}$ cycloalkylsulfinyl group;
(22) an optionally substituted $C_{6-14}$ arylsulfinyl group;
(23) an optionally substituted heterocyclyl-sulfinyl group;
(24) a sulfamoyl group;
(25) a sulfinamoyl group;
(26) a sulfinamoyl group;
(27) a thiocarbamoyl group;
(28) an optionally substituted carbamoyl group;
(29) an optionally substituted $C_{1-10}$ alkoxy-carbonyl group;
(30) an optionally substituted $C_{6-14}$ aryloxy-carbonyl group; and
(31) an optionally substituted $C_{7-16}$ aralkyloxy-carbonyl group, or a salt thereof;

[3A] a medicament comprising the compound of [1A] or a salt thereof;
[4A] the medicament of [3A], which is an RORγt inhibitor;
[5A] the medicament of [4A], which is a prophylactic or therapeutic drug for an inflammatory disease or autoimmune disease;
[6A] the medicament of [4A], which is a prophylactic or therapeutic drug for inflammatory bowel disease (IBD), ulcerative colitis (UC), Crohn's disease (CD), rheumatoid arthritis, multiple sclerosis or psoriasis;
and the like.

Effect of the Invention

The compound of the present invention has a superior RORγt receptor inhibitory action, and is useful as an agent for the prophylaxis or treatment of inflammatory bowel disease (IBD), ulcerative colitis (UC), Crohn's disease (CD), rheumatoid arthritis, multiple sclerosis or psoriasis and the like.

DETAILED DESCRIPTION OF THE INVENTION

The present invention is described in detail in the following.

Unless particularly limited, examples of the "halogen atom" in the present specification include a fluorine atom, a chlorine atom, a bromine atom and an iodine atom.

Unless particularly limited, examples of the "$C_{1-10}$ alkyl" in the present specification include methyl, ethyl, propyl, isopropyl, butyl, isobutyl, sec-butyl, tert-butyl, pentyl, isopentyl, hexyl, neohexyl, heptyl, octyl, nonyl, decyl and the like. As the "$C_{1-6}$ alkyl", the above-mentioned "$C_{1-10}$ alkyl" having 1-6 carbon atoms can be mentioned.

Unless particularly limited, examples of the "$C_{2-10}$ alkenyl" in the present specification include vinyl, propenyl, isopropenyl, 2-buten-1-yl, 4-penten-1-yl, 5-hexen-1-yl and the like. As the "$C_{2-6}$ alkenyl", the above-mentioned "$C_{2-10}$ alkenyl" having 2-6 carbon atoms can be mentioned.

Unless particularly limited, examples of the "$C_{2-10}$ alkynyl" in the present specification include 2-butyn-1-yl, 4-pentyn-1-yl, 5-hexyn-1-yl and the like. As the "$C_{2-6}$ alkynyl", the above-mentioned "$C_{2-10}$ alkynyl" having 2-6 carbon atoms can be mentioned.

Unless particularly limited, examples of the "$C_{1-10}$ alkylene" in the present specification include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$C(CH_3)_2$—, —$C(CH_3)_2$—$CH_2$—$CH_2$— and the like.

Unless particularly limited, examples of the "$C_{2-10}$ alkenylene" in the present specification include —CH═CH—, —$CH_2$—CH═CH—, —CH═CH—$CH_2$—, —$C(CH_3)_2$—CH═CH—, —CH═CH—$C(CH_2)_2$—, —$CH_2$—CH═CH—$CH_2$—, —$CH_2$—$CH_2$—CH═CH—, —CH═CH—$CH_2$—$CH_2$—, —CH═CH—CH═CH—, —CH═CH—$CH_2$—$CH_2$—$CH_2$—, —$CH_2$—$CH_2$—$CH_2$—CH═CH— and the like.

Unless particularly limited, examples of the "$C_{2-10}$ alkynylene" in the present specification include —C≡C—, —$CH_2$—C≡C—, —C≡C—$CH_2$—, —$C(CH_3)$—C≡C—, —C≡C—$C(CH_3)_2$—, —$CH_2$—C≡C—$CH_2$—, —$CH_2$—$CH_2$—C≡C—, —C≡C—$CH_2$—$CH_2$—, —C≡C—$CH_2$—$CH_2$—$CH_2$—, —$CH_2$—$CH_2$—$CH_2$—C≡C— and the like.

Unless particularly limited, examples of the "$C_{3-12}$ cycloalkyl" in the present specification include cyclopropyl, cyclobutyl, cyclopentyl, cyclohexyl, cycloheptyl, cyclooctyl, cyclononyl, cyclodecyl, cycloundecyl, cyclododecyl and the like. As the "$C_{3-7}$ cycloalkyl", the above-mentioned "$C_{3-12}$ cycloalkyl" having 3-7 carbon atoms can be mentioned.

Unless particularly limited, examples of the "$C_{6-14}$ aryl" in the present specification include phenyl, 1-naphthyl, 2-naphthyl, 2-biphenylyl, 3-biphenylyl, 4-biphenylyl, 2-anthryl and the like, examples of "$C_{6-10}$ aryl" include the above-mentioned "$C_{6-14}$ aryl" having 6-10 carbon atoms, and examples of "$C_{10-14}$ aryl" include the above-mentioned "$C_{6-14}$ aryl" having 10-14 carbon atoms.

Unless particularly limited, examples of the "$C_{7-16}$ aralkyl" in the present specification include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

Unless particularly limited, examples of the "cyclic group" in the present specification include cyclic hydrocarbon group, heterocyclic group and the like.

Unless particularly limited, examples of the above-mentioned "cyclic hydrocarbon group" include an aromatic hydrocarbon group, a non-aromatic cyclic hydrocarbon group and the like.

Unless particularly limited, examples of the above-mentioned "aromatic hydrocarbon group" include the above-defined "$C_{6-14}$ aryl" and the like.

Unless particularly limited, examples of the above-mentioned "non-aromatic cyclic hydrocarbon group" include the above-defined "$C_{3-7}$ cycloalkyl", $C_{3-8}$ cycloalkenyl (e.g., cyclopropenyl, cyclobutenyl, cyclopentenyl, cyclohexenyl, cycloheptenyl, cyclooctenyl), $C_{4-10}$ cycloalkadienyl (e.g., cyclobutadienyl, cyclopentadienyl, cyclohexadienyl, cycloheptadienyl, cyclooctadienyl, cyclononadienyl, cyclodecadienyl), a fused ring group wherein these groups are condensed with a benzene ring (e.g., indanyl (e.g., 1-indanyl), tetrahydronaphthyl (e.g., 1,2,3,4-tetrahydronaphthalen-1-yl), fluorenyl (e.g., 9-fluorenyl)), bridged cyclic hydrocarbon group (e.g., adamantyl) and the like.

Unless particularly limited, examples of the above-mentioned "heterocyclic group" include a 5- to 14-membered (preferably 5- to 10-membered, more preferably 5- or 7-membered) heterocyclic group containing, as a ring-constituting atom besides carbon atoms, one or two kinds of 1 to 4 heteroatoms selected from an oxygen atom, a sulfur atom (said sulfur atom is optionally oxidized) and a nitrogen atom (e.g., aromatic heterocyclic group, non-aromatic heterocyclic group) and the like.

Unless particularly limited, examples of the above-mentioned "aromatic heterocyclic group" include a 5- to 10-membered (preferably 5- or 7-membered) monocyclic aromatic heterocyclic group containing, as a ring-constituting atom besides carbon atoms, 1 or 2 kinds of 1 to 4 heteroatoms selected from an oxygen atom, a sulfur atom (said sulfur atom is optionally oxidized) and a nitrogen atom and the like, specifically, furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,3,5-triazin-2-yl) and the like;

a fused aromatic heterocyclic group wherein the above-mentioned "monocyclic aromatic heterocyclic group" and the above-mentioned "$C_{6-10}$ aryl" are condensed, a fused aromatic heterocyclic group wherein the above-mentioned "monocyclic aromatic heterocyclic groups" are condensed and the like, specifically, quinolyl (e.g., 2-quinolyl, 3-quinolyl, 4-quinolyl), isoquinolyl (e.g., 1-isoquinolyl, 3-isoquinolyl, 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-1-yl, benzimidazol-2-yl, benzimidazol-5-yl), indolyl (e.g., indol-1-yl, indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl (e.g., 3-benzisoxazolyl), benzotriazolyl (e.g., 1H-1,2,3-benzotriazol-5-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Unless particularly limited, examples of the above-mentioned "non-aromatic heterocyclic group" include a 3- to 8-membered (preferably 5- or 6-membered) saturated or unsaturated (preferably saturated) monocyclic non-aromatic heterocyclic group and the like, specifically, pyranyl, tetrahydrofuranyl, tetrahydrothiofuranyl, oxiranyl (e.g., 2-oxiranyl), azetidinyl (e.g., 2-azetidinyl), oxetanyl (e.g., 2-oxetanyl), thietanyl (e.g., 2-thietanyl), pyrrolidinyl (e.g., 1-pyrrolidinyl, 2-pyrrolidinyl, 3-pyrrolidinyl), tetrahydrofuryl (e.g., 2-tetrahydrofuryl, 3-tetrahydrofuryl), thiolanyl (e.g., 2-thiolanyl), piperidinyl (e.g., 1-piperidinyl, 2-piperidinyl, 3-piperidinyl, 4-piperidinyl), tetrahydropyranyl (e.g., 2-tetrahydropyranyl, 3-tetrahydropyranyl, 4-tetrahydropyranyl), thiopyranyl, thianyl (e.g., 2-thianyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), piperazinyl (e.g., 1-piperazinyl, 2-piperazinyl), azepanyl (e.g., 2-azepanyl), diazepanyl (e.g., 1,4-diazepan-1-yl), oxepanyl (e.g., 2-oxepanyl), thiepanyl (e.g., 2-thiepanyl), oxazepanyl (e.g., 1,4-oxazepan-4-yl, 1,4-oxazepan-5-yl), thiazepanyl (e.g., 1,4-thiazepan-5-yl), azocanyl (e.g., 2-azocanyl), oxocanyl (e.g., 2-oxocanyl), thiocanyl (e.g., 2-thiocanyl), oxazocanyl (e.g., 1,4-oxazocan-5-yl), thiazocanyl (e.g., 1,4-thiazocan-5-yl), dioxinyl (e.g., 2-dioxinyl) and the like;

a fused non-aromatic heterocyclic group wherein the above-mentioned "monocyclic non-aromatic heterocyclic group" and the above-mentioned "$C_{6-10}$ aryl" are condensed, a fused non-aromatic heterocyclic group wherein the above-mentioned "monocyclic non-aromatic heterocyclic groups" are condensed, a fused non-aromatic heterocyclic group wherein the above-mentioned "monocyclic aromatic heterocyclic group" and the above-mentioned "monocyclic non-aromatic heterocyclic group" are condensed and the like, specifically, benzodioxinyl (e.g., 1,4-benzodioxin-6-yl), isoindolinyl (e.g., isoindolin-1-yl), tetrahydroisoquinolyl (e.g., tetrahydroisoquinolin-1-yl), tetrahydronaphthyridinyl (e.g., tetrahydronaphthyridin-6-yl) and the like;

a spiro ring group wherein the above-mentioned "monocyclic non-aromatic heterocyclic groups" are spiro-bonded and the like, specifically, 2-oxa-7-azaspiro[3.4]oct-7-yl, 2-oxa-8-azaspiro[3.5]non-8-yl, 1-oxa-9-azaspiro[4.5]dec-9-yl and the like.

Unless particularly limited, examples of the "$C_{1-10}$ alkoxy" in the present specification include methoxy, ethoxy, propoxy, isopropoxy, butoxy, isobutoxy, tert-butoxy, pentyloxy, hexyloxy and the like. As the "$C_{1-6}$ alkoxy", the above-mentioned "$C_{1-10}$ alkoxy" having 1-6 carbon atoms can be mentioned.

Unless particularly limited, examples of the "$C_{6-14}$ aryloxy" in the present specification include $C_{6-14}$ aryloxy wherein the $C_{6-14}$ aryl moiety is the "$C_{6-14}$ aryl" defined above, for example, phenoxy, 1-naphthyloxy, 2-naphthyloxy and the like.

Unless particularly limited, examples of the "$C_{7-16}$ aralkyloxy" in the present specification include $C_{7-16}$ aralkyloxy wherein the $C_{7-16}$ aralkyl moiety is the "$C_{7-16}$ aralkyl" defined above, for example, benzyloxy, phenethyloxy and the like.

Unless particularly limited, examples of the "$C_{1-10}$ alkyl-carbonyl" in the present specification include, $C_{1-10}$ alkyl-carbonyl wherein the $C_{1-10}$ alkyl moiety is the "$C_{1-10}$ alkyl" defined above, for example, acetyl, propanoyl, butanoyl, 2-methylpropanoyl, pentanoyl, 3-methylbutanoyl, 2-methylbutanoyl, 2,2-dimethylpropanoyl, hexanoyl, heptanoyl and the like. As the "$C_{1-6}$ alkyl-carbonyl", the above-mentioned "$C_{1-10}$ alkyl-carbonyl" wherein the alkyl moiety has 1-6 carbon atoms can be mentioned.

Unless particularly limited, examples of the "$C_{3-7}$ cycloalkyl-carbonyl" in the present specification include $C_{3-7}$ cycloalkyl-carbonyl wherein the $C_{3-7}$ cycloalkyl moiety is the "$C_{3-7}$ cycloalkyl" defined above, for example, cyclopentylcarbonyl, cyclohexylcarbonyl and the like.

Unless particularly limited, examples of the "$C_{6-14}$ arylcarbonyl" in the present specification include $C_{6-14}$ aryl-carbonyl wherein the $C_{6-14}$ aryl moiety is the "$C_{6-14}$ aryl" defined above, for example, benzoyl, 1-naphthoyl, 2-naphthoyl and the like.

Unless particularly limited, examples of the "$C_{7-16}$ aralkyl-carbonyl" in the present specification include $C_{7-16}$ aralkyl-carbonyl wherein the $C_{7-16}$ aralkyl moiety is the "$C_{7-16}$ aralkyl" defined above, for example, phenylacetyl, phenylpropanoyl, phenylbutanoyl, naphthylacetyl, naphthylpropanoyl and the like.

Unless particularly limited, examples of the "heterocyclyl-carbonyl" in the present specification include heterocyclyl-carbonyl wherein the heterocyclyl moiety is the "heterocyclic group" defined above.

Unless particularly limited, examples of the "$C_{1-10}$ alkoxy-carbonyl" in the present specification include $C_{1-10}$ alkoxy-carbonyl wherein the $C_{1-10}$ alkoxy moiety is the "$C_{1-10}$ alkoxy" defined above, for example, methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl and the like. As the "$C_{1-6}$ alkoxy-carbonyl", the above-mentioned "$C_{1-10}$ alkoxy-carbonyl" wherein the alkoxy moiety has 1-6 carbon atoms can be mentioned.

Unless particularly limited, examples of the "$C_{6-14}$ aryloxy-carbonyl" in the present specification include $C_{6-14}$ aryloxy-carbonyl wherein the $C_{6-14}$ aryloxy moiety is the "$C_{6-14}$ aryloxy" defined above, for example, phenoxycarbonyl, 1-naphthyloxycarbonyl, 2-naphthyloxycarbonyl and the like.

Unless particularly limited, examples of the "$C_{7-16}$-aralkyloxy-carbonyl" in the present specification include $C_{7-16}$ aralkyloxy-carbonyl wherein the $C_{7-16}$ aralkyloxy moiety is the "$C_{7-16}$ aralkyloxy" defined above, for example, benzyloxycarbonyl, phenethyloxycarbonyl and the like.

Unless particularly limited, examples of the "$C_{1-10}$ alkylsulfonyl" in the present specification include $C_{1-10}$ alkylsulfonyl wherein the $C_{1-10}$ alkyl moiety is the "$C_{1-10}$ alkyl" defined above, for example, methylsulfonyl, ethylsulfonyl, propylsulfonyl, isopropylsulfonyl, butylsulfonyl, isobutylsulfonyl, tert-butylsulfonyl and the like. As the "$C_{1-6}$ alkylsulfonyl", the above-mentioned "$C_{1-10}$ alkylsulfonyl" wherein the alkyl moiety has 1-6 carbon atoms can be mentioned.

Unless particularly limited, examples of the "$C_{3-7}$ cycloalkylsulfonyl" in the present specification include $C_{3-7}$ cycloalkylsulfonyl wherein the $C_{3-7}$ cycloalkyl moiety is the "$C_{3-7}$ cycloalkyl" defined above, for example, cyclopropylsulfonyl, cyclobutylsulfonyl, cyclopentylsulfonyl, cyclohexylsulfonyl, cyclopentylsulfonyl and the like.

Unless particularly limited, examples of the "$C_{6-14}$ arylsulfonyl" in the present specification include $C_{6-14}$ arylsulfonyl wherein the $C_{6-14}$ aryl moiety is the "$C_{6-14}$ aryl" defined above, for example, phenylsulfonyl, 1-naphthylsulfonyl, 2-naphthylsulfonyl and the like.

Unless particularly limited, examples of the "heterocyclylsulfonyl" in the present specification include heterocyclylsulfonyl wherein the heterocyclyl moiety is the "heterocyclic group" defined above.

Unless particularly limited, examples of the "$C_{1-10}$ alkylsulfinyl" in the present specification include $C_{1-10}$ alkylsulfinyl wherein the $C_{1-10}$ alkyl moiety is the "$C_{1-10}$ alkyl" defined above, for example, methylsulfinyl, ethylsulfinyl, propylsulfinyl, isopropylsulfinyl, butylsulfinyl, isobutylsulfinyl, tert-butylsulfinyl and the like. As the "$C_{1-6}$ alkylsulfinyl", the above-mentioned "$C_{1-10}$ alkylsulfinyl" wherein the alkyl moiety has 1-6 carbon atoms can be mentioned.

Unless particularly limited, examples of the "$C_{3-7}$ cycloalkylsulfinyl" in the present specification include $C_{3-7}$ cycloalkylsulfinyl wherein the $C_{3-7}$ cycloalkyl moiety is the "$C_{3-7}$ cycloalkyl" defined above, for example, cyclopropylsulfinyl, cyclobutylsulfinyl, cyclopentylsulfinyl, cyclohexylsulfinyl, cyclopentylsulfinyl and the like.

Unless particularly limited, examples of the "$C_{6-14}$ arylsulfinyl" in the present specification include $C_{6-14}$ arylsulfinyl wherein the $C_{6-14}$ aryl moiety is the "$C_{5-14}$ aryl" defined above, for example, for example, phenylsulfinyl, 1-naphthylsulfinyl, 2-naphthylsulfinyl and the like.

Unless particularly limited, examples of the "heterocyclylsulfinyl" in the present specification include heterocyclylsulfinyl wherein the heterocyclyl moiety is the "heterocyclic group" defined above.

Unless particularly limited, examples of the "$C_{1-6}$ alkylsulfanyl" in the present specification include $C_{1-6}$ alkylsulfanyl wherein the $C_{1-6}$ alkyl moiety is the "$C_{1-6}$ alkyl" defined above, for example, methylsulfanyl, ethylsulfanyl, propylsulfanyl, isopropylsulfanyl, butylsulfanyl, isobutylsulfanyl, tert-butylsulfanyl and the like.

Unless particularly limited, examples of the "mono-$C_{1-6}$ alkyl-carbamoyl" in the present specification include carbamoyl mono-substituted by the "$C_{1-10}$ alkyl" defined above, for example, methylcarbamoyl, ethylcarbamoyl, propylcarbamoyl, isopropylcarbamoyl and the like.

Unless particularly limited, examples of the "di-$C_{1-6}$ alkyl-carbamoyl" in the present specification include carbamoyl di-substituted by the same or different "$C_{1-10}$ alkyl" defined above, for example, dimethylcarbamoyl, diethylcarbamoyl, N-ethyl-N-methylcarbamoyl, dipropylcarbamoyl, diisopropylcarbamoyl and the like.

Unless particularly limited, examples of the "mono- or di-(5- or 7-membered heterocyclyl having one or two kinds of 1-4 hetero atoms selected from a nitrogen atom, a sulfur atom and an oxygen atom)-carbamoyl" in the present specification include carbamoyl mono- or di-substituted by the same or different "5- or 7-membered heterocyclic group having one or two kinds of 1-4 hetero atoms selected from a nitrogen atom, a sulfur atom and an oxygen atom" defined above.

Unless particularly limited, examples of the "cyclyl-carbonyl-$C_{1-6}$ alkyl group" in the present specification include cyclyl-carbonyl-$C_{1-6}$ alkyl group wherein the cyclic group moiety is the "cyclic group" defined above and the $C_{1-6}$ alkyl moiety is the "$C_{1-6}$ alkyl" defined above, for example, piperidinocarbonylmethyl, morpholinocarbonylmethyl, piperazinylcarbonylmethyl, azetidinylcarbonylmethyl, thiomorpholinocarbonylmethyl, tetrahydroisoquinolylcarbonylmethyl, isoindolinylcarbonylmethyl, pyrrolidinylcarbonylmethyl, 2-oxa-7-azaspiro[3.4]oct-7-ylcarbonylmethyl, 2-oxa-8-azaspiro[3.5]non-8-ylcarbonylmethyl, 1-oxa-9-azaspiro[4.5]dec-9-ylcarbonylmethyl, 1,4-oxazepanylcarbonylmethyl, 1,4-diazepanylcarbonylmethyl and the like.

Unless particularly limited, examples of the "aminocarbonyl-$C_{1-6}$ alkyl group" in the present specification include aminocarbonyl-$C_{1-6}$ alkyl group wherein the $C_{1-6}$ alkyl moiety is the "$C_{1-6}$ alkyl" defined above, for example, aminocarbonylmethyl and the like.

Unless particularly limited, examples of the "cyclyl-$C_{1-6}$ alkyl group" in the present specification include cyclyl-$C_{1-6}$ alkyl group wherein the cyclic group moiety is the "cyclic group" defined above and the $C_{1-6}$ alkyl moiety is "$C_{1-6}$ alkyl" defined above, for example, thiomorpholinoethyl and the like.

Unless particularly limited, examples of the "cyclyl-$C_{1-6}$ alkylamino-carbonyl group" in the present specification include cyclyl-$C_{1-6}$ alkylamino-carbonyl group wherein the cyclic group moiety is the "cyclic group" defined above and the $C_{1-6}$ alkyl moiety is the "$C_{1-6}$ alkyl" defined above, for example, tetrahydropyranylmethylaminocarbonyl, tetrahydropyranylethylaminocarbonyl, morpholinoethylaminocarbonyl and the like.

Unless particularly limited, examples of the "$C_{1-6}$ alkyl-carbonylamino group" in the present specification include $C_{1-6}$ alkyl-carbonylamino group wherein the $C_{1-6}$ alkyl moiety is the "$C_{1-6}$ alkyl" defined above.

Unless particularly limited, examples of the "hydrocarbon group" in the present specification include "$C_{1-10}$ alkyl", "$C_{2-10}$ alkenyl", "$C_{2-10}$ alkynyl", "$C_{3-12}$ cycloalkyl", "$C_{6-14}$ aryl" and "$C_{7-16}$ aralkyl" defined above.

Unless particularly limited, examples of the "substituent" of the "substituent" and "optionally substituted" in the present specification include the substituents selected from the following. While the number of the substituents is not particularly limited as long as it is a substitutable number, it is preferably 1 to 5, more preferably 1 to 3. When plural substituents are present, the respective substituents may be the same or different.

(1) oxo;
(2) a halogen atom (e.g., a fluorine atom, a chlorine atom);
(3) $C_{1-3}$ alkylenedioxy (e.g., methylenedioxy, ethylenedioxy etc.);
(4) nitro;
(5) cyano;
(6) optionally substituted $C_{1-10}$ alkyl (e.g., methyl, ethyl, propyl, isopropyl, butyl, isobutyl, sec-butyl, tert-butyl, isopentyl, neohexyl) [for example, optionally substituted by 1 to 3 substituents selected from (a) a halogen atom (e.g., a fluorine atom), (b) hydroxy, (c) $C_{1-6}$ alkoxy (e.g., methoxy, ethoxy, isobutoxy) optionally substituted by 1 to 3 halogen atoms (e.g., a fluorine atom), (d) mono-$C_{1-6}$ alkylamino, (e) di-$C_{1-6}$ alkylamino, (f) $C_{3-6}$ cycloalkyl (e.g., cyclopropyl, cyclobutyl, cyclopentyl) optionally substituted by 1 to 3 halogen atoms (e.g., a fluorine atom), (g) cyano, (h) $C_{1-10}$ alkoxy-carbonyl (e.g., ethoxycarbonyl), (i) $C_{6-14}$ aryl (e.g., phenyl) optionally substituted by the same or different 1 to 3 substituents selected from (1) a halogen atom (e.g., a fluorine atom, a chlorine atom), (2) $C_{1-6}$ alkyl (e.g., methyl) substituted by the same or different 1 to 3 halogen atoms (e.g., a fluorine atom), (3) $C_{1-6}$ alkoxy (e.g., methoxy) optionally substituted by the same or different 1 to 3 halogen atoms (e.g., a fluorine atom), (4) cyano, (5) amino substituted by $C_{1-6}$ alkyl (e.g., methyl), (6) $C_{1-10}$ alkylsulfonyl (e.g., methylsulfonyl), and (7) $C_{6-14}$ aryl (e.g., phenyl), and (j) a heterocyclic group (e.g., oxetanyl, tetrahydrofuryl, tetrahydropyranyl, tetrahydrothiopyranyl, piperidyl, morpholino, furyl, pyrazolyl, imidazolyl, oxazolyl, isoxazolyl, thiazolyl, pyridyl, pyrimidinyl) optionally substituted by 1 to 3 substituents selected from (i) a halogen atom, (ii) $C_{1-6}$ alkyl (e.g., methyl) and (iii) $C_{1-6}$ alkoxy];
(7) optionally substituted $C_{2-10}$ alkenyl [for example, optionally having 1-3 halogen atoms];
(8) carboxy-$C_{2-6}$ alkenyl (e.g., 2-carboxyethenyl, 2-carboxy-2-methylethenyl etc.);
(9) optionally substituted $C_{2-10}$ alkynyl [for example, optionally having 1-3 halogen atoms];
(10) optionally substituted $C_{3-7}$ cycloalkyl (e.g., cyclopentyl, cyclobutyl, cyclopentyl, cyclohexyl) [for example, optionally having 1-3 halogen atoms (e.g., a fluorine atom)];
(11) optionally substituted $C_{6-14}$ aryl (e.g., phenyl) [for example, optionally substituted by the same or different 1 to 5 substituents selected from (a) a halogen atom, (b) a hydroxy group, (c) a nitro group, (d) a cyano group, (e) a $C_{6-14}$ aryl group, (f) a $C_{6-14}$ aryloxy group, (g) a $C_{7-16}$ aralkyloxy group, (h) a 5- to 10-membered heterocyclic group having one or two kinds of 1-4 hetero atoms selected from a nitrogen atom, a sulfur atom and an oxygen atom, (i) an amino group, (j) a $C_{3-7}$ cycloalkyl group, (k) a $C_{1-6}$ alkoxy group, (l) a formyl group, (m) a $C_{1-6}$ alkyl-carbonyl group, (n) a $C_{3-7}$ cycloalkyl-carbonyl group, (o) a $C_{6-14}$ aryl-carbonyl group, (p) a $C_{7-16}$ aralkyl-carbonyl group, (q) a $C_{1-6}$ alkoxy-carbonyl group, (r) a $C_{6-14}$ aryloxy-carbonyl group, (s) a $C_{7-16}$ aralkyloxy-carbonyl group, (t) a $C_{1-6}$ alkylsulfanyl group, (u) a $C_{1-6}$ alkylsulfinyl group, (v) a $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- to 7-membered heterocyclyl having one or two kinds of 1-4 hetero atoms selected from a nitrogen atom, a sulfur atom and an oxygen atom)-carbamoyl group, (bb) a $C_{1-6}$ alkyl group, (cc) a $C_{2-6}$ alkenyl group, and (dd) a $C_{2-6}$ alkynyl group];
(12) $C_{7-16}$ aralkyl;
(13) $C_{1-6}$ alkoxy (e.g., methoxy, ethoxy, isopropoxy, isobutoxy) optionally having 1-3 halogen atoms (e.g., a fluorine atom);
(14) $C_{1-6}$ alkoxy-carbonyl-$C_{1-6}$ alkoxy (e.g., ethoxycarbonylmethyloxy etc.);
(15) hydroxy;
(16) $C_{6-10}$ aryloxy (e.g., phenoxy, naphthalen-1-yloxy, naphthalen-2-yloxy etc.) optionally substituted by 1 to 3 substituents selected from a halogen atom, $C_{1-6}$ alkoxy and $C_{1-6}$ alkyl;

(17) $C_{7-12}$ aralkyloxy (e.g., benzyloxy, phenylethyloxy etc.) optionally substituted by 1 to 3 substituents selected from a halogen atom, $C_{1-6}$ alkyl and $C_{1-6}$ alkoxy;
(18) sulfanyl;
(19) $C_{1-6}$ alkylsulfanyl optionally having 1-3 halogen atoms;
(20) $C_{6-10}$ arylsulfanyl (e.g., phenylsulfanyl, naphthalen-1-ylsulfanyl, naphthalen-2-ylsulfanyl etc.) optionally substituted by 1 to 3 substituents selected from a halogen atom, $C_{1-6}$ alkoxy and $C_{1-6}$ alkyl);
(21) $C_{7-12}$ aralkylsulfanyl (e.g., benzylsulfanyl, phenylethylsulfanyl etc.) optionally substituted by 1 to 3 substituents selected from a halogen atom, $C_{1-6}$ alkyl and $C_{1-6}$ alkoxy;
(22) amino;
(23) mono-$C_{1-6}$ alkylamino (e.g., methylamino, ethylamino, propylamino, tert-butylamino, 1-ethylpropylamino, isopentylamino etc.) optionally substituted by 1 to 3 substituents selected from (a) a halogen atom, (b) hydroxy, (c) $C_{1-6}$ alkoxy, (d) mono-$C_{1-6}$ alkylamino, (e) di-$C_{1-6}$ alkylamino, (f) $C_{3-6}$ cycloalkyl and (g) a heterocyclic group optionally substituted by 1 to 3 substituents selected from (i) a halogen atom, (ii) $C_{1-6}$ alkyl and (iii) $C_{1-6}$ alkoxy;
(24) mono-$C_{6-10}$ arylamino (e.g., phenylamino, naphthalen-1-ylamino, naphthalen-2-ylamino etc.) optionally substituted by 1 to 3 substituents selected from a halogen atom, $C_{1-6}$ alkoxy and $C_{1-6}$ alkyl;
(25) $C_{7-12}$ aralkylamino (e.g., benzylamino, 1-phenylethylamino, 2-phenylethylamino etc.) optionally substituted by 1 to 3 substituents selected from a halogen atom, $C_{1-6}$ alkyl and $C_{1-6}$ alkoxy;
(26) di-$C_{1-6}$ alkylamino optionally substituted by 1 to 3 substituents selected from (a) a halogen atom, (b) hydroxy, (c) $C_{1-6}$ alkoxy, (d) mono-$C_{1-6}$ alkylamino, (e) alkylamino, (f) $C_{3-6}$ cycloalkyl and (g) a heterocyclic group optionally substituted by 1 to 3 substituents selected from (i) a halogen atom, (ii) $C_{1-6}$ alkoxy and (iii) $C_{1-6}$ alkyl;
(27) mono-$C_{3-6}$ cycloalkylamino (e.g., cyclopropylamino, cyclobutylamino, cyclopentylamino, cyclohexylamino etc.) optionally condensed with $C_{6-10}$ arene;
(28) di-$C_{3-6}$ cycloalkylamino (e.g., dicyclopropylamino, dicyclopentylamino, dicyclohexylamino, cyclopentylcyclohexylamino etc.);
(29) di-$C_{6-40}$ arylamino (e.g., diphenylamino etc.) optionally substituted by 1 to 3 substituents selected from a halogen atom, $C_{1-6}$ alkoxy and $C_{1-6}$ alkyl;
(30) formyl;
(31) carboxy;
(32) optionally substituted $C_{1-10}$ alkyl-carbonyl (e.g., isobutoxycarbonyl) [for example, optionally substituted by 1-6 substituents selected from a halogen atom (e.g., a fluorine atom), hydroxy and $C_{1-6}$ alkyl-carbonyloxy];
(33) $C_{3-7}$ cycloalkyl-carbonyl (e.g., cyclopropylcarbonyl, cyclopentylcarbonyl, cyclohexylcarbonyl etc.);
(34) optionally substituted $C_{1-10}$ alkoxy-carbonyl (e.g., ethoxycarbonyl, tert-butoxycarbonyl) [for example, optionally having 1-3 halogen atoms];
(35) optionally substituted $C_{6-14}$ aryl-carbonyl (e.g., benzoyl, 4-methoxybenzoyl, 4-methylbenzoyl, 4-fluorobenzoyl, naphthalen-1-ylcarbonyl, naphthalen-2-ylcarbonyl etc.) [for example, optionally substituted by 1 to 3 substituents selected from a halogen atom, cyano, $C_{1-6}$ alkyl and $C_{1-6}$ alkoxy];
(36) optionally substituted $C_{7-16}$ aralkyl-carbonyl (e.g., phenylacetyl, 3-phenylpropanoyl etc.) [for example, optionally substituted by 1 to 3 substituents selected from a halogen atom, $C_{1-6}$ alkyl and $C_{1-6}$ alkoxy];
(37) optionally substituted $C_{6-14}$ aryloxy-carbonyl (e.g., phenoxycarbonyl etc.) [for example, optionally substituted by 1 to 3 substituents selected from a halogen atom, $C_{1-6}$ alkoxy and $C_{1-6}$ alkyl];
(38) optionally substituted $C_{7-16}$ aralkyloxy-carbonyl (e.g., benzyloxycarbonyl, phenylethyloxycarbonyl etc.) [for example, optionally substituted by 1 to 3 substituents selected from a halogen atom, $C_{1-6}$ alkyl and $C_{1-6}$ alkoxy];
(39) optionally substituted heterocyclyl-carbonyl (e.g., pyridin-3-ylcarbonyl, pyridin-4-ylcarbonyl, thiophen-2-ylcarbonyl, thiophen-3-ylcarbonyl, furan-2-ylcarbonyl, furan-3-ylcarbonyl, morpholinocarbonyl, thiomorpholinocarbonyl, piperazin-1-ylcarbonyl, pyrrolidin-1-ylcarbonyl etc. [for example, optionally substituted by 1 to 3 substituents selected from a halogen atom, $C_{1-6}$ alkoxy and $C_{1-6}$ alkyl]);
(40) carbamoyl;
(41) thiocarbamoyl;
(42) mono-$C_{1-6}$ alkyl-carbamoyl (e.g., methylcarbamoyl, ethylcarbamoyl etc.);
(43) di-$C_{1-6}$ alkyl-carbamoyl;
(44) $C_{6-10}$ aryl-carbamoyl (e.g., phenylcarbamoyl, 1-naphthylcarbamoyl, 2-naphthylcarbamoyl etc.) optionally substituted by 1 to 3 substituents selected from a halogen atom, $C_{1-6}$ alkoxy and $C_{1-6}$ alkyl;
(45) heterocyclyl-carbamoyl (e.g., pyridin-2-ylcarbamoyl, pyridin-3-ylcarbamoyl, pyridin-4-ylcarbamoyl, thiophen-2-ylcarbamoyl, thiophen-3-ylcarbamoyl etc.) optionally substituted by 1 to 3 substituents selected from a halogen atom, $C_{1-6}$ alkoxy and $C_{1-6}$ alkyl;
(46) $C_{1-10}$ alkylsulfonyl;
(47) $C_{3-7}$ cycloalkylsulfonyl;
(48) $C_{6-14}$ arylsulfonyl (e.g., phenylsulfonyl, naphthalen-1-ylsulfonyl, naphthalen-2-ylsulfonyl etc.);
(49) heterocyclyl-sulfonyl;
(50) $C_{1-10}$ alkylsulfinyl (e.g., methylsulfinyl, ethylsulfinyl etc.);
(51) $C_{3-7}$ cycloalkylsulfinyl;
(52) optionally substituted $C_{6-14}$ arylsulfinyl (e.g., phenylsulfinyl, naphthalen-1-ylsulfinyl, naphthalen-2-ylsulfinyl etc.) [for example, optionally substituted by 1 to 3 substituents selected from a halogen atom, $C_{1-6}$ alkoxy and $C_{1-6}$ alkyl];
(53) heterocyclyl-sulfinyl;
(54) formylamino;
(55) mono- or bis($C_{1-6}$ alkyl-carbonyl)amino (e.g., acetylamino, propanoylamino, butanoylamino, 2-methylpropanoylamino, 2,2-dimethylpropanoylamino, 3,3-dimethylbutanoylamino, dipropanoylamino etc.) optionally substituted by 1 to 3 substituents selected from $C_{1-6}$ alkyl-carbonyloxy and hydroxy;
(56) mono- or bis($C_{6-10}$ aryl-carbonyl)amino (e.g., benzoylamino, naphthalen-1-ylcarbonylamino, naphthalen-2-ylcarbonylamino etc.) optionally substituted by 1 to 3 substituents selected from $C_{1-6}$ alkyl, $C_{1-6}$ alkoxy and a halogen atom;
(57) $C_{7-12}$ aralkyl-carbonylamino (e.g., benzylcarbonylamino etc.) optionally substituted by 1 to 3 $C_{1-6}$ alkoxy;
(58) $C_{1-6}$ alkoxy-carbonylamino (e.g., ethyloxycarbonylamino) optionally having 1-3 halogen atoms;
(59) $C_{1-6}$ alkyl-carbonylamino (e.g., acetylamino, propanoylamino, butanoylamino, 2-methylpropanoylamino, 2,2-dimethylpropanoylamino, 3,3-dimethylbutanoylamino etc.) optionally substituted by 1 to 3 substituents selected from $C_{1-6}$ alkyl-carbonyloxy (e.g., acetyloxy etc.) and hydroxy;
(60) mono- or di-$C_{3-6}$ cycloalkyl-carbonylamino (e.g., cyclopropylcarbonylamino, bis(cyclopropylcarbonyl)amino etc.);
(61) heterocyclyl-carbonylamino (e.g., thiophen-2-ylcarbonylamino, thiophen-3-ylcarbonylamino, pyridin-3-ylcarbonylamino, pyridin-4-ylcarbonylamino, pyridin-2-ylcarbonylamino, piperidinocarbonylamino, 3,4-dihydroisoquinolylcarbonylamino etc.) optionally substituted by 1 to 3 substituents selected from a halogen atom, $C_{1-6}$ alkyl and $C_{1-6}$ alkoxy;
(62) $C_{1-6}$ alkoxy-carbonylamino (e.g., methoxycarbonylamino, ethoxycarbonylamino, propoxycarbonylamino, butoxycarbonylamino etc.);
(63) $C_{1-6}$ alkylsulfonylamino (e.g., methylsulfonylamino, ethylsulfonylamino etc.);
(64) mono- or bis($C_{6-10}$ arylsulfonyl)amino (e.g., phenylsulfonylamino, naphthalen-2-ylsulfonylamino, naphthalen-1-ylsulfonylamino, bis(phenylsulfonyl)amino etc.);
(65) $C_{6-10}$ aryl-carbamoylamino (e.g., phenylcarbamoylamino etc.) optionally substituted by 1 to 3 substituents selected from $C_{1-6}$ alkyl, $C_{1-6}$ alkoxy and a halogen atom;
(66) $C_{1-6}$ alkyl-carbamoylamino (e.g., ethylcarbamoylamino, propylcarbamoylamino, isopropylcarbamoylamino);
(67) $C_{3-6}$ cycloalkyl-carbamoylamino (e.g., cyclohexylcarbamoylamino);
(68) di-$C_{1-6}$ alkyl-carbamoylamino (e.g., diethylcarbamoylamino);
(69) $C_{1-6}$ alkyl-carbonyloxy (e.g., acetoxy, propanoyloxy etc.);
(70) $C_{6-10}$ aryl-carbonyloxy (e.g., benzoyloxy, naphthylcarbonyloxy etc.) optionally substituted by 1 to 3 substituents selected from a halogen atom, $C_{1-6}$ alkoxy and $C_{1-6}$ alkyl;
(71) $C_{1-6}$ alkoxy-carbonyloxy (e.g., methoxycarbonyloxy, ethoxycarbonyloxy, propoxycarbonyloxy, butoxycarbonyloxy etc.);
(72) mono-$C_{1-6}$ alkyl-carbamoyloxy (e.g., methylcarbamoyloxy, ethylcarbamoyloxy etc.);
(73) di-$C_{1-6}$ alkyl-carbamoyloxy (e.g., dimethylcarbamoyloxy, diethylcarbamoyloxy etc.);
(74) $C_{6-10}$ aryl-carbamoyloxy (e.g., phenylcarbamoyloxy, naphthylcarbamoyloxy etc.);
(75) pyridin-3-ylcarbonyloxy;
(76) an optionally substituted heterocyclic group [e.g., a 5- to 10-membered non-aromatic heterocyclic group (e.g., pyrrolidin-1-yl, piperidino, piperidin-2-yl, piperazin-1-yl, morpholino, thiomorpholino, 3,4-dihydroquinolin-1-yl, 3,4-dihydroisoquinolin-2-yl, 1,2,3,4-tetrahydroquinolin-1-yl, hexahydroazepin-1-yl, oxetanyl, tetrahydrofuryl, tetrahydropyranyl, tetrahydrothiopyranyl etc.), a 5- to 10-membered aromatic heterocyclic group (e.g., furyl, pyrazolyl, imidazolyl, oxazolyl, isoxazolyl, 1,3-thiazolyl, thiophen-2-yl, thiophen-3-yl, pyridin-2-yl, pyridin-3-yl, pyridin-4-yl, pyrimidinyl, quinolin-2-yl, quinolin-3-yl, quinolin-4-yl, quinolin-5-yl, quinolin-8-yl, isoquinolin-1-yl, isoquinolin-3-yl, isoquinolin-4-yl, isoquinolin-5-yl, indol-1-yl, indol-2-yl, indol-3-yl, benzothiazol-2-yl, benzo[b]thiophen-2-yl, benzo[b]thiophen-3-yl, benzo[b]furan-2-yl, benzo[b]furan-3-yl etc.) etc.] [for example, optionally substituted by 1 to 3 substituents selected from a halogen atom, $C_{1-6}$ alkyl (e.g., methyl) optionally substituted by the same or different 1 to 3 halogen atoms (particularly, a fluorine atom), and $C_{1-6}$ alkoxy];
(77) sulfo;
(78) sulfamoyl;
(79) sulfinamoyl;
(80) sulfinamoyl and the like.

The definition of each symbol in the formula (I) is described in detail below.

Ring A is an optionally substituted cyclic group.
As the cyclic group, a $C_{3-7}$ cycloalkyl group (e.g., cyclopropyl, cyclohexyl), a $C_{3-8}$ cycloalkenyl group (e.g., cyclohexenyl), a $C_{6-14}$ aryl group (e.g., phenyl, naphthyl, 3-biphenylyl, 4-biphenylyl), or a heterocyclic group (e.g., furyl, thienyl, pyrazolyl, pyridyl, 1,4-benzodioxinyl, benzofuranyl, benzothienyl, indazolyl, dihydrobenzofuranyl) is preferable, and cyclopropyl, cyclohexyl, cyclohexenyl, phenyl, naphthyl, 3-biphenylyl, 4-biphenylyl, furyl, thienyl, pyrazolyl, pyridyl, 1,4-benzodioxinyl, benzofuranyl, benzothienyl, indazolyl or dihydrobenzofuranyl is more preferable.

Examples of the "substituent" of the "optionally substituted cyclic group" for ring A include a halogen atom (e.g., a fluorine atom, a chlorine atom), optionally substituted $C_{1-6}$ alkyl (e.g., methyl, tert-butyl), optionally substituted $C_{1-6}$ alkoxy (e.g., methoxy, isopropoxy), $C_{6-14}$ aryloxy (e.g., phenoxy), cyano, $C_{1-10}$ alkylsulfonyl (e.g., methylsulfonyl), mono- or bis($C_{1-6}$ alkyl-carbonyl)amino (e.g., acetylamino), and a heterocyclic group (e.g., morpholino). The substituent is present at a substitutable position of the cyclic group, and the number of the substituents is preferably 1 to 5, more preferably 1 to 3, particularly preferably 1 or 2. When the number of the substituents is two or more, the respective substituents may be the same or different.

Ring A is preferably a $C_{3-7}$ cycloalkyl group, a $C_{3-6}$ cycloalkenyl group, an optionally substituted $C_{6-14}$ aryl group, or an optionally substituted heterocyclic group, more preferably,
(1) a $C_{3-7}$ cycloalkyl group (particularly, cyclopropyl, cyclohexyl),
(2) a $C_{3-6}$ cycloalkenyl group (particularly, cyclohexenyl),
(3) a $C_{6-14}$ aryl group (particularly, phenyl, naphthyl, 3-biphenylyl, 4-biphenylyl) optionally substituted by the same or different 1 to 3 substituents selected from (i) a halogen atom (particularly, a fluorine atom, a chlorine atom), (ii) $C_{1-6}$ alkyl (particularly, methyl, tert-butyl) optionally substituted by the same or different 1 to 3 substituents selected from a halogen atom (particularly, a fluorine atom), hydroxy and cyano, (iii) $C_{1-6}$ alkoxy (particularly, methoxy, isopropoxy) optionally substituted by the same or different 1 to 3 halogen atoms (particularly, a fluorine atom), (iv) $C_{6-14}$ aryloxy (particularly, phenoxy), (v) cyano, (vi) $C_{1-10}$ alkylsulfonyl (particularly, methylsulfonyl), (vii) mono- or bis($C_{1-6}$ alkyl-carbonyl)amino (particularly, acetylamino) and (viii) a heterocyclic group (particularly, morpholino), or
(4) a heterocyclic group (particularly, furyl, thienyl, pyrazolyl, pyridyl, 1,4-benzodioxinyl, benzofuranyl, benzothienyl, indazolyl and dihydrobenzofuranyl) optionally substituted by the same or different 1 to 3 substituents selected from (i) a halogen atom (particularly, a chlorine atom), (ii) $C_{1-6}$ alkyl (particularly, methyl) optionally substituted by the same or different 1 to 3 halogen atoms (particularly, a fluorine atom) and (iii) $C_{1-6}$ alkoxy (particularly, methoxy).

Q is a bond, optionally substituted $C_{1-10}$ alkylene, optionally substituted $C_{2-10}$ alkenylene, or optionally substituted $C_{2-10}$ alkynylene.

Q is preferably a bond, optionally substituted $C_{1-10}$ alkylene (e.g., —CH$_2$—, —(CH$_2$)$_2$—) or optionally substituted $C_{2-10}$ alkenylene (e.g., —CH═CH—), more preferably, a bond, —CH$_2$—, —(CH$_2$)$_2$— or —CH═CH—.

$R^1$ is a substituent.
$R^1$ is preferably
(1) an optionally substituted $C_{1-10}$ alkyl group;
(2) an optionally substituted $C_{2-10}$ alkenyl group;
(3) an optionally substituted $C_{2-10}$ alkynyl group;
(4) an optionally substituted $C_{3-12}$ (preferably, $C_{3-7}$) cycloalkyl group;
(5) an optionally substituted $C_{10-14}$ aryl group;
(6) a phenyl group optionally substituted by the same or different 1 to 5 substituents selected from (a) a halogen atom, (b) a hydroxy group, (c) a nitro group, (d) a cyano group, (e)

an optionally substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group;

(7) an optionally substituted $C_{7-16}$ aralkyl group;
(8) an optionally substituted heterocyclic group;
(9) a formyl group;
(10) a carboxy group;
(11) an optionally substituted $C_{1-10}$ alkyl-carbonyl group;
(12) an optionally substituted $C_{3-7}$ cycloalkyl-carbonyl group;
(13) an optionally substituted $C_{6-14}$ aryl-carbonyl group;
(14) an optionally substituted $C_{7-16}$ aralkyl-carbonyl group;
(15) an optionally substituted heterocyclyl-carbonyl group;
(16) an optionally substituted $C_{1-10}$ alkylsulfonyl group;
(17) an optionally substituted $C_{3-7}$ cycloalkylsulfonyl group;
(18) an optionally substituted $C_{6-14}$ arylsulfonyl group;
(19) an optionally substituted heterocyclyl-sulfonyl group
(20) an optionally substituted $C_{1-10}$ alkylsulfinyl group;
(21) an optionally substituted $C_{3-7}$ cycloalkylsulfinyl group;
(22) an optionally substituted $C_{6-14}$ arylsulfinyl group;
(23) an optionally substituted heterocyclyl-sulfinyl group;
(24) a sulfamoyl group;
(25) a sulfinamoyl group;
(26) a sulfinamoyl group;
(27) a thiocarbamoyl group;
(28) an optionally substituted carbamoyl group;
(29) an optionally substituted $C_{1-10}$ alkoxy-carbonyl group;
(30) an optionally substituted $C_{6-14}$ aryloxy-carbonyl group; or
(31) an optionally substituted $C_{7-16}$ aralkyloxy-carbonyl group.

$R^1$ is more preferably
(1) an optionally substituted $C_{1-10}$ alkyl group;
(2) an optionally substituted $C_{2-10}$ alkenyl group;
(3) an optionally substituted $C_{2-10}$ alkynyl group;
(4) an optionally substituted $C_{3-12}$ (preferably, $C_{3-7}$) cycloalkyl group;
(5) an optionally substituted $C_{10-14}$ aryl group;
(6) a phenyl group optionally substituted by the same or different 1 to 5 substituents selected from (a) a halogen atom, (b) a hydroxy group, (c) a nitro group, (d) a cyano group, (e) an optionally substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group;

(7) an optionally substituted $C_{7-16}$ aralkyl group;
(8) an optionally substituted heterocyclic group (bonded to the pyrazole ring via a carbon atom);
(9) a formyl group;
(10) a carboxy group;
(11) an optionally substituted $C_{1-10}$ alkyl-carbonyl group;
(12) an optionally substituted $C_{3-7}$ cycloalkyl-carbonyl group;
(13) an optionally substituted $C_{6-14}$ aryl-carbonyl group;
(14) an optionally substituted $C_{7-16}$ aralkyl-carbonyl group;
(15) an optionally substituted heterocyclyl-carbonyl group;
(27) a thiocarbamoyl group;
(28) an optionally substituted carbamoyl group;
(29) an optionally substituted $C_{1-10}$ alkoxy-carbonyl group;
(30) an optionally substituted $C_{6-14}$ aryloxy-carbonyl group; or
(31) an optionally substituted $C_{7-16}$ aralkyloxy-carbonyl group.

$R^1$ is further more preferably
(1) an optionally substituted $C_{1-10}$ alkyl group;
(4) an optionally substituted $C_{3-12}$ (preferably, $C_{3-7}$) cycloalkyl group;
(6) a phenyl group optionally substituted by the same or different 1 to 5 substituents selected from (a) a halogen atom, (b) a hydroxy group, (c) a nitro group, (d) a cyano group, (e) an optionally substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group; or (8) an optionally substituted heterocyclic group (bonded to the pyrazole ring via a carbon atom).

$R^1$ is particularly preferably (1) a $C_{1-10}$ alkyl group (e.g., methyl, ethyl, propyl, isopropyl, n-butyl, sec-butyl, tert-butyl, isopentyl, neohexyl) optionally substituted by the same or different 1 to 3 substituents selected from (i) a halogen atom (e.g., a fluorine atom), (ii) a hydroxy group, (iii) a $C_{3-7}$ cycloalkyl group (e.g., cyclopropyl, cyclobutyl, cyclopentyl) optionally substituted by the same or different 1-2 halogen atoms (e.g., a fluorine atom), (iv) $C_{1-6}$ alkoxy (e.g., methoxy, ethoxy, isobutoxy) optionally substituted by the same or different 1 to 3 halogen atoms (e.g., a fluorine atom), and (v) a non-aromatic heterocyclic group (e.g., tetrahydrofuranyl, tetrahydropyranyl, tetrahydrothiopyranyl);

(4) a $C_{3-7}$ cycloalkyl group (e.g., cyclopentyl, cyclohexyl, cycloheptyl);

(6) a phenyl group; or (8) a heterocyclic group (bonded to the pyrazole ring via a carbon atom) (e.g., tetrahydrofuranyl, tetrahydrothiopyranyl).

In another embodiment of the present invention, $R^1$ is preferably (1) a $C_{3-12}$ cycloalkyl group optionally substituted by substituent(s) selected from a hydrocarbon group and a halogen atom, or (2) a tert-butyl group optionally substituted by substituent(s) selected from a hydrocarbon group and a halogen atom, more preferably (1) an unsubstituted $C_{3-12}$ cycloalkyl group (e.g., cyclopentyl, cyclohexyl, cycloheptyl), or (2) an unsubstituted tert-butyl group.

Ring B is a thiazole ring, an isothiazole ring or a dihydrothiazole ring, each of which is optionally further substituted by a substituent in addition to $R^2$.

Examples of the "substituent" of the "thiazole ring, isothiazole ring or dihydrothiazole ring, each of which is optionally further substituted by a substituent in addition to $R^2$" for ring B include $C_{1-6}$ alkyl (e.g., methyl).

Ring B is preferably a thiazole ring or a dihydrothiazole ring (particularly, a thiazole ring), each of which is optionally further substituted by a substituent in addition to $R^2$, more preferably, a thiazole ring or a dihydrothiazole ring (particularly, a thiazole ring) each of which is optionally further substituted by $C_{1-6}$ alkyl (e.g., methyl).

$R^2$ is (1) an optionally substituted cyclyl-carbonyl-$C_{1-6}$ alkyl group, (2) an optionally substituted aminocarbonyl-$C_{1-6}$ alkyl group, (3) an optionally substituted cyclyl-$C_{1-6}$ alkyl group, (4) an optionally substituted cyclyl-$C_{1-6}$ alkylaminocarbonyl group, (5) an optionally substituted $C_{1-6}$ alkyl-carbonylamino group, (6) an optionally substituted aminocarbonyl-$C_{2-6}$ alkenyl group, (7) an optionally substituted $C_{1-6}$ alkylcarbonylamino-$C_{1-6}$ alkyl group, (8) an optionally substituted cyclyl-aminocarbonyl group, (9) an optionally substituted cyclyl-carbonyl group or (10) an optionally substituted non-aromatic heterocyclic group.

(1) As the "cyclic group" of the "optionally substituted cyclyl-carbonyl-$C_{1-6}$ alkyl group" for $R^2$, a non-aromatic heterocyclic group (e.g., azetidinyl, pyrrolidinyl, piperidino, morpholino, 1,4-oxazepanyl, piperazinyl, 1,4-diazepanyl, thiomorpholino, 2-oxa-7-azaspiro[3.4]oct-7-yl, 2-oxa-8-azaspiro[3.5]non-8-yl, 1-oxa-9-azaspiro[4.5]dec-9-yl, isoindolinyl, tetrahydroisoquinolyl, tetrahydronaphthyridinyl) is preferable.

As the "$C_{1-6}$ alkyl" of the "optionally substituted cyclyl-carbonyl-$C_{1-6}$ alkyl group" for $R^2$, methyl is preferable.

Examples of the "substituent" of the "optionally substituted cyclyl-carbonyl-$C_{1-6}$ alkyl group" for $R^2$ include oxo, hydroxy, $C_{1-6}$ alkyl (e.g., methyl), carboxy, $C_{1-10}$ alkoxy-carbonyl (e.g., ethoxycarbonyl), and $C_{6-14}$ aryl (e.g., phenyl).

The substituent is present at a substitutable position of the cyclic group and the number of the substituents is preferably 1 to 5, more preferably 1 to 3, particularly preferably 1 or 2. When the number of the substituents is two or more, the respective substituents may be the same or different.

Specific examples of the "cyclyl-carbonyl-$C_{1-6}$ alkyl group" of the "optionally substituted cyclyl-carbonyl-$C_{1-6}$ alkyl group" for $R^2$ include ally, azetidinylcarbonylmethyl, pyrrolidinylcarbonylmethyl, piperidinocarbonylmethyl, morpholinocarbonylmethyl, 1,4-oxazepanylcarbonylmethyl, piperazinylcarbonylmethyl, 1,4-diazepanylcarbonylmethyl, thiomorpholinocarbonylmethyl, 2-oxa-7-azaspiro[3.4]oct-7-ylcarbonylmethyl, 2-oxa-8-azaspiro[3.5]non-8-ylcarbonylmethyl, 1-oxa-9-azaspiro[4.5]dec-9-ylcarbonylmethyl, isoindolinylcarbonylmethyl, tetrahydroisoquinolylcarbonylmethyl, and tetrahydronaphthyridinylcarbonylmethyl.

(2) The "$C_{1-6}$ alkyl" of the "optionally substituted aminocarbonyl-$C_{1-6}$ alkyl group" for $R^2$ is preferably methyl or ethyl.

Examples of the "substituent" of the "optionally substituted aminocarbonyl-$C_{1-6}$ alkyl group" for $R^2$ include (i) optionally substituted $C_{1-6}$ alkyl (e.g., methyl, ethyl, propyl, isobutyl), (ii) optionally substituted $C_{6-14}$ aryl (e.g., phenyl), and (iii) a non-aromatic heterocyclic group (e.g., tetrahydropyranyl). In the "optionally substituted aminocarbonyl-$C_{1-6}$ alkyl group", the "amino" may be substituted and the "$C_{1-6}$ alkyl" may be substituted, and the number of the substituents is preferably 1 to 3. When the number of the substituents is two or more, the respective substituents may be the same or different.

(i) Examples of the "substituent" of the "optionally substituted $C_{1-6}$ alkyl" include a halogen atom (e.g., a fluorine atom), hydroxy, $C_{1-6}$ alkoxy (e.g., methoxy), cyano, $C_{1-10}$ alkoxy-carbonyl (e.g., ethoxycarbonyl), a non-aromatic heterocyclic group (e.g., oxetanyl, tetrahydrofuryl, tetrahydropyranyl, piperidyl, morpholino) optionally substituted by one $C_{1-6}$ alkyl (e.g., methyl) optionally substituted by hydroxy, $C_{6-14}$ aryl (e.g., phenyl) optionally substituted by the same or different 1 to 3 substituents selected from (1) a halogen atom (e.g., a fluorine atom, a chlorine atom), (2) $C_{1-6}$ alkyl (e.g., methyl) substituted by the same or different 1 to 3 halogen atoms (e.g., a fluorine atom), (3) $C_{1-6}$ alkoxy (e.g., methoxy) optionally substituted by the same or different 1 to 3 halogen atoms, (4) cyano, (5) amino substituted by $C_{1-6}$ alkyl (e.g., methyl), (6) alkylsulfonyl (e.g., methylsulfonyl), (7) $C_{6-14}$ aryl (e.g., phenyl) and (8) an aromatic heterocyclic group (e.g., pyrazolyl), and an aromatic heterocyclic group (e.g., furyl, pyrazolyl, imidazolyl, oxazolyl, isoxazolyl, thiazolyl, pyridyl, pyrimidinyl) optionally substituted by the same or different 1 or 2 $C_{1-6}$ alkyl (e.g., methyl). The substituent is present at a substitutable position of the $C_{1-6}$ alkyl and the number of the substituents is preferably 1 to 5, more preferably 1 to 3, particularly preferably 1 or 2. When the number of the substituents is two or more, the respective substituents may be the same or different.

(ii) Examples of the "substituent" of the "optionally substituted $C_{6-14}$ aryl" include $C_{1-6}$ alkoxy (e.g., methoxy), an aromatic heterocyclic group (e.g., pyrazolyl), and mono- or bis($C_{1-6}$ alkyl-carbonyl)amino (e.g., acetylamino). The substituent is present at a substitutable position of the $C_{6-14}$ aryl and the number of the substituents is preferably 1 to 5, more preferably 1 to 3, particularly preferably 1 or 2. When the number of the substituents is two or more, the respective substituents may be the same or different.

Specific examples of the "aminocarbonyl-$C_{1-6}$ alkyl group" of the "optionally substituted aminocarbonyl-$C_{1-6}$ alkyl group" for $R^2$ include aminocarbonylmethyl, 1-(aminocarbonyl)ethyl, and 2-(aminocarbonyl)ethyl.

(3) The "cyclic group" of the "optionally substituted cyclyl-$C_{1-6}$ alkyl group" for $R^2$ is preferably a non-aromatic heterocyclic group (e.g., thiomorpholino).

The "$C_{1-6}$ alkyl" of the "optionally substituted cyclyl-$C_{1-6}$ alkyl group" for $R^2$ is preferably ethyl.

The "optionally substituted cyclyl-$C_{1-6}$ alkyl group" for $R^2$ is preferably an unsubstituted "cyclyl-$C_{1-6}$ alkyl group".

The "cyclyl-$C_{1-6}$ alkyl group" of the "optionally substituted cyclyl-$C_{1-6}$ alkyl group" for $R^2$ is specifically, thiomorpholinoethyl.

(4) The "cyclic group" of the "optionally substituted cyclyl-$C_{1-6}$ alkylamino-carbonyl group" for $R^2$ is preferably a non-aromatic heterocyclic group (e.g., morpholino, tetrahydropyranyl).

The "$C_{1-6}$ alkyl" of the "optionally substituted cyclyl-$C_{1-6}$ alkylamino-carbonyl group" for $R^2$ is preferably methyl or ethyl.

The "optionally substituted cyclyl-$C_{1-6}$ alkylamino-carbonyl group" for $R^2$ is preferably an unsubstituted "cyclyl-$C_{1-6}$ alkylamino-carbonyl group".

The "cyclyl-$C_{1-6}$ alkylamino-carbonyl group" of the "optionally substituted cyclyl-$C_{1-6}$ alkylamino-carbonyl group" for $R^2$ is specifically tetrahydropyranylmethylaminocarbonyl, tetrahydropyranylethylaminocarbonyl, or morpholinoethylaminocarbonyl.

(5) Examples of the "substituent" of the "optionally substituted $C_{1-6}$ alkyl-carbonylamino group" for $R^2$ include oxo, a halogen atom (e.g., a fluorine atom) and the like. Specific examples of the "optionally substituted $C_{1-6}$ alkyl-carbonylamino group" include methylcarbonylamino, ethylcarbonylamino, propylcarbonylamino, methyloxyethylcarbonylamino, methyloxypropylcarbonylamino, 1,1,1-trifluoroethylcarbonylamino, and 1,1,1-trifluoropropylcarbonylamino.

(6) The "$C_{2-6}$ alkenyl" of the "optionally substituted aminocarbonyl-$C_{2-6}$ alkenyl group" for $R^2$ is preferably vinyl.

Examples of the "substituent" of the "optionally substituted aminocarbonyl-$C_{2-6}$ alkenyl group" for $R^2$ include optionally substituted $C_{1-6}$ alkyl (e.g., methyl). In the "optionally substituted aminocarbonyl-$C_{2-6}$ alkenyl group", the "amino" may be substituted and the "$C_{2-6}$ alkenyl" may be substituted, and the number of the substituents is preferably 1 to 3. When the number of the substituents is two or more, the respective substituents may be the same or different.

Examples of the "substituent" of the "optionally substituted $C_{1-6}$ alkyl" include a non-aromatic heterocyclic group (e.g., tetrahydropyranyl). The substituent is present at a substitutable position of the $C_{1-6}$ alkyl and the number of the substituents is preferably 1 to 5, more preferably 1 to 3, particularly preferably 1 or 2. When the number of the substituents is two or more, the respective substituents may be the same or different.

The "aminocarbonyl-$C_{2-6}$ alkenyl group" of the "optionally substituted aminocarbonyl-$C_{2-6}$ alkenyl group" for $R^2$ is specifically 2-(aminocarbonyl)ethenyl.

(7) The "$C_{1-6}$ alkyl" of the "optionally substituted $C_{1-6}$ alkylcarbonylamino-$C_{1-6}$ alkyl group" for $R^2$ is preferably methyl.

Examples of the "substituent" of the "optionally substituted $C_{1-6}$ alkylcarbonylamino-$C_{1-6}$ alkyl group" for $R^2$ include a non-aromatic heterocyclic group (e.g., tetrahydropyranyl). In the "optionally substituted $C_{1-6}$ alkylcarbonylamino-$C_{1-6}$ alkyl group", the "amino" may be substituted and the "$C_{1-6}$ alkyl" may be substituted, and the number of the substituents is preferably 1 to 3. When the number of the substituents is two or more, the respective substituents may be the same or different.

The "$C_{1-6}$ alkylcarbonylamino-$C_{1-6}$ alkyl group" of the "optionally substituted $C_{1-6}$ alkylcarbonylamino-$C_{1-6}$ alkyl group" for $R^2$ is specifically methylcarbonylaminomethyl.

(8) The "cyclic group" of the "optionally substituted cyclyl-aminocarbonyl group" for $R^2$ is preferably a non-aromatic heterocyclic group (e.g., tetrahydropyranyl).

The "optionally substituted cyclyl-aminocarbonyl group" for $R^2$ is preferably an unsubstituted "cyclyl-aminocarbonyl group".

The "cyclyl-aminocarbonyl group" of the "optionally substituted cyclyl-aminocarbonyl group" for $R^2$ is specifically tetrahydropyranylmethylcarbonyl.

(9) The "cyclic group" of the "optionally substituted cyclyl-carbonyl group" for $R^2$ is preferably a non-aromatic heterocyclic group (e.g., tetrahydronaphthyridinyl).

Examples of the "substituent" of the "optionally substituted cyclyl-carbonyl group" for $R^2$ include oxo.

The "cyclyl-carbonyl group" of the "optionally substituted cyclyl-carbonyl group" for $R^2$ is specifically tetrahydronaphthyridinylcarbonyl.

(10) The "non-aromatic heterocyclic group" of the "optionally substituted non-aromatic heterocyclic group" for $R^2$ is preferably pyrrolidinyl, piperidyl, tetrahydrofuranyl, pyranyl, tetrahydrothiofuranyl or thiopyranyl, more preferably piperidyl.

Examples of the "substituent" of the "optionally substituted non-aromatic heterocyclic group" for $R^2$ include $C_{1-10}$ alkoxy-carbonyl (e.g., isobutoxycarbonyl, tert-butoxycarbonyl) optionally substituted by hydroxy or the same or different 1-6 halogen atoms (e.g., a fluorine atom), and $C_{6-14}$ arylcarbonyl (e.g., phenylcarbonyl) optionally substituted by cyano. The substituent is present at a substitutable position of the non-aromatic heterocyclic group and the number of the substituents is preferably 1 to 5, more preferably 1 to 3, particularly preferably 1 or 2. When the number of the substituents is two or more, the respective substituents may be the same or different.

$R^2$ is preferably (1) an optionally substituted cyclyl-carbonyl-$C_{1-6}$ alkyl group, (2) an optionally substituted aminocarbonyl-$C_{1-6}$ alkyl group, (3) an optionally substituted cyclyl-$C_{1-6}$ alkyl group, (4) optionally substituted cyclyl-$C_{1-6}$ alkylamino-carbonyl group, (6) an optionally substituted aminocarbonyl-$C_{2-6}$ alkenyl group, (7) an optionally substituted $C_{1-6}$ alkylcarbonylamino-$C_{1-6}$ alkyl group, (8) an optionally substituted cyclyl-aminocarbonyl group, (9) an optionally substituted cyclyl-carbonyl group or (10) an optionally substituted non-aromatic heterocyclic group.

In a preferable embodiment of the present invention, the partial structural formula in the formula (I):

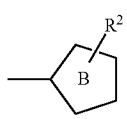

shows the following partial structural formula:

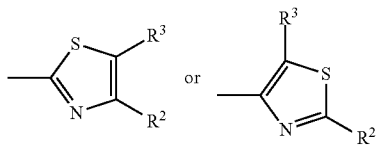

wherein $R^2$ is an optionally substituted cyclyl-carbonyl-$C_{1-6}$ alkyl group, an optionally substituted aminocarbonyl-$C_{1-6}$ alkyl group, an optionally substituted cyclyl-$C_{1-6}$ alkyl group, an optionally substituted cyclyl-$C_{1-6}$ alkylamino-carbonyl group, an optionally substituted $C_{1-6}$ alkyl-carbonylamino group, or an optionally substituted non-aromatic heterocyclic group, and $R^3$ is a hydrogen atom or a substituent.

As the "substituent" for $R^3$, those similar to the "substituent" explained above for $R^1$ can be mentioned.

$R^3$ is preferably a hydrogen atom or $C_{1-6}$ alkyl (e.g., methyl), more preferably, a hydrogen atom.

The partial structural formula in the formula (I):

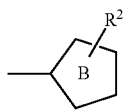

is more preferably the following partial structural formula:

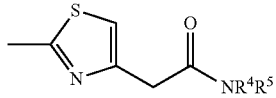

wherein $R^4$ and $R^5$ are as defined above.

One of $R^4$ and $R^5$ is preferably a hydrogen atom or a $C_{1-3}$ alkyl group, and the other is a tetrahydropyranylmethyl group (e.g., tetrahydropyran-4-ylmethyl), a pyridylmethyl group (e.g., pyridin-3-ylmethyl, pyridin-4-ylmethyl), or a benzyl group optionally substituted by a 1-imidazolyl group (e.g., benzyl, 4-(imidazol-1-yl)benzyl), more preferably, one is a hydrogen atom and the other is a tetrahydropyranylmethyl group (e.g., tetrahydropyran-4-ylmethyl).

In a preferable embodiment of the present invention, the partial structural formula in the formula (I):

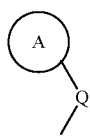

is

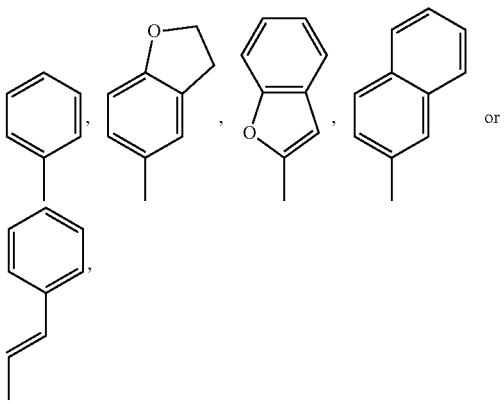

each of which is optionally substituted (more preferably, optionally substituted by the same or different 1 to 3 substituents selected from (i) a halogen atom (e.g., a fluorine atom, a chlorine atom), (ii) $C_{1-6}$ alkyl (e.g., methyl, tert-butyl) optionally substituted by the same or different 1 to 3 substituents selected from a halogen atom (e.g., a fluorine atom), hydroxy and cyano, (iii) $C_{1-6}$ alkoxy (particularly, methoxy, isopropoxy) optionally substituted by the same or different 1 to 3 halogen atoms, (iv) $C_{6-14}$ aryloxy (e.g., phenoxy), (v) cyano, (vi) $C_{1-10}$ alkylsulfonyl (e.g., methylsulfonyl), (vii) mono- or bis($C_{1-6}$ alkyl-carbonyl)amino (e.g., acetylamino) and (viii) a heterocyclic group (e.g., morpholino)).

Preferable examples of the ring, group, substituent and the like explained in the present specification are more preferably used in combination.

As preferable compound (I), the following compound can be mentioned.

A compound wherein
ring A is a $C_{3-7}$ cycloalkyl group, an optionally substituted $C_{6-14}$ aryl group, or a heterocyclic group;
Q is a bond, or optionally substituted $C_{1-10}$ alkylene;
$R^1$ is
(1) an optionally substituted $C_{1-10}$ alkyl group;
(2) an optionally substituted $C_{2-10}$ alkenyl group;
(3) an optionally substituted $C_{2-10}$ alkynyl group;
(4) an optionally substituted $C_{3-7}$ cycloalkyl group;
(5) an optionally substituted $C_{10-14}$ aryl group;
(6) a phenyl group optionally substituted by the same or different 1 to 5 substituents selected from (a) halogen, (b) a hydroxy group, (c) a nitro group, (d) a cyano group, (e) an optionally substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group;

(7) an optionally substituted $C_{7-16}$ aralkyl group;
(8) an optionally substituted heterocyclic group;
(9) a formyl group;
(10) a carboxy group;
(11) an optionally substituted $C_{1-10}$ alkyl-carbonyl group;
(12) an optionally substituted $C_{3-7}$ cycloalkyl-carbonyl group;
(13) an optionally substituted $C_{6-14}$ aryl-carbonyl group;
(14) an optionally substituted $C_{7-16}$ aralkyl-carbonyl group;
(15) an optionally substituted heterocyclyl-carbonyl group;
(16) an optionally substituted $C_{1-10}$ alkylsulfonyl group;
(17) an optionally substituted $C_{3-7}$ cycloalkylsulfonyl group;
(18) an optionally substituted $C_{6-14}$ arylsulfonyl group;
(19) an optionally substituted heterocyclyl-sulfonyl group
(20) an optionally substituted $C_{1-10}$ alkylsulfinyl group;
(21) an optionally substituted $C_{3-7}$ cycloalkylsulfinyl group;
(22) an optionally substituted $C_{6-14}$ arylsulfinyl group;
(23) an optionally substituted heterocyclyl-sulfinyl group;
(24) a sulfamoyl group;
(25) a sulfinamoyl group;
(26) a sulfinamoyl group;
(27) a thiocarbamoyl group;
(28) an optionally substituted carbamoyl group;
(29) an optionally substituted $C_{1-10}$ alkoxy-carbonyl group;
(30) an optionally substituted $C_{6-14}$ aryloxy-carbonyl group; or
(31) an optionally substituted $C_{7-16}$ aralkyloxy-carbonyl group;

ring B is a thiazole ring optionally further substituted by a substituent in addition to $R^2$; and $R^2$ is (1) an optionally substituted cyclyl-carbonyl-$C_{1-6}$ alkyl group, (2) an optionally substituted aminocarbonyl-$C_{1-6}$ alkyl group, (3) an optionally substituted cyclyl-$C_{1-6}$ alkyl group, (4) an optionally substituted cyclyl-$C_{1-6}$ alkylaminocarbonyl group, or (6) an optionally substituted non-aromatic heterocyclic group.

As a more preferable compound (I), the following compound can be mentioned.

A compound wherein
ring A is
(1) a $C_{3-7}$ cycloalkyl group,
(2) a $C_{6-14}$ aryl group optionally substituted by 1 to 5 substituents selected from a halogen atom, $C_{1-6}$ alkyl optionally substituted by the same or different 1 to 3 halogen atoms, $C_{1-6}$ alkoxy, cyano, and a heterocyclic group, or
(3) a heterocyclic group;
Q is a bond, —$CH_2$—, or —$(CH_2)_2$—;
$R^1$ is
(1) an optionally substituted $C_{1-10}$ alkyl group;
(2) an optionally substituted $C_{2-10}$ alkenyl group;
(3) an optionally substituted $C_{2-10}$ alkynyl group;
(4) an optionally substituted $C_{3-7}$ cycloalkyl group;
(5) an optionally substituted $C_{10-14}$ aryl group;
(6) a phenyl group optionally substituted by the same or different 1 to 5 substituents selected from (a) halogen, (b) a hydroxy group, (c) a nitro group, (d) a cyano group, (e) an optionally substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group;

(7) an optionally substituted $C_{7-16}$ aralkyl group;
(8) an optionally substituted heterocyclic group (bonded to the pyrazole ring via a carbon atom);
(9) a formyl group;
(10) a carboxy group;
(11) an optionally substituted $C_{1-10}$ alkyl-carbonyl group;
(12) an optionally substituted $C_{3-7}$ cycloalkyl-carbonyl group;
(13) an optionally substituted $C_{6-14}$ aryl-carbonyl group;
(14) an optionally substituted $C_{7-16}$ aralkyl-carbonyl group;
(15) an optionally substituted heterocyclyl-carbonyl group;
(27) a thiocarbamoyl group;
(28) an optionally substituted carbamoyl group;
(29) an optionally substituted $C_{1-10}$ alkoxy-carbonyl group;
(30) an optionally substituted $C_{6-14}$ aryloxy-carbonyl group; or
(31) an optionally substituted $C_{7-16}$ aralkyloxy-carbonyl group;

ring B is a thiazole ring optionally further substituted by $C_{1-6}$ alkyl (e.g., methyl); and $R^2$ is (1) an optionally substituted non-aromatic heterocyclyl-carbonyl-$C_{1-6}$ alkyl group;
(2) an aminocarbonyl-$C_{1-6}$ alkyl group (e.g., methyl) optionally substituted by 1 or 2 substituents selected from (i) optionally substituted $C_{1-6}$ alkyl (e.g., methyl, ethyl, propyl, isobutyl), (ii) optionally substituted $C_{6-14}$ aryl (e.g., phenyl), and (iii) a non-aromatic heterocyclic group (e.g., tetrahydropyranyl);
(3) an optionally substituted non-aromatic heterocyclic group (e.g., thiomorpholino)-$C_{1-6}$ alkyl group (e.g., ethyl);
(4) an optionally substituted non-aromatic heterocyclic group (e.g., morpholino, tetrahydropyranyl)-$C_{1-6}$ alkyl (e.g., methyl, ethyl)amino-carbonyl group; or
(6) an optionally substituted non-aromatic heterocyclic group (e.g., pyrrolidinyl, piperidyl, tetrahydrofuranyl, pyranyl, tetrahydrothiofuranyl, thiopyranyl).

As a further more preferable compound (I), the following compound can be mentioned.

A compound wherein
ring A is
(1) a $C_{1-7}$ cycloalkyl group (particularly, cyclopropyl),
(2) a $C_{6-14}$ aryl group (particularly, phenyl) optionally substituted by 1 to 5 substituents selected from a halogen atom (particularly, a fluorine atom), $C_{1-6}$ alkyl (particularly, methyl) optionally substituted by the same or different 1 to 3 halogen atoms (particularly, a fluorine atom), $C_{1-6}$ alkoxy (particularly, methoxy, isopropoxy), cyano, and a heterocyclic group (particularly, morpholino), or
(3) a heterocyclic group (particularly, pyridyl and 1,4-benzodioxinyl);

Q is a bond, —CH$_2$—, or —(CH$_2$)$_2$—;
$R^1$ is
(1) an optionally substituted $C_{1-40}$ alkyl group;
(4) an optionally substituted $C_{3-7}$ cycloalkyl group;
(6) a phenyl group optionally substituted by the same or different 1 to 5 substituents selected from (a) a halogen atom, (b) a hydroxy group, (c) a nitro group, (d) a cyano group, (e) an optionally substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group; or
(8) an optionally substituted heterocyclic group;
ring B is a thiazole ring optionally further substituted by methyl; and
$R^2$ is
(1) an optionally substituted non-aromatic heterocyclic group (e.g., azetidinyl, pyrrolidinyl, piperidino, morpholino, 1,4-oxazepanyl, piperazinyl, 1,4-diazepanyl, thiomorpholino, 2-oxa-7-azaspiro[3.4]oct-7-yl, 2-oxa-8-azaspiro[3.5]non-8-yl, 1-oxa-9-azaspiro[4.5]dec-9-yl, isoindolinyl, tetrahydroisoquinolyl)-carbonyl-$C_{1-6}$ alkyl group (e.g., methyl));
(2) an aminocarbonyl-$C_{1-6}$ alkyl group (e.g., methyl) optionally substituted by 1 or 2 substituents selected from (i) $C_{1-6}$ alkyl (e.g., methyl, ethyl, propyl, isobutyl) optionally substituted by substituent(s) selected from a halogen atom (e.g., a fluorine atom), hydroxy, $C_{1-6}$ alkoxy (e.g., methoxy), cyano, $C_{1-10}$ alkoxy-carbonyl (e.g., ethoxycarbonyl), a non-aromatic heterocyclic group (e.g., oxetanyl, tetrahydrofuryl, tetrahydropyranyl, piperidyl, morpholino) optionally substituted by one $C_{1-6}$ alkyl (e.g., methyl), $C_{6-14}$ aryl (e.g., phenyl) optionally substituted by the same or different 1 to 3 substituents selected from (1) a halogen atom (e.g., a fluorine atom, a chlorine atom), (2) $C_{1-6}$ alkyl (e.g., methyl) substituted by the same or different 1 to 3 halogen atoms (e.g., a fluorine atom), (3) $C_{1-6}$ alkoxy (e.g., methoxy) optionally substituted by the same or different 1 to 3 halogen atoms (e.g., a fluorine atom), (4) cyano, (5) amino substituted by $C_{1-6}$ alkyl (e.g., methyl), (6) $C_{1-10}$ alkylsulfonyl (e.g., methylsulfonyl) and (7) $C_{6-14}$ aryl (e.g., phenyl), and an aromatic heterocyclic group (e.g., furyl, pyrazolyl, imidazolyl, oxazolyl, isoxazolyl, thiazolyl, pyridyl, pyrimidinyl) optionally substituted by the same or different 1 or 2 $C_{1-6}$ alkyl (e.g., methyl),
(ii) $C_{6-14}$ aryl (e.g., phenyl) optionally substituted by $C_{1-6}$ alkoxy (e.g., methoxy), and
(iii) a non-aromatic heterocyclic group (e.g., tetrahydropyranyl);
(3) a non-aromatic heterocyclic group (e.g., thiomorpholino)-$C_{1-6}$ alkyl group (e.g., ethyl);
(4) a non-aromatic heterocyclic group (e.g., morpholino, tetrahydropyranyl)-$C_{1-6}$ alkyl (e.g., methyl, ethyl)amino-carbonyl group; or
(6) a non-aromatic heterocyclic group (e.g., pyrrolidinyl, piperidyl, tetrahydrofuranyl, pyranyl, tetrahydrothiofuranyl, thiopyranyl) optionally substituted by 1 to 5 substituents selected from $C_{1-10}$ alkoxy-carbonyl (e.g., isobutoxycarbonyl, tert-butoxycarbonyl) optionally substituted by hydroxy or the same or different 1-6 halogen atoms (e.g., a fluorine atom), and $C_{6-14}$ arylcarbonyl (e.g., phenylcarbonyl) optionally substituted by cyano.

As a particularly preferable compound (I), the following compound can be mentioned.
A compound wherein
ring A is
(1) cyclopropyl,
(2) phenyl optionally substituted by 1 to 5 substituents selected from a fluorine atom, methyl optionally substituted by 1 to 3 fluorine atoms, methoxy, isopropoxy, cyano, and morpholino, or
(3) pyridyl, or 1,4-benzodioxinyl;
Q is a bond, —CH$_2$—, or —(CH$_2$)$_2$—;
$R^1$ is
(1) a $C_{1-10}$ alkyl group (e.g., methyl, ethyl, propyl, isopropyl, n-butyl, sec-butyl, tert-butyl, isopentyl, neohexyl) optionally substituted by the same or different 1 to 3 substituents selected from (i) a halogen atom (e.g., a fluorine atom), (ii) a hydroxy group, (iii) a $C_{3-7}$ cycloalkyl group (e.g., cyclopropyl, cyclobutyl, cyclopentyl) optionally substituted by the same or different 1-2 halogen atoms (e.g., a fluorine atom), (iv) $C_{1-6}$ alkoxy (e.g., methoxy, ethoxy, isobutoxy) optionally substituted by the same or different 1 to 3 halogen atoms (e.g., a fluorine atom), and (v) a non-aromatic heterocyclic group (e.g., tetrahydrofuranyl, tetrahydropyranyl, tetrahydrothiopyranyl);
(4) a $C_{3-7}$ cycloalkyl group (e.g., cyclopentyl, cyclohexyl);
(6) a phenyl group; or
(8) a heterocyclic group (e.g., tetrahydrofuranyl);
ring B is a thiazole ring optionally further substituted by methyl; and
$R^2$ is
(1) an non-aromatic heterocyclic group (e.g., azetidinyl, pyrrolidinyl, piperidino, morpholino, 1,4-oxazepanyl, piperazinyl, 1,4-diazepanyl, thiomorpholino, 2-oxa-7-azaspiro[3.4]oct-7-yl, 2-oxa-8-azaspiro[3.5]non-8-yl, 1-oxa-9-azaspiro[4.5]dec-9-yl, isoindolinyl, a tetrahydroisoquinolyl)-carbonyl-$C_{1-6}$ alkyl group (e.g., methyl) optionally substituted by substituent(s) selected from oxo, hydroxy, $C_{1-6}$ alkyl (e.g., methyl), carboxy, alkoxy-carbonyl (e.g., ethoxycarbonyl), and $C_{6-14}$ aryl (e.g., phenyl);

(2) an aminocarbonyl-$C_{1-6}$ alkyl group (e.g., methyl) substituted by 1 or 2 substituents selected from
(i) $C_{1-6}$ alkyl (e.g., methyl, ethyl, propyl, isobutyl) optionally substituted by substituent(s) selected from a halogen atom (e.g., a fluorine atom), hydroxy, $C_{1-6}$ alkoxy (e.g., methoxy), cyano, $C_{1-10}$ alkoxy-carbonyl (e.g., ethoxycarbonyl), a non-aromatic heterocyclic group (e.g., oxetanyl, tetrahydrofuryl, tetrahydropyranyl, piperidyl, morpholino) optionally substituted by one $C_{1-6}$ alkyl (e.g., methyl), $C_{6-14}$ aryl (e.g., phenyl) optionally substituted by the same or different 1 to 3 substituents selected from (1) a halogen atom (e.g., a fluorine atom, a chlorine atom), (2) $C_{1-6}$ alkyl (e.g., methyl) substituted by the same or different 1 to 3 halogen atoms (e.g., a fluorine atom), (3) $C_{1-6}$ alkoxy (e.g., methoxy) optionally substituted by the same or different 1 to 3 halogen atoms (e.g., a fluorine atom), (4) cyano, (5) amino substituted by $C_{1-6}$ alkyl (e.g., methyl), (6) $C_{1-10}$ alkylsulfonyl (e.g., methylsulfonyl) and (7) $C_{6-14}$ aryl (e.g., phenyl), and an aromatic heterocyclic group (e.g., furyl, pyrazolyl, imidazolyl, oxazolyl, isoxazolyl, thiazolyl, pyridyl, pyrimidinyl) optionally substituted by the same or different 1 or 2 $C_{1-6}$ alkyl (e.g., methyl),
(ii) $C_{6-14}$ aryl (e.g., phenyl) optionally substituted by $C_{1-6}$ alkoxy (e.g., methoxy), and
(iii) a non-aromatic heterocyclic group (e.g., tetrahydropyranyl);
(3) a non-aromatic heterocyclic group (e.g., thiomorpholino)-$C_{1-6}$ alkyl group (e.g., ethyl);
(4) a non-aromatic heterocyclic group (e.g., morpholino, tetrahydropyranyl)-$C_{1-6}$ alkyl (e.g., methyl, ethyl)amino-carbonyl group; or
(6) a non-aromatic heterocyclic group (e.g., piperidyl) optionally substituted by 1 to 5 substituents selected from $C_{1-10}$ to alkoxy-carbonyl (e.g., isobutoxycarbonyl, tert-butoxycarbonyl) optionally substituted by hydroxy or the same or different 1-6 halogen atoms (e.g., a fluorine atom), and $C_{6-14}$ arylcarbonyl (e.g., phenylcarbonyl) optionally substituted by cyano.

In another embodiment of the present invention, preferable compound (I) includes, for example, the following compounds.

[Compound I-1]
Compound (I) wherein
ring A is a $C_{3-7}$ cycloalkyl group, a $C_{3-8}$ cycloalkenyl group, an optionally substituted $C_{6-14}$ aryl group, or an optionally substituted heterocyclic group;
Q is a bond, optionally substituted $C_{1-10}$ alkylene (e.g., —CH$_2$—, —(CH$_2$)$_2$—) or optionally substituted $C_{2-10}$ alkenylene (e.g., —CH═CH—);
$R^1$ is
(1) an optionally substituted $C_{1-10}$ alkyl group,
(2) an optionally substituted $C_{2-10}$ alkenyl group,
(3) an optionally substituted $C_{2-10}$ alkynyl group,
(4) an optionally substituted $C_{3-12}$ cycloalkyl group,
(5) an optionally substituted $C_{10-14}$ aryl group,
(6) a phenyl group optionally substituted by the same or different 1 to 5 substituents selected from (a) a halogen atom, (b) a hydroxy group, (c) a nitro group, (d) a cyano group, (e) an optionally substituted $C_{6-14}$ aryl group, (f) an optionally substituted $C_{6-14}$ aryloxy group, (g) an optionally substituted $C_{7-16}$ aralkyloxy group, (h) an optionally substituted 5- to 10-membered heterocyclic group having one or two kinds of 1-4 hetero atoms selected from a nitrogen atom, a sulfur atom and an oxygen atom, (i) an optionally substituted amino group, (j) an optionally substituted $C_{3-7}$ cycloalkyl group, (k) an optionally substituted $C_{1-6}$ alkoxy group, (l) a formyl group, (m) an optionally substituted $C_{1-6}$ alkyl-carbonyl group, (n) an optionally substituted $C_{3-7}$ cycloalkyl-carbonyl group, (o) an optionally substituted $C_{6-14}$ aryl-carbonyl group, (p) an optionally substituted $C_{7-16}$ aralkyl-carbonyl group, (q) an optionally substituted $C_{1-6}$ alkoxy-carbonyl group, (r) an optionally substituted $C_{6-14}$ aryloxy-carbonyl group, (s) an optionally substituted $C_{7-16}$ aralkyloxy-carbonyl group, (t) an optionally substituted $C_{1-6}$ alkylsulfanyl group, (u) an optionally substituted $C_{1-6}$ alkylsulfinyl group, (v) an optionally substituted $C_{1-6}$ alkylsulfonyl group, (w) a carbamoyl group, (x) a thiocarbamoyl group, (y) a mono-$C_{1-6}$ alkyl-carbamoyl group, (z) a di-$C_{1-6}$ alkyl-carbamoyl group, (aa) a mono- or di-(5- or 7-membered heterocyclyl having one or two kinds of 1-4 hetero atoms selected from a nitrogen atom, a sulfur atom and an oxygen atom)-carbamoyl group, (bb) an optionally substituted $C_{1-6}$ alkyl group, (cc) an optionally substituted $C_{2-6}$ alkenyl group, and (dd) an optionally substituted $C_{2-6}$ alkynyl group;
(7) an optionally substituted $C_{7-16}$ aralkyl group,
(8) an optionally substituted heterocyclic group,
(9) a formyl group,
(10) a carboxy group,
(11) an optionally substituted $C_{1-10}$ alkyl-carbonyl group,
(12) an optionally substituted $C_{3-7}$ cycloalkyl-carbonyl group,
(13) an optionally substituted $C_{6-14}$ aryl-carbonyl group,
(14) an optionally substituted $C_{7-16}$ aralkyl-carbonyl group,
(15) an optionally substituted heterocyclyl-carbonyl group,
(16) an optionally substituted $C_{1-10}$ alkylsulfonyl group,
(17) an optionally substituted $C_{3-7}$ cycloalkylsulfonyl group,
(18) an optionally substituted $C_{6-14}$ arylsulfonyl group,
(19) an optionally substituted heterocyclyl-sulfonyl group,
(20) an optionally substituted $C_{1-10}$ alkylsulfinyl group,
(21) an optionally substituted $C_{3-7}$ cycloalkylsulfinyl group,
(22) an optionally substituted $C_{6-14}$ arylsulfinyl group,
(23) an optionally substituted heterocyclyl-sulfinyl group,
(24) a sulfamoyl group,
(25) a sulfinamoyl group,
(26) a sulfinamoyl group,
(27) a thiocarbamoyl group,
(28) an optionally substituted carbamoyl group,
(29) an optionally substituted $C_{1-10}$ alkoxy-carbonyl group,
(30) an optionally substituted $C_{6-14}$ aryloxy-carbonyl group, or
(31) an optionally substituted $C_{7-16}$ aralkyloxy-carbonyl group;
ring B is a thiazole ring optionally further substituted by a substituent in addition to $R^2$; and
$R^2$ is
(1) an optionally substituted non-aromatic heterocyclyl-carbonyl-$C_{1-6}$ alkyl group,
(2) an aminocarbonyl-$C_{1-6}$ alkyl group (e.g., methyl, ethyl) optionally substituted by 1 or 2 substituents selected from (i) optionally substituted $C_{1-6}$ alkyl (e.g., methyl, ethyl, propyl, isobutyl), (ii) optionally substituted $C_{6-14}$ aryl (e.g., phenyl), and (iii) a non-aromatic heterocyclic group (e.g., tetrahydropyranyl),
(3) an optionally substituted non-aromatic heterocyclic group (e.g., thiomorpholino)-$C_{1-6}$ alkyl group (e.g., ethyl),
(4) an optionally substituted non-aromatic heterocyclic group (e.g., morpholino, tetrahydropyranyl)-$C_{1-6}$ alkyl (e.g., methyl, ethyl)amino-carbonyl group,
(6) an aminocarbonyl-$C_{2-6}$ alkenyl group (e.g., vinyl) optionally substituted by optionally substituted $C_{1-6}$ alkyl (e.g., methyl),
(7) a $C_{1-6}$ alkylcarbonylamino-$C_{1-6}$ alkyl group (e.g., methyl) optionally substituted by a non-aromatic heterocyclic group (e.g., tetrahydropyranyl), (8) an optionally substituted non-aromatic heterocyclic group (e.g., tetrahydropyranyl)-aminocarbonyl group, (9) a non-aromatic heterocyclic group (e.g., tetrahydronaphthyridinyl)-carbonyl group optionally substituted by oxo, or

(10) an optionally substituted non-aromatic heterocyclic group (e.g., pyrrolidinyl, piperidyl, tetrahydrofuranyl, pyranyl, tetrahydrothiofuranyl, thiopyranyl).

[Compound I-2]

Compound (I) wherein ring A is (1) a $C_{3-7}$ cycloalkyl group (e.g., cyclopropyl, cyclohexyl), (2) a $C_{3-8}$ cycloalkenyl group (e.g., cyclohexenyl), (3) a $C_{6-14}$ aryl group (e.g., phenyl, naphthyl, 3-biphenylyl, 4-biphenylyl) optionally substituted by the same or different 1 to 3 substituents selected from (i) a halogen atom (e.g., a fluorine atom, a chlorine atom), (ii) $C_{1-6}$ alkyl (e.g., methyl, tert-butyl) optionally substituted by the same or different 1 to 3 substituents selected from a halogen atom (e.g., a fluorine atom), hydroxy and cyano, (iii) $C_{1-6}$ alkoxy (e.g., methoxy, isopropoxy) optionally substituted by the same or different 1 to 3 halogen atoms (e.g., a fluorine atom), (iv) $C_{6-14}$ aryloxy (e.g., phenoxy), (v) cyano, (vi) $C_{1-10}$ alkylsulfonyl (e.g., methylsulfonyl), (vii) mono- or bis($C_{1-6}$ alkyl-carbonyl)amino (e.g., acetylamino) and (viii) a heterocyclic group (e.g., morpholino), or (4) a heterocyclic group (e.g., furyl, thienyl, pyrazolyl, pyridyl, 1,4-benzodioxinyl, benzofuranyl, benzothienyl, indazolyl and dihydrobenzofuranyl) optionally substituted by the same or different 1 to 3 substituents selected from (i) a halogen atom (e.g., a chlorine atom), (ii) $C_{1-6}$ alkyl (e.g., methyl) optionally substituted by the same or different 1 to 3 halogen atoms (e.g., a fluorine atom) and (iii) $C_{1-6}$ alkoxy (e.g., methoxy);

Q is a bond, —CH$_2$—, —(CH$_2$)$_2$— or —CH=CH—;

R$^1$ is (1) a $C_{1-10}$ alkyl group (e.g., methyl, ethyl, propyl, isopropyl, n-butyl, sec-butyl, tert-butyl, isopentyl, neohexyl) optionally substituted by the same or different 1 to 3 substituents selected from (i) a halogen atom (e.g., a fluorine atom), (ii) a hydroxy group, (iii) a $C_{3-7}$ cycloalkyl group (e.g., cyclopropyl, cyclobutyl, cyclopentyl) optionally substituted by the same or different 1-2 halogen atoms (e.g., a fluorine atom), (iv) $C_{1-6}$ alkoxy (e.g., methoxy, ethoxy, isobutoxy) optionally substituted by the same or different 1 to 3 halogen atoms (e.g., a fluorine atom), and (v) a non-aromatic heterocyclic group (e.g., tetrahydrofuranyl, tetrahydropyranyl, tetrahydrothiopyranyl);

(4) a $C_{3-7}$ cycloalkyl group (e.g., cyclopentyl, cyclohexyl, cycloheptyl), (6) a phenyl group, or (8) a heterocyclic group (bonded to the pyrazole ring via a carbon atom) (e.g., tetrahydrofuranyl, tetrahydrothiopyranyl);

ring B is a thiazole ring optionally further substituted by $C_{1-6}$ alkyl (e.g., methyl); and R$^2$ is (1) an non-aromatic heterocyclic group (e.g., azetidinyl, pyrrolidinyl, piperidino, morpholino, 1,4-oxazepanyl, piperazinyl, 1,4-diazepanyl, thiomorpholino, 2-oxa-7-azaspiro[3.4]oct-7-yl, 2-oxa-8-azaspiro[3.5]non-8-yl, 1-oxa-9-azaspiro[4.5]dec-9-yl, isoindolinyl, tetrahydroisoquinolyl, a tetrahydronaphthyridinyl)-carbonyl-$C_{1-6}$ alkyl group (e.g., methyl) optionally substituted by substituent(s) selected from oxo, hydroxy, $C_{1-6}$ alkyl (e.g., methyl), carboxy, $C_{1-10}$ alkoxy-carbonyl (e.g., ethoxycarbonyl), and $C_{6-14}$ aryl (e.g., phenyl);

(2) an aminocarbonyl-$C_{1-6}$ alkyl group (e.g., methyl, ethyl) substituted by 1 or 2 substituents selected from (i) $C_{1-6}$ alkyl (e.g., methyl, ethyl, propyl, isobutyl) optionally substituted by substituent(s) selected from a halogen atom (e.g., a fluorine atom), hydroxy, $C_{1-6}$ alkoxy (e.g., methoxy), cyano, $C_{1-10}$ alkoxy-carbonyl (e.g., ethoxycarbonyl), a non-aromatic heterocyclic group (e.g., oxetanyl, tetrahydrofuryl, tetrahydropyranyl, piperidyl, morpholino) optionally substituted by one $C_{1-6}$ alkyl (e.g., methyl) optionally substituted by hydroxy, $C_{6-14}$ aryl (e.g., phenyl) optionally substituted by the same or different 1 to 3 substituents selected from (1) a halogen atom (e.g., a fluorine atom, a chlorine atom), (2) $C_{1-6}$ alkyl (e.g., methyl) substituted by the same or different 1 to 3 halogen atoms (e.g., a fluorine atom), (3) $C_{1-6}$ alkoxy (e.g., methoxy) optionally substituted by the same or different 1 to 3 halogen atoms (e.g., a fluorine atom), (4) cyano, (5) amino substituted by $C_{1-6}$ alkyl (e.g., methyl), (6) $C_{1-10}$ alkylsulfonyl (e.g., methylsulfonyl), (7) $C_{6-14}$ aryl (e.g., phenyl), and (8) an aromatic heterocyclic group (e.g., pyrazolyl), and an aromatic heterocyclic group (e.g., furyl, pyrazolyl, imidazolyl, oxazolyl, isoxazolyl, thiazolyl, pyridyl, pyrimidinyl) optionally substituted by the same or different 1 or 2 $C_{1-6}$ alkyl (e.g., methyl), (ii) $C_{6-14}$ aryl (e.g., phenyl) optionally substituted by substituent(s) selected from $C_{1-6}$ alkoxy (e.g., methoxy), an aromatic heterocyclic group (e.g., pyrazolyl), and mono- or bis($C_{1-6}$ alkyl-carbonyl)amino (e.g., acetylamino), and (iii) a non-aromatic heterocyclic group (e.g., tetrahydropyranyl);

(3) a non-aromatic heterocyclic group (e.g., thiomorpholino)-$C_{1-6}$ alkyl group (e.g., ethyl);

(4) a non-aromatic heterocyclic group (e.g., morpholino, tetrahydropyranyl)-$C_{1-6}$ alkyl (e.g., methyl, ethyl)amino-carbonyl group;

(6) an aminocarbonyl-$C_{2-6}$ alkenyl group (e.g., vinyl) optionally substituted by $C_{1-6}$ alkyl (e.g., methyl) optionally substituted by a non-aromatic heterocyclic group (e.g., tetrahydropyranyl), (7) a $C_{1-6}$ alkylcarbonylamino-$C_{1-6}$ alkyl group (e.g., methyl) optionally substituted by a non-aromatic heterocyclic group (e.g., tetrahydropyranyl), (8) a non-aromatic heterocyclic group (e.g., tetrahydropyranyl)-aminocarbonyl group, (9) a non-aromatic heterocyclic group (e.g., tetrahydronaphthyridinyl)-carbonyl group optionally substituted by oxo, or

(10) a non-aromatic heterocyclic group (e.g., piperidyl) optionally substituted by 1 to 5 substituents selected from $C_{1-10}$ alkoxy-carbonyl (e.g., isobutoxycarbonyl, tert-butoxycarbonyl) optionally substituted by hydroxy or the same or different 1-6 halogen atoms (e.g., a fluorine atom), and $C_{6-14}$ arylcarbonyl (e.g., phenylcarbonyl) optionally substituted by cyano.

Specific examples of the above-mentioned compound (I) include Example compounds, and 2-{2-[1-tert-butyl-5-(4-methoxyphenyl)-1H-pyrazol-4-yl]-1,3-thiazol-4-yl}-N-(tetrahydro-2H-pyran-4-ylmethyl)acetamide or a salt thereof (Example 39), 2-{2-[1-cyclohexyl-5-(4-fluorophenyl)-1H-pyrazol-4-yl]-1,3-thiazol-4-yl}-N-(tetrahydro-2H-pyran-4-ylmethyl)acetamide or a salt thereof (Example 51), and 2-{2-[1-tert-butyl-5-(4-fluorophenyl)-1H-pyrazol-4-yl]-1,3-thiazol-4-yl}-N-[4-(1H-imidazol-1-yl)benzyl]acetamide or a salt thereof (Example 170)

are particularly preferable.

Examples of a salt of compound (I) include metal salts, ammonium salts, salts with organic base, salts with inorganic acid, salts with organic acid, salts with basic or acidic amino acids. Preferable examples of the metal salt include alkaline metal salts such as sodium salt and potassium salt; alkaline earth metal salts such as calcium salt, magnesium salt and barium salt; and aluminum salt. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine and N,N'-dibenzylethylenediamine. Preferable examples of the salt with inorganic acid include salts with hydrochloric acid, hydrobromic acid, nitric acid, sulfuric acid and phosphoric acid. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid. Preferable examples of the salt with basic amino acid include salts with arginine, lysine and ornithine. Preferable examples of the salt with acidic amino acid include salt with aspartic acid and glutamic acid.

Among them, pharmaceutically acceptable salts are preferable. For example, if the compound has an acidic functional group therein, examples of the salt include inorganic salts such as alkaline metal salts (e.g., sodium salt and potassium salt) and alkaline earth metal salts (e.g., calcium salt, magnesium salt and barium salt); and ammonium salt. If the compound has a basic functional group therein, examples of the salt thereof include salts with inorganic acids such as hydrochloric acid, hydrobromic acid, nitric acid, sulfuric acid and phosphoric acid, and salts with organic acids such as acetic acid, phthalic acid, fumaric acid, oxalic acid, tartaric acid, maleic acid, citric aid, succinic acid, methanesulfonic acid and p-toluenesulfonic acid.

The production methods of the compound (I) of the present invention or a salt thereof are explained below.

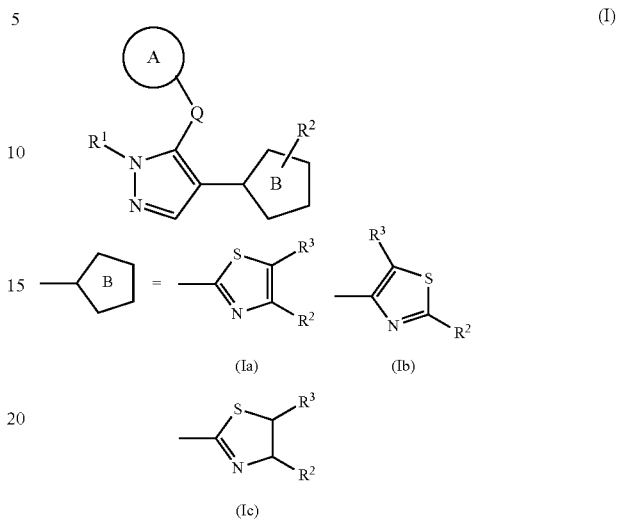

The intermediates produced in the following production methods may be isolated and purified by methods such as column chromatography, recrystallization, distillation and the like, or may be directly used without isolation in the next step.

The compound (I), compound (Ia), compound (Ib), compound (Ic) or a salt thereof of the present invention can be produced by the following Method A to Method F.

[Method A]

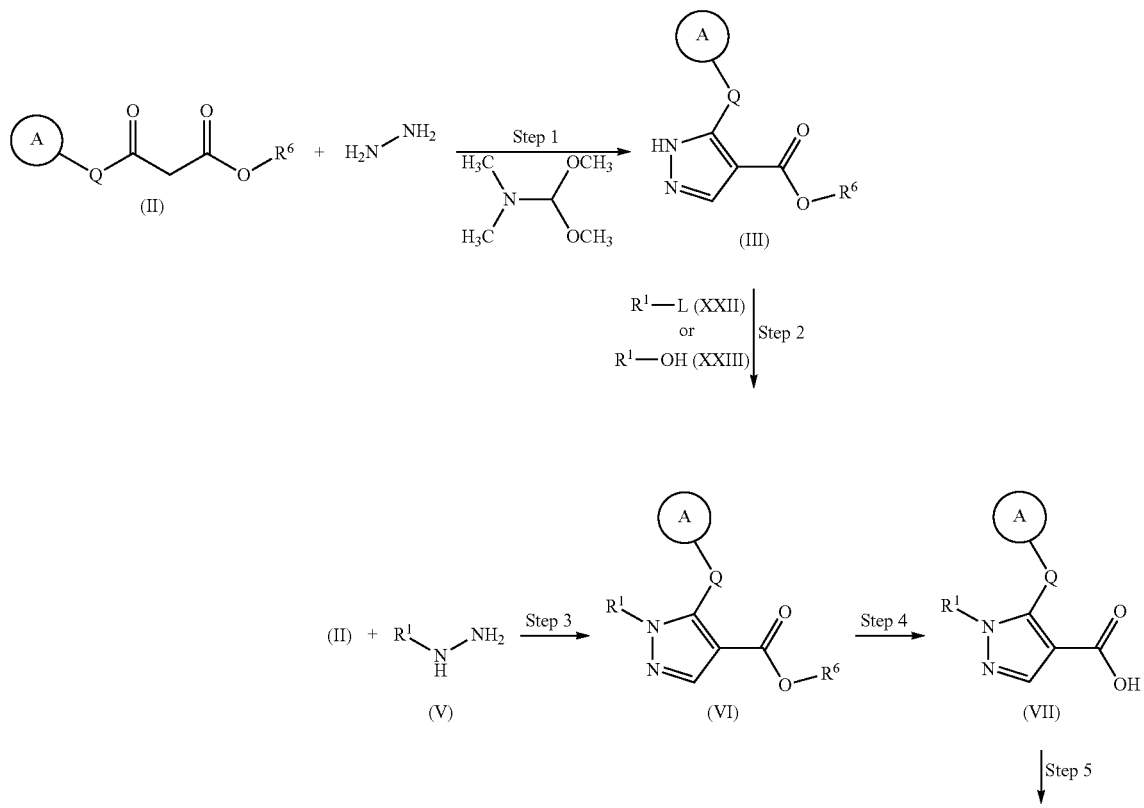

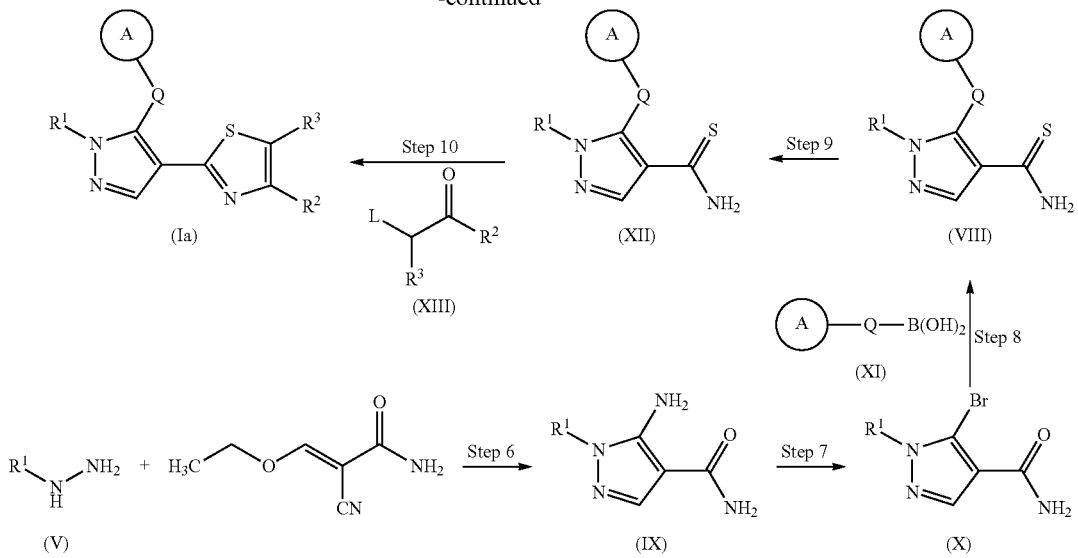

wherein R[6] is a hydrocarbon group optionally having substituent(s), L is a leaving group, and other symbols are as defined above.

As the leaving group for L, a halogen atom (a chlorine atom, a bromine atom, an iodine atom and the like), a substituted sulfonyloxy group ($C_{1-6}$ alkylsulfonyloxy group such as methanesulfonyloxy, ethanesulfonyloxy and the like; a $C_{6-14}$ arylsulfonyloxy group such as benzenesulfonyloxy, p-toluenesulfonyloxy and the like; a $C_{7-16}$ aralkylsulfonyloxy group such as benzylsulfonyloxy group and the like, and the like), acyloxy (acetoxy, benzoyloxy and the like), an oxy group substituted by a heterocycle or an aryl group (succinimide, benzotriazole, quinoline, 4-nitrophenyl and the like), a heterocycle (imidazole and the like) and the like are used.

(Step 1)

In this step, compound (II) or a salt thereof is treated with dimethylformamide dimethylacetal (DMFDMA), and reacted with hydrazine or a salt thereof in the presence of a base or an inorganic salt to produce compound (III) or a salt thereof.

The treatment of compound (II) or a salt thereof with DMFDMA is performed without a solvent or in a solvent that does not adversely influence the reaction.

Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylformamide and the like), sulfoxides (dimethyl sulfoxide and the like) and the like. Of these, toluene is preferable. Two or more kinds of these solvents may be used in a mixture in an appropriate ratio.

The reaction temperature is within the range of, for example, about 0-200° C., preferably about 50-100° C. The reaction time varies depending on the kind of compound (II) or a salt thereof, the reaction temperature and the like, and is, for example, about 0.5-100 hr, preferably about 0.5-24 hr.

The amount of DMFDMA to be used varies depending on the kind of the solvent, and other reaction conditions, and is generally about 1-10 molar equivalents, preferably about 1-5 molar equivalents, per 1 mol of compound (II).

As the base to be used for reacting the reactive intermediate, which is obtained by treating compound (II) or a salt thereof with DMFDMA, with hydrazine or a salt thereof, inorganic bases (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate and the like, alkoxides such as sodium methoxide, sodium ethoxide and the like, and the like), organic bases (amines such as trimethylamine, triethylamine, diisopropylethylamine and the like, cyclic amines such as pyridine, 4-dimethylaminopyridine and the like, and the like) and the like are used, and triethylamine is preferable. The amount of the base to be used varies depending on the kind of the solvent, and other reaction conditions, and is generally about 0.1-10 molar equivalents, preferably about 1-5 molar equivalents, per 1 mol of compound (II).

As the inorganic salt, carbonates (lithium carbonate, sodium carbonate, potassium carbonate and the like), acetates (lithium acetate, sodium acetate, potassium acetate, magnesium acetate, calcium acetate and the like) and the like are used, and sodium acetate is preferable. The amount of the inorganic salt to be used is generally about 0.1-10 molar equivalents, preferably about 1-5 molar equivalents, per 1 mol of the substrate.

Examples of the solvent to be used in reacting the active intermediate, which is obtained by treating compound (II) or a salt thereof with DMFDMA, with hydrazine or a salt thereof, include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), carboxylic acids (acetic acid and the like), amides (dimethylformamide and the like), sulfoxides (dimethyl sulfoxide and the like), water and the like, with preference to given to ethanol. Two or more kinds of these solvents may be used in a mixture in an appropriate ratio.

The amount of the hydrazine or a salt thereof to be used varies depending on the kind of the solvent, and other reaction conditions, and is generally about 1-10 molar equivalents, preferably about 1-5 molar equivalents, per 1 mol of compound (II).

The reaction temperature is, for example, within the range of about −50-200° C., preferably about 50-100° C. The reaction time varies depending on the kind of compound (II) or a salt thereof, the reaction temperature and the like, and it is, for example, about 0.5-100 hr, preferably about 0.5-24 hr.

(Step 2)

In this step, compound (VI) or a salt thereof is produced by reacting, in the presence of a base, compound (III) or a salt thereof with a compound represented by the formula:

wherein each symbol is as defined above,
or a salt thereof, or by reacting, in the presence of a Mitsunobu reagent and an organic phosphorous reagent, compound (III) or a salt thereof with a compound represented by the formula:

wherein each symbol is as defined above,
or a salt thereof.

The amount of the compound represented by the formula (XXII) to be used varies depending on the kind of the solvent, and other reaction conditions, and is generally about 1-10 molar equivalents, preferably about 1-5 molar equivalents, per 1 mol of compound (III).

As the base to be used when reacting compound (III) or a salt thereof with a compound represented by the formula (XXII) or a salt thereof, inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, alkali metal alkoxides such as sodium methoxide, sodium ethoxide, etc. and the like), organic base (amines such as trimethylamine, triethylamine, diisopropylethylamine and the like, cyclic amines such as pyridine, 4-dimethylaminopyridine, etc. and the like) and the like are used and, of these, sodium hydride, potassium carbonate and cesium carbonate are preferable. The amount of the base to be used varies depending on the kind of the solvent, and other reaction conditions, and is generally about 1-10 molar equivalents, preferably about 1-5 molar equivalents, per 1 mol of compound (III).

Compound (III) or a salt thereof is generally reacted with a compound represented by the formula (XXII) or a salt thereof in a solvent that does not adversely influence the reaction.

Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylformamide and the like), sulfoxides (dimethyl sulfoxide and the like) and the like. Of these, tetrahydrofuran, acetonitrile and dimethylformamide are preferable. Two or more kinds of these solvents may be used in a mixture in an appropriate ratio.

The reaction temperature is within the range of, for example, about 0-200° C., preferably about 50-100° C. The reaction time varies depending on the kind of compound (III) or a salt thereof, the reaction temperature and the like, and it is, for example, about 0.5-100 hr, preferably about 0.5-24 hr.

The amount of the compound represented by the formula (XXIII) to be used varies depending on the kind of the solvent, and other reaction conditions, and is generally about 1-10 molar equivalents, preferably about 1-5 molar equivalents, per 1 mol of compound (III).

As the Mitsunobu reagent to be used when reacting compound (III) or a salt thereof with a compound represented by the formula (XXIII) or a salt thereof, azodicarboxylates such as diethyl azodicarboxylate, diisopropyl azodicarboxylate and the like, and the like are used and, of these, diisopropyl azodicarboxylate is preferable. The amount of the Mitsunobu reagent to be used varies depending on the kind of the solvent, and other reaction conditions, and is generally about 1-10 molar equivalents, preferably about 1-5 molar equivalents, per 1 mol of compound (III).

As the organic phosphorous reagent to be used when reacting compound (III) or a salt thereof with a compound represented by the formula (XXIII) or a salt thereof, organic phosphorous compounds such as tributylphosphine, triphenylphosphine and the like are used and, of these, triphenylphosphine is preferable. The amount of the organic phosphorous reagent to be used varies depending on the kind of the solvent, and other reaction conditions, and is generally about 1-10 molar equivalents, preferably about 1-5 molar equivalents, per 1 mol of compound (III).

Compound (III) or a salt thereof is generally reacted with a compound represented by the formula (XXIII) or a salt thereof in a solvent that does not adversely influence the reaction.

Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylformamide and the like), sulfoxides (dimethyl sulfoxide and the like) and the like. Of these, toluene and tetrahydrofuran are preferable. Two or more kinds of these solvents may be used in a mixture in an appropriate ratio.

The reaction temperature is within the range of, for example, about 0-200° C., preferably about 50-100° C. The reaction time varies depending on the kind of compound (III) or a salt thereof, the reaction temperature and the like, and it is, for example, about 0.5-100 hr, preferably about 0.5-24 hr.

(Step 3)

In this step, compound (II) or a salt thereof is treated with dimethylformamide dimethylacetal (DMFDMA), and reacted with compound (V) or a salt thereof in the presence of a base or an inorganic salt to produce compound (VI) or a salt thereof. This step can be performed by a method similar to that described in Method A, step 1.

(Step 4)

In this step, compound (VI) or a salt thereof is subjected to hydrolysis to be converted to compound (VII) or a salt thereof. While this reaction can be performed by a method known per se, it is generally performed in the presence of an acid or a base and, where necessary, in a solvent that does not adversely influence the reaction.

As the acid, mineral acids (hydrochloric acid, hydrobromic acid, sulfuric acid and the like), carboxylic acids (acetic acid, trifluoroacetic acid, trichloroacetic acid and the like), sulfonic acids (methanesulfonic acid, toluenesulfonic acid and the like), Lewis acids (aluminum chloride, tin chloride, zinc bromide and the like) and the like are used, and two or more kinds thereof may be mixed as necessary. The amount of the acid to be used varies depending on the kind of the solvent, and other reaction conditions, and is generally about 0.1 mol or more equivalents per 1 mol of compound (VI). It can also be used as a solvent.

As the base, inorganic bases (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate and the like, alkoxides such as sodium methoxide, sodium ethoxide and the like, and the like), organic bases (amines such as trimethylamine, triethylamine, diisopropylethylamine and the like, cyclic amines such as pyridine, 4-dimethylaminopyridine and the like, and the like) and the like are used. Of these, sodium hydroxide is preferable. The amount of the base to be used varies depending on the kind of the solvent, and other reaction conditions, and is generally about 0.1-10 molar equivalents, preferably about 1-5 molar equivalents, per 1 mol of compound (VI).

Examples of the solvent that does not adversely influence the reaction include alcohols (methanol, ethanol, propanol, 2-propanol, butanol, isobutanol, t-butanol and the like), hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), carboxylic acids (acetic acid and the like), amides (dimethylformamide, dimethylacetamide and the like), sulfoxides (dimethyl sulfoxide and the like), water and the like. Of these, ethanol, tetrahydrofuran and water are preferable. Two or more kinds of these solvents may be used in a mixture in an appropriate ratio.

The reaction temperature is within the range of, for example, about −50-200° C., preferably about 0-100° C. The reaction time varies depending on the kind of compound (VI) or a salt thereof, the reaction temperature and the like, and it is, for example, about 0.5-100 hr, preferably about 0.5-24 hr.
(Step 5)

In this step, compound (VII) or a salt thereof is subjected to dehydration condensation with ammonia or a salt thereof to be converted to compound (VIII) or a salt thereof.

The amount of the ammonia or a salt thereof to be used varies depending on the kind of the solvent, and other reaction conditions, and is generally about 1-10 molar equivalents, preferably about 1-5 molar equivalents, per 1 mol of compound (VII).

The method for the dehydration condensation is a method known per se, for example, the method described in The Chemical Society of Japan ed. 1991 "4th Edition Jikken Kagaku Kouza 22, organic synthesis IV" and the like, or a method analogous thereto. Examples of the method include a method using a condensing agent, a method via a reactive derivative, and the like.

Examples of the condensing agent to be used for the "method using a condensing agent" include dicyclohexylcarbodiimide, diisopropylcarbodiimide, N-ethyl-N'-3-dimethylaminopropylcarbodiimide and hydrochlorides thereof, benzotriazol-1-yl-tris(dimethylamino)phosphonium hexafluorophosphate, diphenylphosphoryl azide and the like. These may be used alone, or may also be used in combination with an additive (e.g., N-hydroxysuccinimide, 1-hydroxybenzotriazole, 3-hydroxy-4-oxo-3,4-dihydro-1,2,3-benzotriazine and the like). The amount of the condensing agent to be used is about 1-10 molar equivalents, preferably about 1-2 molar equivalents, per 1 mol of compound (VII). The amount of the additive to be used is about 1-10 molar equivalents, preferably about 1-2 molar equivalents, per 1 mol of compound (VII).

The above-mentioned reaction is generally performed in a solvent that does not adversely influence the reaction, and a base may be added to accelerate the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), water and the like, and they may be mixed as appropriate. Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1-100 molar equivalents, preferably about 1-5 molar equivalents, per 1 mol of the substrate. The reaction temperature is generally about −80-150° C., preferably about 0-50° C. The reaction time is generally about 0.5-48 hr, preferably 0.5-16 hr.

Examples of the reactive derivative shown for the "method via a reactive derivative" include acid halides, acid anhydrides, mixed acid anhydrides, active esters and the like. While the conversion to a reactive derivative can be performed according to a method known per se, for example, as conversion to an acid halide, a method using an acid halide (e.g., thionyl chloride, oxalyl chloride and the like), a method using a halide of phosphorous or phosphoric acid (e.g., phosphorous trichloride, phosphorous pentachloride and the like) and the like can be mentioned. The reaction using the above-mentioned reactive derivative is generally performed in a solvent that does not adversely influence the reaction, though subject to change depending on the kind of the reactive derivative or substrate, and a base may be added to accelerate the reaction. The kind of the solvent and base to be used for the reaction, the amounts of use, the reaction temperature and reaction time are the same as those described in the above-mentioned "method using a condensing agent".
(Step 6)

In this step, compound (V) or a salt thereof is reacted with (2E)-2-cyano-3-ethoxyprop-2-enamide to be converted to compound (IX) or a salt thereof.

The amount of the (2E)-2-cyano-3-ethoxyprop-2-enamide to be used varies depending on the kind of the solvent, and other reaction conditions, and is generally about 1-10 molar equivalents, preferably 1-5 molar equivalents, per 1 mol of compound (V).

The above-mentioned reaction is generally performed in a solvent that does not adversely influence the reaction, and a base may be added to accelerate the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), water and the like, and they may be mixed as appropriate. Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1-100 molar equivalents, preferably about 1-5 molar equivalents, per 1 mol of the substrate. The reaction temperature is generally about −80-200° C., preferably about 0-100° C. The reaction time is generally about 0.5-48 hr, preferably 0.5-24 hr.
(Step 7)

In this step, compound (IX) or a salt thereof is subjected to a diazotization reaction and reacted with copper(I) bromide to be converted to compound (X) or a salt thereof.

The diazotization reaction is performed in the presence of a diazotization reagent in a solvent that does not adversely influence the reaction.

As the diazotization reagent, nitrous acid, salts of nitrous acid (e.g., sodium nitrite), esters of nitrous acid (e.g., pentyl nitrite) and the like are used. Of these, pentyl nitrite is preferable. The amount of the diazotization reagent to be used is generally about 1-100 molar equivalents, preferably about 1-5 molar equivalents, per 1 mol of the substrate.

Examples of the solvent that does not adversely influence the reaction include nitriles (acetonitrile and the like), ethers (diethyl ether, dioxane, tetrahydrofuran and the like), amides (N,N-dimethylformamide and the like), water and the like, and they may be mixed as appropriate. An acid may be added to accelerate the reaction.

As the acid to accelerate the reaction, mineral acids (hydrochloric acid, hydrobromic acid, sulfuric acid and the like), carboxylic acids (acetic acid, trifluoroacetic acid, trichloroacetic acid and the like), sulfonic acids (methanesulfonic acid, toluenesulfonic acid and the like). Lewis acids (aluminum chloride, tin chloride, zinc bromide and the like) and the like are used, and two or more kinds may be mixed as necessary. The amount of the acid to be used varies depending on the kind of the solvent, and other reaction conditions, and it is generally about 0.1 mol or more equivalents per 1 mol of compound (IX). The acid may also be used as a solvent.

The amount of copper(I) bromide varies depending on the kind of the solvent, and other reaction conditions, and is generally about 1-10 molar equivalents, preferably about 1-5 molar equivalents, per 1 mol of compound (IX).
(Step 8)

In this step, compound (X) or a salt thereof is subjected to a coupling reaction with compound (XI) or a salt thereof, and subjected to a reduction reaction as necessary to produce compound (VIII) or a salt thereof.

The amount of compound (XI) to be used varies depending on the kind of the solvent, and other reaction conditions, and is generally about 1-10 molar equivalents, preferably about 1-5 molar equivalents, per 1 mol of compound (X).

The coupling reaction can be performed in the presence of a transition metal catalyst and a base, in a solvent that does not adversely influence the reaction.

As the transition metal catalyst to be used, palladium catalysts (palladium acetate, palladium chloride, tetrakistriphenylphosphinepalladium and the like), nickel catalysts (nickel chloride and the like) and the like are used and, where necessary, a ligand (triphenylphosphine, tri-t-butylphosphine, S-Phos and the like) may be added, and a metal oxide (copper oxide, silver oxide and the like) and the like may be used as a co-catalyst. The amount of the catalyst to be used varies depending on the kind of the catalyst, and it is generally about 0.0001-1 mol equivalents, preferably about 0.01-0.5 molar equivalents, per 1 mol of compound (X). The amount of the ligand to be used is generally about 0.0001-4 molar equivalents, preferably about 0.01-2 molar equivalents, per 1 mol of compound (X). The amount of the co-catalyst to be used is about 0.0001-4 molar equivalents, preferably about 0.01-2 molar equivalents, per 1 mol of compound (X).

Examples of the base to be used include organic amines (trimethylamine, triethylamine, diisopropylamine, N-methylmorpholine, 1,8-diazabicyclo[5,4,0]undec-7-ene, pyridine, N,N-dimethylaniline and the like), alkali metal salts (sodium hydrogen carbonate, potassium hydrogen carbonate, sodium carbonate, potassium carbonate, cesium carbonate, sodium phosphate, potassium phosphate, sodium hydroxide, potassium hydroxide and the like), metal hydrides (potassium hydride, sodium hydride and the like), alkali metal alkoxides (sodium methoxide, sodium ethoxide, sodium-t-butoxide, potassium-t-butoxide and the like), alkali disilazides (lithium disilazide, sodium disilazide, potassium disilazide and the like) and the like. Of these, alkali metal salts such as potassium carbonate, cesium carbonate, sodium phosphate, potassium phosphate and the like, alkali metal alkoxides such as sodium-t-butoxide, potassium-t-butoxide and the like, organic amines such as triethylamine, diisopropylamine and the like, and the like are preferable. The amount of the base to be used is about 0.1-10 molar equivalents, preferably about 1-5 molar equivalents, per 1 mol of compound (X).

The solvent to be used only needs to be free from an adverse influence on the reaction and, for example, hydrocarbons (benzene, toluene, xylene and the like), halogenated hydrocarbons (chloroform, 1,2-dichloroethane and the like), nitriles (acetonitrile and the like), ethers (dimethoxyethane, tetrahydrofuran), alcohols (methanol, ethanol and the like), aprotic polar solvents (dimethylformamide, dimethyl sulfoxide, hexamethylphosphoramide and the like), water or a mixture thereof are used. The reaction temperature is generally −10-200° C., preferably about 0-150° C. The reaction time is generally 0.5-48 hr, preferably 0.5-24 hr.

The reduction reaction following the coupling reaction can be performed by reduction using a metal or a metal salt or reduction by catalytic hydrogenenation using a transition metal catalyst, in a solvent that does not adversely influence the reaction.

As the metal or metal salt to be used for the "reduction using a metal or a metal salt", alkali metals (lithium, sodium, potassium and the like), alkaline earth metals (magnesium, calcium and the like), other metals (zinc, chrome, titanium, iron, samarium, selenium and the like), metal salts (zinc-amalgam, zinc-copper alloy, aluminum-amalgam, sodium hydrosulfite and the like) and the like are preferable. The amount of the metal or metal salt to be used is, for example, 1-50 molar equivalents, preferably 1-5 molar equivalents, per 1 mol of the substrate.

Examples of the solvent to be used for the reaction include alcohols (methanol, ethanol, 2-propanol, t-butanol, benzyl alcohol and the like), amines (liquid ammonia, methylamine, ethylamine, ethylenediamine and the like), ethers (diethyl ether, tetrahydrofuran, dioxane, dimethoxyethane and the like), mineral acids (hydrochloric acid, hydrobromic acid, sulfuric acid and the like), carboxylic acids (acetic acid and the like), amides (hexamethylphosphoramide), water and the like, and these solvents can be used alone or in a mixture.

The reaction temperature is generally about −80-150° C., preferably about −80-100° C. The reaction time is generally 5 min-48 hr, preferably 1-24 hr.

Examples of the transition metal catalyst to be used for the "reduction by catalytic hydrogenenation using a transition metal catalyst" include palladiums (palladium carbon, palladium hydroxide, palladium oxide and the like), nickels (Raney-nickel and the like), platinums (platinum oxide, platinum carbon and the like), rhodiums (rhodium acetate, rhodium carbon and the like) and the like. The amount thereof to be used is, for example, about 0.001-1 equivalents, preferably about 0.01-0.5 equivalents, per 1 mol of the substrate. The hydrogenation reaction is generally performed in a solvent inert to the reaction. Examples of the solvent include alcohols (methanol, ethanol, propanol, butanol and the like), hydrocarbons (benzene, toluene, xylene and the like), halogenated hydrocarbons (dichloromethane, chloroform and the like), ethers (diethyl ether, dioxane, tetrahydrofuran and the like), esters (ethyl acetate and the like), amides (N,N-dimethylformamide and the like), carboxylic acids (acetic acid and the like), water and a mixture thereof. The reaction is performed at a hydrogen pressure of generally about 1-500 atm, preferably about 1-100 atm. The reaction temperature is generally about 0-150° C., preferably about 20-100° C. The reaction time is generally 5 min-72 hr, preferably 0.5-40 hr.

(Step 9)

In this step, compound (VIII) or a salt thereof is reacted with Lawesson's reagent (2,4-bis(4-methoxyphenyl)-1,3,2,4-dithiadiphosphetane-2,4-disulfide) to produce compound (XII) or a salt thereof.

The amount of the Lawesson's reagent to be used varies depending on the kind of the solvent, and other reaction conditions, and is generally about 1-10 molar equivalents, preferably about 1-5 molar equivalents, per 1 mol of compound (VIII).

This step can be performed in a solvent that does not adversely influence the reaction. As the solvent, tetrahydrofuran is preferably used. The reaction temperature is generally about 0-100° C. The reaction time is generally 5 min-24 hr.

(Step 10)

In this step, compound (XII) or a salt thereof is reacted with compound (XIII) or a salt thereof to be converted to compound (Ia) or a salt thereof.

The amount of compound (XIII) to be used varies depending on the kind of the solvent, and other reaction conditions, and is generally about 1-10 molar equivalents, preferably about 1-5 molar equivalents, per 1 mol of compound (XII).

The above-mentioned reaction is generally performed in a solvent that does not adversely influence the reaction. Examples of the solvent include alcohols (methanol, ethanol, propanol, 2-propanol, butanol, isobutanol, t-butanol and the like), hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), water and the like, and they may be mixed as appropriate. Of these, ethanol is preferably used.

The reaction temperature is generally about −80-200° C., preferably about 0-100° C. The reaction time is generally about 0.5-48 hr, preferably 0.5-24 hr.

[Method B]

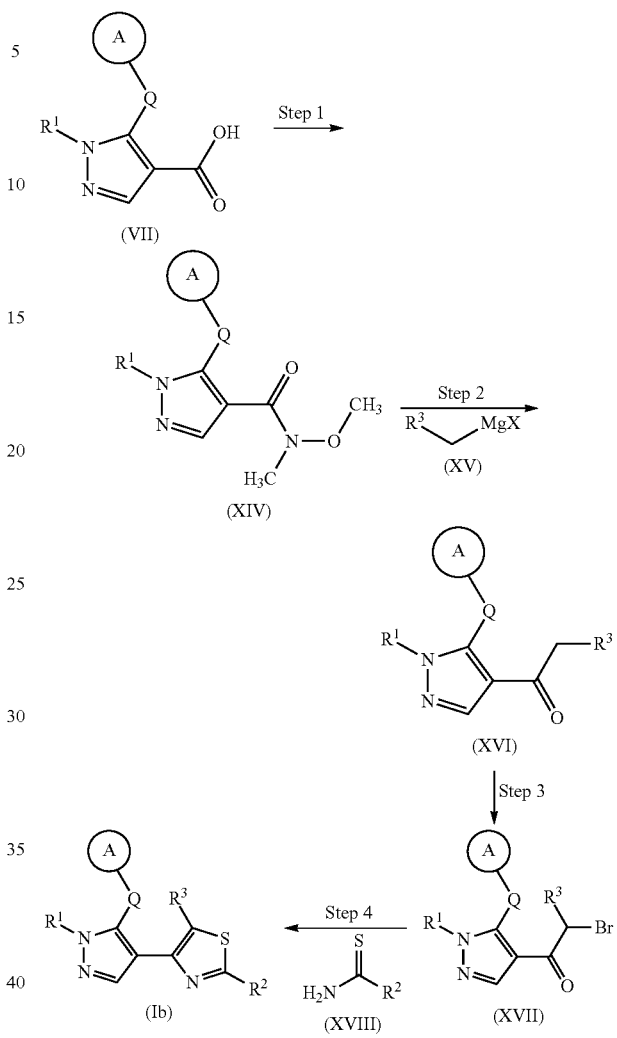

wherein X is a halogen atom (a chlorine atom, a bromine atom, an iodine atom and the like), and other symbols are as defined above.

(Step 1)

In this step, compound (VII) or a salt thereof is subjected to dehydration condensation with N,O-dimethylhydroxylamine or a salt thereof to be converted to compound (XIV) or a salt thereof. This step can be performed by a method similar to that described in Method A, step 5.

(Step 2)

In this step, compound (XIV) or a salt thereof is coupled with compound (XV) or a salt thereof to be converted to compound (XVI) or a salt thereof.

As compound (XV) or a salt thereof, a commercially available product may be used, or can also be produced by a method known per se (e.g., Journal of the Chemical Society, Perkin Transaction 1: Organic and Bioorganic Chemistry (1972-1999) 1981, vol. 6, pages 1754-1762).

As the Grignard reagent represented by the formula (XV), a commercially available product may be used, or may also be prepared by a method known per se, for example, the method described in The Chemical Society of Japan ed. 1991 "4th Edition Jikken Kagaku Kouza 24, organic synthesis VI" and the like, or a method analogous thereto.

The amount of compound (XV) to be used varies depending on the kind of the solvent, and other reaction conditions, and is generally about 1-10 molar equivalents, preferably about 1-5 molar equivalents, per 1 mol of compound (XIV).

This step is performed in a solvent inert to the reaction. As the solvent, hydrocarbons (hexane, benzene, toluene, xylene and the like), halogenated hydrocarbons (dichloromethane, chloroform and the like), ethers (diethyl ether, dioxane, tetrahydrofuran and the like) or a mixture thereof are used. The reaction temperature is generally about −80-50° C., preferably about −35-25° C. The reaction time is generally 5 min-48 hr, preferably 1-24 hr.

(Step 3)

In this step, compound (XVI) or a salt thereof is treated with trimethylphenylammonium tribromide to be converted to compound (XVII) or a salt thereof.

The amount of the trimethylphenylammonium tribromide to be used varies depending on the kind of the solvent, and other reaction conditions, and is generally about 1-10 molar equivalents, preferably about 1-5 molar equivalents, per 1 mol of compound (XVI).

This step is generally performed in a solvent that does not adversely influence the reaction. Examples of the solvent include alcohols (methanol, ethanol, propanol, 2-propanol, butanol, isobutanol, t-butanol and the like), hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), water and the like, and they may be mixed as appropriate. Of these, tetrahydrofuran is preferably used.

The reaction temperature is generally about −80-100° C., preferably about 0-50° C. The reaction time is generally about 0.5-48 hr, preferably 0.5-24 hr.

(Step 4)

In this step, compound (XVII) or a salt thereof is reacted with compound (XVIII) or a salt thereof to be converted to compound (Ib) or a salt thereof. This step can be performed by a method similar to that described in Method A, step 10.

[Method C]

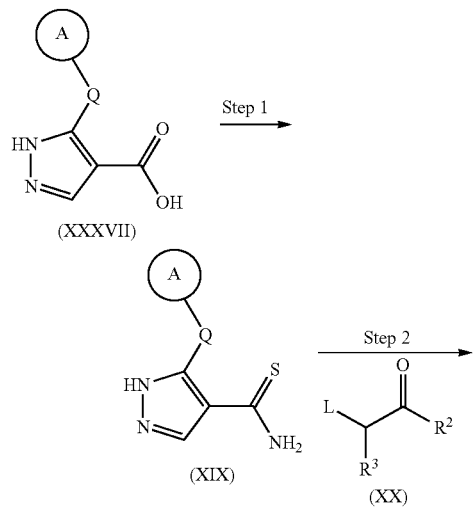

(XXXVII)

(XIX)

(XX)

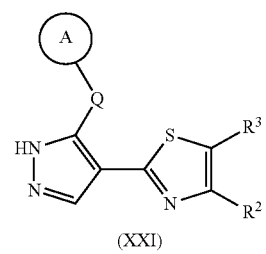

(XXI)

R¹—L (XXII)
or                Step 3
R¹—OH (XXIII)

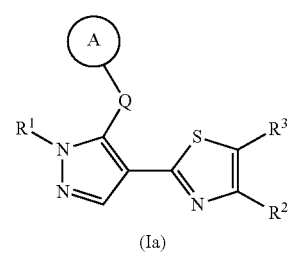

(Ia)

wherein each symbol is as defined above.

(Step 1)

In this step, compound (XXXVII) or a salt thereof is subjected to amidation and thioamidation to be converted to compound (XIX) or a salt thereof. This step can be performed by a method similar to that described in Method A, step 5 and Method A, step 9.

(Step 2)

In this step, compound (XIX) or a salt thereof is reacted with compound (XX) or a salt thereof to be converted to compound (XXI) or a salt thereof. This step can be performed by a method similar to that described in Method A, step 10.

(Step 3)

In this step, compound (XXI) or a salt thereof is reacted with a compound represented by the formula:

R¹-L                                    (XXII)

wherein each symbol is as defined above, or a salt thereof, in the presence of a base or reacted with a compound represented by formula:

R¹—OH                                  (XXIII)

wherein each symbol is as defined above, or a salt thereof, in the presence of a Mitsunobu reagent and an organic phosphorous reagent, to produce compound (Ia) or a salt thereof. This step can be performed by a method similar to that described in Method A, step 2.

[Method D]

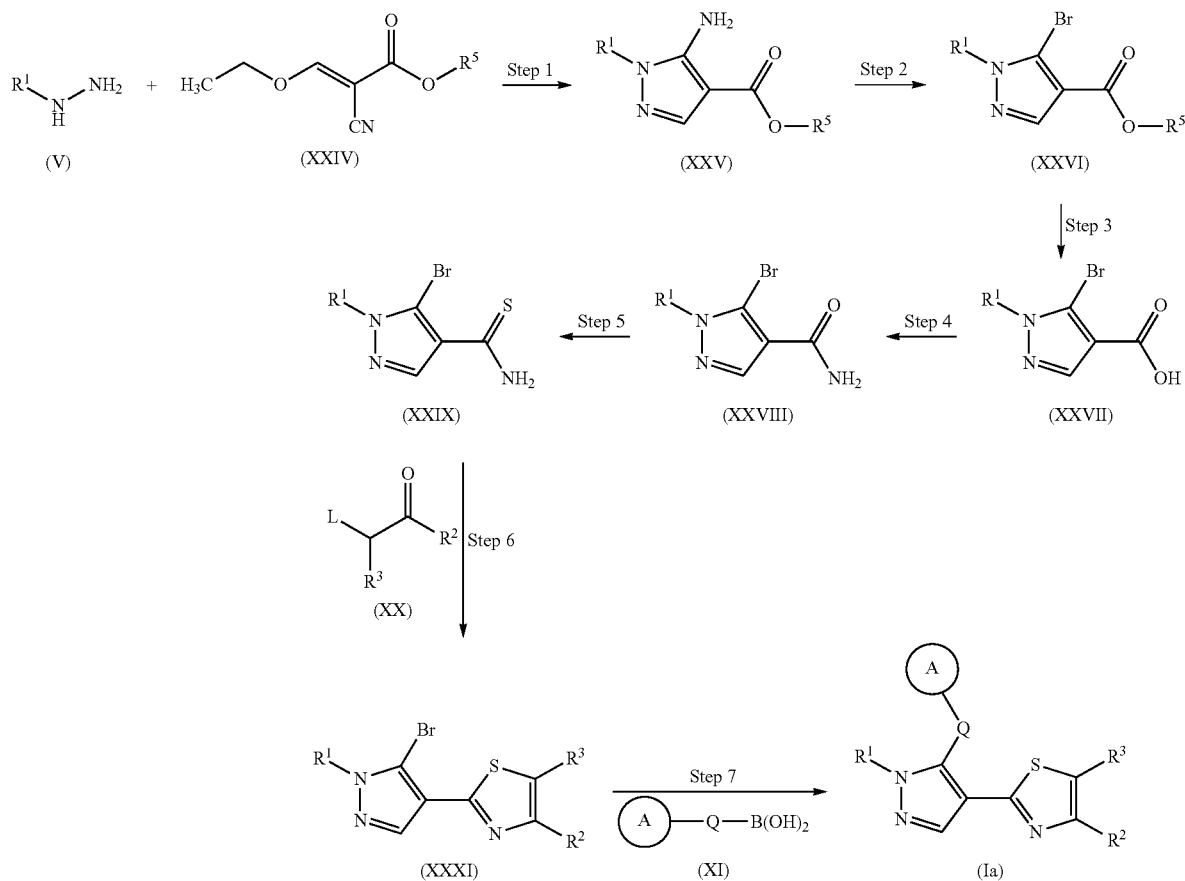

wherein each symbol is as defined above.

(Step 1)
In this step, compound (V) or a salt thereof is reacted with compound (XXIV) (2-(ethoxymethylene)-2-cyanoacetate) to be converted to compound (XXV) or a salt thereof. This step can be performed by a method similar to that described in Method A, step 6.

(Step 2)
In this step, compound (XXV) or a salt thereof is subjected to a diazotization reaction and reacted with copper(I) bromide to be converted to compound (XXVI) or a salt thereof. This step can be performed by a method similar to that described in Method A, step 7.

(Step 3)
In this step, compound (XXVI) or a salt thereof is subjected to hydrolysis to be converted to compound (XXVII) or a salt thereof. This step can be performed by a method similar to that described in Method A, step 4.

(Step 4)
In this step, compound (XXVII) or a salt thereof is subjected to dehydration condensation with ammonia or a salt thereof to be converted to compound (XXVIII) or a salt thereof. This step can be performed by a method similar to that described in Method A, step 5.

(Step 5)
In this step, compound (XXVIII) or a salt thereof is reacted with Lawesson's reagent to produce compound (XXIX) or a salt thereof. This step can be performed by a method similar to that described in Method A, step 9.

(Step 6)
In this step, compound (XXIX) or a salt thereof is reacted with compound (XX) or a salt thereof to be converted to compound (XXXI) or a salt thereof. This step can be performed by a method similar to that described in Method A, step 10.

(Step 7)
In this step, compound (XXXI) or a salt thereof is subjected to a coupling reaction with compound (XI) or a salt thereof and, where necessary, subjected to a reduction reaction to produce compound (Ia) or a salt thereof. This step can be performed by a method similar to that described in Method A, step 8.

[Method E]

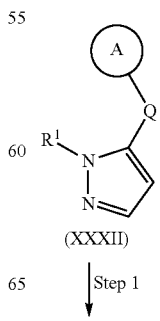

(XXXII)

Step 1

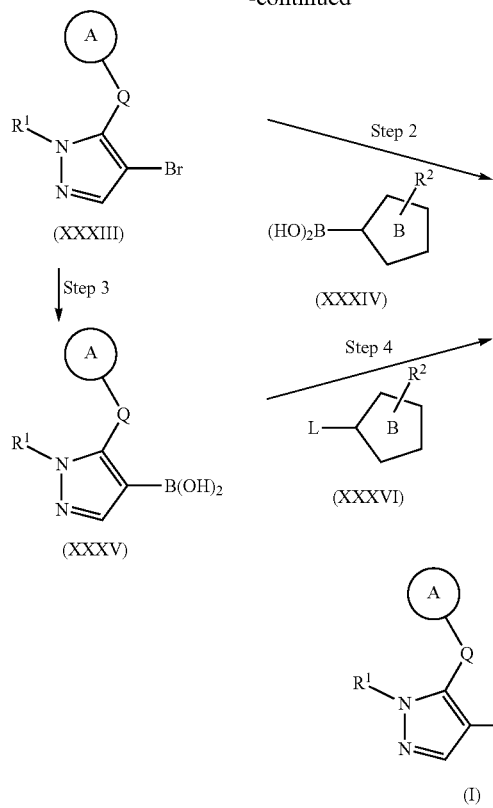

wherein each symbol is as defined above.

(Step 1)

In this step, compound (XXXII) or a salt thereof is treated with N-bromosuccinimide to be converted to compound (XXXIII) or a salt thereof.

The amount of the N-bromosuccinimide to be used varies depending on the kind of the solvent, and other reaction conditions, and is generally about 1-10 molar equivalents, preferably about 1-5 molar equivalents, per 1 mol of compound (XXXII).

This step is generally performed in a solvent that does not adversely influence the reaction. Examples of the solvent include alcohols (methanol, ethanol, propanol, 2-propanol, butanol, isobutanol, t-butanol and the like), hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), mineral acids (hydrochloric acid, sulfuric acid, hydrobromic acid and the like), carboxylic acids (acetic acid and the like), water and the like, and they may be mixed as appropriate. Of these, N,N-dimethylformamide is preferably used.

The reaction temperature is generally about −80-100° C., preferably about 0-50° C. The reaction time is generally about 0.5-48 hr, preferably 0.5-24 hr.

(Step 2)

In this step, compound (XXXIII) or a salt thereof is subjected to a coupling reaction with compound (XXXIV) or a salt thereof to produce compound (I) or a salt thereof.

The coupling reaction can be performed in the presence of a transition metal catalyst and a base, in a solvent that does not adversely influence the reaction, and can be performed by a method similar to that described in Method A, step 8.

(Step 3)

In this step, compound (XXXIII) or a salt thereof is treated with n-butyllithium, and reacted with triisopropyl borate to be converted to compound (XXXV) or a salt thereof.

The amount of the n-butyllithium to be used varies depending on the kind of the solvent, and other reaction conditions, and is generally about 1-10 molar equivalents, preferably about 1-5 molar equivalents, per 1 mol of compound (XXXIII).

The amount of the triisopropyl borate to be used varies depending on the kind of the solvent, and other reaction conditions, and is generally about 1-10 molar equivalents, preferably about 1-5 molar equivalents, per 1 mol of compound (XXXIII).

This step is generally performed in a solvent that does not adversely influence the reaction. Examples of the solvent include hydrocarbons (benzene, toluene and the like), ethers (diethyl ether, dioxane, tetrahydrofuran and the like) and the like, and they may be mixed as appropriate. Of these, tetrahydrofuran is preferably used.

The reaction temperature is generally about −200-40° C., preferably about −80-0° C. The reaction time is generally about 0.5-48 hr, preferably 0.5-12 hr.

(Step 4)

In this step, compound (XXXV) or a salt thereof is subjected to a coupling reaction with compound (XXXVI) or a salt thereof to produce compound (I) or a salt thereof.

The coupling reaction can be performed in the presence of a transition metal catalyst and a base, in a solvent that does not adversely influence the reaction, and can be performed by a method similar to that described in Method A, step 8.

[Method F]

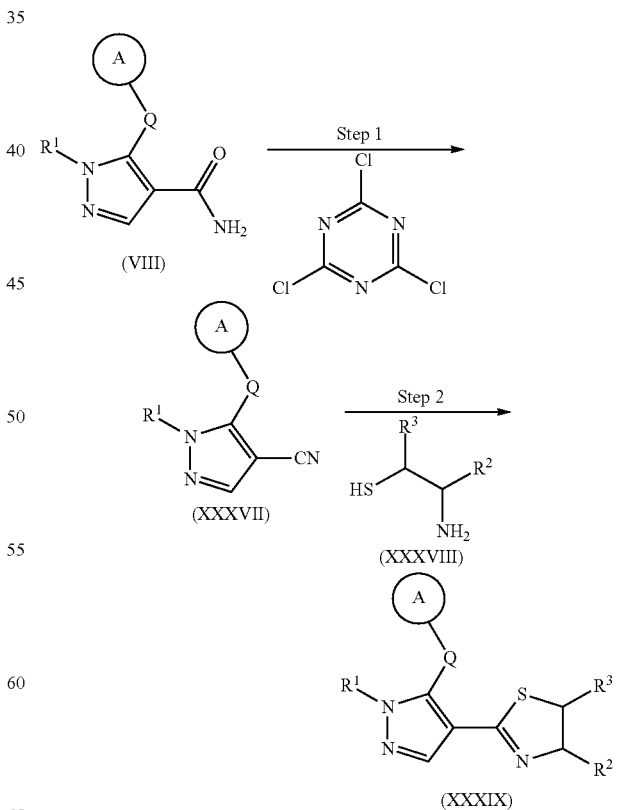

wherein each symbol is as defined above.

(Step 1)

In this step, compound (VIII) or a salt thereof is treated with cyanuric chloride to be converted to compound (XXXVII) or a salt thereof.

The amount of the cyanuric chloride to be used varies depending on the kind of the solvent, and other reaction conditions, and is generally about 1-10 molar equivalents, preferably about 1-5 molar equivalents, per 1 mol of compound (VIII).

This step is generally performed in a solvent that does not adversely influence the reaction. Examples of the solvent include hydrocarbons (benzene, toluene and the like), ethers (diethyl ether, dioxane, tetrahydrofuran and the like), amides (N,N-dimethylformamide and the like) and the like, and they may be mixed as appropriate. Of these, N,N-dimethylformamide is preferably used.

The reaction temperature is generally about −200-40° C., preferably about 0-30° C. The reaction time is generally about 0.5-48 hr, preferably 0.5-12 hr.

(Step 2)

In this step, compound (XXXVII) or a salt thereof is reacted with compound (XXXVIII) or a salt thereof in the presence of a base to be converted to compound (XXXIX) or a salt thereof.

The amount of compound (XXXVIII) to be used varies depending on the kind of the solvent, and other reaction conditions, and is generally about 1-10 molar equivalents, preferably about 1-5 molar equivalents, per 1 mol of compound (XXXVII).

As the base to be used in this step, inorganic bases (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate and the like, alkali metal alkoxides such as sodium methoxide, sodium ethoxide and the like, and the like), organic bases (amines such as trimethylamine, triethylamine, diisopropylethylamine and the like, cyclic amines such as pyridine, 4-dimethylaminopyridine and the like, and the like) and the like are used. Of these, sodium hydroxide is preferable. The amount of the base to be used varies depending on the kind of the solvent, and other reaction conditions, and is generally about 1-10 molar equivalents, preferably about 1-5 molar equivalents, per 1 mol of compound (XXXVII).

This step is generally performed in a solvent that does not adversely influence the reaction. Examples of the solvent include water, alcohols (methanol, ethanol and the like), hydrocarbons (benzene, toluene and the like), ethers (diethyl ether, dioxane, tetrahydrofuran and the like), amides (N,N-dimethylformamide and the like) and the like, and they may be mixed as appropriate. Of these, water and ethanol is preferably used.

The reaction temperature is generally about 0-200° C., preferably about 0-100° C. The reaction time is generally about 0.5-48 hr, preferably 0.5-12 hr.

In each reaction for the synthesis of the object compounds and the starting materials, when the starting compound has an amino group, a carboxyl group or a hydroxy group as a substituent, these groups may be protected by a protecting group generally used in the peptide chemistry and the like. In this case, the object compound can be obtained by removing the protecting group as necessary after the reaction.

Examples of the protecting group include those described in Wiley-Interscience, 1999, "Protective Groups in Organic Synthesis, 3rd Ed." (Theodora W. Greene, Peter G. M. Wuts).

Examples of the amino-protecting group include formyl group, $C_{1-6}$ alkyl-carbonyl group (acetyl, propionyl group etc.), phenylcarbonyl group, $C_{1-6}$ alkyl-oxycarbonyl group (methoxycarbonyl, ethoxycarbonyl group etc.), aryloxycarbonyl group (phenyloxycarbonyl group etc.), $C_{7-10}$ aralkyl-carbonyl group (benzyloxycarbonyl group etc.), benzyl group, benzhydryl group, trityl group, phthaloyl group and the like. These protecting groups optionally have substituent(s). Examples of the substituent include halogen atom (fluorine, chlorine, bromine, iodine atom etc.), $C_{1-6}$ alkyl-carbonyl group (acetyl, propionyl, butylcarbonyl group etc.), nitro group and the like, wherein the number of the substituents is about 1-3.

Examples of the carboxyl-protecting group include $C_{1-6}$ alkyl group (methyl, ethyl, n-propyl, isopropyl, n-butyl, tert-butyl group etc.), phenyl group, trityl group, silyl group and the like. These protecting groups optionally have substituent(s). Examples of the substituent include halogen atom (fluorine, chlorine, bromine, iodine atom etc.), formyl group, $C_{1-6}$ alkyl-carbonyl group (acetyl, propionyl, butylcarbonyl group etc.), nitro group and the like, wherein the number of the substituents is about 1-3.

Examples of the hydroxyl-protecting group include $C_{1-6}$ alkyl group (methyl, ethyl, n-propyl, isopropyl, n-butyl, tert-butyl group etc.), phenyl group, $C_{7-10}$ aralkyl group (benzyl group etc.), formyl group, $C_{1-6}$ alkyl-carbonyl group (acetyl, propionyl group etc.), aryloxycarbonyl group (phenyloxycarbonyl group etc.), $C_{7-10}$ aralkyl-carbonyl group (benzyloxycarbonyl group etc.), pyranyl group, furanyl group, silyl group and the like. These protecting groups optionally have substituent(s). Examples of the substituent include halogen atom (fluorine, chlorine, bromine, iodine atom etc.), $C_{1-6}$ alkyl group, phenyl group, $C_{7-10}$ aralkyl group, nitro group and the like, wherein the number of the substituents is about 1-4.

The protecting group can be removed by a known method or a method described in Wiley-Interscience, 1999, "Protective Groups in Organic Synthesis, 3rd Ed." (Theodora W. Greene, Peter G. M. Wuts) and the like, or a method analogous thereto. For example, a method of treating with an acid, base, reducing agent, ultraviolet radiation, hydrazine, phenylhydrazine, sodium N-methyldithiocarbamate, tetrabutylammonium fluoride, palladium acetate and the like can be utilized.

When the object product is obtained in a free form by the aforementioned reaction, it may be converted to a salt by a conventional method. When it is obtained as a salt, it can also be converted to a free form or other salt by a conventional method. The thus-obtained compound (I) can be isolated and purified from the reaction solution by a known means, for example, phase transfer, concentration, solvent extraction, fractionation, crystallization, recrystallization, chromatography and the like.

When compound (I) contains an isomer such as a tautomer, an optical isomer, a stereoisomer, a regioisomer, a rotamer and the like, any isomer and a mixture thereof are also encompassed in the compound of the present invention. Furthermore, when compound (I) has an optical isomer, an optical isomer resolved from this compound is also encompassed in compound (I).

The compound (I) may be a crystal. Even if compound (I) is in a single crystal form or mixed crystal form, it can be provided as compound (I) of the present invention.

Compound (I) may be a pharmaceutically acceptable co-crystal or co-crystal salt. Here, the co-crystal or co-crystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

The compound (I) may be a solvate (e.g., a hydrate) or a nonsolvate. Any of them can be provided as compound (I) of the present invention.

Any of the above compounds may be labeled or substituted with an isotope (e.g., $^2H$, $^3H$, $^{11}C$, $^{14}C$, $^{18}F$, $^{35}S$, or $^{125}I$) and provided as compound (I) of the present invention.

The prodrug of compound (I) means a compound which can be converted into compound (I) by reaction with an enzyme, gastric acid, or the like under physiological conditions in the living body. In other words, it means a compound which can be converted into compound (I) by enzymatic oxidation, reduction, hydrolysis or the like, or a compound which can be converted into compound (I) by hydrolysis with gastric acid or the like. Examples of the prodrug of compound (I) include a compound in which amino of compound (I) is acylated, alkylated, or phosphorylated (e.g., the amino of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); a compound in which hydroxyl of compound (I) is acylated, alkylated, phosphorylated, or borated (e.g., hydroxyl of compound (I) is acetylated, palmitoylated, propanoylated, pivaloylated, succinylated, fumarylated, alanylated, or dimethylaminomethylcarbonylated); a compound in which carboxy of compound (I) is esterified or amidated (e.g., a compound in which carboxy of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, or methylamidated). These compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

Since compound (I) and a prodrug thereof [hereinafter sometimes to be abbreviated as the compound of the present invention] show superior RORγt inhibitory activity, they are also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for RORγt associated diseases, Th17 cell associated diseases and IL-17A or IL-17F associated diseases, more specifically, the diseases described in (1)-(4) below.

(1) inflammatory diseases (e.g., rheumatoid arthritis, acute pancreatitis, chronic pancreatitis, asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis etc.), (2) autoimmune diseases (e.g., rheumatoid arthritis, ankylosing spondylitis, psoriasis, multiple sclerosis (MS), polymyositis, dermatomyositis (DM), polyarteritis nodosa (PN), mixed connective tissue disease (MCTD), Sjogren's syndrome nephritis, systemic lupus erythematosus, scleroderma, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, inflammatory bowel disease (IBD), ulcerative colitis, Crohn's disease, graft versus host disease, Addison's disease, abnormal immunoresponse, arthritis, dermatitis, radiodermatitis, uveoretinitis (Bechet's uveitis), cystic fibrosis etc.), (3) bone or joint degenerative diseases (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor and the like), lung cancer (e.g., non-small cell lung cancer, small cell lung cancer, malignant mesothelioma and the like), mesothelioma, pancreatic cancer (e.g., pancreatic duct cancer and the like), gastric cancer (e.g., papillary adenocarcinoma, mucinous adenocarcinoma, adenosquamous carcinoma and the like), breast cancer (e.g., invasive ductal carcinoma, ductal carcinoma in situ, inflammatory breast cancer and the like), ovarian cancer (e.g., ovarian epithelial carcinoma, extragonadal germ cell tumor, ovarian germ cell tumor, ovarian low malignant potential tumor and the like), prostate cancer (e.g., hormone-dependent prostate cancer, non-hormone dependent prostate cancer and the like), liver cancer (e.g., primary liver cancer, extrahepatic bile duct cancer and the like), thyroid cancer (e.g., medullary thyroid carcinoma and the like), kidney cancer (e.g., renal cell carcinoma, transitional cell carcinoma in kidney and urinary duct and the like), uterine cancer, brain tumor (e.g., pineal astrocytoma, pilocytic astrocytoma, diffuse astrocytoma, anaplastic astrocytoma and the like), melanoma (melanoma), sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, cancer of the bile duct, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary).

The medicament of the present invention can be used as a prophylactic or therapeutic agent for preferably autoimmune disease, inflammatory disease, bone or articular disease or neoplastic disease, particularly preferably, rheumatoid arthritis, inflammatory bowel disease, psoriasis, ankylosing spondylitis, bronchial asthma, chronic obstructive pulmonary diseases, ovarian cancer, non-small cell lung cancer, breast cancer, gastric cancer, cervical cancer, prostate cancer or uterine body cancer.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. While the dose varies depending on the subject of administration, administration route, disease and the like, for example, for oral administration to an adult inflammatory bowel disease (IBD) patient (body weight about 60 kg), it is about 0.1 mg/kg body weight to 30 mg/kg body weight, preferably about 1 mg/kg body weight to 20 mg/kg body weight as an active ingredient (compound (I)) for one day, which is administered once to several times (e.g., 4 times).

The pharmaceutically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as an RORγt inhibitor, Th17 cell inhibitor, IL-17A or IL-17F inhibitor, it can be used in combination with the following drugs.
(1) non-steroidal anti-inflammatory drug (NSAIDs)
(i) Classical NSAIDs
  alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.

(ii) cyclooxygenase inhibitor (COX-1 selective inhibitor, COX-2 selective inhibitor and the like)
salicylic acid derivatives (e.g., celecoxib, aspirin), etoricoxib, valdecoxib, diclofenac, indomethacin, loxoprofen and the like.
(iii) nitric oxide-releasing NSAIDs
(2) disease-modifying anti-rheumatic drugs (DMARDs)
(i) Gold preparation
auranofin and the like.
(ii) penicillamine
D-penicillamine.
(iii) aminosalicylic acid preparation
sulfasalazine, mesalizine, olsalazine, balsalazide.
(iv) antimalarial drug
chloroquine and the like.
(v) pyrimidine synthesis inhibitor
leflunomide and the like.
(vi) prograf
(3) anti-cytokine drug
(I) protein drug
(i) TNF inhibitor
etanercept, infliximab, adalimumab, certolizumab pegol, golimumab, PASSTNF-α, soluble TNF-α receptor, TNF-α binding protein, anti-TNF-α antibody and the like.
(ii) interleukin-1 inhibitor
anakinra (interleukin-1 receptor antagonist), soluble interleukin-1 receptor and the like.
(iii) interleukin-6 inhibitor
tocilizumab (anti-interleukin-6 receptor antibody), anti-interleukin-6 antibody and the like.
(iv) interleukin-10 drug
interleukin-10 and the like.
(v) interleukin-12/23 inhibitor
ustekinumab, briakinumab (anti-interleukin-12/23 antibody) and the like.
(II) non-protein drug
(i) MAPK inhibitor
BMS-582949 and the like.
(ii) gene modulator
inhibitor of molecule involved in signal transduction, such as NF-κ, NF-κB, IKK-1, IKK-2, AP-1 and the like, and the like.
(iii) cytokine production inhibitor
iguratimod, tetomilast and the like.
(iv) TNF-α converting enzyme inhibitor
(v) interleukin-1β converting enzyme inhibitor
VX-765 and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (CCX-282, CCX-025), MCP-1 antagonist and the like.
(ix) interleukin-2 receptor antagonist
denileukin, diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor, soluble TNF-α receptor and the like.
(xii) antisense compound
ISIS 104838 and the like.

(4) integrin inhibitor
natalizumab, vedolizumab, AJM300, TRK-170, E-6007 and the like.
(5) immunomodulator (immunosuppressant)
methotrexate, cyclophosphamide, MX-68, atiprimod dihydrochloride, BMS-188667, CKD-461, rimexolone, cyclosporine, tacrolimus, gusperimus, azathiopurine, anti-lymphocyte serum, freeze-dried sulfonated normal immunoglobulin, erythropoietin, colony stimulating factor, interleukin, interferon and the like.
(6) steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(7) angiotensin converting enzyme inhibitor
enalapril, captopril, ramipril, lisinopril, cilazapril, perindopril and the like.
(8) angiotensin II receptor antagonist
candesartan, candesartan cilexetil, valsartan, irbesartan, olmesartan, eprosartan and the like.
(9) diuretic drug
hydrochlorothiazide, spironolactone, furosemide, indapamide, bendrofluazide, cyclopenthiazide and the like.
(10) cardiotonic drug
digoxin, dobutamine and the like.
(11) β receptor antagonist
carvedilol, metoprolol, atenolol and the like.
(12) Ca sensitizer
MCC-135 and the like.
(13) Ca channel antagonist
nifedipine, diltiazem, verapamil and the like.
(14) anti-platelet drug, anticoagulator
heparin, aspirin, warfarin and the like.
(15) HMG-CoA reductase inhibitor
atorvastatin, simvastatin and the like.
(16) contraceptive
(i) sex hormone or derivatives thereof
gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
ormeloxifene, mifepristone, Org-33628 and the like.
(iii) spermatocide
ushercell and the like.
(17) others
(i) T cell inhibitors
(ii) inosine monophosphate dehydrogenase (IMPDH) inhibitor
mycophenolate mofetil and the like.
(iii) adhesion molecule inhibitor
ISIS 2302, selectin inhibitor, ELAM-1, VCAM-1, ICAM-1 and the like.

(iv) thalidomide
(v) cathepsin inhibitor
(vi) matrix metalloprotease (MMPs) inhibitor
V-85546 and the like.
(vii) glucose-6-phosphate dehydrogenase inhibitor
(viii) Dihydroorotate dehydrogenase (DHODH) inhibitor
(ix) phosphodiesterase IV (PDE IV) inhibitor roflumilast, CG-1088 and the like.
(x) phospholipase $A_2$ inhibitor
(xi) iNOS inhibitor
VAS-203 and the like.
(xii) microtubule stimulating drug
paclitaxel and the like.
(xiii) microtuble inhibitor
reumacon and the like.
(xiv) MHC class II antagonist
(xv) prostacyclin agonist
iloprost and the like.
(xvi) CD4 antagonist
zanolimumab and the like.
(xvii) CD23 antagonist
(xviii) LTB4 receptor antagonist
DW-1305 and the like.
(xix) 5-lipoxygenase inhibitor
zileuton and the like.
(xx) cholinesterase inhibitor
galanthamine and the like.
(xxi) tyrosine kinase inhibitor
Tyk2 inhibitor (WO2010142752) and the like.
(xxii) cathepsin B inhibitor
(xxiii) adenosine deaminase inhibitor
pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
synvisc (hylan G-F 20), orthovisc and the like.
(xxix) glucosamine sulfate
(xxx) amiprilose
(xxxi) CD-20 inhibitor
rituximab, ibritumomab, tositumomab, ofatumumab and the like.
(xxxii) BAFF inhibitor
belimumab, tabalumab, atacicept, A-623 and the like.
(xxxiii) CD52 inhibitor
alemtuzumab and the like.

Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, hypotensive diuretic, therapeutic drug for diabetes, antinarcotic, vitamin, vitamin derivative, antiasthmatic, therapeutic agent for pollakisuria/anischuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial agent
(i) sulfa drug
sulfamethizole, sulfisoxazole, sulfamonomethoxine, sulfamethizole, salazosulfapyridine, silver sulfadiazine and the like.
(ii) quinolone antibacterial agent
nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
diaphenylsulfone, rifampicin and the like.
(v) antiviral drug
idoxuridine, acyclovir, vidarabine, gancyclovir and the like.
(vi) anti-HIV agent
zidovudine, didanosine, zalcitabine, indinavir sulfate ethanolate, ritonavir and the like.
(vii) antispirochetele
(viii) antibiotic
tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefinetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885 (1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like] and the like.
(2) antifungal agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.
(3) antiprotozoal agent
metronidazole, tinidazole, diethylcarbamazine citrate, quinine hydrochloride, quinine sulfate and the like.
(4) antitussive and expectorant drug
ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline, oxymetebanol, morphine hydrochloride, dextromethorphan, hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) anesthetic (6-1) local anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(6-2) general anesthetic (i) inhalation anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) antiulcer drug histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(8) antiarrhythmic agent (i) sodium channel blocker (e.g., quinidine, procainamide, disopyramide, ajmaline, lidocaine, mexiletine, phenytoin), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride), (iii) potassium channel blocker (e.g., amiodarone), (iv) calcium channel blocker (e.g., verapamil, diltiazem) and the like.

(9) hypotensive diuretic drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) anticoagulant heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) antitumor drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) hypolipidemic drug clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], pravastatin, simvastatin, probucol, bezafibrate, clinofibrate, nicomol, cholestyramine, dextran sulfate sodium and the like.

(15) muscle relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) antiepileptic drug phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(17) antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) antiallergic drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) cardiac stimulants trans-π-oxocamphor, terephyllol, aminophylline, etilefrine, dopamine, dobutamine, denopamine, aminophylline, vesinarinone, amrinone, pimobendan, ubidecarenone, digitoxin, digoxin, methyldigoxin, lanatoside C, G-strophanthin and the like.

(20) vasodilator oxyfedrine, diltiazem, tolazoline, hexobendine, bamethan, clonidine, methyldopa, guanabenz and the like.

(21) vasoconstrictor dopamine, dobutamine denopamine and the like.

(22) hypotensive diuretic hexamethonium bromide, pentolinium, mecamylamine, ecarazine, clonidine, diltiazem, nifedipine and the like.

(23) therapeutic drug for diabetes tolbutamide, chlorpropamide, acetohexamide, glibenclamide, tolazamide, acarbose, epalrestat, troglitazone, glucagon, glymidine, glipizide, phenformin, buformin, metformin and the like.

(24) antinarcotic levallorphan, nalorphine, naloxone or a salt thereof and the like.

(25) liposoluble vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, δ-tocopherol, dl-α-tocopherol nicotinate
(iv) vitamin K: vitamin $K_1$, $K_2$, $K_3$ and $K_4$
(v) folic acid (vitamin M) and the like.

(26) vitamin derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(27) antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate and the like.

(28) therapeutic agent for pollakisuria/anischuria flavoxate hydrochloride and the like.

(29) therapeutic agent for atopic dermatitis sodium cromoglicate and the like.

30) therapeutic agent for allergic rhinitis sodium cromoglicate, chlorpheniramine maleate, alimemazine tartrate, clemastine fumarate, homochlorcyclizine hydrochloride, fexofenadine, mequitazine and the like.

(31) hypertensor dopamine, dobutamine, denopamine, digitoxin, digoxin, methyldigoxin, lanatoside C, G-strophanthin and the like.

(32) others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with inflammatory bowel disease (IBD), about 0.1 mg/kg body weight-about 30 mg/kg body weight, preferably about 1 mg/kg body weight-20 mg/kg body weight, of compound (I) can be administered once to several portions (e.g., 4 times) per day.

The dose of the medicament of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human and the like), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in more detail in the following by referring to Examples, preparation Examples and Experimental Examples, which are not to be construed as limitative and may be modified without departing from the scope of the invention.

Unless particularly indicated, the elution in column chromatography in the Examples was performed under observation by TLC (Thin Layer Chromatography). For TLC observation, 60F254 manufactured by Merck was used as a TLC plate, and the solvent used as an elution solvent for column chromatography was used. For detection, moreover, a UV detector was adopted. As silica gel for column chromatography, silica gel 60 (70-230 mesh) manufactured by Merck was used. The room temperature generally means a temperature about 10° C. to 35° C. For drying extracts, sodium sulfate or magnesium sulfate was used.

The abbreviations in the Examples mean as follows.
LC: liquid chromatography
MS: mass spectrometry spectrum
API: atmospheric pressure ionization method
M: molecular weight of the compound
NMR: nuclear magnetic resonance spectrum
Hz: hertz
J: coupling constant
m: multiplet
q: quartet
t: triplet
d: doublet
s: singlet
br: broad
dt: double triplet
ddd: double double doublet
brs: broad singlet
$^t$Bu: tert-butyl group
Boc: tert-butyloxycarbonyl group
N: normal concentration
THF: tetrahydrofuran
HOBt: 1H-benzo[d][1,2,3]triazol-1-ol hydrate
WSC: $N^1$-((ethylimino)methylene)-$N^3$,$N^3$-dimethylpropane-1,3-diamine hydrochloride
DMF: dimethylformamide
DIEA, DEIA: diisopropylethylamine
HATU: 2-(1H-7-azabenzotriazol-1-yl)-1,1,3,3-tetramethyluronium hexafluorophosphate
TFA: trifluoroacetic acid
TEA: triethylamine
DMAP: dimethylaminopyridine
mCPBA: m-chloroperbenzoic acid
(Boc)$_2$O: di-t-butyl carbonate
DIAD: diisopropyl azodicarboxylate
DMFDMA: dimethylformamide dimethylacetal The purification by preparative HPLC in the Examples was performed under the following conditions.
  instrument: Gilson Inc. High throughput purification system
  column: CombiPrep ODS-A S-5 µm, 50×20 mm (YMC)
    solvent: SOLUTION A; 0.1% trifluoroacetic acid-containing water, SOLUTION B; 0.1% trifluoroacetic acid-containing acetonitrile
    gradient cycle: 0.00 min (SOLUTION A/SOLUTION B=95/5), 1.00 min (SOLUTION A/SOLUTION B=95/5), 5.20 min (SOLUTION A/SOLUTION B=5/95), 6.40 min (SOLUTION A/SOLUTION B=5/95), 6.50 min (SOLUTION A/SOLUTION B=95/5), 6.60 min (SOLUTION A/SOLUTION B=95/5)
    flow rate: 25 mL/min, detection method: UV 220 nm Example 1

1-({2-[1-tert-butyl-5-(4-fluorophenyl)-1H-pyrazol-4-yl]-1,3-thiazol-4-yl}acetyl)piperidin-4-one (Step 1)
A solution of ethyl 3-(4-fluorophenyl)-3-oxopropanoate (19.8 g, 94.20 mmol) and DMFDMA (13.76 mL, 103.61 mmol) in toluene (150 mL) was stirred at 100° C. for 14 hr, and concentrated under reduced pressure. The residue was dissolved in ethanol (150 ml), tert-butylhydrazine hydrochloride (11.74 g, 94.20 mmol) and TEA (14.44 mL, 103.61 mmol) were added thereto. The reaction mixture was stirred at 80° C. for 3 hr, and concentrated under reduced pressure. The residue was dissolved in ethyl acetate, and the solution was washed with water and saturated brine and dried, and the solvent was evaporated under reduced pressure to give ethyl 1-tert-butyl-5-(4-fluorophenyl)-1H-pyrazole-4-carboxylate (18.67 g, 64.3 mmol, 68.3%) as a white powder.
$^1$H-NMR (300 MHz, DMSO-d$_6$): δ0.97 (3H, t, J=7.16 Hz), 1.37, (9H, s) 3.94 (2H, q, J=7.03 Hz), 7.23-7.33 (2H, m), 7.37-7.45 (2H, m), 7.90 (1H, s)

(Step 2)
A solution of the compound (18.67 g, 64.31 mmol) obtained in step 1 and 1N aqueous sodium hydroxide solution (70.0 mL, 70 mmol) in ethanol (180 mL) was stirred at 70° C. for 14 hr, and concentrated under reduced pressure. To the residue were added water and 1N hydrochloric acid, and the precipitate was collected by filtration to give 1-tert-butyl-5-(4-fluorophenyl)-1H-pyrazole-4-carboxylic acid (16.87 g, 64.3 mmol, 100%) as a white powder.
$^1$H-NMR (300 MHz, DMSO-d$_6$): δ1.36 (9H, s), 7.21-7.31 (2H, m), 7.35-7.45 (2H, m), 7.85 (1H, s)

(Step 3)
A solution of the compound (16.87 g, 64.32 mmol) obtained in step 2, WSC (16.03 g, 83.62 mmol), HOBt (11.30 g, 83.62 mmol), TEA (11.65 mL, 83.62 mmol) and ammonium chloride (4.47 g, 83.62 mmol) in DMF (200 mL) was stirred at room temperature for 2 days. Water was added to the reaction solution, and the mixture was extracted with ethyl acetate. The organic layer was washed with water and saturated brine and dried, and the solvent was evaporated under reduced pressure. The obtained residue was purified by silica gel column chromatography (solvent gradient; 5→85% ethyl acetate/hexane) to give 1-tert-butyl-5-(4-fluorophenyl)-1H-pyrazole-4-carboxamide (14.72 g, 56.3 mmol, 88%) as a white powder.
$^1$H-NMR (300 MHz, DMSO-d$_6$): δ1.34 (9H, s), 6.80 (1H, brs), 6.84 (1H, brs), 7.18-7.31 (2H, m), 7.33-7.42 (2H, m), 7.89 (1H, s)

(Step 4)
A solution of the compound (4.00 g, 15.31 mmol) obtained in step 3 and Lawesson's reagent (6.19 g, 15.31 mmol) in THF (50 mL) was stirred at 50° C. for 1.5 hr. The reaction mixture was concentrated under reduced pressure, and the residue was purified by NH-silica gel column chromatography (solvent gradient; 2→65% ethyl acetate/hexane) to give 1-tert-butyl-5-(4-fluorophenyl)-1H-pyrazole-4-carbothioamide (2.75 g, 9.91 mmol, 65%) as a pale-yellow powder.
$^1$H-NMR (300 MHz, CDCl$_3$): δ1.42 (9H, s), 5.99 (1H, brs), 6.91 (1H, brs), 7.19-7.32 (2H, m), 7.35-7.50 (2H, m), 8.27 (1H, s)

(Step 5)

A solution of the compound (2.90 g, 10.46 mmol) obtained in step 4 and ethyl 4-chloroacetoacetate (1.554 mL, 11.50 mmol) in ethanol (30 mL) was stirred at 80° C. for 16 hr. The reaction mixture was concentrated under reduced pressure, and the residue was crystallized from ethyl acetate and hexane to give ethyl 2-(2-(1-tert-butyl-5-(4-fluorophenyl)-1H-pyrazol-4-yl)thiazol-4-yl)acetate (3.96 g, 10.22 mmol, 98%) as a pale-yellow powder.

$^1$H-NMR (300 MHz, CDCl$_3$): δ1.29 (3H, t, J=7.18 Hz), 1.48 (9H, s), 4.21 (2H, q, J=7.18 Hz), 4.26 (2H, s), 7.15 (1H, s), 7.28-7.39 (4H, m), 9.17 (1H, s)

(Step 6)

A solution of the compound (3.96 g, 10.22 mmol) obtained in step 5 and 1N aqueous sodium hydroxide solution (15.33 mL, 15.33 mmol) in ethanol (50 mL) was stirred at room temperature for 2 hr. To the reaction mixture was further added 1N aqueous sodium hydroxide solution (5.0 mL, 5.0 mmol), and the mixture was stirred at room temperature for 30 min. The reaction mixture was concentrated under reduced pressure, and water was added to the residue. 1N Hydrochloric acid was added thereto, and the precipitate was collected by filtration, and crystallized from ethyl acetate and hexane to give 2-(2-(1-tert-butyl-5-(4-fluorophenyl)-1H-pyrazol-4-yl) thiazol-4-yl)acetic acid (2.52 g, 7.01 mmol, 69%) as a pale-yellow powder.

$^1$H-NMR (300 MHz, CDCl$_3$): δ1.49 (9H, s), 3.75 (2H, s), 6.77 (1H, s), 7.19-7.28 (2H, m), 7.32-7.41 (2H, m), 8.01 (1H, s)

(Step 7)

A solution of the compound (60 mg, 0.17 mmol) obtained in step 6, HATU (76 mg, 0.20 mmol), DIEA (0.035 mL, 0.20 mmol) and piperidin-4-one monohydrochloride monohydrate (30.8 mg, 0.20 mmol) in DMF (1.5 mL) was stirred at room temperature for 4 hr. Water was added to the reaction solution, and the mixture was extracted with ethyl acetate. The organic layer was washed with water and saturated brine and dried, and the solvent was evaporated under reduced pressure. The obtained residue was purified by silica gel column chromatography (solvent gradient; 5→100% ethyl acetate/hexane) to give the title compound (44 mg, 0.100 mmol, 60%) as a white powder.

$^1$H-NMR (300 MHz, CDCl$_3$): δ1.48 (9H, s), 2.37-2.47 (4H, m), 3.83-3.93 (4H, m), 3.97 (2H, t, J=6.23 Hz), 6.86 (1H, s), 7.16-7.25 (2H, m), 7.31-7.39 (2H, m), 8.00 (1H, s)

MS (API): 441 (M+H)

Example 2

4-({2-[1-tert-butyl-5-(4-fluorophenyl)-1H-pyrazol-4-yl]-1,3-thiazol-4-yl}acetyl)morpholine Using 2-(2-(1-tert-butyl-5-(4-fluorophenyl)-1H-pyrazol-4-yl)thiazol-4-yl)acetic acid and morpholine and by reaction and purification in the same manner as in the method described in Example 1, step 7, the title compound was obtained.

MS (API): 429 (M+H)

Example 3

1-({2-[1-tert-butyl-5-(4-fluorophenyl)-1H-pyrazol-4-yl]-1,3-thiazol-4-yl}acetyl)piperidin-4-ol Using 2-(2-(1-tert-butyl-5-(4-fluorophenyl)-1H-pyrazol-4-yl)thiazol-4-yl)acetic acid and piperidin-4-ol and by reaction and purification in the same manner as in the method described in Example 1, step 7, the title compound was obtained.

MS (API): 443 (M+H)

Example 4

2-{2-[1-tert-butyl-5-(4-fluorophenyl)-1H-pyrazol-4-yl]-1,3-thiazol-4-yl}-N-(2-methoxyethyl)-N-methylacetamide Using 2-(2-(1-tert-butyl-5-(4-fluorophenyl)-1H-pyrazol-4-yl)thiazol-4-yl)acetic acid and 2-methoxy-N-methylethanamine and by reaction and purification in the same manner as in the method described in Example 1, step 7, the title compound was obtained.

MS (API): 431 (M+H)

Example 5

2-{2-[1-tert-butyl-5-(4-fluorophenyl)-1H-pyrazol-4-yl]-1,3-thiazol-4-yl}-N-(2,2,2-trifluoroethyl)acetamide Using 2-(2-(1-tert-butyl-5-(4-fluorophenyl)-1H-pyrazol-4-yl)thiazol-4-yl)acetic acid and 2,2,2-trifluoroethanamine and by reaction and purification in the same manner as in the method described in Example 1, step 7, the title compound was obtained.

MS (API): 441 (M+H)

Example 6

1-({2-[1-tert-butyl-5-(4-fluorophenyl)-1H-pyrazol-4-yl]-1,3-thiazol-4-yl}acetyl)-4-methylpiperazine Using 2-(2-(1-tert-butyl-5-(4-fluorophenyl)-1H-pyrazol-4-yl)thiazol-4-yl)acetic acid and 1-methylpiperazine and by reaction and purification in the same manner as in the method described in Example 1, step 7, the title compound was obtained.

MS (API): 442 (M+H)

Example 7

1-({2-[1-tert-butyl-5-(4-fluorophenyl)-1H-pyrazol-4-yl]-1,3-thiazol-4-yl}acetyl)azetidin-3-ol Using 2-(2-(1-tert-butyl-5-(4-fluorophenyl)-1H-pyrazol-4-yl)thiazol-4-yl)acetic acid and azetidin-3-ol monohydrochloride and by reaction and purification in the same manner as in the method described in Example 1, step 7, the title compound was obtained.

MS (API): 415 (M+H)

Example 8

2-{2-[1-tert-butyl-5-(4-fluorophenyl)-1H-pyrazol-4-yl]-1,3-thiazol-4-yl}-N,N-dimethylacetamide Using 2-(2-(1-tert-butyl-5-(4-fluorophenyl)-1H-pyrazol-4-yl)thiazol-4-yl)acetic acid and dimethylammonium chloride and by reaction and purification in the same manner as in the method described in Example 1, step 7, the title compound was obtained.

MS (API): 387 (M+H)

Example 9

2-{2-[1-tert-butyl-5-(4-fluorophenyl)-1H-pyrazol-4-yl]-1,3-thiazol-4-yl}-N-(2-hydroxy-2-methylpropyl) acetamide Using 2-(2-(1-tert-butyl-5-(4-fluorophenyl)-1H-pyrazol-4-yl)thiazol-4-yl)acetic acid and 1-amino-2-methyl-propan-2-ol and by reaction and purification in the same manner as in the method described in Example 1, step 7, the title compound was obtained.
MS (API): 431 (M+H)

Example 10

2-{2-[1-tert-butyl-5-(4-fluorophenyl)-1H-pyrazol-4-yl]-1,3-thiazol-4-yl}-N-(2-methoxyethyl)acetamide Using 2-(2-(1-tert-butyl-5-(4-fluorophenyl)-1H-pyrazol-4-yl)thiazol-4-yl)acetic acid and 2-methoxyethylamine and by reaction and purification in the same manner as in the method described in Example 1, step 7, the title compound was obtained.
MS (API): 417 (M+H)

Example 11

4-({2-[1-tert-butyl-5-(4-fluorophenyl)-1H-pyrazol-4-yl]-1,3-thiazol-4-yl}acetyl)thiomorpholine Using 2-(2-(1-tert-butyl-5-(4-fluorophenyl)-1H-pyrazol-4-yl)thiazol-4-yl)acetic acid and thiomorpholine and by reaction and purification in the same manner as in the method described in Example 1, step 7, the title compound was obtained.
MS (API): 445 (M+H)

Example 12

4-({2-[1-tert-butyl-5-(4-fluorophenyl)-1H-pyrazol-4-yl]-1,3-thiazol-4-yl}acetyl)thiomorpholine 1,1-dioxide To a mixed solution of 4-({2-[1-tert-butyl-5-(4-fluorophenyl)-1H-pyrazol-4-yl]-1,3-thiazol-4-yl}acetyl)thiomorpholine (100 mg, 0.22 mmol) in THF (2 mL), MeOH (2 mL) and water (2 mL) was added Oxone (290 mg, 0.47 mmol) at 0° C., and the mixture was stirred at 0° C. for 3 hr. Water was added to the reaction solution, and the mixture was extracted with ethyl acetate. The organic layer was washed with aqueous sodium hydrogen carbonate solution and saturated brine and dried, and the solvent was evaporated under reduced pressure to give the title compound (82 mg, 0.172 mmol, 76%) as a white powder.
MS (API): 477 (M+H)

Example 13

Ethyl 1-({2-[1-tert-butyl-5-(4-fluorophenyl)-1H-pyrazol-4-yl]-1,3-thiazol-4-yl}acetyl)piperidine-4-carboxylate Using 2-(2-(1-tert-butyl-5-(4-fluorophenyl)-1H-pyrazol-4-yl)thiazol-4-yl)acetic acid and ethyl isonipecotate and by reaction and purification in the same manner as in the method described in Example 1, step 7, the title compound was obtained.
MS (API): 499 (M+H)

Example 14

2-{2-[1-tert-butyl-5-(4-fluorophenyl)-1H-pyrazol-4-yl]-1,3-thiazol-4-yl}-N-(tetrahydro-2H-pyran-4-ylmethyl)acetamide A solution of 2-(2-(1-tert-butyl-5-(4-fluorophenyl)-1H-pyrazol-4-yl)thiazol-4-yl)acetic acid (60 mg, 0.17 mmol), HATU (76 mg, 0.20 mmol), DEIA (0.035 mL, 0.20 mmol) and (tetrahydro-2H-pyran-4-yl)methanamine (0.023 mL, 0.20 mmol) in DMF (1 mL) was stirred at room temperature for 1 day. Water was added to the reaction solution, and the mixture was extracted with ethyl acetate. The organic layer was washed with water and saturated brine and dried, and the solvent was evaporated under reduced pressure. The obtained residue was purified by silica gel column chromatography (solvent gradient; 20→100% ethyl acetate/hexane⇒0→5% methanol/ethyl acetate) to give the title compound (44 mg, 0.100 mmol, 60%) as a white powder.
$^1$H-NMR (300 MHz, CDCl$_3$): δ1.19-1.37 (2H, m), 1.49 (9H, s), 1.53-1.63 (2H, m), 1.65-1.81 (2H, m), 3.14 (2H, t, J=6.44 Hz), 3.34 (2H, td, J=11.74, 1.89 Hz), 3.63 (2H, s), 3.94 (2H, dd, J=11.17, 3.60 Hz), 6.73 (1H, s), 7.17-7.25 (2H, m), 7.33-7.41 (2H, m), 8.03 (1H, s)
MS (API): 457 (M+H)

Example 15

2-{2-[1-tert-butyl-5-(4-fluorophenyl)-1H-pyrazol-4-yl]-1,3-thiazol-4-yl}-N-(2-cyanoethyl)acetamide Using 2-(2-(1-tert-butyl-5-(4-fluorophenyl)-1H-pyrazol-4-yl)thiazol-4-yl)acetic acid and 3-aminopropionitrile and by reaction and purification in the same manner as in the method described in Example 1, step 7, the title compound was obtained.
MS (API): 412 (M+H)

Example 16

1-({2-[1-tert-butyl-5-(4-fluorophenyl)-1H-pyrazol-4-yl]-1,3-thiazol-4-yl}acetyl)piperidine-4-carboxylic acid A mixed solution of 2-(2-(1-tert-butyl-5-(4-fluorophenyl)-1H-pyrazol-4-yl)thiazol-4-yl)acetic acid (95 mg, 0.19 mmol) and 1N aqueous sodium hydroxide solution (0.286 mL, 0.29 mmol) in ethanol (2 mL) and THF (2 mL) was stirred at room temperature for 3 hr. The reaction mixture was concentrated under reduced pressure, and water and 1N hydrochloric acid were added to the residue. After extraction with ethyl acetate, washing with water and saturated brine and drying, the solvent was evaporated under reduced pressure to give the title compound (74 mg, 0.157 mmol, 83%) as a white powder.
$^1$H-NMR (300 MHz, CDCl$_3$): δ1.48 (9H, s), 1.56-1.75 (2H, m), 1.86-2.02 (2H, m), 2.50-2.64 (1H, m), 2.82-2.94 (1H, m), 3.12-3.26 (1H, m), 3.72-3.84 (1H, m), 3.87-3.97 (1H, m), 3.99-4.10 (1H, m), 4.30-4.44 (1H, m), 6.81 (1H, s), 7.14-7.25 (2H, m), 7.31-7.42 (2H, m), 8.06 (1H, s)

Example 17

4-(2-{2-[1-tert-butyl-5-(4-fluorophenyl)-1H-pyrazol-4-yl]-1,3-thiazol-4-yl}ethyl)thiomorpholine To a solution of lithium aluminum hydride (4.93 mg, 0.13 mmol) in THF (3 mL) was added 2-(2-(1-tert-butyl-5-(4- fluorophenyl)-1H-pyrazol-4-yl)thiazol-4-yl)acetic acid (68 mg, 0.15 mmol) at room temperature, and the mixture was stirred at 80° C. for 2 hr. To the reaction mixture was added 1N aqueous sodium hydroxide solution (2 drops), and the mixture was stirred at room temperature for 1 hr. After extraction with ethyl acetate, washing with saturated brine and drying, the solvent was evaporated under reduced pressure. The residue was purified by NH-silica gel column chromatography (solvent gradient; 3→50% ethyl acetate/hexane) to give the title compound (8 mg, 0.019 mmol, 12.15%) as a pale-yellow oil.

MS (API): 431 (M+H)

Example 18

2-{2-[1-tert-butyl-5-(4-fluorophenyl)-1H-pyrazol-4-yl]-1,3-thiazol-4-yl}-N-methyl-N-(pyridin-4-ylmethyl)acetamide A solution of 2-(2-(1-tert-butyl-5-(4-fluorophenyl)-1H-pyrazol-4-yl)thiazol-4-yl)acetic acid (60 mg, 0.17 mmol), HATU (76 mg, 0.20 mmol), DIEA (0.035 mL, 0.20 mmol) and N-methyl-1-(pyridin-4-yl)methanamine (20.39 mg, 0.17 mmol) in DMF (1 mL) was stirred at room temperature for 2 hr. Water was added to the reaction solution, and the mixture was extracted with ethyl acetate. The organic layer was washed with saturated brine and dried, and the solvent was evaporated under reduced pressure. The obtained residue was purified by NH-silica gel column chromatography (solvent gradient; 5→80% ethyl acetate/hexane) to give the title compound (50 mg, 0.108 mmol, 65%) as a white powder.

MS (API): 464 (M+H)

Example 19

2-[1-tert-butyl-5-(4-fluorophenyl)-1H-pyrazol-4-yl]-N-etrahydro-2H-pyran-4-ylmethyl)-1,3-thiazole-4-carboxamide (Step 1)

A solution of the compound (710 mg, 2.56 mmol) obtained in Example 1, step 4 and ethyl bromopyruvate (0.322 mL, 2.56 mmol) in ethanol (15 mL) was stirred at 80° C. for 16 hr. The reaction mixture was concentrated under reduced pressure, and the residue was purified by silica gel column chromatography (solvent gradient; 3→50% ethyl acetate/hexane) to give ethyl 2-(1-tert-butyl-5-(4-fluorophenyl)-1H-pyrazol-4-yl)thiazole-4-carboxylate (50 mg, 0.108 mmol, 64.6%) as a white powder.

$^1$H-NMR (300 MHz, CDCl$_3$): δ1.39 (3H, t, J=7.16 Hz), 1.48 (9H, s), 4.39 (2H, q, J=6.91 Hz), 7.17-7.25 (2H, m), 7.31-7.41 (2H, m), 7.80 (1H, s), 8.22 (1H, s)

(Step 2)

A mixed solution of the compound (0.57 g, 1.53 mmol) obtained in step 1 and 1N aqueous sodium hydroxide solution (2.289 ml, 2.29 mmol) in ethanol (5 mL) and THF (5 mL) was stirred at 60° C. for 3 hr. The reaction mixture was concentrated under reduced pressure, and 1N hydrochloric acid was added to the residue. The precipitate was collected by filtration to give 2-(1-tert-butyl-5-(4-fluorophenyl)-1H-pyrazol-4-yl)thiazole-4-carboxylic acid (0.50 g, 1.448 mmol, 95%) as a white powder.

$^1$H-NMR (300 MHz, DMSO-d$_6$): δ1.43 (9H, s), 7.38-7.48 (2H, m), 7.52-7.62 (2H, m), 7.90-8.14 (2H, m)

(Step 3)

A solution of the compound (60 mg, 0.17 mmol) obtained in step 2, HATU (79 mg, 0.21 mmol), DIEA (0.036 mL, 0.21 mmol) and (tetrahydro-2H-pyran-4-yl)methanamine (0.024 mL, 0.21 mmol) in DMF (1.5 mL) was stirred at room temperature for 14 hr. Water was added to the reaction solution, and the mixture was extracted with ethyl acetate. The organic layer was washed with water and saturated brine and dried, and the solvent was evaporated under reduced pressure to give the title compound (50 mg, 0.113 mmol, 65.0%) as a white powder.

$^1$H-NMR (300 MHz, CDCl$_3$): δ1.25-1.46 (2H, m), 1.46-1.52 (9H, m), 1.60-1.69 (2H, m), 1.75-1.93 (1H, m), 3.31 (2H, t, J=6.61 Hz), 3.39 (2H, td, J=11.80, 2.08 Hz), 3.99 (2H, dd, J=11.14, 3.21 Hz), 7.18-7.26 (3H, m), 7.32-7.42 (2H, m), 7.75 (1H, s), 8.02 (1H, s)

Example 20

2-{2-[1-tert-butyl-5-(4-fluorophenyl)-1H-pyrazol-4-yl]-1,3-thiazol-4-yl}-N-(2-morpholin-4-ylethyl)acetamide Using 2-(2-(1-tert-butyl-5-(4-fluorophenyl)-1H-pyrazol-4-yl)thiazol-4-yl)acetic acid and 2-morpholinoethanamine and by reaction and purification in the same manner as in the method described in Example 1, step 7, the title compound was obtained.

MS (API): 472 (M+H)

Example 21

2-{2-[1-tert-butyl-5-(4-fluorophenyl)-1H-pyrazol-4-yl]-1,3-thiazol-4-yl}-N-(3-morpholin-4-ylpropyl)acetamide Using 2-(2-(1-tert-butyl-5-(4-fluorophenyl)-1H-pyrazol-4-yl)thiazol-4-yl)acetic acid and 3-morpholinopropan-1-amine and by reaction and purification in the same manner as in the method described in Example 1, step 7, the title compound was obtained.

MS (API): 486 (M+H)

Example 22

2-[1-tert-butyl-5-(4-fluorophenyl)-1H-pyrazol-4-yl]-N-(2-morpholin-4-ylethyl)-1,3-thiazole-4-carboxamide Using 2-(1-tert-butyl-5-(4-fluorophenyl)-1H-pyrazol-4-yl)thiazole-4-carboxylic acid and 2-morpholinoethanamine and by reaction and purification in the same manner as in the method described in Example 1, step 7, the title compound was obtained.

MS (API): 458 (M+H)

Example 23

2-[1-tert-butyl-5-(4-fluorophenyl)-1H-pyrazol-4-yl]-N-[2-(tetrahydro-2H-pyran-4-yl)ethyl]-1,3-thiazole-4-carboxamide Using 2-(1-tert-butyl-5-(4-fluorophenyl)-1H-pyrazol-4-yl)thiazole-4-carboxylic acid and 2-(tetrahydro-2H-pyran-4-yl)ethanamine and by reaction and purification in the same manner as in the method described in Example 1, step 7, the title compound was obtained.

MS (API): 457 (M+H)

Example 24

2-{2-[1-tert-butyl-5-(4-fluorophenyl)-1H-pyrazol-4-yl]-1,3-thiazol-4-yl}-N-[2-(tetrahydro-2H-pyran-4-yl)ethyl]acetamide Using 2-(2-(1-tert-butyl-5-(4-fluorophenyl)-1H-pyrazol-4-yl)thiazol-4-yl)acetic acid and 2-(tetrahydro-2H-pyran-4-yl)ethanamine and by reaction and purification in the same manner as in the method described in Example 1, step 7, the title compound was obtained.
MS (API): 471 (M+H)

Example 25

2-{2-[1-tert-butyl-5-(4-fluorophenyl)-1H-pyrazol-4-yl]-1,3-thiazol-4-yl}-N-(4-cyanobenzyl)acetamide Using 2-(2-(1-tert-butyl-5-(4-fluorophenyl)-1H-pyrazol-4-yl)thiazol-4-yl)acetic acid and p-(aminomethyl)benzonitrile hydrochloride and by reaction and purification in the same manner as in the method described in Example 1, step 7, the title compound was obtained.
MS (API): 474 (M+H)

Example 26

2-{2-[1-tert-butyl-5-(4-fluorophenyl)-1H-pyrazol-4-yl]-1,3-thiazol-4-yl}-N-(tetrahydro-2H-pyran-4-yl)acetamide Using 2-(2-(1-tert-butyl-5-(4-fluorophenyl)-1H-pyrazol-4-yl)thiazol-4-yl)acetic acid and 4-aminotetrahydropyran and by reaction and purification in the same manner as in the method described in Example 1, step 7, the title compound was obtained.
MS (API): 443 (M+H)

Example 27 tert-butyl 4-{(2-[1-tert-butyl-5-(4-fluorophenyl)-1H-pyrazol-4-yl]-1,3-thiazol-4-yl}piperidine-1-carboxylate Using 1-tert-butyl-5-(4-fluorophenyl)-1H-pyrazole-4-carbothioamide and tert-butyl 4-(2-bromoacetyl)piperidine-1-carboxylate and by reaction and purification in the same manner as in the method described in Example 19, step 1, the title compound was obtained.
MS (API): 485 (M+H)

Example 28

4-{2-[1-tert-butyl-5-(4-fluorophenyl)-1H-pyrazol-4-yl]-1,3-thiazol-4-yl}piperidine monohydrochloride To a solution of 4-(2-(1-tert-butyl-5-(4-fluorophenyl)-1H-pyrazol-4-yl)thiazol-4-yl)piperidine-1-carboxylic acid (338 mg, 0.70 mmol) in ethyl acetate (1 mL) was added 4N hydrogen chloride/ethyl acetate (1 mL, 4.00 mmol), and the mixture was stirred at room temperature for 14 hr. The precipitate was collected by filtration, and washed with ethyl acetate to give the title compound (294 mg, 0.698 mmol, 100%) as a pale-yellow powder.
$^1$H-NMR (300 MHz, CDCl$_3$): δ1.48 (9H, s), 2.11-2.32 (2H, m), 2.33-2.55 (2H, m), 2.93-3.25 (2H, m), 3.47-3.66 (2H, m), 3.66-3.83 (1H, m), 7.00 (1H, brs), 7.30-7.48 (4H, m), 9.16 (1H, s), 9.70 (2H, brs)

Example 29

4-(4-{2-[1-tert-butyl-5-(4-fluorophenyl)-1H-pyrazol-4-yl]-1,3-thiazol-4-yl}piperidin-1-yl)-2-methyl-4-oxobutan-2-ol Using 4-{2-[1-tert-butyl-5-(4-fluorophenyl)-1H-pyrazol-4-yl]-1,3-thiazol-4-yl}piperidine monohydrochloride and 3-hydroxy-3-methylbutyric acid and by reaction and purification in the same manner as in the method described in Example 1, step 7, the title compound was obtained.
MS (API): 485 (M+H)

Example 30

4-{2-[1-tert-butyl-5-(4-fluorophenyl)-1H-pyrazol-4-yl]-1,3-thiazol-4-yl}-1-[4,4,4-trifluoro-3-(trifluoromethyl)butanoyl]piperidine Using 4-{2-[1-tert-butyl-5-(4-fluorophenyl)-1H-pyrazol-4-yl]-1,3-thiazol-4-yl}piperidine monohydrochloride and 4,4,4-trifluoro-3-(trifluoromethyl)butyric acid and by reaction and purification in the same manner as in the method described in Example 1, step 7, the title compound was obtained.
$^1$H-NMR (300 MHz, CDCl$_3$): δ1.48 (9H, s), 1.55-1.71 (2H, m), 1.96-2.20 (2H, m), 2.74 (2H, d, J=5.3 Hz), 2.77-2.88 (1H, m), 2.92-3.04 (1H, m), 3.12-3.30 (1H, m), 3.80-3.95 (1H, m), 4.06-4.29 (1H, m), 4.55-4.70 (1H, m), 6.55 (1H, d, J=0.8 Hz), 7.14-7.23 (2H, m), 7.32-7.40 (2H, m), 8.04 (1H, s)

Example 31

4-[(4-{2-[1-tert-butyl-5-(4-fluorophenyl)-1H-pyrazol-4-yl]-1,3-thiazol-4-yl}piperidin-1-yl)carbonyl]benzonitrile Using 4-{2-[1-tert-butyl-5-(4-fluorophenyl)-1H-pyrazol-4-yl]-1,3-thiazol-4-yl}piperidine monohydrochloride and 4-cyanobenzoic acid and by reaction and purification in the same manner as in the method described in Example 1, step 7, the title compound was obtained.
MS (API): 514 (M+H)

Example 32

2-{2-[1-tert-butyl-5-(4-fluorophenyl)-1H-pyrazol-4-yl]-1,3-thiazol-5-yl}-N-(tetrahydro-2H-pyran-4-ylmethyl)acetamide (Step 1)
Using 1-tert-butyl-5-(4-fluorophenyl)-1H-pyrazole-4-carbothioamide and methyl 3-bromo-4-oxobutanoate and by reaction and purification in the same manner as in the method described in Example 19, step 1, ethyl 2-(2-(1-tert-butyl-5-(4-fluorophenyl)-1H-pyrazol-4-yl)thiazol-5-yl)acetate was obtained.
MS (API): 388 (M+H)
(Step 2)
Using the compound obtained in step 1 and by reaction and purification in the same manner as in the method described in Example 1, step 2, 2-(2-(1-tert-butyl-5-(4-fluorophenyl)-1H-pyrazol-4-yl)thiazol-5-yl)acetic acid was obtained.
MS (API): 360 (M+H)

(Step 3)

Using the compound obtained in step 2 and (tetrahydro-2H-pyran-4-yl)methanamine and by reaction and purification in the same manner as in the method described in Example 1, step 7, the title compound was obtained.

MS (API): 457 (M+H)

Example 33

2-{4-[1-tert-butyl-5-(4-methoxyphenyl)-1H-pyrazol-4-yl]-1,3-thiazol-2-yl}-N-(tetrahydro-2H-pyran-4-ylmethyl)acetamide (Step 1)

A solution of ethyl 3-(4-methoxyphenyl)-3-oxopropanoate (3 g, 13.5 mmol) and 1,1-dimethoxy-N,N-dimethylmethanamine (2.152 mL, 16.20 mmol) in toluene (10 ml) was stirred at 90° C. for 14 hr. The reaction mixture was concentrated under reduced pressure, and ethanol (15 mL) was added thereto. To the residue were added tert-butylhydrazine monohydrochloride (1.85 g, 14.85 mmol) and TEA (2.07 mL, 14.85 mmol), and the mixture was stirred at 80° C. for 20 hr. The reaction mixture was concentrated under reduced pressure, and ethyl acetate was added thereto. The organic layer was washed with water and saturated brine and dried, and the solvent was evaporated under reduced pressure. The obtained residue was purified by silica gel column chromatography (solvent gradient; 3→60% ethyl acetate/hexane) to give ethyl 1-tert-butyl-5-(4-methoxyphenyl)-1H-pyrazole-4-carboxylate (2.86 g, 9.46 mmol, 70.1%) as a pale-yellow powder.

MS (API): 303 (M+H)

(Step 2)

To a mixed solution of the compound (2.86 g, 9.46 mmol) obtained in step 1 in THF (15 mL) and ethanol (15 mL) was added 1N aqueous sodium hydroxide solution (14.19 mL, 14.19 mmol) at room temperature, and the mixture was stirred at room temperature for 1 hr. The reaction mixture was concentrated under reduced pressure, and 1N hydrochloric acid was added thereto. The precipitate was collected by filtration to give 1-tert-butyl-5-(4-methoxyphenyl)-1H-pyrazole-4-carboxylic acid (2.59 g, 9.44 mmol, 100%) as a white powder.

MS (API): 275 (M+H)

(Step 3)

A solution of the compound (300 mg, 1.09 mmol) obtained in step 2, N,O-dimethylhydroxylamine monohydrochloride (160 mg, 1.64 mmol), HOBt (222 mg, 1.64 mmol), WSC (314 mg, 1.64 mmol) and TEA (0.228 mL, 1.64 mmol) in DMF (5 mL) was stirred at room temperature for 3 days. Water was added to the reaction mixture, and the mixture was extracted with ethyl acetate. The organic layer was washed with water and aqueous sodium hydrogen carbonate solution and dried, and the solvent was evaporated under reduced pressure to give a crude product 1-tert-butyl-N-methoxy-5-(4-methoxyphenyl)-N-methyl-1H-pyrazole-4-carboxamide (320 mg, 1.008 mmol, 92%) as a pale-yellow powder.

MS (API): 318 (M+H)

(Step 4)

To a solution of the compound (320 mg, 1.01 mmol) obtained in step 3 in THF (5 mL) was added 3 mol/L methylmagnesium chloride, and the mixture was stirred at room temperature for 14 hr. To the reaction mixture was added 1N hydrochloric acid, and the mixture was extracted with ethyl acetate. The organic layer was washed with saturated brine and dried, and the solvent was evaporated under reduced pressure to give 1-(1-tert-butyl-5-(4-methoxyphenyl)-1H-pyrazol-4-yl)ethanone (260 mg, 0.955 mmol, 95%) as a white powder.

$^1$H-NMR (300 MHz, CDCl$_3$): δ1.45 (9H, s), 1.96 (3H, s), 3.88 (3H, s), 6.94-7.01 (2H, m), 7.21-7.25 (2H, m), 7.96 (1H, s)

(Step 5)

To a solution of the compound (260 mg, 0.95 mmol) obtained in step 4 in THF (5 mL) was added dropwise a solution of trimethylphenylammonium tribromide (359 mg, 0.95 mmol) in THF (5 mL) at 0° C. The reaction mixture was stirred at 0° C. for 14 hr, and the precipitate was filtered. The filtrate was concentrated under reduced pressure, and the residue was purified by silica gel column chromatography (solvent gradient; 2→45% ethyl acetate/hexane) to give 2-bromo-1-(1-tert-butyl-5-(4-methoxyphenyl)-1H-pyrazol-4-yl)ethanone (107 mg, 0.305 mmol, 31.9%) as a white powder.

$^1$H-NMR (300 MHz, CDCl$_3$): δ1.45 (9H, s), 3.77 (2H, s), 3.88 (3H, s), 6.94-7.02 (2H, m, J=1.1 Hz), 7.22-7.30 (2H, m), 8.01 (1H, s)

(Step 6)

A solution of the compound (107 mg, 0.30 mmol) obtained in step 5 and methyl 3-amino-3-thioxopropanoate (48.7 mg, 0.37 mmol) in EtOH (3 mL) was stirred at 90° C. for 14 hr. The reaction mixture was concentrated under reduced pressure, and the residue was purified by NH-silica gel column chromatography (solvent gradient; 5→80% ethyl acetate/hexane) to give a crude product ethyl 2-(4-(1-tert-butyl-5-(4-methoxyphenyl)-1H-pyrazol-4-yl)thiazol-2-yl)acetate as a colorless oil, which was used for the next step without purification.

MS (API): 400 (M+H)

(Step 7)

A mixed solution of the compound (53 mg, 0.13 mmol) obtained in step 6 and 1N aqueous sodium hydroxide solution (0.199 mL, 0.199 mmol) in ethanol (2 mL) and THF (2 mL) was stirred at room temperature for 2 hr. The reaction mixture was concentrated under reduced pressure, and 1N hydrochloric acid and ethyl acetate were added thereto. The organic layer was washed with saturated brine and dried, and the solvent was evaporated under reduced pressure to give 2-(4-(1-tert-butyl-5-(4-methoxyphenyl)-1H-pyrazol-4-yl)thiazol-2-yl)acetic acid (49 mg, 0.132 mmol, 99%) as a white powder.

MS (API): 372 (M+H)

(Step 8)

A solution of the compound (54 mg, 0.15 mmol) obtained in step 7, HATU (66.3 mg, 0.17 mmol), DIEA (0.030 mL, 0.17 mmol) and (tetrahydro-2H-pyran-4-yl)methanamine (0.020 mL, 0.17 mmol) in DMF (2 mL) was stirred at room temperature for 3 days. Water was added to the reaction mixture, and the mixture was extracted with ethyl acetate. The organic layer was washed with water, aqueous sodium hydrogen carbonate solution and saturated brine and dried, and the solvent was evaporated under reduced pressure. The residue was purified by silica gel column chromatography (solvent gradient; 80→100% ethyl acetate/hexane) to give the title compound (12 mg, 0.026 mmol, 18%)

$^1$H-NMR (300 MHz, CDCl$_3$): δ1.25-1.40 (2H, m), 1.49 (9H, s), 1.55-1.64 (2H, m), 1.68-1.84 (1H, m), 3.18 (2H, t, J=6.4 Hz), 3.36 (2H, td, J=11.6, 2.1 Hz), 3.88 (2H, s), 3.90 (3H, s), 3.92-3.99 (2H, m), 5.92 (1H, s), 6.98-7.06 (2H, m), 7.24-7.30 (2H, m), 7.69 (1H, brs), 7.94 (1H, s)

Example 34

2-{2-[5-(4-fluorophenyl)-1-phenyl-1H-pyrazol-4-yl]-1,3-thiazol-4-yl}-N-(tetrahydro-2H-pyran-4-ylmethyl)acetamide (Step 1)

A solution of ethyl 3-(4-fluorophenyl)-3-oxopropanoate (1.50 g, 7.14 mmol) and DMFDMA (1.15 mL, 8.56 mmol) in toluene (23 mL) was heated under reflux for 15 hr. The reaction mixture was concentrated under reduced pressure, and the residue was dissolved in ethanol (23 mL). To the ethanol solution was added phenylhydrazine (0.779 mL, 7.85 mmol) at room temperature, and the mixture was heated under reflux for 3 hr. The reaction mixture was concentrated under reduced pressure, and the residue was purified by silica gel column chromatography (solvent; 2% ethyl acetate/hexane) to give ethyl 5-(4-fluorophenyl)-1-phenyl-1H-pyrazole-4-carboxylate (1.90 g, 86%) as a yellow powder.

$^1$H-NMR (400 MHz, CDCl$_3$): δ1.25 (3H, t, J=7.2 Hz), 4.23 (2H, q, J=7.2 Hz), 7.01-7.05 (2H, m), 7.18-7.21 (2H, m), 7.26-7.33 (5H, m), 8.18 (1H, s)

(Step 2)

To a solution of the compound (1.00 g, 3.22 mmol) obtained in step 1 in ethanol (5.0 ml) was added 2N aqueous sodium hydroxide solution (4.70 mL, 9.40 mmol) at room temperature, and the mixture was heated under reflux for 3 hr. The reaction mixture was cooled to room temperature, and 2N hydrochloric acid was added until the mixture became pH 6. The precipitate was collected by filtration with ethyl acetate to give 5-(4-fluorophenyl)-1-phenyl-1H-pyrazole-4-carboxylic acid (852 mg, 94%) as a white powder.

$^1$H-NMR (400 MHz, DMSO-d$_6$): δ7.17-7.23 (4H, m), 7.32-7.38 (5H, m), 8.14 (1H, s) (* hydrogen of carboxyl group was not observed)

(Step 3)

To a solution of the compound (852 mg, 3.02 mmol) obtained in step 2 in DMF (10 mL) were added WSC (868 mg, 4.53 mmol), HOBt (693 mg, 4.53 mmol), TEA (916 mg, 9.06 mmol) and ammonium chloride (484 mg, 9.06 mmol) at room temperature. The reaction mixture was heated at 100° C. for 1 hr, cooled to room temperature, and poured into ethyl acetate. The solution was washed with saturated brine and water and dried, and the solvent was evaporated under reduced pressure. The residue was purified by silica gel column chromatography (solvent; 50% ethyl acetate/hexane) to give 5-(4-fluorophenyl)-1-phenyl-1H-pyrazole-4-carboxamide (820 mg, 97%) as a yellow powder.

$^1$H-NMR (400 MHz, CDCl$_3$): δ7.03-7.08 (2H, m), 7.19-7.21 (2H, m), 7.28-7.30 (2H, m), 7.31-7.35 (3H, m), 8.13 (1H, s) (* hydrogen of NH$_2$ group was not observed)

(Step 4)

A solution of the compound (820 mg, 2.92 mmol) obtained in step 3 and Lawesson's reagent (943 mg, 2.33 mmol) in THF (10 mL) was heated under reflux for 1 hr. The reaction mixture was concentrated under reduced pressure, and the residue was purified by silica gel column chromatography (solvent; 50% ethyl acetate/hexane) to give 5-(4-fluorophenyl)-1-phenyl-1H-pyrazole-4-carbothioamide (678 mg, 78%) as a yellow powder.

$^1$H-NMR (400 MHz, CDCl$_2$): δ7.06-7.10 (2H, m), 7.19-7.21 (2H, m), 7.27-7.31 (2H, m), 7.33-7.35 (3H, m), 8.10 (1H, s) (* hydrogen of NH$_2$ group was not observed)

(Step 5)

A solution of the compound (520 mg, 1.74 mmol) obtained in step 4 and ethyl 4-chloroacetoacetate (314 mg, 1.91 mmol) in ethanol (5.0 mL) was heated under reflux for 12 hr. The reaction mixture was concentrated under reduced pressure, and the residue was purified by silica gel column chromatography (solvent; 33% ethyl acetate/hexane) to give ethyl {2-[5-(4-fluorophenyl)-1-phenyl-1H-pyrazol-4-yl]-1,3-thiazol-4-yl}acetate (220 mg, 32%) as a yellow powder.

$^1$H-NMR (400 MHz, CDCl$_3$): δ1.29 (3H, t, J=7.2 Hz), 3.82 (2H, s), 4.20 (2H, q, J=7.2 Hz), 7.00 (1H, s), 7.07-7.23 (2H, m), 7.23-7.28 (3H, m), 7.32-7.40 (4H, m), 8.26 (1H, s)

(Step 6)

A solution of the compound (220 mg, 0.540 mmol) obtained in step 5 and 1N aqueous sodium hydroxide solution (1.08 mmol, 1.08 mL) in ethanol (5.0 mL) was heated under reflux for 1 hr. The reaction mixture was cooled to room temperature, and concentrated hydrochloric acid was added until the mixture became pH 6. The mixture was concentrated under reduced pressure, and the residue was purified by silica gel column chromatography (solvent; 33% ethyl acetate/hexane) to give {2-[5-(4-fluorophenyl)-1-phenyl-1H-pyrazol-4-yl]-1,3-thiazol-4-yl}acetic acid (140 mg, 68%) as a yellow powder.

$^1$H-NMR (400 MHz, CD$_3$OD): δ3.79 (2H, s), 7.14-7.19 (3H, m), 7.24-7.30 (2H, m), 7.34-7.39 (5H, m), 8.27 (1H, s) (* hydrogen of CO$_2$H group was not observed)

(Step 7)

A solution of the compound (140 mg, 0.369 mmol) obtained in step 6, WSC (106 mg, 0.553 mmol), HOBt (85.0 mg, 0.553 mmol), TEA (112 mg, 1.11 mmol) and (tetrahydro-2H-pyran-4-yl)methanamine (51.0 mg, 0.443 mmol) in DMF (10 mL) was stirred at 100° C. for 1 hr. The reaction solution was cooled, and added to water, and the mixture was extracted with ethyl acetate. The organic layer was washed with water and saturated brine and dried, and the solvent was evaporated under reduced pressure. The obtained residue was purified by silica gel column chromatography (solvent; 20% methanol/ethyl acetate) to give the title compound (70.0 mg, 41%) as a yellow powder.

$^1$H-NMR (400 MHz, CD$_3$OD): δ1.19-1.29 (2H, m), 1.58-1.62 (2H, m), 1.71-1.75 (1H, m), 3.09 (2H, d, J=6.8 Hz), 3.35 (2H, dt, J=12 Hz, 2 Hz), 3.658 (2H, s), 3.88-3.91 (2H, m), 7.11-7.17 (3H, m), 7.26-7.29 (2H, s), 7.33-7.38 (5H, m), 8.22 (1H, s) (* hydrogen of NH group was not observed)

Example 35

2-{2-[5-(4-fluorophenyl)-1-methyl-1H-pyrazol-4-yl]-1,3-thiazol-4-yl}-N-(tetrahydro-2H-pyran-4-ylmethyl)acetamide (Step 1)

To a solution of ethyl 3-(4-fluorophenyl)-1H-pyrazole-4-carboxylate (15.0 g, 64.0 mmol) in THF was added sodium hydride (55 wt % paraffin oil, 3.35 g, 77.0 mmol) at room temperature and methyl iodide (8.01 mL, 128 mmol) was successively added at room temperature. After stirring at room temperature for 15 min, the reaction mixture was poured into ice water. The mixture was extracted with ethyl acetate, the organic layer was washed with saturated brine and dried, and the solvent was evaporated under reduced pressure. The residue was purified by silica gel column chromatography (solvent; 33% ethyl acetate/hexane) to give a mixture (1:1 (mol/mol), 14.2 g, 90%) of ethyl 5-(4-fluorophenyl)-1-methyl-1H-pyrazole-4-carboxylate and ethyl 3-(4-fluorophenyl)-1-methyl-1H-pyrazole-4-carboxylate as a brown oil.

$^1$H-NMR (400 MHz, CDCl$_3$): δ1.20 (1.5H, t, J=7.2 Hz), 1.29 (1.5H, t, J=7.2 Hz), 3.73 (1.5H, s), 3.95 (1.5H, s), 4.16

(1H, q, J=7.2 Hz), 4.24 (1H, q, J=7.2 Hz), 7.07-7.12 (1H, m), 7.16-7.21 (1H, m), 7.35-7.39 (1H, m), 7.75-7.78 (1H, m), 7.95 (0.5H, s), 7.99 (0.5H, s)

(Step 2)

To a solution of the compound (14.2 g, 57.4 mmol) obtained in step 1 in ethanol (50 mL) was added 2N aqueous sodium hydroxide solution (63.2 mL, 126 mmol) at room temperature, and the mixture was heated under reflux for 1 hr. The reaction mixture was cooled to room temperature, and 2N hydrochloric acid was added until the mixture became pH 6. The precipitate was collected by filtration with ethyl acetate to give a mixture (3:2.2 (mol/mol), 13.0 g, 100%) of 5-(4-fluorophenyl)-1-methyl-1H-pyrazole-4-carboxylic acid and 3-(4-fluorophenyl)-1-methyl-1H-pyrazole-4-carboxylic acid as a white powder.

$^1$H-NMR (400 MHz, CDCl$_3$) of isomer 1: δ3.73 (3H, s), 7.16-7.21 (2H, m), 7.35-7.39 (2H, m), 8.04 (1H, s) (* hydrogen of carboxyl group was not observed)

$^1$H-NMR (400 MHz, CDCl$_3$) of isomer 2: δ3.96 (3H, s), 7.07-7.11 (2H, m), 7.74-7.78 (2H, m), 8.01 (1H, s) (* hydrogen of carboxyl group was not observed)

(Step 3)

To a solution of the compound (822 mg, 3.73 mmol) obtained in step 2 in DMF (9 mL) were added WSC (859 mg, 4.48 mmol), HOBt (686 mg, 4.48 mmol), TEA (0.624 mL, 4.48 mmol) and ammonium chloride (240 mg, 4.48 mmol) at room temperature, and the mixture was stirred for 14 hr and poured into water and ethyl acetate. The organic layer was washed with saturated brine and water and dried, and the solvent was evaporated under reduced pressure. The residue was purified by silica gel column chromatography (solvent; 50% ethyl acetate/hexane) to give a mixture (3:2.7 (mol/mol), 446 mg, 55%) of 5-(4-fluorophenyl)-1-methyl-1H-pyrazole-4-carboxamide and 3-(4-fluorophenyl)-1-methyl-1H-pyrazole-4-carboxamide as a white powder.

$^1$H-NMR (400 MHz, CDCl$_3$) of isomer 1: δ3.70 (3H, s), 5.28 (2H, brs), 7.22-7.29 (2H, m), 7.41-7.45 (2H, m), 8.00 (1H, s)

$^1$H-NMR (400 MHz, CDCl$_3$) of isomer 2: δ3.95 (3H, s), 5.47 (2H, brs), 7.12-7.19 (2H, m), 7.57-7.63 (2H, m), 7.97 (1H, s)

(Step 4)

A solution of the compound (446 mg, 2.04 mmol) obtained in step 3 and Lawesson's reagent (658 mg, 1.63 mmol) in THF (8.5 mL) was heated at 60° C. for 1 hr. The reaction mixture was concentrated under reduced pressure, and the residue was purified by NH-silica gel column chromatography (solvent gradient; 20→50% ethyl acetate/hexane) to give a mixture (3:2 (mol/mol), 319 mg, 67%) of 5-(4-fluorophenyl)-1-methyl-1H-pyrazole-4-carbothioamide and 3-(4-fluorophenyl)-1-methyl-1H-pyrazole-4-carbothioamide as a yellow powder.

$^1$H-NMR (400 MHz, CDCl$_3$) of isomer 1: δ3.66 (3H, s), 6.33 (1H, brs), 7.00 (1H, brs), 7.26-7.31 (2H, m), 7.42-7.46 (2H, m), 8.26 (1H, s) (* hydrogen of NH group and CSNH$_2$ group was not observed)

$^1$H-NMR (400 MHz, CDCl$_3$) of isomer 2: δ3.93 (3H, s), 6.71 (1H, brs), 7.15-7.20 (2H, m), 7.55-7.59 (2H, m), 8.23 (1H, s) (*hydrogen of NH group and CSNH$_2$ group was not observed)

(Step 4)

A solution of the compound (319 mg, 1.36 mmol) obtained in step 3 and ethyl 4-chloroacetoacetate (0.202 mL, 1.49 mmol) in EtOH (3.8 mL) was heated under reflux for 2 hr. The reaction mixture was concentrated under reduced pressure, and ethyl acetate was added thereto. The precipitate was collected by filtration to give ethyl {2-[5-(4-fluorophenyl)-1-methyl-1H-pyrazol-4-yl]-1,3-thiazol-4-yl}acetate (245 mg, 52%) as a white powder. The filtrate was concentrated under reduced pressure, and ethyl acetate and hexane were added thereto. The precipitate was collected by filtration to give ethyl {2-[3-(4-fluorophenyl)-1-methyl-1H-pyrazol-4-yl]-1,3-thiazol-4-yl}acetate (115 mg, 25%) as a yellow powder.

$^1$H-NMR (400 MHz, CDCl$_3$) of ethyl {2-[5-(4-fluorophenyl)-1-methyl-1H-pyrazol-4-yl]-1,3-thiazol-4-yl}acetate: δ1.30 (3H, t, J=7.2 Hz), 3.75 (3H, s), 4.22 (2H, q, J=7.2 Hz), 4.26 (2H, s), 7.22 (1H, s), 7.33-7.41 (4H, m), 9.17 (1H, s)

$^1$H-NMR (400 MHz, CDCl$_3$) of ethyl {2-[3-(4-fluorophenyl)-1-methyl-1H-pyrazol-4-yl]-1,3-thiazol-4-yl}acetate: δ1.31 (3H, t, J=7.2 Hz), 4.04 (3H, s), 4.21 (2H, s), 4.24 (2H, q, J=7.2 Hz), 7.20-7.25 (3H, m), 7.45-7.49 (2H, m), 9.48 (1H, s)

(Step 5)

A solution of ethyl {2-[5-(4-fluorophenyl)-1-methyl-1H-pyrazol-4-yl]-1,3-thiazol-4-yl}acetate (245 mg, 0.709 mmol) and 6N aqueous sodium hydroxide solution (0.355 mL, 2.13 mmol) in ethanol (2.8 mL) was heated under reflux for 2 hr. Ethanol was evaporated, and 2N hydrochloric acid was added until the mixture became pH2. The precipitate was collected by filtration to give {2-[5-(4-fluorophenyl)-1-methyl-1H-pyrazol-4-yl]-1,3-thiazol-4-yl}acetic acid (235 mg, 100%) as a yellow powder.

$^1$H-NMR (400 MHz, DMSO-d$_6$): δ3.67 (5H, s), 7.18 (1H, s), 7.41-7.45 (2H, m), 7.57-7.60 (2H, m), 7.96 (1H, s), 12.42 (1H, brs)

(Step 6)

A solution of the compound (225 mg, 0.709 mmol) obtained in step 5, WSC (204 mg, 1.06 mmol), HOBt (163 mg, 1.06 mmol), TEA (0.198 mL, 1.42 mmol) and (tetrahydro-2H-pyran-4-yl)methanamine (98.0 mg, 0.851 mmol) in DMF (2.8 mL) was stirred at 100° C. for 1 hr. The reaction solution was cooled, added to water, and the mixture was extracted with ethyl acetate. The organic layer was washed with water and saturated brine and dried, and the solvent was evaporated under reduced pressure. The obtained residue was purified by silica gel column chromatography (solvent gradient; 1→10% methanol/ethyl acetate) to give the title compound (192 mg, 65%) as a yellow powder.

$^1$H-NMR (400 MHz, CDCl$_3$): δ1.21-1.31 (2H, m), 1.51-1.55 (2H, m), 1.63-1.73 (1H, m), 3.11 (2H, t, J=6.4 Hz), 3.33 (2H, td, J=12.0, 2.0 Hz), 3.64 (2H, s), 3.74 (3H, s), 3.94 (2H, dd, J=11.2, 3.2 Hz), 6.82 (1H, s), 7.10 (1H, brs), 7.23-7.28 (2H, m), 7.39-7.43 (2H, m), 8.02 (1H, s)

Example 36

2-{2-[5-(4-fluorophenyl)-1-(2,2,2-trifluoroethyl)-1H-pyrazol-4-yl]-1,3-thiazol-4-yl}-N-(tetrahydro-2H-pyran-4-ylmethyl)acetamide (Step 1)

A solution of 5-(4-fluorophenyl)-1-(2,2,2-trifluoroethyl)-1H-pyrazole-4-carboxylic acid (400 mg, 1.39 mmol) and thionyl chloride (0.506 mL, 6.94 mmol) in toluene (6 mL) was stirred at 100° C. for 2.5 hr. The reaction mixture was concentrated under reduced pressure, and the residue was dissolved in THF (4 mL). To the solution was added 25% aqueous ammonia (3 mL), and the mixture was stirred at room temperature for 14 hr. Water was added to the reaction mixture, and the precipitate was collected by filtration to give 5-(4-fluorophenyl)-1-(2,2,2-trifluoroethyl)-1H-pyrazole-4-carboxamide (350 mg, 1.219 mmol, 88%) as a white powder.

MS (API): 288 (M+H)

(Step 2)

Using the compound obtained in step 1 and by reaction and purification in the same manner as in the method described in Example 1, step 4, 5-(4-fluorophenyl)-1-(2,2,2-trifluoroethyl)-1H-pyrazole-4-carbothioamide was obtained.

MS (API): 304 (M+H)

(Step 3)

Using the compound obtained in step 2 and by reaction and purification in the same manner as in the method described in Example 1, step 5, ethyl 2-(2-(5-(4-fluorophenyl)-1-(2,2,2-trifluoroethyl)-1H-pyrazol-4-yl)thiazol-4-yl)acetate was obtained.

MS (API): 414 (M+H)

(Step 4)

Using the compound obtained in step 3 and by reaction and purification in the same manner as in the method described in Example 1, step 6, 2-(2-(5-(4-fluorophenyl)-1-(2,2,2-trifluoroethyl)-1H-pyrazol-4-yl)thiazol-4-yl)acetic acid was obtained.

MS (API): 386 (M+H)

(Step 5)

Using the compound obtained in step 4 and by reaction and purification in the same manner as in the method described in Example 14, the title compound was obtained.

MS (API): 483 (M+H)

Example 37

2-{2-[1-(difluoromethyl)-5-(4-fluorophenyl)-1H-pyrazol-4-yl]-1,3-thiazol-4-yl}-N-(tetrahydro-2H-pyran-4-ylmethyl)acetamide (Step 1)

To a solution of ethyl 3-(4-fluorophenyl)-1H-pyrazole-4-carboxylate (4.50 g, 19.2 mmol) in DMF (96 mL) was added cesium carbonate (7.51 g, 77.0 mmol) at room temperature, and dichlorofluoromethane gas was blown into the reaction solution at room temperature for 2 hr. The mixture was stirred at room temperature for 2 hr, water was poured into the reaction solution, and the mixture was extracted with ethyl acetate. The organic layer was washed with saturated brine and dried, and the solvent was evaporated under reduced pressure. The obtained residue was purified by silica gel column chromatography (solvent; 5% ethyl acetate/hexane) to give a mixture (3.10 g, 57%, 1:1.5 mol/mol) of ethyl 1-(difluoromethyl)-3-(4-fluorophenyl)-1H-pyrazole-4-carboxylate and ethyl 1-(difluoromethyl)-5-(4-fluorophenyl)-1H-pyrazole-4-carboxylate as a pale-yellow oil.

Ethyl 1-(difluoromethyl)-3-(4-fluorophenyl)-1H-pyrazole-4-carboxylate; $^1$H-NMR (400 MHz, CDCl$_3$): δ1.32 (3H, t, J=7.2 Hz), 4.29 (2H, q, J=7.0 Hz), 7.09-7.15 (2H, m), 7.21 (1H, t, J=60.4 Hz), 7.77-7.81 (2H, m), 8.41 (1H, s).

(Step 2)

To a solution of the mixture (2.88 g, 10.1 mmol) obtained in step 1 in ethanol (8.4 mL) was added 2N aqueous sodium hydroxide solution (11.2 mL, 22.3 mmol) at room temperature, and the mixture was heated under reflux for 1 hr. After cooling to room temperature, 2N hydrochloric acid was added until the mixture became pH 6. The precipitate was collected by filtration, and the precipitate was washed with ethyl acetate to give a mixture (2.57 g, 99%, 1.18:1 mol/mol) of 1-(difluoromethyl)-3-(4-fluorophenyl)-1H-pyrazole-4-carboxylic to acid and 1-(difluoromethyl)-5-(4-fluorophenyl)-1H-pyrazole-4-carboxylic acid as a pale-green powder.

1-(difluoromethyl)-3-(4-fluorophenyl)-1H-pyrazole-4-carboxylic acid; $^1$H-NMR (400 MHz, DMSO-d$_6$): δ7.24-7.30 (2H, m), 7.81-7.86 (2H, m), 7.87 (1H, t, J=58.4 Hz), 8.79 (1H, s) (* hydrogen of carboxyl group was not observed)

(Step 3)

To a solution of the mixture (2.57 g, 10.0 mmol) obtained in step 2 in DMF (25 mL) were added WSC (2.31 g, 12.0 mmol), HOBt (1.84 g, 12.0 mmol), TEA (3.05 g, 30.1 mmol) and ammonium chloride (1.61 g, 30.1 mmol), and the mixture was stirred at room temperature for 1 hr. Water was poured into the reaction solution, and the mixture was extracted with ethyl acetate. The organic layer was washed with saturated brine and dried, and the solvent was evaporated under reduced pressure. The obtained residue was purified by silica gel column chromatography (solvent gradient; 30→50% ethyl acetate/hexane) to give a mixture (1.16 g, 45%, 1:1.03 mol/mol) of 1-(difluoromethyl)-3-(4-fluorophenyl)-1H-pyrazole-4-carboxamide and 1-(difluoromethyl)-5-(4-fluorophenyl)-1H-pyrazole-4-carboxamide as a pale-yellow oil.

(Step 4)

To a solution of the mixture (1.15 g, 4.51 mmol) obtained in step 3 in THF (18.8 mL) was added Lawesson's reagent (1.46 g, 3.61 mmol) at room temperature, and the mixture was stirred at 60° C. for 3 hr. After cooling to room temperature, and the reaction mixture was concentrated under reduced pressure. The obtained residue was purified by silica gel column chromatography (solvent; 7% ethyl acetate/hexane) to give a mixture (0.840 g, 68%, 1:1.92 mol/mol) of 1-(difluoromethyl)-3-(4-fluorophenyl)-1H-pyrazole-4-carbothioamide and 1-(difluoromethyl)-5-(4-fluorophenyl)-1H-pyrazole-4-carbothioamide as a pale-green powder.

(Step 5)

To a solution of the mixture (0.840 g, 3.10 mmol) obtained in step 4 in ethanol (8.7 mL) was added ethyl 4-chloro-3-oxobutanoate (0.560 g, 3.41 mmol) at room temperature, and the mixture was heated under reflux for 3 hr. After cooling to room temperature, the reaction mixture was concentrated under reduced pressure. The obtained residue was purified by silica gel column chromatography (solvent; 10% ethyl acetate/hexane) to give ethyl(2-[1-(difluoromethyl)-5-(4-fluorophenyl)-1H-pyrazol-4-yl]-1,3-thiazol-4-yl)acetate (0.380 g, 49%) as a white powder.

$^1$H-NMR (400 MHz, CDCl$_3$): δ1.30 (3H, t, J=7.2 Hz), 4.20-4.26 (4H, m), 7.18 (1H, t, J=58.0 Hz), 7.31-7.36 (3H, m), 7.44-7.48 (2H, m), 9.27 (1H, s)

(Step 6)

To a solution of the compound (0.380 g, 1.00 mmol) obtained in step 5 in ethanol (4.0 mL) was added 6N aqueous sodium hydroxide solution (0.500 mL, 2.99 mmol) at room temperature, and the mixture was heated under reflux for 30 min. After cooling to room temperature, concentrated hydrochloric acid was added until the mixture became pH 6. The reaction mixture was extracted with dichloromethane. The organic layer was washed with saturated brine and dried, and the solvent was evaporated under reduced pressure to give (2-[1-(difluoromethyl)-5-(4-fluorophenyl)-1H-pyrazol-4-yl]-1,3-thiazol-4-yl)acetic acid (0.320 g, 91%) as a yellow powder.

$^1$H-NMR (400 MHz, CDCl$_3$): δ3.83 (2H, s), 7.08 (1H, t, J=58.4 Hz), 6.98 (1H, s), 7.23-7.28 (2H, m), 7.43-7.47 (2H, m), 8.22 (1H, s), 10.38 (1H, brs)

(Step 7)

To a solution of the compound (320 mg, 0.910 mmol) obtained in step 6 in DMF (3.6 mL) were added WSC (260 mg, 1.34 mmol), HOBt (208 mg, 1.36 mmol), TEA (180 mg, 1.81 mmol) and (tetrahydro-2H-pyran-4-yl)methanamine (125 mg, 1.09 mmol) at room temperature, and the mixture was heated under reflux for 30 min. The reaction mixture was poured into water, and the mixture was extracted with ethyl acetate. The organic layer was washed with saturated brine and dried, and the solvent was evaporated under reduced pressure. The obtained residue was purified by silica gel column chromatography (solvent; 17% methanol/ethyl acetate) to give the title compound (150 mg, 37%) as a yellow oil.

$^1$H-NMR (400 MHz, CDCl$_3$): δ1.22-1.33 (2H, m), 1.53-1.57 (2H, m), 1.67-1.76 (1H, m), 3.14 (2H, t, J=6.8 Hz), 3.34 (2H, td, J=12.2, 3.4 Hz), 3.67 (2H, s), 3.95 (2H, dd, J=10.8, 3.6 Hz), 6.84-7.00 (1H, m), 6.92 (1H, s), 7.09 (1H, J=58.4 Hz), 7.23-7.29 (2H, m), 7.45-7.50 (2H, m), 8.20 (1H, s)

Example 38

2-{2-[5-(4-fluorophenyl)-1-(2-hydroxy-1,1-dimethylethyl)-1H-pyrazol-4-yl]-1,3-thiazol-4-yl}-N-(tetrahydro-2H-pyran-4-ylmethyl)acetamide (Step 1)

Using 1-(1-acetoxy-2-methylpropan-2-yl)-5-(4-fluorophenyl)-1H-pyrazole-4-carboxylic acid and by reaction and purification in the same manner as in the method described in Example 36, step 1, 2-(4-carbamoyl-5-(4-fluorophenyl)-1H-pyrazol-1-yl)-2-methylpropyl acetate was obtained.

MS (API): 320 (M+H)

(Step 2)

To a solution of the compound (95 mg, 0.30 mmol) obtained in step 1 in methanol (3 mL) was added 6N aqueous sodium hydroxide solution (0.05 mL), and the mixture was stirred at 60° C. for 1 hr. To the reaction mixture were added water and 6M hydrochloric acid, and the mixture was extracted with ethyl acetate. The organic layer was washed with saturated brine and dried, and the solvent was evaporated under reduced pressure to give 5-(4-fluorophenyl)-1-(1-hydroxy-2-methylpropan-2-yl)-1H-pyrazole-4-carboxamide (60 mg, 0.216 mmol, 73%) as a white powder.

MS (API): 278 (M+H)

(Step 3)

Using the compound obtained in step 2 and by reaction and purification in the same manner as in the method described in Example 1, step 4, 5-(4-fluorophenyl)-1-(1-hydroxy-2-methylpropan-2-yl)-1H-pyrazole-4-carbothioamide was obtained.

(Step 4)

Using the compound obtained in step 3 and by reaction and purification in the same manner as in the method described in Example 1, step 5, ethyl 2-(2-(5-(4-fluorophenyl)-1-(1-hydroxy-2-methylpropan-2-yl)-1H-pyrazol-4-yl)thiazol-4-yl)acetate was obtained.

MS (API): 404 (M+H)

(Step 5)

Using the compound obtained in step 4 and by reaction and purification in the same manner as in the method described in Example 1, step 6, 2-(2-(5-(4-fluorophenyl)-1-(1-hydroxy-2-methylpropan-2-yl)-1H-pyrazol-4-yl)thiazol-4-yl)acetic acid was obtained.

MS (API): 376 (M+H)

(Step 6)

Using the compound obtained in step 5 and by reaction and purification in the same manner as in the method described in Example 14, the title compound was obtained.

MS (API): 473 (M+H)

Example 39

2-{2-[1-tert-butyl-5-(4-methoxyphenyl)-1H-pyrazol-4-yl]-1,3-thiazol-4-yl}-N-(tetrahydro-2H-pyran-4-ylmethyl)acetamide (Step 1)

A solution of tert-butylhydrazine monohydrochloride (13.9 g, 111.55 mmol), sodium acetate (11.44 g, 139.43 mmol) and ethyl 2-(ethoxymethylene)-2-cyanoacetate (19 g, 112.31 mmol) in ethanol (130 mL) was heated under reflux for 20 hr. Ethanol was evaporated under reduced pressure, and ethyl acetate was added to the residue. The solution was washed with aqueous sodium hydrogen carbonate solution and saturated brine and dried, and the solvent was evaporated under reduced pressure. The residue was purified by silica gel column chromatography (solvent gradient; 2→35% ethyl acetate/hexane) to give ethyl 5-amino-1-tert-butyl-1H-pyrazole-4-carboxylate (24 g, 111.55 mmol, 102%) as a pale-yellow oil.

$^1$H-NMR (300 MHz, CDCl$_3$): δ1.33 (3H, t, J=7.16 Hz), 1.63 (9H, s), 4.26 (2H, q, J=7.03 Hz), 5.25 (2H, br.s.), 7.57 (1H, s)

(Step 2)

To a solution of pentyl nitrite (16.64 g, 142.00 mmol) and copper(II) bromide (5.32 mL, 113.60 mmol) in acetonitrile (100 mL) was added dropwise a solution of the compound (20 g, 94.67 mmol) obtained in step 1 in acetonitrile (50 mL), and the mixture was stirred at room temperature for 4 hr. Then, 6N hydrochloric acid was added thereto, and the mixture was extracted with ethyl acetate. The organic layer was washed with water, aqueous sodium hydrogen carbonate solution and saturated brine and dried, and the solvent was evaporated under reduced pressure. The residue was purified by silica gel column chromatography (solvent gradient; 2→30% ethyl acetate/hexane) to give ethyl 5-bromo-1-tert-butyl-1H-pyrazole-4-carboxylate (23.5 g, 85 mmol, 90%) as a brown oil.

$^1$H-NMR (300 MHz, CDCl$_3$): δ1.35 (3H, t, J=7.19 Hz), 1.77 (9H, s), 4.31 (2H, q, J=7.19 Hz), 7.87 (1H, s)

(Step 3)

A mixed solution of the compound (13.5 g, 49.07 mmol) obtained in step 2 and 1N aqueous sodium hydroxide solution (65 mL, 65.00 mmol) in ethanol (70 mL) and THF (70 mL) was stirred at 60° C. for 2.5 hr. The organic solvent was evaporated under reduced pressure, and water and 1N hydrochloric acid (70 mL) were added thereto. The precipitate was collected by filtration, and washed with diethyl ether and hexane to give 5-bromo-1-tert-butyl-1H-pyrazole-4-carboxylic acid (10.29 g, 41.6 mmol, 85%) as a white powder.

$^1$H-NMR (300 MHz, CDCl$_3$): δ1.76-1.81 (9H, m), 7.95 (1H, s)

(Step 4)

A solution of the compound (10.29 g, 41.64 mmol) obtained in step 3, WSC (9.58 g, 49.97 mmol), HOBt (6.75 g, 49.97 mmol), TEA (6.97 ml, 49.97 mmol) and ammonium chloride (2.67 g, 49.97 mmol) in DMF (100 mL) was stirred at room temperature for 14 hr. The reaction mixture was concentrated under reduced pressure, and water and ethyl acetate were added to the residue. The organic layer was washed with water, aqueous sodium hydrogen carbonate solution and saturated brine and dried, and the solvent was evaporated under reduced pressure to give 5-bromo-1-tert-butyl-1H-pyrazole-4-carboxamide (6.18 g, 25.1 mmol, 60%) as a white powder.

$^1$H-NMR (300 MHz, CDCl$_3$): δ1.77 (9H, s), 7.91 (1H, s)

(Step 5)

A solution of the compound (3.59 g, 14.59 mmol) obtained in step 4 and Lawesson's reagent (5.31 g, 13.13 mmol) in THF (60 mL) was stirred at 60° C. for 2 hr. The reaction mixture was concentrated under reduced pressure, and the residue was purified by NH-silica gel column chromatography (solvent gradient; 2→50% ethyl acetate/hexane) to give 5-bromo-1-tert-butyl-1H-pyrazole-4-carbothioamide (2.8 g, 10.68 mmol, 73%) as a pale-yellow powder.

MS (API): 262 (M+H)

(Step 6)

A solution of the compound (2.80 g, 10.68 mmol) obtained in step 5 and ethyl 4-chloroacetoacetate (1.588 mL, 11.75 mmol) in ethanol (30 mL) was stirred at 80° C. for 16 hr. The reaction mixture was concentrated under reduced pressure, and the residue was purified by NH-silica gel column chromatography (solvent gradient; 3→50% ethyl acetate/hexane) to give ethyl 2-(2-(5-bromo-1-tert-butyl-1H-pyrazol-4-yl)thiazol-4-yl)acetate (2.55 g, 6.85 mmol, 64%) as a colorless oil $^1$H-NMR (300 MHz, CDCl$_3$): δ1.29 (3H, t, J=7.19 Hz), 1.78 (9H, s), 3.88 (2H, s), 4.21 (2H, q, J=7.07 Hz), 7.17 (1H, s), 8.00 (1H, s)

(Step 7)

A mixed solution of the compound (2.55 g, 6.85 mmol) obtained in step 6 and 1N aqueous sodium hydroxide solution (10.27 mL, 10.27 mmol) in ethanol (10 mL) and THF (10 ml) was stirred at room temperature for 2 hr. The reaction mixture was concentrated under reduced pressure, and water was added to the residue. 1N Hydrochloric acid was added thereto, and the precipitate was collected by filtration, and washed with diethyl ether and hexane to give 2-(2-(5-bromo-1-tert-butyl-1H-pyrazol-4-yl)thiazol-4-yl)acetic acid (2.23 g, 6.48 mmol, 95%) as a white powder.

MS (API): 344 (M+H)

(Step 8)

A solution of the compound (1.8 g, 5.23 mmol) obtained in step 7, HATU (2.386 g, 6.27 mmol), DIEA (1.093 mL, 6.27 mmol) and (tetrahydro-2H-pyran-4-yl)methanamine (0.723 g, 6.27 mmol) in DMF (1 mL) was stirred at room temperature for 2 hr. Water was added to the reaction solution, and the mixture was extracted with ethyl acetate. The organic layer was washed with saturated brine and dried, and the solvent was evaporated under reduced pressure. The obtained residue was purified by silica gel column chromatography (solvent gradient; 50% ethyl acetate/hexane→5% methanol/ethyl acetate) to give 2-(2-(5-bromo-1-tert-butyl-1H-pyrazol-4-yl)thiazol-4-yl)-N-((tetrahydro-2H-pyran-4-yl)methyl)acetamide (2.31 g, 5.23 mmol, 100%) as a colorless oil $^1$H-NMR (300 MHz, CDCl$_3$): δ1.16-1.38 (2H, m), 1.44-1.62 (2H, m), 1.65-1.77 (1H, m), 1.80 (9H, s), 3.17 (2H, t, J=6.61 Hz), 3.33 (2H, td, J=11.80, 2.08 Hz), 3.75 (2H, s), 3.93 (2H, dd, J=10.95, 3.40 Hz), 7.05 (1H, s), 7.33 (1H, br.s.), 7.95 (1H, s)

(Step 9)

A solution of the compound (100 mg, 0.23 mmol) obtained in step 8, 4-methoxyphenylboronic acid (51.6 mg, 0.34 mmol), tripotassium phosphate (96 mg, 0.45 mmol), S-Phos (6.51 mg, 0.02 mmol) and palladium(II) acetate (1.8 mg, 8.02 µmol) in toluene (1.5 mL) was stirred under an argon atmosphere at 90° C. for 18 hr. The reaction mixture was purified by silica gel column chromatography (solvent gradient; 50% ethyl acetate/hexane→5% methanol/ethyl acetate) to give the title compound (55 mg, 0.117 mmol, 52%) as a white powder.

$^1$H-NMR (300 MHz, CDCl$_3$): δ1.21-1.37 (2H, m), 1.49 (9H, s), 1.54-1.61 (2H, m) 1.66-1.79 (1H, m), 3.14 (2H, t, J=6.44 Hz) 3.34 (2H, td, J=11.74, 1.89 Hz), 3.63 (2H, s), 3.89-3.99 (5H, m), 6.70 (1H, s), 7.04 (2H, m, J=8.33 Hz), 7.27-7.37 (3H, m), 8.03 (1H, s)

MS (API): 469 (M+H)

(Step 10)

A solution of 1-tert-butyl-5-(4-methoxyphenyl)-1H-pyrazole-4-carboxylic acid (1.5 g, 5.47 mmol) and thionyl chloride (3 mL, 41.13 mmol) in toluene (6 mL) was stirred at 100° C. for 2.5 hr. The reaction mixture was concentrated under reduced pressure, and the residue was dissolved in THF (5 mL). To the solution was added 25% aqueous ammonia (4 mL), and the mixture was stirred at room temperature for 14 hr. Water was added to the reaction mixture, and the precipitate was collected by filtration to give 1-tert-butyl-5-(4-methoxyphenyl)-1H-pyrazole-4-carboxamide (1.45 mg, 5.30 mmol, 97%) as a white powder.

MS (API): 274 (M+H)

(Step 11)

A solution of the compound (1.45 g, 5.30 mmol) obtained in step 10 and Lawesson's reagent (2.146 g, 5.30 mmol) in THF (25 mL) was stirred at 60° C. for 20 min. The reaction mixture was concentrated under reduced pressure, and the residue was purified by NH-silica gel column chromatography (solvent gradient; 2→60% ethyl acetate/hexane) to give 1-tert-butyl-5-(4-methoxyphenyl)-1H-pyrazole-4-carbothioamide (0.81 g, 2.80 mmol, 53%) as a pale-yellow powder.

MS (API): 290 (M+H)

(Step 12)

A solution of the compound (700 mg, 2.42 mmol) obtained in step 11 and ethyl 4-chloroacetoacetate (0.392 mL, 2.90 mmol) in ethanol (5 mL) was stirred at 80° C. for 16 hr. The reaction mixture was concentrated under reduced pressure, and the residue was crystallized from diethyl ether and hexane to give ethyl 2-(2-(1-tert-butyl-5-(4-methoxyphenyl)-1H-pyrazol-4-yl)thiazol-4-yl)acetate (920 mg, 2.33 mmol, 95%) as a pale-yellow powder.

MS (API): 400 (M+H)

(Step 13)

A mixed solution of the compound (920 mg, 2.30 mmol) obtained in step 12 and 1N aqueous sodium hydroxide solution (3.45 mL, 3.45 mmol) in ethanol (10 mL) and THF (10 ml) was stirred at room temperature for 1 hr. The reaction mixture was concentrated under reduced pressure, and water was added to the residue. 1N Hydrochloric acid was added thereto, and the precipitate was collected by filtration to give 2-(2-(1-tert-butyl-5-(4-methoxyphenyl)-1H-pyrazol-4-yl)thiazol-4-yl)acetic acid (780 mg, 2.10 mmol, 91%) as a white powder.

MS (API): 372 (M+H)

(Step 14)

A solution of the compound (780 mg, 2.10 mmol) obtained in step 13, HATU (958 mg, 2.52 mmol), DIEA (0.439 ml, 2.52 mmol) and (tetrahydro-2H-pyran-4-yl)methanamine (290 mg, 2.52 mmol) in DMF (10 mL) was stirred at room temperature for 14 hr. Water was added to the reaction solution, and the mixture was extracted with ethyl acetate. The organic layer was washed with saturated aqueous sodium hydrogen carbonate solution, water and saturated brine and dried, and the solvent was evaporated under reduced pressure to give the title compound (918 mg, 1.959 mmol, 93%) as a white powder.

MS (API): 469 (M+H)

Example 40

2-(2-{1-tert-butyl-5-[4-(trifluoromethyl)phenyl]-1H-pyrazol-4-yl}-1,3-thiazol-4-yl)-N-(tetrahydro-2H-pyran-4-ylmethyl)acetamide Using 2-(2-(5-bromo-1-tert-butyl-1H-pyrazol-4-yl)thiazol-4-yl)-N-((tetrahydro-2H-pyran-4-yl)methyl)acetamide and 4-(trifluoromethyl)phenylboronic acid and by reaction and purification in the same manner as in the method described in Example 30, step 9, the title compound was obtained. MS (API): 507 (M+H)

Example 41

2-[2-(1-tert-butyl-5-phenyl-1H-pyrazol-4-yl)-1,3-thiazol-4-yl]-Netrahydro-2H-pyran-4-ylmethyl)acetamide A solution of 2-(2-(5-bromo-1-tert-butyl-1H-pyrazol-4-yl)thiazol-4-yl)-N-((tetrahydro-2H-pyran-4-yl)methyl)acetamide (105 mg, 0.24 mmol), phenylboronic acid (43.5 mg, 0.36 mmol), tripotassium phosphate (101 mg, 0.48 mmol), S-Phos (6.84 mg, 0.02 mmol) and palladium(II) acetate (1.8 mg, 8.02 μmol) in toluene (1.5 mL) was stirred under an argon atmosphere at 90° C. for 24 hr. Water was added to the reaction solution, and the mixture was extracted with ethyl acetate. The organic layer was washed with saturated brine and dried, and the solvent was evaporated under reduced pressure. The residue was purified by NH-silica gel column chromatography (solvent gradient; 50% ethyl acetate/hexane→5% methanol/ethyl acetate) to give the title compound (38 mg, 0.087 mmol, 36%) as a white powder.
$^1$H-NMR (300 MHz, CDCl$_3$): δ1.19-1.37 (2H, m), 1.49 (9H, s), 1.52-1.61 (2H, m), 1.65-1.81 (1H, m), 3.14 (2H, t, J=6.40 Hz), 3.34 (2H, td, J=11.77, 2.07 Hz), 3.62 (2H, s), 3.88-4.00 (2H, m), 6.69 (1H, s), 7.34-7.42 (2H, m), 7.47-7.58 (3H, m), 8.04 (1H, s)

Example 42

2-[2-(1-tert-butyl-5-pyridin-2-yl-1H-pyrazol-4-yl)-1,3-thiazol-4-yl]-Netrahydro-2H-pyran-4-ylmethyl)acetamide (Step 1)
Using ethyl 3-oxo-3-(pyridin-2-yl)propanoate and by reaction and purification in the same manner as in the method described in Example 1, step 1, ethyl 1-tert-butyl-5-(pyridin-2-yl)-1H-pyrazole-4-carboxylate was obtained.
MS (API): 274 (M+H)
(Step 2)
Using the compound obtained in step 1 and by reaction and purification in the same manner as in the method described in Example 1, step 2, 1-tert-butyl-5-(pyridin-2-yl)-1H-pyrazole-4-carboxylic acid was obtained.
MS (API): 246 (M+H)
(Step 3)
Using the compound obtained in step 2 and by reaction and purification in the same manner as in the method described in Example 1, step 3, 1-tert-butyl-5-(pyridin-2-yl)-1H-pyrazole-4-carboxamide was obtained.
MS (API): 245 (M+H)
(Step 4)
Using the compound obtained in step 3 and by reaction and purification in the same manner as in the method described in Example 1, step 4, 1-tert-butyl-5-(pyridin-2-yl)-1H-pyrazole-4-carbothioamide was obtained.
MS (API): 261 (M+H)
(Step 5)
Using the compound obtained in step 4 and by reaction and purification in the same manner as in the method described in Example 1, step 5, ethyl 2-(2-(1-tert-butyl-5-(pyridin-2-yl)-1H-pyrazol-4-yl)thiazol-4-yl)acetate was obtained.
MS (API): 371 (M+H)

(Step 6)
Using the compound obtained in step 5 and by reaction and purification in the same manner as in the method described in Example 1, step 6, 2-(2-(1-tert-butyl-5-(pyridin-2-yl)-1H-pyrazol-4-yl)thiazol-4-yl)acetic acid was obtained.
MS (API): 343 (M+H)
(Step 7)
Using the compound obtained in step 6 and (tetrahydro-2H-pyran-4-yl)methanamine and by reaction and purification in the same manner as in the method described in Example 1, step 7, the title compound was obtained.
MS (API): 440 (M+H)

Example 43

2-{2-[1-tert-butyl-5-(4-cyanophenyl)-1H-pyrazol-4-yl]-1,3-thiazol-4-yl}-N-(tetrahydro-2H-pyran-4-ylmethyl)acetamide A solution of 2-(2-(5-bromo-1-tert-butyl-1H-pyrazol-4-yl)thiazol-4-yl)-N-((tetrahydro-2H-pyran-4-yl)methyl)acetamide (102 mg, 0.23 mmol), 4-cyanophenylboronic acid (50.9 mg, 0.35 mmol), tripotassium phosphate (98 mg, 0.46 mmol), S-Phos (7.59 mg, 0.02 mmol) and palladium(II) acetate (2.075 mg, 9.24 μmol) in toluene (1.5 ml) was stirred under an argon atmosphere at 90° C. for 20 hr. Water was added to the reaction solution, and the mixture was extracted with ethyl acetate. The organic layer was washed with saturated brine and dried, and the solvent was evaporated under reduced pressure. The residue was purified by NH-silica gel column chromatography (solvent gradient; 50% ethyl acetate/hexane→5% methanol/ethyl acetate) to give the title compound (60 mg, 0.129 mmol, 56.0%) as a white powder.
$^1$H-NMR (300 MHz, CDCl$_3$): δ1.20-1.37 (2H, m), 1.48 (9H, s), 1.52-1.60 (2H, m), 1.65-1.79 (1H, m), 3.10-3.18 (2H, m), 3.34 (2H, t, J=11.9 Hz), 3.62 (2H, s), 3.87-3.99 (2H, m), 6.76 (1H, s), 7.05 (1H, s), 7.55 (2H, d, J=8.7 Hz), 7.82 (2H, d, J=8.3 Hz), 8.03 (1H, s).

Example 44

2-[2-(1-tert-butyl-5-pyridin-4-yl-1H-pyrazol-4-yl)-1,3-thiazol-4-yl]-Netrahydro-2H-pyran-4-ylmethyl)acetamide (Step 1)
Using ethyl 3-oxo-3-(pyridin-4-yl)propanoate and by reaction and purification in the same manner as in the method described in Example 1, step 1, ethyl 1-tert-butyl-5-(pyridin-4-yl)-1H-pyrazole-4-carboxylate was obtained.
MS (API): 274 (M+H)
(Step 2)
Using the compound obtained in step 1 and by reaction and purification in the same manner as in the method described in Example 1, step 2, 1-tert-butyl-5-(pyridin-4-yl)-1H-pyrazole-4-carboxylic acid was obtained.
MS (API): 246 (M+H)
(Step 3)
Using the compound obtained in step 2 and by reaction and purification in the same manner as in the method described in Example 1, step 3, 1-tert-butyl-5-(pyridin-4-yl)-1H-pyrazole-4-carboxamide was obtained.
MS (API): 245 (M+H)
(Step 4)
Using the compound obtained in step 3 and by reaction and purification in the same manner as in the method described in Example 1, step 4, 1-tert-butyl-5-(pyridin-4-yl)-1H-pyrazole-4-carbothioamide was obtained.
MS (API): 261 (M+H)
(Step 5)
Using the compound obtained in step 4 and by reaction and purification in the same manner as in the method described in Example 1, step 5, ethyl 2-(2-(1-tert-butyl-5-(pyridin-4-yl)-1H-pyrazol-4-yl)thiazol-4-yl)acetate was obtained.
MS (API): 371 (M+H)
(Step 6)
Using the compound obtained in step 5 and by reaction and purification in the same manner as in the method described in Example 1, step 6, 2-(2-(1-tert-butyl-5-(pyridin-4-yl)-1H-pyrazol-4-yl)thiazol-4-yl)acetic acid was obtained.
MS (API): 343 (M+H)
(Step 7)
Using the compound obtained in step 6 and (tetrahydro-2H-pyran-4-yl)methanamine and by reaction and purification in the same manner as in the method described in Example 1, step 7, the title compound was obtained.
MS (API): 440 (M+H)

Example 45

2-[2-(1-tert-butyl-5-pyridin-3-yl-1H-pyrazol-4-yl)-1,3-thiazol-4-yl]-N-tetrahydro-2H-pyran-4-ylmethyl)acetamide (Step 1)
Using ethyl 3-oxo-3-(pyridin-3-yl)propanoate and by reaction and purification in the same manner as in the method described in Example 1, step 1, ethyl 1-tert-butyl-5-(pyridin-3-yl)-1H-pyrazole-4-carboxylate was obtained.
MS (API): 274 (M+H)
(Step 2)
Using the compound obtained in step 1 and by reaction and purification in the same manner as in the method described in Example 1, step 2, 1-tert-butyl-5-(pyridin-3-yl)-1H-pyrazole-4-carboxylic acid was obtained.
(Step 3)
Using the compound obtained in step 2 and by reaction and purification in the same manner as in the method described in Example 1, step 3, 1-tert-butyl-5-(pyridin-3-yl)-1H-pyrazole-4-carboxamide was obtained.
MS (API): 245 (M+H)
(Step 4)
Using the compound obtained in step 3 and by reaction and purification in the same manner as in the method described in Example 1, step 4, 1-tert-butyl-5-(pyridin-3-yl)-1H-pyrazole-4-carbothioamide was obtained.
MS (API): 261 (M+H)
(Step 5)
Using the compound obtained in step 4 and by reaction and purification in the same manner as in the method described in Example 1, step 5, ethyl 2-(2-(1-tert-butyl-5-(pyridin-3-yl)-1H-pyrazol-4-yl)thiazol-4-yl)acetate was obtained.
(Step 6)
Using the compound obtained in step 5 and by reaction and purification in the same manner as in the method described in Example 1, step 6, 2-(2-(1-tert-butyl-5-(pyridin-3-yl)-1H-pyrazol-4-yl)thiazol-4-yl)acetic acid was obtained.
MS (API): 343 (M+H)
(Step 7)
Using the compound obtained in step 6 and (tetrahydro-2H-pyran-4-yl)methanamine and by reaction and purification in the same manner as in the method described in Example 1, step 7, the title compound was obtained.
MS (API): 440 (M+H)

Example 46

2-[2-(1-tert-butyl-5-cyclopropyl-1H-pyrazol-4-yl)-1,3-thiazol-4-yl]-N-tetrahydro-2H-pyran-4-ylmethyl)acetamide Using 2-(2-(5-bromo-1-tert-butyl-1H-pyrazol-4-yl)thiazol-4-yl)-N-((tetrahydro-2H-pyran-4-yl)methyl)acetamide and cyclopropylboronic acid and by reaction and purification in the same manner as in the method described in Example 30, step 9, the title compound was obtained.
MS (API): 403 (M+H)

Example 47

2-{2-[1-tert-butyl-5-(4-fluorobenzyl)-1H-pyrazol-4-yl]-1,3-thiazol-4-yl}-N-(tetrahydro-2H-pyran-4-ylmethyl)acetamide (Step 1)
Using 1-tert-butyl-5-(4-fluorobenzyl)-1H-pyrazole-4-carboxylic acid and by reaction and purification in the same manner as in the method described in Example 1, step 3, 1-tert-butyl-5-(4-fluorobenzyl)-1H-pyrazole-4-carboxamide was obtained.
MS (API): 276 (M+H)
(Step 2)
Using the compound obtained in step 1 and by reaction and purification in the same manner as in the method described in Example 1, step 4, 1-tert-butyl-5-(4-fluorobenzyl)-1H-pyrazole-4-carbothioamide was obtained.
MS (API): 292 (M+H)
(Step 3)
Using the compound obtained in step 2 and by reaction and purification in the same manner as in the method described in Example 1, step 5, ethyl 2-(2-(1-tert-butyl-5-(4-fluorobenzyl)-1H-pyrazol-4-yl)thiazol-4-yl)acetate was obtained.
MS (API): 402 (M+H)
(Step 4)
Using the compound obtained in step 3 and by reaction and purification in the same manner as in the method described in Example 1, step 6, 2-(2-(1-tert-butyl-5-(4-fluorobenzyl)-1H-pyrazol-4-yl)thiazol-4-yl)acetic acid was obtained.
MS (API): 374 (M+H)
(Step 5)
Using the compound obtained in step 4 and (tetrahydro-2H-pyran-4-yl)methanamine and by reaction and purification in the same manner as in the method described in Example 1, step 7, the title compound was obtained.
MS (API): 471 (M+H)

Example 48

2-(2-{1-tert-butyl-5-[2-(4-methoxyphenyl)ethyl]-1H-pyrazol-4-yl}-1,3-thiazol-4-yl)-N-(tetrahydro-2H-pyran-4-ylmethyl)acetamide (Step 1)
A solution of 5-bromo-1-tert-butyl-1H-pyrazole-4-carboxamide (100 mg, 0.41 mmol), trans-2-(4-methoxyphenyl)vinylboronic acid (108 mg, 0.61 mmol), S-phos (3.34 mg, 8.13 μmol), palladium(II) acetate (0.912 mg, 4.06 μmol) and tripotassium phosphate (173 mg, 0.81 mmol) in THF (2 mL) was stirred under an argon atmosphere at 40° C. for 14 hr. Water was added to the reaction solution, and the mixture was extracted with ethyl acetate. The organic layer was washed with saturated brine and dried, and the solvent was evaporated under reduced pressure. The residue was purified by silica gel column chromatography (solvent gradient; 3→100% ethyl acetate/hexane) to give (E)-1-tert-butyl-5-(4-methoxystyryl)-1H-pyrazole-4-carboxamide (20 mg, 0.067 mmol, 16.4%) as a white powder.

MS (API): 300 (M+H)

(Step 2)

A mixed solution of the compound (80 mg, 0.27 mmol) obtained in step 1, 10% palladium carbon (28.4 mg, 0.27 mmol) in THF (15 mL) and ethanol (15 mL) was stirred under 1 atm hydrogen atmosphere at room temperature for 6 hr. The catalyst was filtered off, and the filtrate was concentrated under reduced pressure to give 1-tert-butyl-5-(4-methoxyphenethyl)-1H-pyrazole-4-carboxamide (80 mg, 0.265 mmol, 99%) as a white powder.

MS (API): 302 (M+H)

(Step 3)

Using the compound obtained in step 2 and by reaction and purification in the same manner as in the method described in Example 1, step 4, 1-tert-butyl-5-(4-methoxyphenethyl)-1H-pyrazole-4-carbothioamide was obtained.

MS (API): 318 (M+H)

(Step 4)

Using the compound obtained in step 3 and by reaction and purification in the same manner as in the method described in Example 1, step 5, ethyl 2-(2-(1-tert-butyl-5-(4-methoxyphenethyl)-1H-pyrazol-4-yl)thiazol-4-yl)acetate was obtained.

MS (API): 428 (M+H)

(Step 5)

Using the compound obtained in step 4 and by reaction and purification in the same manner as in the method described in Example 1, step 6, 2-(2-(1-tert-butyl-5-(4-methoxyphenethyl)-1H-pyrazol-4-yl)thiazol-4-yl)acetic acid was obtained.

MS (API): 400 (M+H)

(Step 6)

Using the compound obtained in step 5 and (tetrahydro-2H-pyran-4-yl)methanamine and by reaction and purification in the same manner as in the method described in Example 1, step 7, the title compound was obtained.

MS (API): 497 (M+H)

Example 49

2-{2-[1-tert-butyl-5-(4-fluorophenyl)-1H-pyrazol-4-yl]-5-methyl-1,3-thiazol-4-yl}-N-(tetrahydro-2H-pyran-4-ylmethyl)acetamide (Step 1)

Using 1-tert-butyl-5-(4-fluorophenyl)-1H-pyrazole-4-carbothioamide and methyl 4-bromo-3-oxopentanoate and by reaction and purification in the same manner as in the method described in Example 1, step 5, ethyl 2-(2-(1-tert-butyl-5-(4-fluorophenyl)-1H-pyrazol-4-yl)-5-methylthiazol-4-yl)acetate was obtained.

MS (API): 402 (M+H)

(Step 2)

Using the compound obtained in step 1 and by reaction and purification in the same manner as in the method described in Example 1, step 6, 2-(2-(1-tert-butyl-5-(4-fluorophenyl)-1H-pyrazol-4-yl)-5-methylthiazol-4-yl)acetic acid was obtained.

MS (API): 374 (M+H)

(Step 3)

Using the compound obtained in step 2 and (tetrahydro-2H-pyran-4-yl)methanamine and by reaction and purification in the same manner as in the method described in Example 1, step 7, the title compound was obtained.

MS (API): 471 (M+H)

Example 50

2-{2-[5-(4-fluorophenyl)-1-(1-methylethyl)-1H-pyrazol-4-yl]-1,3-thiazol-4-yl}-N-(tetrahydro-2H-pyran-4-ylmethyl)acetamide (Step 1)

Using 5-(4-fluorophenyl)-1-isopropyl-1H-pyrazole-4-carboxylic acid and by reaction and purification in the same manner as in the method described in Example 38, step 1, 5-(4-fluorophenyl)-1-isopropyl-1H-pyrazole-4-carboxamide was obtained.

MS (API): 248 (M+H)

(Step 2)

Using the compound obtained in step 1 and by reaction and purification in the same manner as in the method described in Example 1, step 4, 5-(4-fluorophenyl)-1-isopropyl-1H-pyrazole-4-carbothioamide was obtained.

MS (API): 264 (M+H)

(Step 3)

Using the compound obtained in step 2 and by reaction and purification in the same manner as in the method described in Example 1, step 5, ethyl 2-(2-(5-(4-fluorophenyl)-1-isopropyl-1H-pyrazol-4-yl)thiazol-4-yl)acetate was obtained.

MS (API): 374 (M+H)

(Step 4)

Using the compound obtained in step 3 and by reaction and purification in the same manner as in the method described in Example 1, step 6, 2-(2-(5-(4-fluorophenyl)-1-isopropyl-1H-pyrazol-4-yl)thiazol-4-yl)acetic acid was obtained.

MS (API): 346 (M+H)

(Step 5)

Using the compound obtained in step 4 and (tetrahydro-2H-pyran-4-yl)methanamine and by reaction and purification in the same manner as in the method described in Example 1, step 7, the title compound was obtained.

MS (API): 443 (M+H)

Example 51

2-{2-[1-cyclohexyl-5-(4-fluorophenyl)-1H-pyrazol-4-yl]-1,3-thiazol-4-yl}-N-(tetrahydro-2H-pyran-4-ylmethyl)acetamide (Step 1)

A solution of 1-cyclohexyl-5-(4-fluorophenyl)-1H-pyrazole-4-carboxylic acid (300 mg, 1.04 mmol) and thionyl chloride (0.379 mL, 5.20 mmol) in toluene (3 mL) was stirred at 90° C. for 2 hr. The reaction mixture was concentrated under reduced pressure, and the residue was dissolved in THF (3 mL). 28% Aqueous ammonia (2 mL, 22.87 mmol) was added to the THF solution, and the mixture was stirred at room temperature for 14 hr. The reaction mixture was poured into water, and the precipitate was collected by filtration to give 1-cyclohexyl-5-(4-fluorophenyl)-1H-pyrazole-4-carboxamide (284 mg, 0.988 mmol, 95%) as a white powder.

MS (API): 288 (M+H)

(Step 2)

A solution of the compound (284 mg, 0.99 mmol) obtained in step 1 and Lawesson's reagent (360 mg, 0.89 mmol) in THF (4 mL) was stirred at 60° C. for 30 min. The reaction mixture was concentrated under reduced pressure, and the residue was purified by NH-silica gel column chromatography (solvent gradient; 5→95% ethyl acetate/hexane) to give 1-cyclohexyl-5-(4-fluorophenyl)-1H-pyrazole-4-carbothioamide (236 mg, 0.778 mmol, 79%) as a white powder.

MS (API): 304 (M+H)

(Step 3)

A solution of the compound (236 mg, 0.78 mmol) obtained in step 2 and ethyl 4-chloroacetoacetate (0.126 ml, 0.93 mmol) in ethanol (4 mL) was stirred at 90° C. for 18 hr. The reaction mixture was concentrated under reduced pressure, and the residue was crystallized from hexane to give ethyl 2-(2-(1-cyclohexyl-5-(4-fluorophenyl)-1H-pyrazol-4-yl)thiazol-4-yl)acetate (269 mg, 0.651 mmol, 84%) as a white powder.

MS (API): 414 (M+H)

(Step 4)

A mixed solution of the compound (269 mg, 0.65 mmol) obtained in step 3 and 1N aqueous sodium hydroxide solution (0.976 mL, 0.98 mmol) in ethanol (4 mL) and THF (4 mL) was stirred at room temperature for 3 hr. The reaction mixture was concentrated under reduced pressure, and water was added to the residue. 1N Hydrochloric acid was added thereto, and the precipitate was collected by filtration, and crystallized from diethyl ether and hexane to give 2-(2-(1-cyclohexyl-5-(4-fluorophenyl)-1H-pyrazol-4-yl)thiazol-4-yl)acetic acid (226 mg, 0.586 mmol, 90%) as a white powder.

MS (API): 386 (M+H)

(Step 5)

A solution of the compound (50 mg, 0.13 mmol) obtained in step 4, HATU (74.0 mg, 0.19 mmol), DIEA (0.034 ml, 0.19 mmol) and (tetrahydro-2H-pyran-4-yl)methanamine (0.022 ml, 0.19 mmol) in DMF (2 mL) was stirred at room temperature for 2 days. Water was added to the reaction solution, and the mixture was extracted with ethyl acetate. The organic layer was washed with water and saturated brine and dried, and the solvent was evaporated under reduced pressure. The obtained residue was crystallized from ethyl acetate and hexane to give the title compound (45 mg, 0.093 mmol, 71.9%) as a white powder.

$^1$H-NMR (300 MHz, CDCl$_3$): δ1.16-1.35 (5H, m), 1.49-1.60 (2H, m), 1.62-1.75 (2H, m), 1.80-1.91 (4H, m), 1.93-2.10 (2H, m), 3.11 (2H, t, J=6.4 Hz), 3.33 (2H, td, J=11.7, 1.9 Hz), 3.63 (2H, s), 3.72-3.86 (1H, m), 3.93 (2H, dd, J=11.5, 3.6 Hz), 6.78 (1H, s), 7.13 (1H, brs), 7.20-7.30 (2H, m), 7.33-7.41 (2H, m), 8.04 (1H, s).

MS (API): 483 (M+H)

Example 52

2-{2-[1-methyl-5-(2-methylphenyl)-1H-pyrazol-4-yl]-1,3-thiazol-4-yl}-N-(tetrahydro-2H-pyran-4-ylmethyl)acetamide (Step 1)

Using 1-methyl-5-(o-tolyl)-1H-pyrazole-4-carboxylic acid, and by reaction and purification in the same manner as in the method described in Example 51, step 1 and the method described in Example 1, step 4, 1-methyl-5-(o-tolyl)-1H-pyrazole-4-carbothioamide was obtained.

(Step 2)

Using the compound obtained in step 1 and by reaction and purification in the same manner as in the method described in Example 1, step 5, ethyl 2-(2-(1-methyl-5-(o-tolyl)-1H-pyrazol-4-yl)thiazol-4-yl)acetate was obtained.

MS (API): 342 (M+H)

(Step 3)

Using the compound obtained in step 2 and by reaction and purification in the same manner as in the method described in Example 1, step 6, 2-(2-(1-methyl-5-(o-tolyl)-1H-pyrazol-4-yl)thiazol-4-yl)acetic acid was obtained.

MS (API): 314 (M+H)

(Step 4)

Using the compound obtained in step 3 and (tetrahydro-2H-pyran-4-yl)methanamine and by reaction and purification in the same manner as in the method described in Example 1, step 7, the title compound was obtained.

MS (API): 411 (M+H)

The compounds described in Examples 53-99 were obtained using 2-(2-(1-(tert-butyl)-5-(4-fluorophenyl)-1H-pyrazol-4-yl)thiazol-4-yl)acetic acid and 3-fluorobenzylamine, 4-fluorobenzylamine, 2-chlorobenzylamine, 3-chlorobenzylamine, 4-chlorobenzylamine, 2-methoxybenzylamine, 3-methoxybenzylamine, 4-methoxybenzylamine, 3-(trifluoromethoxy)benzylamine, 4-(trifluoromethoxy)benzylamine, (2-(methylsulfonyl)phenyl)methanamine, 4-(methylsulfonyl)benzylamine, N-[2-(aminomethyl)phenyl]-N,N-dimethylamine, 3-(difluoromethoxy)benzylamine, 4-dimethylaminobenzylamine, 1-oxa-7-azaspiro[4.5]decane, (1-methyl-2-piperidinyl)methanamine, 2-oxa-6-azaspiro[3.5]nonane, 2-oxa-6-azaspiro[3.4]octane, N-methyl-1-(3-methyloxetan-3-yl)methanamine, 3-oxetanemethanamine, p-anisidine, m-anisidine, o-anisidine, 1,4-oxazepane, [1,4]diazepan-5-one, 3-(aminomethyl)pyridine, 2-(aminomethyl)-5-methylpyrazine, 2-(aminomethyl)pyridine, methyl-(5-methylthiazol-2-ylmethyl)-amine, (1-methyl-1H-imidazol-4-yl)methylamine, (3-methylisoxazol-5-ylmethyl)amine, (2,5-dimethyl-1,3-oxazol-4-yl)methylamine, (1,5-dimethyl-1H-pyrazol-3-yl)methylamine, 5-methylfurfurylamine, 2-phenylbenzylamine, 3-phenylbenzylamine, 4-phenylbenzylamine, 1,2,3,4-tetrahydroisoquinoline, isoindoline, 2-phenylpyrrolidine, tetrahydrofurfurylamine, (tetrahydrofuran-3-yl)methanamine, benzylamine, N-benzyl-N-propylamine, N-phenylglycine ethyl ester or 3-(trifluoromethyl)benzylamine, and by reaction and purification in the same manner as in the method described in Example 1, step 7.

Example 53

2-(2-(1-tert-butyl-5-(4-fluorophenyl)-1H-pyrazol-4-yl)-1,3-thiazol-4-yl)-N-(3-fluorobenzyl)acetamide

MS (API): 467 (M+H)

Example 54

2-(2-(1-tert-butyl-5-(4-fluorophenyl)-1H-pyrazol-4-yl)-1,3-thiazol-4-yl)-N-(4-fluorobenzyl)acetamide

MS (API): 467 (M+H)

Example 55

2-(2-(1-tert-butyl-5-(4-fluorophenyl)-1H-pyrazol-4-yl)-1,3-thiazol-4-yl)-N-(2-chlorobenzyl)acetamide

MS (API): 483 (M+H)

Example 56

2-(2-(1-tert-butyl-5-(4-fluorophenyl)-1H-pyrazol-4-yl)-1,3-thiazol-4-yl)-N-(3-chlorobenzyl)acetamide

MS (API): 483 (M+H)

Example 57

2-(2-(1-tert-butyl-5-(4-fluorophenyl)-1H-pyrazol-4-yl)-1,3-thiazol-4-yl)-N-(4-chlorobenzyl)acetamide

MS (API): 483 (M+H)

Example 58

2-(2-(1-tert-butyl-5-(4-fluorophenyl)-1H-pyrazol-4-yl)-1,3-thiazol-4-yl)-N-(2-methoxybenzyl)acetamide

MS (API): 479 (M+H)

Example 59

2-(2-(1-tert-butyl-5-(4-fluorophenyl)-1H-pyrazol-4-yl)-1,3-thiazol-4-yl)-N-(3-methoxybenzyl)acetamide

MS (API): 479 (M+H)

Example 60

2-(2-(1-tert-butyl-5-(4-fluorophenyl)-1H-pyrazol-4-yl)-1,3-thiazol-4-yl)-N-(4-methoxybenzyl)acetamide

MS (API): 479 (M+H)

Example 61

2-(2-(1-tert-butyl-5-(4-fluorophenyl)-1H-pyrazol-4-yl)-1,3-thiazol-4-yl)-N-(3-(trifluoromethoxy)benzyl)acetamide

MS (API): 533 (M+H)

Example 62

2-(2-(1-tert-butyl-5-(4-fluorophenyl)-1H-pyrazol-4-yl)-1,3-thiazol-4-yl)-N-(4-(trifluoromethoxy)benzyl)acetamide

MS (API): 533 (M+H)

Example 63

2-(2-(1-tert-butyl-5-(4-fluorophenyl)-1H-pyrazol-4-yl)-1,3-thiazol-4-yl)-N-(2-(methylsulfonyl)benzyl)acetamide

MS (API): 527 (M+H)

Example 64

2-(2-(1-tert-butyl-5-(4-fluorophenyl)-1H-pyrazol-4-yl)-1,3-thiazol-4-yl)-N-(4-(methylsulfonyl)benzyl)acetamide

MS (API): 527 (M+H)

Example 65

2-(2-(1-tert-butyl-5-(4-fluorophenyl)-1H-pyrazol-4-yl)-1,3-thiazol-4-yl)-N-(2-(dimethylamino)benzyl)acetamide

MS (API): 492 (M+H)

Example 66

2-(2-(1-tert-butyl-5-(4-fluorophenyl)-1H-pyrazol-4-yl)-1,3-thiazol-4-yl)-N-(3-(difluoromethoxy)benzyl)acetamide

MS (API): 515 (M+H)

Example 67

2-{2-[1-tert-butyl-5-(4-fluorophenyl)-1H-pyrazol-4-yl]-1,3-thiazol-4-yl}-N-[4-(dimethylamino)benzyl]acetamide

MS (API): 492 (M+H)

Example 68

7-({2-[1-tert-butyl-5-(4-fluorophenyl)-1H-pyrazol-4-yl]-1,3-thiazol-4-yl}acetyl)-1-oxa-7-azaspiro[4.5]decane

MS (API): 483 (M+H)

Example 69

2-{2-[1-tert-butyl-5-(4-fluorophenyl)-1H-pyrazol-4-yl]-1,3-thiazol-4-yl}-N-[(1-methylpiperidin-2-yl)methyl]acetamide

MS (API): 470 (M+H)

Example 70

6-({2-[1-tert-butyl-5-(4-fluorophenyl)-1H-pyrazol-4-yl]-1,3-thiazol-4-yl}acetyl)-2-oxa-6-azaspiro[3.5]nonane

MS (API): 469 (M+H)

Example 71

6-({2-[1-tert-butyl-5-(4-fluorophenyl)-1H-pyrazol-4-yl]-1,3-thiazol-4-yl}acetyl)-2-oxa-6-azaspiro[3.4]octane

MS (API): 455 (M+H)

Example 72

2-{2-[1-tert-butyl-5-(4-fluorophenyl)-1H-pyrazol-4-yl]-1,3-thiazol-4-yl}-N-methyl-N-[(3-methyloxetan-3-yl)methyl]acetamide

MS (API): 457 (M+H)

Example 73

2-{2-[1-tert-butyl-5-(4-fluorophenyl)-1H-pyrazol-4-yl]-1,3-thiazol-4-yl}-N-(oxetan-3-ylmethyl)acetamide

MS (API): 429 (M+H)

Example 74

2-{2-[1-tert-butyl-5-(4-fluorophenyl)-1H-pyrazol-4-yl]-1,3-thiazol-4-yl}-N-(4-methoxyphenyl)acetamide

MS (API): 465 (M+H)

Example 75

2-{2-[1-tert-butyl-5-(4-fluorophenyl)-1H-pyrazol-4-yl]-1,3-thiazol-4-yl}-N-(3-methoxyphenyl)acetamide

MS (API): 465 (M+H)

Example 76

2-{2-[1-tert-butyl-5-(4-fluorophenyl)-1H-pyrazol-4-yl]-1,3-thiazol-4-yl}-N-(2-methoxyphenyl)acetamide

MS (API): 465 (M+H)

Example 77

4-({2-[1-tert-butyl-5-(4-fluorophenyl)-1H-pyrazol-4-yl]-1,3-thiazol-4-yl}acetyl)-1,4-oxazepane

MS (API): 443 (M+H)

Example 78

1-({2-[1-tert-butyl-5-(4-fluorophenyl)-1H-pyrazol-4-yl]-1,3-thiazol-4-yl}acetyl)-1,4-diazepan-5-one

MS (API): 456 (M+H)

Example 79

2-{2-[1-tert-butyl-5-(4-fluorophenyl)-1H-pyrazol-4-yl]-1,3-thiazol-4-yl}-N-(pyridin-3-ylmethyl)acetamide

MS (API): 450 (M+H)

Example 80

2-{2-[1-tert-butyl-5-(4-fluorophenyl)-1H-pyrazol-4-yl]-1,3-thiazol-4-yl}-N-[(5-methylpyrazin-2-yl)methyl]acetamide

MS (API): 465 (M+H)

Example 81

2-{2-[1-tert-butyl-5-(4-fluorophenyl)-1H-pyrazol-4-yl]-1,3-thiazol-4-yl}-N-(pyridin-2-ylmethyl)acetamide

MS (API): 450 (M+H)

Example 82

2-{2-[1-tert-butyl-5-(4-fluorophenyl)-1H-pyrazol-4-yl]-1,3-thiazol-4-yl}-N-methyl-N-[(5-methyl-1,3-thiazol-2-yl)methyl]acetamide

MS (API): 484 (M+H)

Example 83

2-{2-[1-tert-butyl-5-(4-fluorophenyl)-1H-pyrazol-4-yl]-1,3-thiazol-4-yl}-N-[(1-methyl-1H-imidazol-4-yl)methyl]acetamide

MS (API): 453 (M+H)

Example 84

2-{2-[1-tert-butyl-5-(4-fluorophenyl)-1H-pyrazol-4-yl]-1,3-thiazol-4-yl}-N-[(3-methylisoxazol-5-yl)methyl]acetamide

MS (API): 454 (M+H)

Example 85

2-{2-[1-tert-butyl-5-(4-fluorophenyl)-1H-pyrazol-4-yl]-1,3-thiazol-4-yl}-N-[(2,5-dimethyl-1,3-oxazol-4-yl)methyl]acetamide

MS (API): 468 (M+H)

Example 86

2-{2-[1-tert-butyl-5-(4-fluorophenyl)-1H-pyrazol-4-yl]-1,3-thiazol-4-yl}-N-[(1,5-dimethyl-1H-pyrazol-3-yl)methyl]acetamide

MS (API): 467 (M+H)

Example 87

2-{2-[1-tert-butyl-5-(4-fluorophenyl)-1H-pyrazol-4-yl]-1,3-thiazol-4-yl}-N-[(5-methylfuran-2-yl)methyl]acetamide

MS (API): 453 (M+H)

Example 88

N-(biphenyl-2-ylmethyl)-2-{2-[1-tert-butyl-5-(4-fluorophenyl)-1H-pyrazol-4-yl]-1,3-thiazol-4-yl}acetamide

MS (API): 525 (M+H)

Example 89

N-(biphenyl-3-ylmethyl)-2-{2-[1-tert-butyl-5-(4-fluorophenyl)-1H-pyrazol-4-yl]-1,3-thiazol-4-yl}acetamide

MS (API): 525 (M+H)

Example 90

N-(biphenyl-4-ylmethyl)-2-{2-[1-tert-butyl-5-(4-fluorophenyl)-1H-pyrazol-4-yl]-1,3-thiazol-4-yl}acetamide

MS (API): 525 (M+H)

Example 91

2-({2-[1-tert-butyl-5-(4-fluorophenyl)-1H-pyrazol-4-yl]-1,3-thiazol-4-yl}acetyl)-1,2,3,4-tetrahydroisoquinoline

MS (API): 475 (M+H)

Example 92

2-({2-[1-tert-butyl-5-(4-fluorophenyl)-1H-pyrazol-4-yl]-1,3-thiazol-4-yl}acetyl)-2,3-dihydro-1H-isoindole

MS (API): 461 (M+H)

Example 93

2-[1-tert-butyl-5-(4-fluorophenyl)-1H-pyrazol-4-yl]-4-[2-oxo-2-(2-phenylpyrrolidin-1-yl)ethyl]-1,3-thiazole

MS (API): 489 (M+H)

Example 94

2-{2-[1-tert-butyl-5-(4-fluorophenyl)-1H-pyrazol-4-yl]-1,3-thiazol-4-yl}-N-(tetrahydrofuran-2-ylmethyl)acetamide

MS (API): 443 (M+H)

Example 95

2-{2-[1-tert-butyl-5-(4-fluorophenyl)-1H-pyrazol-4-yl]-1,3-thiazol-4-yl}-N-(tetrahydrofuran-3-ylmethyl)acetamide

MS (API): 443 (M+H)

Example 96

N-benzyl-2-{2-[1-tert-butyl-5-(4-fluorophenyl)-1H-pyrazol-4-yl]-1,3-thiazol-4-yl}acetamide

MS (API): 449 (M+H)

Example 97

N-benzyl-2-{2-[1-tert-butyl-5-(4-fluorophenyl)-1H-pyrazol-4-yl]-1,3-thiazol-4-yl}-N-propylacetamide

MS (API): 491 (M+H)

Example 98 ethyl N-({2-[1-tert-butyl-5-(4-fluorophenyl)-1H-pyrazol-4-yl]-1,3-thiazol-4-yl}acetyl)-N-phenylglycinate

MS (API): 521 (M+H)

Example 99

2-{2-[1-tert-butyl-5-(4-fluorophenyl)-1H-pyrazol-4-yl]-1,3-thiazol-4-yl}-N-[3-(trifluoromethyl)benzyl]acetamide

MS (API): 517 (M+H)

Example 100

2-(2-{1-tert-butyl-5-[4-(1-methylethoxy)phenyl]-1H-pyrazol-4-yl}-1,3-thiazol-4-yl)-N-(tetrahydro-2H-pyran-4-ylmethyl)acetamide Using 2-(2-(5-bromo-1-tert-butyl-1H-pyrazol-4-yl)thiazol-4-yl)-N-((tetrahydro-2H-pyran-4-yl)methyl)acetamide and (4-isopropoxyphenyl)boronic acid and by reaction and purification in the same manner as in the method described in Example 43, the title compound was obtained.

MS (API): 497 (M+H)

Example 101

2-{2-[1-tert-butyl-5-(4-(morpholin-4-yl)phenyl)-1H-pyrazol-4-yl]-1,3-thiazol-4-yl}-N-(tetrahydro-2H-pyran-4-ylmethyl)acetamide Using 2-(2-(5-bromo-1-tert-butyl-1H-pyrazol-4-yl)thiazol-4-yl)-N-((tetrahydro-2H-pyran-4-yl)methyl)acetamide and (4-morpholinophenyl)boronic acid and by reaction and purification in the same manner as in the method described in Example 43, the title compound was obtained.

MS (API): 524 (M+H)

Example 102

2-{2-[1-tert-butyl-5-(2,3-dihydro-1,4-benzodioxin-6-yl)-1H-pyrazol-4-yl]-1,3-thiazol-4-yl}-N-(tetrahydro-2H-pyran-4-ylmethyl)acetamide Using 2-(2-(5-bromo-1-tert-butyl-1H-pyrazol-4-yl)thiazol-4-yl)-N-((tetrahydro-2H-pyran-4-yl)methyl)acetamide and (2,3-dihydrobenzo[b][1,4]dioxin-6-yl)boronic acid and by reaction and purification in the same manner as in the method described in Example 43, the title compound was obtained.

MS (API): 497 (M+H)

Example 103

2-{2-[1-cyclopentyl-5-(4-fluorophenyl)-1H-pyrazol-4-yl]-1,3-thiazol-4-yl}-N-(tetrahydro-2H-pyran-4-ylmethyl)acetamide (Step 1)

To a suspension of diethyl carbonate (47.4 mL, 391 mmol) and sodium hydride (55 wt % paraffin oil, 23.7 g, 543 mmol) in THF was added 4'-fluoroacetophenone (26.4 mL, 271 mmol) at 60° C. The reaction mixture was heated under reflux for 1 hr, cooled to room temperature, and poured into acetic acid (33.6 ml, 586 mmol) and ice water (1 L). The reaction mixture was extracted with diethyl ether (2×500 mL), the organic layer was washed with saturated aqueous sodium hydrogen carbonate solution and saturated brine and dried, and the solvent was evaporated under reduced pressure to give ethyl 3-(4-fluorophenyl)-3-oxopropanoate (45.7 g, 100%, keto form: enol for m=5:1) as a yellow oil.

$^1$H-NMR (400 MHz, CDCl$_3$), keto form: δ1.26 (3H, t, J=7.2 Hz), 3.97 (3H, s), 4.22 (2H, q, J=7.2 Hz), 7.13-7.19 (2H, m), 7.96-8.01 (2H, m)

$^1$H-NMR (400 MHz, CDCl$_3$), enol form: δ1.34 (0.6H, t, J=7.2 Hz), 4.27 (0.4H, q, J=7.2 Hz), 5.61 (0.2H, s), 7.08-7.12 (0.4H, m), 7.76-7.80 (0.4H, m), 12.62 (0.2H, s)

(Step 2)

A solution of the compound (45.7 g, 217 mmol) obtained in step 1 and DMFDMA (34.9 mL, 261 mmol) in toluene (700 mL) was heated under reflux for 15 hr. The reaction mixture was concentrated under reduced pressure, and the residue was dissolved in ethanol (700 mL). To the ethanol solution was added hydrazine monohydrate (11.6 mL, 239 mmol) at room temperature, and the mixture was heated under reflux for 3 hr. The reaction mixture was concentrated under reduced pressure, and the residue was treated with ethyl acetate and hexane. The insoluble material was filtered off, and the filtrate was concentrated to give ethyl 3-(4-fluorophenyl)-1H-pyrazole-4-carboxylate (46.2 g, 91%) as a yellow powder.

$^1$H-NMR (400 MHz, CDCl$_3$): δ1.30 (3H, t, J=7.2 Hz), 4.26 (2H, q, J=7.2 Hz), 7.10-7.15 (2H, m), 7.68-7.71 (2H, m), 8.07 (1H, s), 11.08 (1H, brs)

(Step 3)

To a solution of the compound (25.0 g, 107 mmol) obtained in step 2 in ethanol (90 mL) was added 2N aqueous sodium hydroxide solution (117 mL, 235 mmol) at room temperature, and the mixture was heated under reflux for 24 hr. The organic solvent was evaporated, and ethyl acetate was added to the residue. The aqueous layer was separated, and 2N hydrochloric acid was added until the aqueous layer became pH2. The precipitate was collected by filtration to give 3-(4-fluorophenyl)-1H-pyrazole-4-carboxylic acid (22.8 g, 100%) as a yellow powder.

$^1$H-NMR (400 MHz, DMSO-d$_6$): δ7.26 (2H, t, J=8.8 Hz), 7.82 (2H, dd, J=8.8, 6.0 Hz), 8.11 (1H, brs), 12.68 (1H, brs), 13.17 (1H, brs)

(Step 4)

To a solution of the compound (21.0 g, 102 mmol) obtained in step 3 in DMF (400 mL) was added DMAP (27.4 g, 224 mmol), and (Boc)$_2$O (28.4 mL, 122 mmol) was added thereto at room temperature. The reaction mixture was stirred for 10 min, and poured into ethyl acetate and water. 1N Hydrochloric acid was added until the mixture became pH3-4, and the organic layer was separated. The organic layer was washed with saturated brine and dried, and the solvent was evaporated under reduced pressure to give a mixture (35.6 g, 100%) of 1-(tert-butoxycarbonyl)-5-(4-fluorophenyl)-1H-pyrazole-4-carboxylic acid and 1-(tert-butoxycarbonyl)-3-(4-fluorophenyl)-1H-pyrazole-4-carboxylic acid as a brown oil.

$^1$H-NMR (400 MHz, CDCl$_3$): δ1.68 (9H, s), 7.10 (2H, t, J=8.4 Hz), 7.82-7.86 (2H, m), 8.69 (1H, s) (* hydrogen of carboxyl group was not observed)

(Step 5)

A solution of the mixture (31.2 g, 102 mmol) obtained in step 4, ammonium chloride (6.54 g, 122 mmol), WSC (23.4 g, 122 mmol), HOBt (18.7 g, 122 mmol) and TEA (35.5 mL, 255 mmol) in DMF (255 mL) was stirred at room temperature for 14 hr. Water was added to the reaction mixture, and the mixture was extracted with ethyl acetate (3×300 mL). The organic layer was washed with saturated brine and dried, and the solvent was evaporated under reduced pressure. The residue was treated with ethyl acetate and diethyl ether to give a mixture (17.5 g, 56%) of tert-butyl 4-carbamoyl-5-(4-fluorophenyl)-1H-pyrazole-1-carboxylate and tert-butyl 4-carbamoyl-3-(4-fluorophenyl)-1H-pyrazole-1-carboxylate as a yellow powder.

$^1$H-NMR (400 MHz, DMSO-d$_6$): δ1.61 (9H, s), 7.24-7.28 (2H, m), 7.36 (1H, brs), 7.78-7.82 (2H, m), 7.85 (1H, brs), 8.77 (1H, s)

(Step 6)

A solution of the mixture (711 mg, 2.33 mmol) obtained in step 5 and Lawesson's reagent (754 mg, 1.86 mmol) in THF (10 mL) was stirred at 60° C. for 1 hr. The reaction mixture was concentrated under reduced pressure, and the residue was treated with ethyl acetate and diethyl ether to give a mixture (415 mg, 55%) of tert-butyl 4-carbamothioyl-5-(4-fluorophenyl)-1H-pyrazole-1-carboxylate and tert-butyl 4-carbamothioyl-3-(4-fluorophenyl)-1H-pyrazole-1-carboxylate as a yellow powder.

$^1$H-NMR (400 MHz, DMSO-d$_6$): δ1.60 (9H, s), 7.27-7.31 (2H, m), 7.65-7.69 (2H, m), 8.46 (1H, s), 9.43 (1H, brs), 9.92 (1H, brs)

(Step 7)

A solution of the mixture (415 mg, 1.29 mmol) obtained in step 6 and ethyl 4-chloroacetoacetate (0.192 mL, 1.42 mmol) in EtOH (3.6 mL) was heated under reflux for 4 hr. The reaction mixture was concentrated under reduced pressure, and the residue was dissolved in ethyl acetate. The solution was washed with saturated aqueous sodium hydrogen carbonate solution and saturated brine and dried, and the solvent was evaporated under reduced pressure. The residue was purified by NH-silica gel column chromatography (solvent gradient; 50→66% ethyl acetate/hexane) to give ethyl {2-[5-(4-fluorophenyl)-1H-pyrazol-4-yl]-1,3-thiazol-4-yl}acetate (294 mg, 69%) was obtained as a colorless oil $^1$H-NMR (400 MHz, CDCl$_3$): δ1.28 (3H, t, J=7.2 Hz), 3.83 (2H, s), 4.20 (2H, q, J=7.2 Hz), 7.07 (1H, s), 7.11-7.15 (2H, m), 7.60-7.64 (2H, m), 8.04 (1H, s), 10.54 (1H, brs)

(Step 8)

To a solution of the compound (178 mg, 0.537 mmol) obtained in step 7 in ethanol (2.2 mL) was added 6N aqueous sodium hydroxide solution (0.269 mL, 1.61 mmol) at room temperature, and the mixture was heated under reflux for 1 hr. The organic solvent was evaporated, and 2N hydrochloric acid was added until the mixture became pH2. The precipitate was collected by filtration to give {2-[5-(4-fluorophenyl)-1H-pyrazol-4-yl]-1,3-thiazol-4-yl}acetic acid (122 mg, 75%) as a yellow powder.

$^1$H-NMR (400 MHz, DMSO-d$_6$): δ3.71 (2H, s), 7.26 (2H, brs), 7.33 (1H, s), 7.74-7.79 (2H, m), 8.28 (1H, brs), 12.46 (1H, brs), 13.39 (1H, brs)

(Step 9)

A solution of the compound (122 mg, 0.402 mmol) obtained in step 8, WSC (116 mg, 0.603 mmol), HOBt (92.0 mg, 0.603 mmol), TEA (0.112 mL, 0.804 mmol) and 2-(tetrahydro-2H-pyran-4-yl)ethanamine (56.0 mg, 0.483 mmol) in DMF (1.6 mL) was stirred at 100° C. for 1 hr. The reaction mixture was cooled, water was added to the reaction mixture, and the mixture was extracted with ethyl acetate (3×10 mL). The organic layer was washed with water and saturated brine and dried, and the solvent was evaporated under reduced pressure. The obtained residue was purified by silica gel column chromatography (solvent gradient; 0→10% methanol/ethyl acetate) to give 2-{2-[5-(4-fluorophenyl)-1H-pyrazol-4-yl]-1,3-thiazol-4-yl}-N-(tetrahydro-2H-pyran-4-ylmethyl)acetamide (117 mg, 73%) as a yellow powder.

¹H-NMR (400 MHz, CDCl₃): δ1.15-1.26 (2H, m), 1.43-1.50 (2H, m), 1.56-1.64 (1H, m), 3.08 (2H, t, J=6.8 Hz), 3.29 (2H, td, J=12.0, 2.0 Hz), 3.69 (2H, s), 3.91 (2H, dd, J=6.4, 3.2 Hz), 6.97 (1H, s), 7.00 (1H, brs), 7.15-7.19 (2H, m), 7.60-7.63 (2H, m), 8.06 (1H, s) (* hydrogen of NH group was not observed)

(Step 10)

To a mixed solution of the compound (58 mg, 0.14 mmol) obtained in step 9, cyclopentanol (0.020 mL, 0.22 mmol) and triphenylphosphine (57.0 mg, 0.22 mmol) in THF (2 mL) and toluene (2 mL) was added DIAD (0.114 mL, 0.22 mmol), and the mixture was stirred at 80° C. for 1.5 hr. To the reaction mixture were further added cyclopentanol (0.020 mL, 0.22 mmol), triphenylphosphine (57.0 mg, 0.22 mmol) and diisopropyl azodicarboxylate (0.114 mL, 0.22 mmol), and the mixture was further stirred at 80° C. for 2 hr. The reaction mixture was concentrated under reduced pressure, and the residue was purified by silica gel column chromatography (solvent gradient; 0→5% methanol/ethyl acetate) to give a mixture (1:2 (mol/mol), 50 mg, 0.107 mmol, 76%) of the title compound and 2-(2-(1-cyclopentyl-3-(4-fluorophenyl)-1H-pyrazol-4-yl)thiazol-4-yl)-N-((tetrahydro-2H-pyran-4-yl)methyl)acetamide as a pale-yellow solid.

MS (API): 469 (M+H)

Example 104

2-{2-[1-(cyclobutylmethyl)-5-(4-fluorophenyl)-1H-pyrazol-4-yl]-1,3-thiazol-4-yl}-N-(tetrahydro-2H-pyran-4-ylmethyl)acetamide A solution of 2-{2-[5-(4-fluorophenyl)-1H-pyrazol-4-yl]-1,3-thiazol-4-yl}-N-(tetrahydro-2H-pyran-4-ylmethyl)acetamide (58 mg, 0.14 mmol), (bromomethyl)cyclobutane (0.033 mL, 0.29 mmol) and potassium carbonate (40.0 mg, 0.29 mmol) in acetonitrile (3 mL) was stirred at 80° C. for 1 hr. To the reaction mixture were further added potassium carbonate (40.0 mg, 0.29 mmol) and (bromomethyl)cyclobutane (0.033 mL, 0.29 mmol), and the mixture was further stirred at 80° C. for 2 hr. Water was added to the reaction mixture, and the mixture was extracted with ethyl acetate. The organic layer was washed with water and saturated brine and dried, and the solvent was evaporated under reduced pressure. The obtained residue was purified by NH-silica gel column chromatography (solvent gradient; 30→90% ethyl acetate/hexane) to give a mixture (1:3 (mol/mol), 55 mg, 0.118 mmol, 84%) of the title compound and 2-(2-(1-(cyclobutylmethyl)-3-(4-fluorophenyl)-1H-pyrazol-4-yl)thiazol-4-yl)-N-((tetrahydro-2H-pyran-4-yl)methyl)acetamide as a pale-yellow solid.

MS (API): 469 (M+H)

Example 105

2-{2-[5-(4-fluorophenyl)-1-(tetrahydrofuran-3-yl)-1H-pyrazol-4-yl]-1,3-thiazol-4-yl}-N-(tetrahydro-2H-pyran-4-ylmethyl)acetamide To a mixed solution of 2-{2-[5-(4-fluorophenyl)-1H-pyrazol-4-yl]-1,3-thiazol-4-yl}-N-(tetrahydro-2H-pyran-4-ylmethyl)acetamide (32.0 mg, 80 μmol) and 3-hydroxytetrahydrofuran (14 mg, 160 μmol) in THF (500 μL) and toluene (500 μL) were added DIAD (31.1 μL, 160 μmol) and triphenylphosphine (42.0 mg, 160 μmol), and the mixture was stirred at 80° C. for 14 hr. To the reaction mixture were added water and ethyl acetate, and the mixture was stirred for 10 min. The organic layer was filtered with a Top-Phase Separation Filter Tube. The filtrate was concentrated. The residue was purified by preparative HPLC to give a mixture (1:3, mol/mol) of a racemic title compound and racemic 2-{2-[3-(4-fluorophenyl)-1-(tetrahydrofuran-3-yl)-1H-pyrazol-4-yl]-1,3-thiazol-4-yl}-N-(tetrahydro-2H-pyran-4-ylmethyl)acetamide.

MS (API): 471 (M+H)

Example 106

2-(2-{5-(4-fluorophenyl)-1-[2-(2-methylpropoxy)ethyl]-1H-pyrazol-4-yl}-1,3-thiazol-4-yl)-N-(tetrahydro-2H-pyran-4-ylmethyl)acetamide Using 2-isobutoxyethanol and by reaction and purification in the same manner as in the method described in Example 105, a mixture (1:1, mol/mol) of the title compound and 2-(2-{3-(4-fluorophenyl)-1-[2-(2-methylpropoxy)ethyl]-1H-pyrazol-4-yl}-1,3-thiazol-4-yl)-N-(tetrahydro-2H-pyran-4-ylmethyl)acetamide was obtained.

MS (API): 501 (M+H)

Example 107

2-{2-[1-butyl-5-(4-fluorophenyl)-1H-pyrazol-4-yl]-1,3-thiazol-4-yl}-N-(tetrahydro-2H-pyran-4-ylmethyl)acetamide Using 1-butanol and by reaction and purification in the same manner as in the method described in Example 105, a mixture (1:1, mol/mol) of the title compound and 2-{2-[1-butyl-3-(4-fluorophenyl)-1H-pyrazol-4-yl]-1,3-thiazol-4-yl}-N-(tetrahydro-2H-pyran-4-ylmethyl)acetamide was obtained.

MS (API): 557 (M+H)

Example 108

2-{2-[5-(4-fluorophenyl)-1-(3-methylbutyl)-1H-pyrazol-4-yl]-1,3-thiazol-4-yl}-N-(tetrahydro-2H-pyran-4-ylmethyl)acetamide Using isoamyl alcohol and by reaction and purification in the same manner as in the method described in Example 105, a mixture (1:1, mol/mol) of the title compound and 2-{2-[3-(4-fluorophenyl)-1-(3-methylbutyl)-1H-pyrazol-4-yl]-1,3-thiazol-4-yl}-N-(tetrahydro-2H-pyran-4-ylmethyl)acetamide was obtained.

MS (API): 471 (M+H)

Example 109

2-{2-[5-(4-fluorophenyl)-1-(3-methoxypropyl)-1H-pyrazol-4-yl]-1,3-thiazol-4-yl}-N-(tetrahydro-2H-pyran-4-ylmethyl)acetamide Using 3-methoxy-1-propanol and by reaction and purification in the same manner as in the method described in Example 105, a mixture (1:1, mol/mol) of the title compound and 2-{2-[3-(4-fluorophenyl)-1-(3-methoxypropyl)-1H-pyrazol-4-yl]-1,3-thiazol-4-yl}-N-(tetrahydro-2H-pyran-4-ylmethyl)acetamide was obtained.

MS (API): 473 (M+H)

Example 110

2-{2-[1-(3,3-dimethylbutyl)-5-(4-fluorophenyl)-1H-pyrazol-4-yl]-1,3-thiazol-4-yl}-N-(tetrahydro-2H-pyran-4-ylmethyl)acetamide Using 3,3-dimethyl-1-butanol and by reaction and purification in the same manner as in the method described in Example 105, a mixture (1:2, mol/mol) of the title compound and 2-{2-[1-(3,3-dimethylbutyl)-3-(4-fluorophenyl)-1H-pyrazol-4-yl]-1,3-thiazol-4-yl}-N-(tetrahydro-2H-pyran-4-ylmethyl)acetamide was obtained.
MS (API): 485 (M+H)

Example 111

2-(2-{5-(4-fluorophenyl)-1-[2-(2,2,2-trifluoroethoxy)ethyl]-1H-pyrazol-4-yl}-1,3-thiazol-4-yl)-N-(tetrahydro-2H-pyran-4-ylmethyl)acetamide Using 2-(2,2,2-trifluoroethoxy)ethanol and by reaction and purification in the same manner as in the method described in Example 105, a mixture (1:6, mol/mol) of the title compound and 2-(2-{3-(4-fluorophenyl)-1-[2-(2,2,2-trifluoroethoxy)ethyl]-1H-pyrazol-4-yl}-1,3-thiazol-4-yl)-N-(tetrahydro-2H-pyran-4-ylmethyl)acetamide was obtained.
MS (API): 527 (M+H)

Example 112

2-(2-{1-[2-ethoxy-1-(ethoxymethyl)ethyl]-5-(4-fluorophenyl)-1H-pyrazol-4-yl}-1,3-thiazol-4-yl)-N-(tetrahydro-2H-pyran-4-ylmethyl)acetamide Using 1,3-diethoxy-2-propanol and by reaction and purification in the same manner as in the method described in Example 105, a mixture (1:2, mol/mol) of the title compound and 2-(2-{1-[2-ethoxy-1-(ethoxymethyl)ethyl]-3-(4-fluorophenyl)-1H-pyrazol-4-yl}-1,3-thiazol-4-yl)-N-(tetrahydro-2H-pyran-4-ylmethyl)acetamide was obtained.
MS (API): 531 (M+H)

Example 113

2-{2-[1-(cyclopentylmethyl)-5-(4-fluorophenyl)-1H-pyrazol-4-yl]-1,3-thiazol-4-yl}-N-(tetrahydro-2H-pyran-4-ylmethyl)acetamide Using cyclopentanemethanol and by reaction and purification in the same manner as in the method described in Example 105, a mixture (1:1, mol/mol) of the title compound and 2-{2-[1-(cyclopentylmethyl)-3-(4-fluorophenyl)-1H-pyrazol-4-yl]-1,3-thiazol-4-yl}-N-(tetrahydro-2H-pyran-4-ylmethyl)acetamide was obtained.
MS (API): 483 (M+H)

Example 114

2-{2-[5-(4-fluorophenyl)-1-(tetrahydro-2H-pyran-4-ylmethyl)-1H-pyrazol-4-yl]-1,3-thiazol-4-yl}-N-(tetrahydro-2H-pyran-4-ylmethyl)acetamide Using tetrahydro-2H-pyran-4-ylmethanol and by reaction and purification in the same manner as in the method described in Example 105, a mixture (1:2, mol/mol) of the title compound and 2-{2-[3-(4-fluorophenyl)-1-(tetrahydro-2H-pyran-4-ylmethyl)-1H-pyrazol-4-yl]-1,3-thiazol-4-yl}-N-(tetrahydro-2H-pyran-4-ylmethyl)acetamide was obtained.
MS (API): 499 (M+H)

Example 115

2-{2-[5-(4-fluorophenyl)-1-(2-methoxy-1-methylethyl)-1H-pyrazol-4-yl]-1,3-thiazol-4-yl}-N-(tetrahydro-2H-pyran-4-ylmethyl)acetamide Using 1-methoxy-2-propanol and by reaction and purification in the same manner as in the method described in Example 105, a mixture (1:1, mol/mol) of a racemic title compound and racemic 2-{2-[3-(4-fluorophenyl)-1-(2-methoxy-1-methylethyl)-1H-pyrazol-4-yl]-1,3-thiazol-4-yl}-N-(tetrahydro-2H-pyran-4-ylmethyl)acetamide was obtained.
MS (API): 473 (M+H)

Example 116

2-{2-[5-(4-fluorophenyl)-1-(1-methylpropyl)-1H-pyrazol-4-yl]-1,3-thiazol-4-yl}-N-(tetrahydro-2H-pyran-4-ylmethyl)acetamide Using 2-butanol and by reaction and purification in the same manner as in the method described in Example 105, a mixture (1:1, mol/mol) of a racemic title compound and racemic 2-{2-[3-(4-fluorophenyl)-1-(1-methylpropyl)-1H-pyrazol-4-yl]-1,3-thiazol-4-yl}-N-(tetrahydro-2H-pyran-4-ylmethyl)acetamide was obtained.
MS (API): 457 (M+H)

Example 117

2-{2-[5-(4-fluorophenyl)-1-(tetrahydrofuran-3-ylmethyl)-1H-pyrazol-4-yl]-1,3-thiazol-4-yl}-N-(tetrahydro-2H-pyran-4-ylmethyl)acetamide Using tetrahydro-3-furanmethanol and by reaction and purification in the same manner as in the method described in Example 105, a mixture (1:1, mol/mol) of a racemic title compound and racemic 2-{2-[3-(4-fluorophenyl)-1-(tetrahydrofuran-3-ylmethyl)-1H-pyrazol-4-yl]-1,3-thiazol-4-yl}-N-(tetrahydro-2H-pyran-4-ylmethyl)acetamide was obtained.
MS (API): 485 (M+H)

Example 118

2-{2-[1-(2-cyclopropylethyl)-5-(4-fluorophenyl)-1H-pyrazol-4-yl]-1,3-thiazol-4-yl}-N-(tetrahydro-2H-pyran-4-ylmethyl)acetamide Using 2-cyclopropylethanol and by reaction and purification in the same manner as in the method described in Example 105, a mixture (1:1, mol/mol) of the title compound and 2-{2-[1-(2-cyclopropylethyl)-3-(4-fluorophenyl)-1H-pyrazol-4-yl]-1,3-thiazol-4-yl}-N-(tetrahydro-2H-pyran-4-ylmethyl)acetamide was obtained.
MS (API): 469 (M+H)

Example 119

2-(2-{1-[(3,3-difluorocyclobutyl)methyl]-5-(4-fluorophenyl)-1H-pyrazol-4-yl}-1,3-thiazol-4-yl)-N-(tetrahydro-2H-pyran-4-ylmethyl)acetamide Using (3,3-difluorocyclobutyl)methanol and by reaction and purification in the same manner as in the method described in Example 105, a mixture (1:1, mol/mol) of the title compound and 2-(2-{1-[(3,3-difluorocyclobutyl)methyl]-3-(4-fluorophenyl)-1H-pyrazol-4-yl}-1,3-thiazol-4-yl)-N-(tetrahydro-2H-pyran-4-ylmethyl)acetamide was obtained.

MS (API): 505 (M+H)

Example 120

2-{2-[5-(4-fluorophenyl)-1-(tetrahydro-2H-thiopyran-4-ylmethyl)-1H-pyrazol-4-yl]-1,3-thiazol-4-yl}-N-(tetrahydro-2H-pyran-4-ylmethyl)acetamide Using tetrahydrothiopyran-4-ylmethanol and by reaction and purification in the same manner as in the method described in Example 105, a mixture (1:1, mol/mol) of the title compound and 2-{2-[3-(4-fluorophenyl)-1-(tetrahydro-2H-thiopyran-4-ylmethyl)-1H-pyrazol-4-yl]-1,3-thiazol-4-yl}-N-(tetrahydro-2H-pyran-4-ylmethyl)acetamide was obtained.

MS (API): 515 (M+H)

Example 121

2-{2-[1-tert-butyl-5-(4-fluorophenyl)-1H-pyrazol-4-yl]-1,3-thiazol-4-yl}-3-phenyl-N-(tetrahydro-2H-pyran-4-ylmethyl)propanamide (Step 1)

To a solution of ethyl 2-(2-(1-tert-butyl-5-(4-fluorophenyl)-1H-pyrazol-4-yl)thiazol-4-yl)acetate (50 mg, 0.13 mmol) in DMF (2.0 mL) was added sodium hydride (60 wt % oil 6.19 mg, 0.15 mmol) at 0° C., and the mixture was stirred at room temperature for 15 min. To the reaction mixture was added benzyl bromide (0.018 mL, 0.15 mmol) at 0° C., and the mixture was stirred at room temperature for 4 hr. Water was added to the reaction mixture, and the mixture was extracted with ethyl acetate. The organic layer was washed with saturated brine and dried, and the solvent was evaporated under reduced pressure. The obtained residue was purified by silica gel column chromatography (solvent gradient; 0→10% ethyl acetate/hexane) to give ethyl 2-(2-(1-(tert-butyl)-5-(4-fluorophenyl)-1H-pyrazol-4-yl)thiazol-4-yl)-3-phenylpropanoate (15.9 mg, 0.033 mmol, 25.8%) as a colorless oil.

MS (API): 478 (M+H)

(Step 2)

To a mixed solution of the compound (14 mg, 0.03 mmol) obtained in step 1 in ethanol (1.0 mL) and THF (1.0 mL) was added 1N aqueous sodium hydroxide solution (0.059 mL, 0.06 mmol) at room temperature, and the mixture was stirred at 60° C. for 3 hr. The reaction mixture was diluted with water, 1N hydrochloric acid was added until the mixture became pH 2-3, and the mixture was extracted with ethyl acetate. The organic layer was washed with saturated brine and dried, and the solvent was evaporated under reduced pressure to give 2-(2-(1-(tert-butyl)-5-(4-fluorophenyl)-1H-pyrazol-4-yl)thiazol-4-yl)-3-phenylpropanoic acid (11.4 mg, 0.025 mmol, 87%) as a colorless oil.

MS (API): 450 (M+H)

(Step 3)

A solution of the compound (11 mg, 0.02 mmol) obtained in step 2, HATU (76 mg, 0.20 mmol), DEIA (5.13 µL, 0.03 mmol) and (tetrahydro-2H-pyran-4-yl)methanamine (3.04 µL, 0.03 mmol) in DMF (2 mL) was stirred at room temperature for 1 day. Water was added to the reaction solution, and the mixture was extracted with ethyl acetate. The organic layer was washed to with water and saturated brine and dried, and the solvent was evaporated under reduced pressure. The obtained residue was purified by NH-silica gel column chromatography (solvent gradient; 0→50% ethyl acetate/hexane) to give the title compound (1.9 mg, 3.48 µmol, 14.2%) as a white powder.

MS (API): 547 (M+H)

Example 122

2-{2-[5-(4-fluorophenyl)-1-(tetrahydro-2H-thiopyran-4-yl)-1H-pyrazol-4-yl]-1,3-thiazol-4-yl}-N-(tetrahydro-2H-pyran-4-ylmethyl)acetamide Using tetrahydro-2H-thiopyran-4-ol and by reaction and purification in the same manner as in the method described in Example 105, a mixture (1:1, mol/mol) of the title compound and 2-{2-[3-(4-fluorophenyl)-1-(tetrahydro-2H-thiopyran-4-yl)-1H-pyrazol-4-yl]-1,3-thiazol-4-yl}-N-(tetrahydro-2H-pyran-4-ylmethyl)acetamide was obtained.

MS (API): 501 (M+H)

Example 123

2-{2-[5-(4-fluorophenyl)-1-(3,3,3-trifluoropropyl)-1H-pyrazol-4-yl]-1,3-thiazol-4-yl}-N-(tetrahydro-2H-pyran-4-ylmethyl)acetamide Using 2,2,2-trifluoroethanol and by reaction and purification in the same manner as in the method described in Example 105, a mixture (1:2, mol/mol) of the title compound and 2-{2-[3-(4-fluorophenyl)-1-(3,3,3-trifluoropropyl)-1H-pyrazol-4-yl]-1,3-thiazol-4-yl}-N-(tetrahydro-2H-pyran-4-ylmethyl)acetamide was obtained.

MS (API): 497 (M+H)

Example 124

2-{2-[1-cycloheptyl-5-(4-fluorophenyl)-1H-pyrazol-4-yl]-1,3-thiazol-4-yl}-N-(tetrahydro-2H-pyran-4-ylmethyl)acetamide To a mixed solution of 2-{2-[5-(4-fluorophenyl)-1H-pyrazol-4-yl]-1,3-thiazol-4-yl}-N-(tetrahydro-2H-pyran-4-ylmethyl)acetamide (32.0 mg, 80 µmol) and cycloheptanol (18 mg, 160 µmol) in THF (500 µL) and toluene (500 µL) were added DIAD (31.1 µL, 160 µmol) and triphenylphosphine (42.0 mg, 160 µmol), and the mixture was stirred at 80° C. for 14 hr. To the reaction mixture were added water and ethyl acetate, and the mixture was stirred for 10 min. The organic layer was filtered with Top-Phase Separation Filter Tube. The filtrate was concentrated, and the residue was purified by preparative HPLC to give a mixture (1:2, mol/mol) of a racemic title compound and racemic 2-{2-[1-cycloheptyl-3-(4-fluorophenyl)-1H-pyrazol-4-yl]-1,3-thiazol-4-yl}-N-(tetrahydro-2H-pyran-4-ylmethyl)acetamide.

MS (API): 497 (M+H)

Example 125

2-{2-[1-tert-butyl-5-(4-fluorophenyl)-1H-pyrazol-4-yl]-1,3-thiazol-4-yl}-N-(tetrahydro-2H-pyran-4-ylmethyl)propanamide (Step 1)
Using ethyl 2-(2-(1-tert-butyl-5-(4-fluorophenyl)-1H-pyrazol-4-yl)thiazol-4-yl)acetate and methyl iodide and by reaction and purification in the same manner as in the method described in Example 121, step 1, ethyl 2-(2-(1-(tert-butyl)-5-(4-fluorophenyl)-1H-pyrazol-4-yl)thiazol-4-yl)propanoate was obtained as a colorless oil
MS (API): 402 (M+H)

(Step 2)
Using the compound obtained in step 1 and by reaction and purification in the same manner as in the method described in Example 121, step 2, crude 2-(2-(1-(tert-butyl)-5-(4-fluorophenyl)-1H-pyrazol-4-yl)thiazol-4-yl)propanoic acid was obtained as a colorless oil (Step 3)
Using the compound obtained in step 2 and by reaction and purification in the same manner as in the method described in Example 121, step 2, the title compound was obtained as a white powder.
MS (API): 471 (M+H)

Example 126

(2E)-3-{2-[1-tert-butyl-5-(4-methoxyphenyl)-1H-pyrazol-4-yl]-1,3-thiazol-4-yl}-N-(tetrahydro-2H-pyran-4-ylmethyl)prop-2-enamide (Step 1)
A solution of 1-tert-butyl-5-(4-methoxyphenyl)-1H-pyrazole-4-carbothioamide (1.24 g, 4.28 mmol) and ethyl bromopyruvate (0.647 mL, 5.14 mmol) in ethanol (24 mL) was stirred at 90° C. for 14 hr. The reaction mixture was concentrated under reduced pressure, and hexane was added thereto to give ethyl 2-(1-(tert-butyl)-5-(4-methoxyphenyl)-1H-pyrazol-4-yl)thiazole-4-carboxylate (1.27 g, 3.29 mmol, 77%) as a white powder.
$^1$H-NMR (300 MHz, CDCl$_3$): δ1.39 (3H, t, J=7.2 Hz), 1.49 (9H, s), 3.91 (3H, s), 4.34-4.43 (2H, m), 6.97-7.07 (2H, m), 7.22-7.31 (2H, m), 7.78 (1H, s), 8.22 (1H, s).

(Step 2)
To a suspension of lithium aluminum hydride (39.4 mg, 1.04 mmol) in THF (2.0 mL) was added a solution of the compound (200 mg, 0.52 mmol) obtained in step 1 in THF (2.0 mL) at 0° C., and the mixture was stirred at 0° C. for 2 hr. To the reaction mixture was added Na$_2$SO$_4$ 10H$_2$O (excess amount), and the mixture was stirred at room temperature for 30 min. The reaction mixture was filtered, and the filtrate was concentrated under reduced pressure to give crude (2-(1-(tert-butyl)-5-(4-methoxyphenyl)-1H-pyrazol-4-yl)thiazol-4-yl)methanol as a white solid, which was used for the next step without purification.
MS (API): 344 (M+H)

(Step 3)
To a solution of the compound (663 mg, 1.93 mmol) obtained in step 2 and TEA (0.807 mL, 5.79 mmol) in DMSO (14 mL) was added a sulfur trioxide-pyridine complex (922 mg, 5.79 mmol) at room temperature, and the mixture was stirred at room temperature for 14 hr. Water was added to the reaction mixture, and the mixture was extracted with ethyl acetate. The organic layer was washed with water and dried, and the solvent was evaporated under reduced pressure. The obtained residue was purified by silica gel column chromatography (solvent; ethyl acetate) to give 2-(1-(tert-butyl)-5-(4-methoxyphenyl)-1H-pyrazol-4-yl)thiazole-4-carbaldehyde (607.5 mg, 1.779 mmol, 92%) as a white powder.
MS (API): 342 (M+H)

(Step 4)
To a solution of triethyl phosphonoacetate (0.026 ml, 0.13 mmol) in THF (2.0 mL) was added sodium hydride (55 wt % paraffin oil, 5.15 mg, 0.13 mmol) at 0° C., and the mixture was stirred at room temperature for 15 min. To the reaction mixture was added a solution of the compound (40 mg, 0.12 mmol) obtained in step 3 in THF (2.0 mL) at 0° C., and the mixture was stirred at room temperature for 5 hr. Water was added to the reaction mixture, and the mixture was extracted with ethyl acetate. The organic layer was washed with water and dried, and the solvent was evaporated under reduced pressure, and the residue was crystallized from diethyl ether-hexane to give ethyl(E)-3-(2-(1-(tert-butyl)-5-(4-methoxyphenyl)-1H-pyrazol-4-yl)thiazol-4-yl)acrylate (12.2 mg, 0.030 mmol, 25.3%) as a white powder.
MS (API): 412 (M+H)

(Step 5)
To a mixed solution of the compound (200 mg, 0.49 mmol) obtained in step 4 in THF (2 mL) and methanol (2 mL) was added 1N aqueous sodium hydroxide solution (0.972 ml, 0.97 mmol) at room temperature, and the mixture was stirred at 60° C. for 3 hr. The reaction mixture was cooled to room temperature, and 1N hydrochloric acid was added until the mixture became pH 2-3. The mixture was extracted with ethyl acetate, the organic layer was dried, and the solvent was evaporated under reduced pressure to give (E)-3-(2-(1-(tert-butyl)-5-(4-methoxyphenyl)-1H-pyrazol-4-yl)thiazol-4-yl)acrylic acid (180.7 mg, 0.471 mmol, 97%) as a white powder.
MS (API): 383 (M+H)

(Step 6)
A solution of the compound (90 mg, 0.23 mmol) obtained in step 5, 4-(aminomethyl)tetrahydropyran (0.029 mL, 0.26 mmol), DIEA (0.049 mL, 0.28 mmol) and HATU (107 mg, 0.28 mmol) in DMF (2.0 mL) was stirred at room temperature for 14 hr. Water was added to the reaction solution, and the mixture was extracted with ethyl acetate. The organic layer was washed with water and saturated brine and dried, and the solvent was evaporated under reduced pressure. The obtained residue was purified by NH-silica gel column chromatography (solvent gradient; 50→80% ethyl acetate/hexane) and crystallized from ethyl acetate and hexane to give the title compound (52.7 mg, 0.110 mmol, 46.7%) as a white powder.
$^1$H-NMR (300 MHz, DMSO-d$_6$): δ1.07-1.26 (2H, m), 1.43 (9H, s), 1.50-1.76 (3H, m), 2.99-3.13 (2H, m), 3.19-3.30 (2H, m), 3.77-3.85 (2H, m), 3.86 (3H, s), 6.81 (1H, d, J=15.4 Hz), 7.08-7.16 (2H, m), 7.28 (1H, d, J=15.4 Hz), 7.33-7.41 (2H, m), 7.54 (1H, s), 7.98 (1H, s), 8.24 (1H, t, J=5.7 Hz).

Example 127

3-{2-[1-tert-butyl-5-(4-methoxyphenyl)-1H-pyrazol-4-yl]-1,3-thiazol-4-yl}-N-(tetrahydro-2H-pyran-4-ylmethyl)propanamide A solution of (2E)-3-{2-[1-tert-butyl-5-(4-methoxyphenyl)-1H-pyrazol-4-yl]-1,3-thiazol-4-yl}-N-(tetrahydro-2H-pyran-4-ylmethyl)prop-2-enamide (46.7 mg, 0.10 mmol) and 10% palladium carbon (10 mg, 0.09 mmol) in methanol (15 mL) was stirred under 1 atm hydrogen atmosphere at room temperature for 14 hr. The catalyst was filtered off, and the filtrate was concentrated under reduced pressure. The obtained residue was purified by NH-silica gel column chromatography (solvent gradient; 0→50% ethyl acetate/hexane) and crystallized from ethyl acetate and hexane to give the title compound (26.2 mg, 0.054 mmol, 55.9%) as a white powder.
$^1$H-NMR (300 MHz, DMSO-$d_6$): δ0.94-1.21 (2H, m), 1.41 (9H, s), 1.44-1.65 (3H, m), 2.35-2.46 (2H, m), 2.77-2.97 (4H, m), 3.08-3.24 (2H, m), 3.69-3.82 (2H, m), 3.85 (3H, s), 6.87 (1H, s), 7.11 (2H, d, J=8.7 Hz), 7.32 (2H, d, J=8.7 Hz), 7.83 (1H, t, J=5.8 Hz), 7.95 (1H, s).

Example 128

2-{2-[1-tert-butyl-5-(4-chlorophenyl)-1H-pyrazol-4-yl]-1,3-thiazol-4-yl}-N-(tetrahydro-2H-pyran-4-ylmethyl)acetamide A mixed solution of 2-[2-(5-bromo-1-tert-butyl-1H-pyrazol-4-yl)thiazol-4-yl]-N-[(tetrahydro-2H-pyran-4-yl)methyl]acetamide (44.1 mg, 100 μmol), 4-chlorophenylboronic acid (15.6 mg, 100 μmol), potassium carbonate (27.6 mg, 200 μmol) and bis[di-tert-butyl(4-dimethylaminophenyl)phosphine]dichloropalladium(II) (7.08 mg, 10.00 μmol) in 1,2-dimethoxyethane (0.5 mL) and water (0.5 mL) was stirred at 150° C. for 30 min under ultrasonic irradiation. To the reaction solution was added water (1 mL), the mixture was extracted with ethyl acetate (2 mL), and the organic layer was concentrated. The residue was purified by preparative HPLC to give the title compound (17.9 mg, 0.038 mmol, 38%).
MS (API): 473 (M+H)

Example 129

2-{2-[1-tert-butyl-5-(3-chlorophenyl)-1H-pyrazol-4-yl]-1,3-thiazol-4-yl}-N-(tetrahydro-2H-pyran-4-ylmethyl)acetamide Using 4-chlorophenylboronic acid and by reaction and purification in the same manner as in the method described in Example 129, the title compound was obtained.
MS (API): 473 (M+H)

Example 130

2-[2-(5-(biphenyl-4-yl)-1-tert-butyl-1H-pyrazol-4-yl)-1,3-thiazol-4-yl]-Netrahydro-2H-pyran-4-ylmethyl)acetamide Using 4-biphenylboronic acid and by reaction and purification in the same manner as in the method described in Example 129, the title compound was obtained.
MS (API): 515 (M+H)

Example 131

2-(2-{1-tert-butyl-5-[4-(hydroxymethyl)phenyl]-1H-pyrazol-4-yl}-1,3-thiazol-4-yl)-N-(tetrahydro-2H-pyran-4-ylmethyl)acetamide Using 4-(hydroxymethyl)phenylboronic acid and by reaction and purification in the same manner as in the method described in Example 129, the title compound was obtained.
MS (API): 469 (M+H)

Example 132

2-{2-[1-tert-butyl-5-(4-tert-butylphenyl)-1H-pyrazol-4-yl]-1,3-thiazol-4-yl}-N-(tetrahydro-2H-pyran-4-ylmethyl)acetamide Using 4-tert-butylphenylboronic acid and by reaction and purification in the same manner as in the method described in Example 129, the title compound was obtained.
MS (API): 495 (M+H)

Example 133

2-(2-{1-tert-butyl-5-[4-(trifluoromethoxy)phenyl]-1H-pyrazol-4-yl}-1,3-thiazol-4-yl)-N-(tetrahydro-2H-pyran-4-ylmethyl)acetamide Using 4-(trifluoromethoxy)phenylboronic acid and by reaction and purification in the same manner as in the method described in Example 129, the title compound was obtained.
MS (API): 523 (M+H)

Example 134

2-(2-{1-tert-butyl-5-[4-(methylsulfonyl)phenyl]-1H-pyrazol-4-yl}-1,3-thiazol-4-yl)-N-(tetrahydro-2H-pyran-4-ylmethyl)acetamide Using 4-(methylsulfonyl)phenylboronic acid and by reaction and purification in the same manner as in the method described in Example 129, the title compound was obtained.
MS (API): 517 (M+H)

Example 135

2-(2-[1-tert-butyl-5-[4-(cyanomethyl)phenyl]-1H-pyrazol-4-yl]-1,3-thiazol-4-yl)-N-(tetrahydro-2H-pyran-4-ylmethyl)acetamide Using 4-(cyanomethyl)benzeneboronic acid and by reaction and purification in the same manner as in the method described in Example 129, the title compound was obtained.
MS (API): 478 (M+H)

Example 136

2-[2-(5-(biphenyl-3-yl)-1-tert-butyl-1H-pyrazol-4-yl)-1,3-thiazol-4-yl]-Netrahydro-2H-pyran-4-ylmethyl)acetamide Using 3-biphenylboronic acid and by reaction and purification in the same manner as in the method described in Example 129, the title compound was obtained.
MS (API): 515 (M+H)

Example 137

2-(2-{5-[3-(acetylamino)phenyl]-1-tert-butyl-1H-pyrazol-4-yl}-1,3-thiazol-4-yl)-N-(tetrahydro-2H-pyran-4-ylmethyl)acetamide Using 4-acetamidophenylboronic acid and by reaction and purification in the same manner as in the method described in Example 129, the title compound was obtained.
MS (API): 496 (M+H)

Example 138

2-{2-[1-tert-butyl-5-(3-cyanophenyl)-1H-pyrazol-4-yl]-1,3-thiazol-4-yl}-N-(tetrahydro-2H-pyran-4-ylmethyl)acetamide Using 3-cyanophenylboronic acid and by reaction and purification in the same manner as in the method described in Example 129, the title compound was obtained.
MS (API): 464 (M+H)

Example 139

2-(2-[(1-tert-butyl-5-[3-(trifluoromethoxy)phenyl]-1H-pyrazol-4-yl]-1,3-thiazol-4-yl)-N-(tetrahydro-2H-pyran-4-ylmethyl)acetamide Using 3-(trifluoromethoxy)phenylboronic acid and by reaction and purification in the same manner as in the method described in Example 129, the title compound was obtained.
MS (API): 523 (M+H)

Example 140

2-{2-[1-tert-butyl-5-(3-phenoxyphenyl)-1H-pyrazol-4-yl]-1,3-thiazol-4-yl}-N-(tetrahydro-2H-pyran-4-ylmethyl)acetamide Using 3-phenoxyphenylboronic acid and by reaction and purification in the same manner as in the method described in Example 129, the title compound was obtained.
MS (API): 531 (M+H)

Example 141

2-{2-[1-tert-butyl-5-(2,3-dihydro-1-benzofuran-5-yl)-1H-pyrazol-4-yl]-1,3-thiazol-4-yl}-N-(tetrahydro-2H-pyran-4-ylmethyl)acetamide Using 2,3-dihydrobenzofuran-5-boronic acid and by reaction and purification in the same manner as in the method described in Example 129, the title compound was obtained.
MS (API): 481 (M+H)

Example 142

2-[2-(1-tert-butyl-5-(naphthalen-2-yl)-1H-pyrazol-4-yl)-1,3-thiazol-4-yl]-N-etrahydro-2H-pyran-4-ylmethyl)acetamide Using 2-naphthaleneboronic acid and by reaction and purification in the same manner as in the method described in Example 129, the title compound was obtained.
MS (API): 489 (M+H)

Example 143

2-(2-{1-tert-butyl-5-[6-(trifluoromethyl)pyridin-3-yl]-1H-pyrazol-4-yl}-1,3-thiazol-4-yl)-N-(tetrahydro-2H-pyran-4-ylmethyl)acetamide Using 2-trifluoromethyl-5-pyridineboric acid and by reaction and purification in the same manner as in the method described in Example 129, the title compound was obtained.
MS (API): 508 (M+H)

Example 144

2-[2-(1-tert-butyl-5-(furan-3-yl)-1H-pyrazol-4-yl)-1,3-thiazol-4-yl]-N-etrahydro-2H-pyran-4-ylmethyl)acetamide Using furan-3-boronic acid and by reaction and purification in the same manner as in the method described in Example 129, the title compound was obtained.
MS (API): 429 (M+H)

Example 145

2-[2-(1-tert-butyl-5-(thiophen-3-yl)-1H-pyrazol-4-yl)-1,3-thiazol-4-yl]-N-etrahydro-2H-pyran-4-ylmethyl)acetamide Using thiophene-3-boronic acid and by reaction and purification in the same manner as in the method described in Example 129, the title compound was obtained.
MS (API): 445 (M+H)

Example 146

2-(2-{1-tert-butyl-5-[(E)-2-cyclopropylethenyl]-1H-pyrazol-4-yl}-1,3-thiazol-4-yl)-N-(tetrahydro-2H-pyran-4-ylmethyl)acetamide Using [(E)-2-cyclopropylethenyl]boranediol and by reaction and purification in the same manner as in the method described in Example 129, the title compound was obtained.
MS (API): 429 (M+H)

Example 147

2-{2-[1-tert-butyl-5-(6-methoxypyridin-3-yl)-1H-pyrazol-4-yl]-1,3-thiazol-4-yl}-N-(tetrahydro-2H-pyran-4-ylmethyl)acetamide Using 2-methoxy-5-pyridineboronic acid and by reaction and purification in the same manner as in the method described in Example 129, the title compound was obtained.
MS (API): 470 (M+H)

Example 148

2-[2-(1-tert-butyl-5-(cyclohex-1-en-1-yl)-1H-pyrazol-4-yl)-1,3-thiazol-4-yl]-N-etrahydro-2H-pyran-4-ylmethyl)acetamide Using 1-cyclohexen-1-yl-boronic acid and by reaction and purification in the same manner as in the method described in Example 129, the title compound was obtained.
MS (API): 443 (M+H)

Example 149

2-{2-[5-(1-benzofuran-2-yl)-1-tert-butyl-1H-pyrazol-4-yl]-1,3-thiazol-4-yl}-N-(tetrahydro-2H-pyran-4-ylmethyl)acetamide Using benzofuran-2-boronic acid and by reaction and purification in the same manner as in the method described in Example 129, the title compound was obtained.
MS (API): 479 (M+H)

Example 150

2-{2-[5-(1-benzothiophen-2-yl)-1-tert-butyl-1H-pyrazol-4-yl]-1,3-thiazol-4-yl}-N-(tetrahydro-2H-pyran-4-ylmethyl)acetamide Using benzo[b]thiophene-2-boronic acid and by reaction and purification in the same manner as in the method described in Example 129, the title compound was obtained.
MS (API): 495 (M+H)

Example 151

2-{2-[1-tert-butyl-5-(3,4-dimethoxyphenyl)-1H-pyrazol-4-yl]-1,3-thiazol-4-yl}-N-(tetrahydro-2H-pyran-4-ylmethyl)acetamide Using 3,4-dimethoxyphenylboronic acid and by reaction and purification in the same manner as in the method described in Example 129, the title compound was obtained.
MS (API): 499 (M+H)

Example 152

2-{2-[1-tert-butyl-5-(3-fluoro-4-methoxyphenyl)-1H-pyrazol-4-yl]-1,3-thiazol-4-yl}-N-(tetrahydro-2H-pyran-4-ylmethyl)acetamide Using 3-fluoro-4-methoxyphenylboronic acid and by reaction and purification in the same manner as in the method described in Example 129, the title compound was obtained.
MS (API): 487 (M+H)

Example 153

2-{2-[1-tert-butyl-5-(5-chlorothiophen-2-yl)-1H-pyrazol-4-yl]-1,3-thiazol-4-yl}-N-(tetrahydro-2H-pyran-4-ylmethyl)acetamide Using 5-chlorothiophene-2-boronic acid and by reaction and purification in the same manner as in the method described in Example 129, the title compound was obtained.
MS (API): 480 (M+H)

Example 154

2-(2-{1-tert-butyl-5-[(E)-2-cyclohexylethenyl]-1H-pyrazol-4-yl}-1,3-thiazol-4-yl)-N-(tetrahydro-2H-pyran-4-ylmethyl)acetamide Using 2-cyclohexylethenylboronic acid and by reaction and purification in the same manner as in the method described in Example 129, the title compound was obtained.
MS (API): 471 (M+H)

Example 155

2-(2-{1-tert-butyl-5-[(E)-2-phenylethenyl]-1H-pyrazol-4-yl}-1,3-thiazol-4-yl)-N-(tetrahydro-2H-pyran-4-ylmethyl)acetamide Using trans-2-phenylvinylboronic acid and by reaction and purification in the same manner as in the method described in Example 129, the title compound was obtained.
MS (API): 465 (M+H)

Example 156

2-{2-[1-tert-butyl-5-(2-methyl-2H-indazol-5-yl)-1H-pyrazol-4-yl]-1,3-thiazol-4-yl}-N-(tetrahydro-2H-pyran-4-ylmethyl)acetamide Using 2-methylindazole-5-boronic acid and by reaction and purification in the same manner as in the method described in Example 129, the title compound was obtained.
MS (API): 493 (M+H)

Example 157

2-{2-[1-tert-butyl-5-(2-methyl-2H-indazol-6-yl)-1H-pyrazol-4-yl]-1,3-thiazol-4-yl}-N-(tetrahydro-2H-pyran-4-ylmethyl)acetamide Using 2-methyl-2H-indazole-6-boronic acid and by reaction and purification in the same manner as in the method described in Example 129, the title compound was obtained.
MS (API): 493 (M+H)

Example 158

2-[2-(1-tert-butyl-5-(furan-2-yl)-1H-pyrazol-4-yl)-1,3-thiazol-4-yl]-N-tetrahydro-2H-pyran-4-ylmethyl)acetamide Using furan-2-boronic acid and by reaction and purification in the same manner as in the method described in Example 129, the title compound was obtained.
MS (API): 429 (M+H)

Example 159

2-[2-(2-tert-butyl-1'-methyl-1'H, 2H-3,4'-bipyrazol-4-yl)-1,3-thiazol-4-yl]-N-tetrahydro-2H-pyran-4-ylmethyl)acetamide Using 1-methyl-1H-pyrazole-4-boronic acid and by reaction and purification in the same manner as in the method described in Example 129, the title compound was obtained.
MS (API): 443 (M+H)

Example 160

2-{2-[1-tert-butyl-5-(3-methoxyphenyl)-1H-pyrazol-4-yl]-1,3-thiazol-4-yl}-N-(tetrahydro-2H-pyran-4-ylmethyl)acetamide Using 3-methoxyphenylboronic acid and by reaction and purification in the same manner as in the method described in Example 129, the title compound was obtained.
MS (API): 469 (M+H)

Example 161

3-{2-[1-tert-butyl-5-(4-methoxyphenyl)-1H-pyrazol-4-yl]-1,3-thiazol-4-yl}-N-(tetrahydro-2H-pyran-4-yl)propanamide (Step 1)
A mixed solution of (E)-3-(2-(1-(tert-butyl)-5-(4-methoxyphenyl)-1H-pyrazol-4-yl)thiazol-4-yl)acrylic acid (70 mg, 0.18 mmol) and 10% palladium carbon (19.43 mg, 0.18 mmol) in THF (2 mL) and methanol (2 mL) was stirred under 1 atm hydrogen atmosphere at room temperature for 14 hr.

The catalyst was filtered off, and the filtrate was concentrated under reduced pressure. The residue was crystallized from diethyl ether to give 3-(2-(1-(tert-butyl)-5-(4-methoxyphenyl)-1H-pyrazol-4-yl)thiazol-4-yl)propanoic acid (62.0 mg, 0.161 mmol, 88%) as a white powder. PMS (API): 386 (M+H) P(Step 2) PUsing the compound obtained in step 1 and 4-aminotetrahydropyran and by reaction and purification in the same manner as in the method described in Example 1, step 7, the title compound was obtained. P¹H-NMR (300 MHz, DMSO-d$_6$): δ1.24-1.38 (3H, m), 1.41 (9H, s), 1.56-1.70 (2H, m), 2.33-2.44 (2H, m), 2.79-2.91 (2H, m), 3.22-3.36 (1H, m), 3.64-3.83 (3H, m), 3.85 (3H, s), 6.87 (1H, s), 7.05-7.15 (2H, m), 7.28-7.38 (2H, m), 7.80 (1H, d, J=7.6 Hz), 7.94 (1H, s). PMS (API): 469 (M+H)

Example 162

N-({2-[1-tert-butyl-5-(4-fluorophenyl)-1H-pyrazol-4-yl]-1,3-thiazol-4-yl}methyl)-2-(tetrahydro-2H-pyran-4-yl)acetamide P(Step 1) PA solution of 2-(2-(1-(tert-butyl)-5-(4-fluorophenyl)-1H-pyrazol-4-yl)thiazol-4-yl)acetic acid (100 mg, 0.28 mmol), diphenylphosphoryl azide (0.066 mL, 0.31 mmol), TEA (0.047 mL, 0.33 mmol) and tert-butyl alcohol (0.052 mL, 0.56 mmol) in toluene (2.0 mL) was stirred at room temperature for 14 hr. Water was added to the reaction solution, and the mixture was extracted with ethyl acetate. The organic layer was washed with water and saturated brine and dried, and the solvent was evaporated under reduced pressure. The obtained residue was purified by NH-silica gel column chromatography (solvent gradient; 50→80% ethyl acetate/hexane) to give ((2-(1-tert-butyl-5-(4-fluorophenyl)-1H-pyrazol-4-yl)thiazol-4-yl)methyl)carbamic acid (13.6 mg, 0.032 mmol, 11.35%) as a pale-yellow oil. PMS (API): 431 (M+H) P(Step 2) PA solution of the compound (13.6 mg, 0.03 mmol) obtained in step 1 in TFA (1.0 mL) was stirred at room temperature for 1 hr, and concentrated under reduced pressure. To the residue were added saturated aqueous sodium hydrogen carbonate solution and ethyl acetate. The organic layer was dried, and the solvent was evaporated under reduced pressure to give (2-(1-tert-butyl-5-(4-fluorophenyl)-1H-pyrazol-4-yl)thiazol-4-yl)methanamine (7.2 mg, 0.022 mmol, 69.0%) as a pale-yellow oil. PMS (API): 331 (M+H)

(Step 3)

Using the compound obtained in step 2 and tetrahydropyranyl-4-acetic acid and by reaction and purification in the same manner as in the method described in Example 1, step 7, the title compound was obtained.

¹H-NMR (300 MHz, DMSO-d$_6$): δ1.05-1.28 (2H, m), 1.43 (9H, brs), 1.46-1.63 (2H, m), 1.77-1.97 (1H, m), 2.00-2.11 (2H, m), 3.17-3.29 (2H, m), 3.69-3.86 (2H, m), 4.28 (2H, d, J=5.7 Hz), 6.96 (1H, s), 7.33-7.46 (2H, m), 7.47-7.59 (2H, m), 7.96 (1H, s), 8.30 (1H, t, J=5.5 Hz).

Example 163

2-[1-tert-butyl-5-(4-fluorophenyl)-1H-pyrazol-4-yl]-Netrahydro-2H-pyran-4-ylmethyl)-4,5-dihydro-1,3-thiazole-4-carboxamide (Step 1)
To a solution of 1-(tert-butyl)-5-(4-fluorophenyl)-1H-pyrazole-4-carboxamide (500 mg, 1.91 mmol) in DMF (4 mL) was added cyanuric chloride (0.267 mL, 1.91 mmol) at 0° C., and the mixture was stirred at 0° C. for 14 hr. Water was added to the reaction solution, and the mixture was extracted with ethyl acetate. The organic layer was washed with water and saturated brine and dried, and the solvent was evaporated under reduced pressure. The obtained residue was purified by silica gel column chromatography (solvent gradient; 5→50% ethyl acetate/hexane) to give 1-(tert-butyl)-5-(4-fluorophenyl)-1H-pyrazole-4-carbonitrile (430 mg, 1.77 mmol, 92%) as a white powder.

¹H-NMR (300 MHz, CDCl$_3$): δ1.47 (9H, s), 7.12-7.24 (2H, m), 7.30-7.39 (2H, m), 7.78 (1H, s).

(Step 2)

A mixed solution of 1N aqueous sodium hydroxide solution (2.65 ml, 2.65 mmol) of the compound (430 mg, 1.77 mmol) obtained in step 1 and DL-cysteine (321 mg, 2.65 mmol), and ethanol (5.3 mL) was stirred at 80° C. for 3 hr. DL-cysteine (200 mg) and 1N aqueous sodium hydroxide solution (1.5 mL) were further added thereto, and the mixture was stirred at 80° C. for 14 hr. DL-cysteine (321 mg) and 1N aqueous sodium hydroxide solution (2.65 mL) were further added thereto, and the mixture was stirred at 80° C. for 5 hr. The reaction mixture was concentrated under reduced pressure, and 1N hydrochloric acid and ethyl acetate were added thereto. The organic layer was washed with saturated brine and dried, and the solvent was evaporated under reduced pressure. The residue was crystallized from ethyl acetate and diethyl ether to give 2-(1-(tert-butyl)-5-(4-fluorophenyl)-1H-pyrazol-4-yl)-4,5-dihydrothiazole-4-carboxylic acid (385 mg, 1.108 mmol, 62.7%) as a pale-yellow powder.

¹H-NMR (300 MHz, CDCl$_3$): δ1.46 (9H, s), 3.39-3.53 (2H, m), 5.04 (1H, t, J=9.4 Hz), 7.12-7.21 (2H, m), 7.28-7.40 (2H, m), 7.93 (1H, s).

(Step 3)

A solution of the compound (50 mg, 0.14 mmol) obtained in step 2, HATU (65.7 mg, 0.17 mmol), DIEA (0.030 mL, 0.17 mmol) and 4-aminomethyltetrahydropyran (0.020 mL, 0.17 mmol) in DMF (2 mL) was stirred at room temperature for 48 hr. Water was added to the reaction solution, and the mixture was extracted with ethyl acetate. The organic layer was washed with water and saturated brine and dried, and the solvent was evaporated under reduced pressure. The obtained residue was purified by silica gel column chromatography (solvent; ethyl acetate) to give the title compound (50 mg, 0.112 mmol, 78%) as a white powder.

¹H-NMR (300 MHz, CDCl$_3$): δ1.20-1.37 (2H, m), 1.46 (9H, s), 1.50-1.59 (2H, m), 1.63-1.78 (1H, m), 2.90-3.05 (1H, m), 3.17 (1H, dt, J=13.3, 6.6 Hz), 3.29-3.42 (3H, m), 3.42-3.54 (1H, m), 3.97 (2H, dd, J=11.5, 4.7 Hz), 4.88 (1H, t, J=9.5 Hz), 6.39 (1H, brs), 7.15 (2H, q, J=8.2 Hz), 7.30-7.44 (2H, m), 7.88 (1H, s).

MS (API): 445 (M+H)

Example 164

2-[1-tert-butyl-5-(4-fluorophenyl)-1H-pyrazol-4-yl]-Netrahydro-2H-pyran-4-yl)-4,5-dihydro-1,3-thiazole-4-carboxamide Using 2-(1-(tert-butyl)-5-(4-fluorophenyl)-1H-pyrazol-4-yl)-4,5-dihydrothiazole-4-carboxylic acid and tetrahydro-pyran-4-ylamine and by reaction and purification in the same manner as in the method described in Example 1, step 7, the title compound was obtained.

MS (API): 431 (M+H)

Example 165

2-[1-tert-butyl-5-(4-fluorophenyl)-1H-pyrazol-4-yl]-N-[2-(tetrahydro-2H-pyran-4-yl)ethyl]-4,5-dihydro-1,3-thiazole-4-carboxamide Using 2-(1-(tert-butyl)-5-(4-fluorophenyl)-1H-pyrazol-4-yl)-4,5-dihydrothiazole-4-carboxylic acid and 2-(tetrahydropyran-4-yl)-ethylamine and by reaction and purification in the same manner as in the method described in Example 1, step 7, the title compound was obtained.
MS (API): 459 (M+H)

Example 166

6-({2-[1-tert-butyl-5-(4-fluorophenyl)-1H-pyrazol-4-yl]-4,5-dihydro-1,3-thiazol-4-yl}carbonyl)-5,6,7,8-tetrahydro-1,6-naphthyridin-2(1H)-one Using 2-(1-(tert-butyl)-5-(4-fluorophenyl)-1H-pyrazol-4-yl)-4,5-dihydrothiazole-4-carboxylic acid and 5,6,7,8-tetrahydro-1,6-naphthyridin-2(1H)-one and by reaction and purification in the same manner as in the method described in Example 1, step 7, the title compound was obtained.
MS (API): 480 (M+H)

Example 167

6-({2-[1-tert-butyl-5-(4-fluorophenyl)-1H-pyrazol-4-yl]-1,3-thiazol-4-yl}acetyl)-5,6,7,8-tetrahydro-1,6-naphthyridin-2(1H)-one Using 2-(2-(1-tert-butyl-5-(4-fluorophenyl)-1H-pyrazol-4-yl)thiazol-4-yl)acetic acid and 5,6,7,8-tetrahydro-1,6-naphthyridin-2(1H)-one and by reaction and purification in the same manner as in the method described in Example 1, step 7, the title compound was obtained.
MS (API): 492 (M+H)

Example 168

2-{2-[1-tert-butyl-5-(4-fluorophenyl)-1H-pyrazol-4-yl]-1,3-thiazol-4-yl}-N-[4-(1H-imidazol-1-yl)phenyl]acetamide Using 2-(2-(1-tert-butyl-5-(4-fluorophenyl)-1H-pyrazol-4-yl)thiazol-4-yl)acetic acid and 4-(1H-imidazol-1-yl)aniline and by reaction and purification in the same manner as in the method described in Example 1, step 7, the title compound was obtained.
MS (API): 501 (M+H)
$^1$H-NMR (300 MHz, DMSO-$d_6$): δ1.41 (9H, s), 3.77 (2H, s), 7.08 (1H, s), 7.14 (1H, s), 7.36-7.46 (2H, m), 7.48-7.62 (4H, m), 7.65-7.77 (3H, m), 7.98 (1H, s), 8.17 (1H, s), 10.33 (1H, s).

Example 169

N-[4-(acetylamino)phenyl]-2-{2-[1-tert-butyl-5-(4-fluorophenyl)-1H-pyrazol-4-yl]-1,3-thiazol-4-yl}acetamide Using 2-(2-(1-tert-butyl-5-(4-fluorophenyl)-1H-pyrazol-4-yl)thiazol-4-yl)acetic acid and 4-aminoacetanilide and by reaction and purification in the same manner as in the method described in Example 1, step 7, the title compound was obtained.
MS (API): 492 (M+H)
$^1$H-NMR (300 MHz, DMSO-$d_6$): δ1.41 (9H, s), 2.01 (3H, s), 3.72 (2H, s), 7.11 (1H, s), 7.35-7.46 (2H, m), 7.47-7.59 (6H, m), 7.97 (1H, s), 9.85 (1H, s), 10.07 (1H, s).

Example 170

2-{2-[1-tert-butyl-5-(4-fluorophenyl)-1H-pyrazol-4-yl]-1,3-thiazol-4-yl}-N-[4-(1H-imidazol-1-yl)benzyl]acetamide A solution of 2-(2-(1-tert-butyl-5-(4-fluorophenyl)-1H-pyrazol-4-yl)thiazol-4-yl)acetic acid (50 mg, 0.14 mmol), HATU (106 mg, 0.28 mmol), DIEA (0.049 mL, 0.28 mmol) and 4-(1H-imidazol-1-yl)benzylamine (96 mg, 0.56 mmol) in DMF (2.0 mL) was stirred at room temperature for 14 hr. Water was added to the reaction solution, and the mixture was extracted with ethyl acetate. The organic layer was washed with water and saturated brine and dried, and the solvent was evaporated under reduced pressure. The obtained residue was purified by NH-silica gel column chromatography (solvent gradient; 50→70% ethyl acetate/hexane) to give the title compound (33.4 mg, 0.065 mmol, 46.7%) as a white powder.
MS (API): 515 (M+H)
$^1$H-NMR (300 MHz, DMSO-$d_6$): δ1.41 (9H, s), 3.60 (2H, s), 4.32 (2H, d, J=5.7 Hz), 7.07 (1H, s), 7.10 (1H, t, J=1.1 Hz), 7.36-7.45 (4H, m), 7.49-7.60 (4H, m), 7.70 (1H, t, J=1.1 Hz), 7.97 (1H, s), 8.21 (1H, t, J=1.1 Hz), 8.53 (1H, t, J=5.7 Hz).

Example 171

2-{2-[1-tert-butyl-5-(4-fluorophenyl)-1H-pyrazol-4-yl]-1,3-thiazol-4-yl}-N-[3-(1H-imidazol-1-yl)benzyl]acetamide Using 2-(2-(1-tert-butyl-5-(4-fluorophenyl)-1H-pyrazol-4-yl)thiazol-4-yl)acetic acid and (3-(1H-imidazol-1-yl)phenyl)methanamine and by reaction and purification in the same manner as in the method described in Example 1, step 7, the title compound was obtained.
MS (API): 515 (M+H)
$^1$H-NMR (300 MHz, DMSO-$d_6$): δ1.42 (9H, s), 3.61 (2H, s), 4.36 (2H, d, J=6.0 Hz), 7.05-7.09 (2H, m), 7.27 (1H, d, J=7.6 Hz), 7.36-7.45 (3H, m), 7.46-7.56 (4H, m), 7.65 (1H, t, J=1.3 Hz), 7.94 (1H, s), 8.14-8.19 (1H, m), 8.54 (1H, t, J=6.0 Hz).

Example 172

2-{2-[1-tert-butyl-5-(4-fluorophenyl)-1H-pyrazol-4-yl]-1,3-thiazol-4-yl}-N-{[4-(hydroxymethyl)tetrahydro-2H-pyran-4-yl]methyl}acetamide Using 2-(2-(1-tert-butyl-5-(4-fluorophenyl)-1H-pyrazol-4-yl)thiazol-4-yl)acetic acid and [4-(aminomethyl)tetrahydro-2H-pyran-4-yl]methanol and by reaction and purification in the same manner as in the method described in Example 1, step 7, the title compound was obtained.
MS (API): 487 (M+H)
$^1$H-NMR (300 MHz, DMSO-$d_6$): δ1.22-1.37 (4H, m), 1.41 (9H, s), 3.15 (2H, d, J=6.0 Hz), 3.22 (2H, d, J=6.0 Hz), 3.45-3.62 (6H, m), 4.50 (1H, t, J=6.0 Hz), 7.03 (1H, s), 7.35-7.46 (2H, m), 7.48-7.58 (2H, m), 7.91-8.02 (2H, m).

Example 173

2-{2-[1-tert-butyl-5-(4-fluorophenyl)-1H-pyrazol-4-yl]-1,3-thiazol-4-yl}-N-[3-(1H-imidazol-1-yl)phenyl]acetamide Using 2-(2-(1-tert-butyl-5-(4-fluorophenyl)-1H-pyrazol-4-yl)thiazol-4-yl)acetic acid and 3-(1H-imidazol-1-yl)aniline and by reaction and purification in the same manner as in the method described in Example 1, step 7, the title compound was obtained.

MS (API): 501 (M+H)

$^1$H-NMR (300 MHz, DMSO-$d_6$): δ1.41 (9H, s), 3.79 (2H, s), 7.10 (1H, s), 7.15 (1H, s), 7.27-7.34 (1H, m), 7.36-7.57 (6H, m), 7.61 (1H, t, J=1.3 Hz), 7.89 (1H, t, J=1.9 Hz), 7.97 (1H, s), 8.13 (1H, s), 10.39 (1H, s).

The compounds described in Examples 1-173 are as described below (Table 1). The "free" in Table 1 shows a free form.

TABLE 1

| Example No. | 1 | 2 | 3 |
|---|---|---|---|
| structural formula | (structure) | (structure) | (structure) |
| salt | free | free | free |

| Example No. | 4 | 5 | 6 |
|---|---|---|---|
| structural formula | (structure) | (structure) | (structure) |

TABLE 1-continued
| salt | free | free | free |
|---|---|---|---|
| Example No. | 7 | 8 | 9 |
| structural formula | 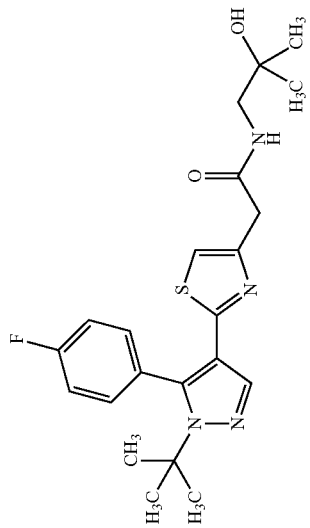 | 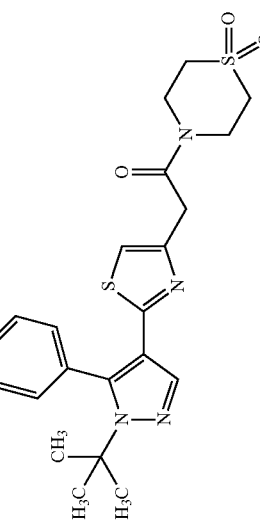 | 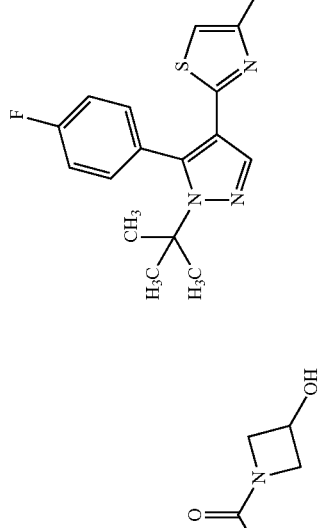 |
| salt | free | free | free |
|---|---|---|---|
| Example No. | 10 | 11 | 12 |
| structural formula | 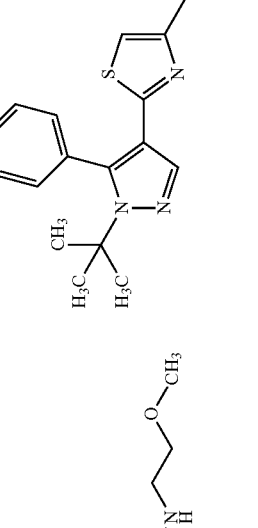 | 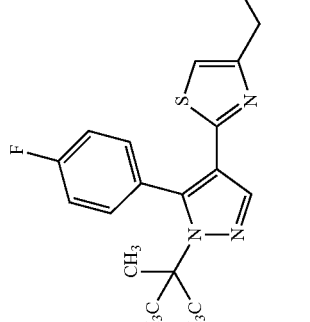 | 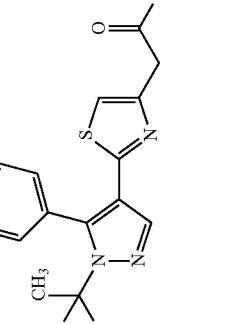 |

TABLE 1-continued

| salt | free | free | free |
|---|---|---|---|
| Example No. | 13 | 14 | 15 |
| structural formula | (structure) | (structure) | (structure) |

| salt | free | free | free |
|---|---|---|---|
| Example No. | 16 | 17 | 18 |
| structural formula | (structure) | (structure) | (structure) |

TABLE 1-continued

| salt | free | free | free |
|---|---|---|---|
| Example No. | 19 | 20 | 21 |
| structural formula | (structure) | (structure) | (structure) |

| salt | free | free | free |
|---|---|---|---|
| Example No. | 22 | 23 | 24 |
| structural formula | (structure) | (structure) | (structure) |

TABLE 1-continued

| salt | free | free | free |
|---|---|---|---|
| Example No. | 25 | 26 | 27 |
| structural formula | (structure) | (structure) | (structure) |

| salt | free | free | free |
|---|---|---|---|
| Example No. | 28 | 29 | 30 |
| structural formula | (structure) | (structure) | (structure) |

| salt | HCl | free | free |
|---|---|---|---|
| Example No. | 31 | 32 | 33 |
| structural formula | | | |

TABLE 1-continued

| salt | Example No. | structural formula |
|---|---|---|
| free | 34 | (structure) |
| free | 35 | (structure) |
| free | 36 | (structure) |

TABLE 1-continued

| salt | free | free | free |
|---|---|---|---|
| Example No. | 37 | 38 | 39 |
| structural formula | (structure) | (structure) | (structure) |

TABLE 1-continued

| salt | free | free | free |
|---|---|---|---|
| Example No. | 40 | 41 | 42 |
| structural formula | (structure) | (structure) | (structure) |

| salt | free | free | free |
|---|---|---|---|
| Example No. | 43 | 44 | 45 |
| structural formula | (structure) | (structure) | (structure) |

TABLE 1-continued

| structural formula | Example No. | salt |
|---|---|---|
| (structure) | 46 | free |
| (structure) | 47 | free |
| (structure) | 48 | free |
| (structure) | 49 | free |
| (structure) | 50 | free |
| (structure) | 51 | free |

TABLE 1-continued

| salt | free | free | free |
|---|---|---|---|
| Example No. | 52 | 53 | 54 |
| structural formula | (structure) | (structure) | (structure) |

| salt | free | free | free |
|---|---|---|---|
| Example No. | 55 | 56 | 57 |
| structural formula | (structure) | (structure) | (structure) |

TABLE 1-continued

| salt | Example No. | structural formula | salt | Example No. | structural formula |
|---|---|---|---|---|---|
| free | 58 | (structure) | free | 61 | (structure) |
| free | 59 | (structure) | free | 62 | (structure) |
| free | 60 | (structure) | free | 63 | (structure) |

TABLE 1-continued

| salt | free | free | free |
|---|---|---|---|
| Example No. | 64 | 65 | 66 |
| structural formula | (structure) | (structure) | (structure) |

TABLE 1-continued

| salt | free | free | free |
|---|---|---|---|
| Example No. | 67 | 68 | 69 |
| structural formula | | | |

TABLE 1-continued

| salt | free | free | free |
|---|---|---|---|
| Example No. | 70 | 71 | 72 |
| structural formula | (structure) | (structure) | (structure) |

| salt | free | free | free |
|---|---|---|---|
| Example No. | 73 | 74 | 75 |
| structural formula | (structure) | (structure) | (structure) |

TABLE 1-continued

| Example No. | 76 | 77 | 78 |
|---|---|---|---|
| salt | free | free | free |

| Example No. | 79 | 80 | 81 |
|---|---|---|---|
| salt | free | free | free |

TABLE 1-continued

| salt | Example No. | structural formula |
|---|---|---|
| free | 82 | |
| free | 83 | |
| free | 84 | |

TABLE 1-continued

| salt | free | free | free |
|---|---|---|---|
| Example No. | 85 | 86 | 87 |
| structural formula | (structure) | (structure) | (structure) |

| salt | free | free | free |
|---|---|---|---|
| Example No. | 88 | 89 | 90 |
| structural formula | (structure) | (structure) | (structure) |

TABLE 1-continued

| salt | free | free | free |
|---|---|---|---|
| Example No. | 91 | 92 | 93 |
| structural formula | (structure) | (structure) | (structure) |

| salt | free | free | free |
|---|---|---|---|
| Example No. | 94 | 95 | 96 |
| structural formula | (structure) | (structure) | (structure) |

TABLE 1-continued

| salt | free | free | free |
|---|---|---|---|
| Example No. | 97 | 98 | 99 |
| structural formula | (structure) | (structure) | (structure) |

TABLE 1-continued

| salt | free | free | free |
|---|---|---|---|
| Example No. | 100 | 101 | 102 |
| structural formula | (structure) | (structure) | (structure) |

| salt | free | free | free |
|---|---|---|---|
| Example No. | 103 | 104 | 105 |
| structural formula | (structure) | (structure) | (structure) |

TABLE 1-continued

| salt | free | free | free |
|---|---|---|---|
| Example No. | 106 | 107 | 108 |
| structural formula | (structure) | (structure) | (structure) |

| salt | free | free | free |
|---|---|---|---|
| Example No. | 109 | 110 | 111 |
| structural formula | (structure) | (structure) | (structure) |

TABLE 1-continued
| salt | free | free | free |
|---|---|---|---|
| Example No. | 112 | 113 | 114 |
| structural formula | 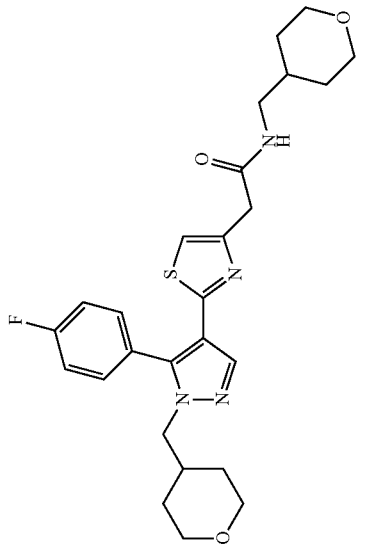 | 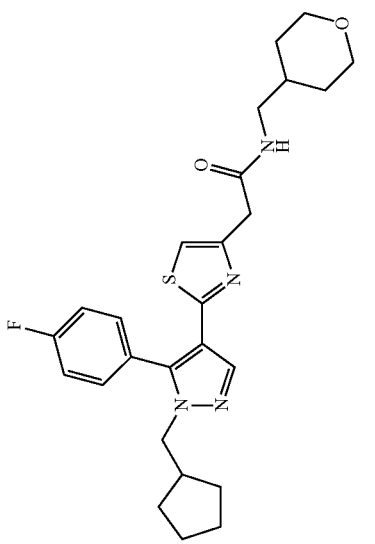 | 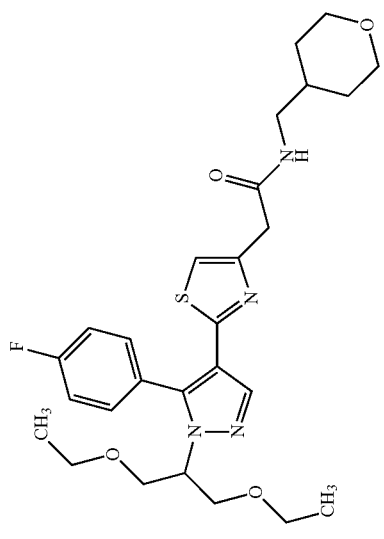 |
| salt | free | free | free |
|---|---|---|---|
| Example No. | 115 | 116 | 117 |
| structural formula | 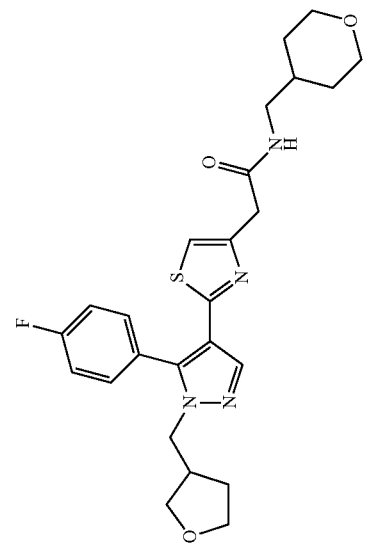 | 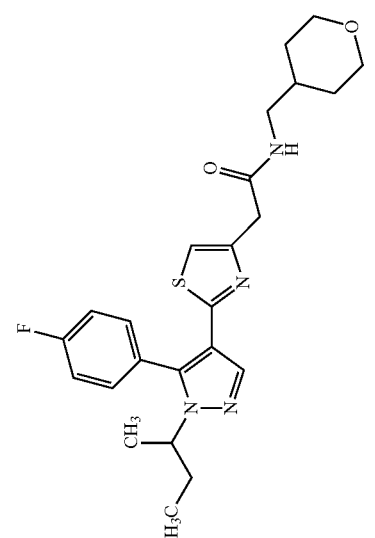 | 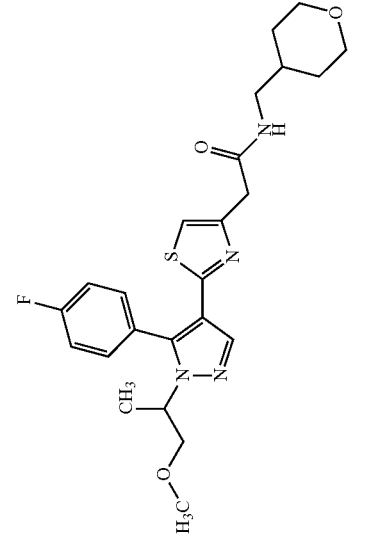 |

TABLE 1-continued

| salt | free | free | free |
|---|---|---|---|
| Example No. | 118 | 119 | 120 |
| structural formula | | | |

| salt | free | free | free |
|---|---|---|---|
| Example No. | 121 | 122 | 123 |
| structural formula | | | |

TABLE 1-continued

| salt | free | free | free |
|---|---|---|---|
| Example No. | 124 | 125 | 126 |
| structural formula | (structure) | (structure) | (structure) |

| salt | free | free | free |
|---|---|---|---|
| Example No. | 127 | 128 | 129 |
| structural formula | (structure) | (structure) | (structure) |

TABLE 1-continued
| salt | free | free | free |
|---|---|---|---|
| Example No. | 130 | 131 | 132 |
| structural formula | 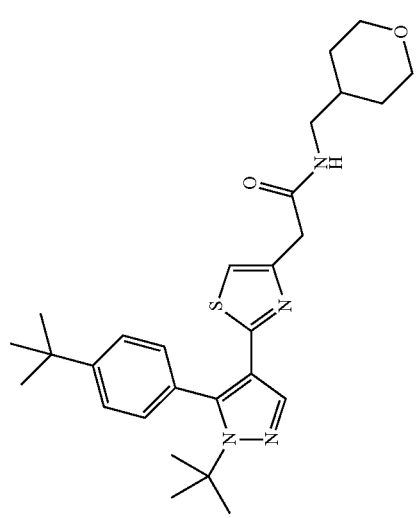 | 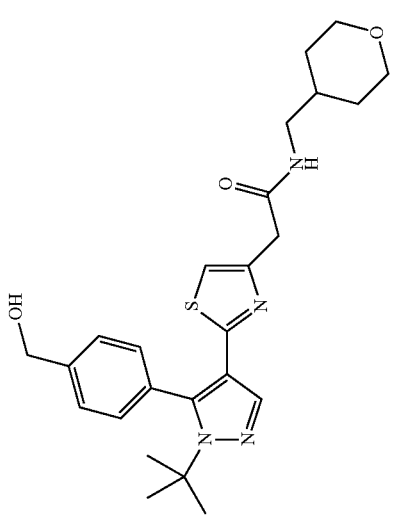 | 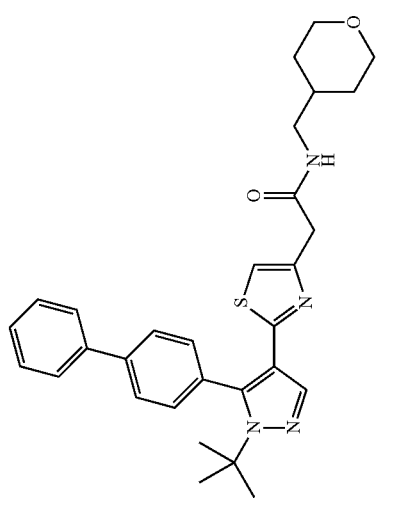 |

| salt | free | free | free |
|---|---|---|---|
| Example No. | 133 | 134 | 135 |
| structural formula | | | |

TABLE 1-continued

| salt | free | free | free |
|---|---|---|---|
| Example No. | 136 | 137 | 138 |
| structural formula | (structure) | (structure) | (structure) |

TABLE 1-continued
| salt | free | free | free |
|---|---|---|---|
| Example No. | 141 | 140 | 139 |
| structural formula | 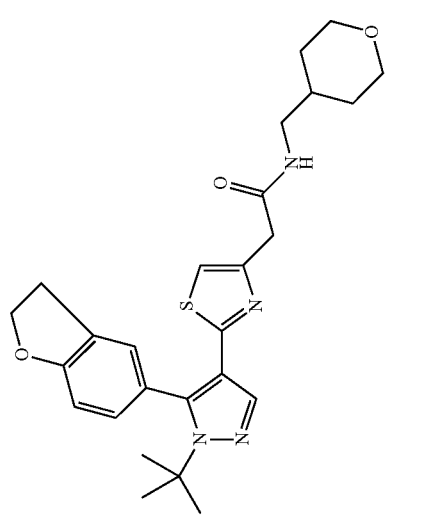 | 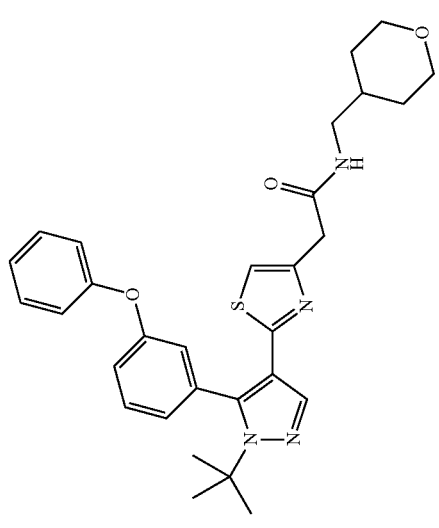 | 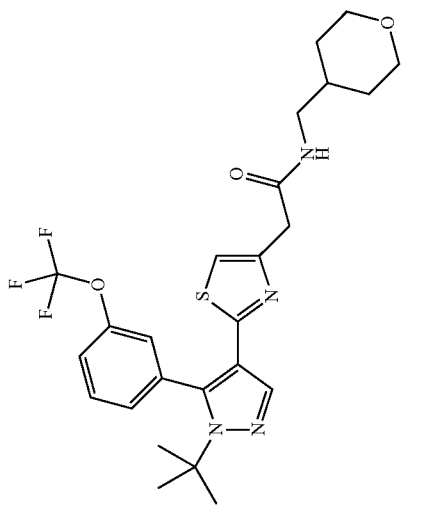 |

TABLE 1-continued

| salt | free | free | free |
|---|---|---|---|
| Example No. | 142 | 143 | 144 |
| structural formula | | | |

| salt | free | free | free |
|---|---|---|---|
| Example No. | 145 | 146 | 147 |
| structural formula | | | |

TABLE 1-continued

| salt | free | free | free | free | free | free |
|---|---|---|---|---|---|---|
| Example No. | 148 | 149 | 150 | 151 | 152 | 153 |
| structural formula | | | | | | |

TABLE 1-continued

| salt | free | free | free |
|---|---|---|---|
| Example No. | 154 | 155 | 156 |
| structural formula | | | |

TABLE 1-continued
| salt | free | free | free |
|---|---|---|---|
| Example No. | 157 | 158 | 159 |
| structural formula | 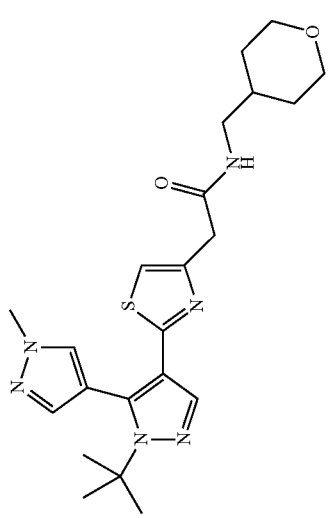 | 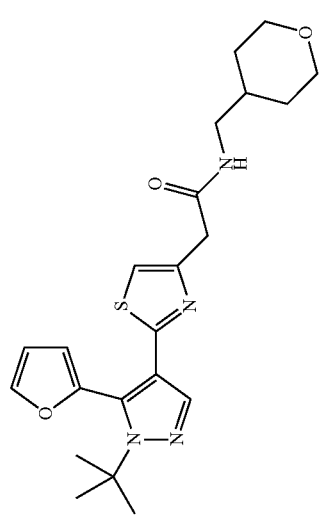 | 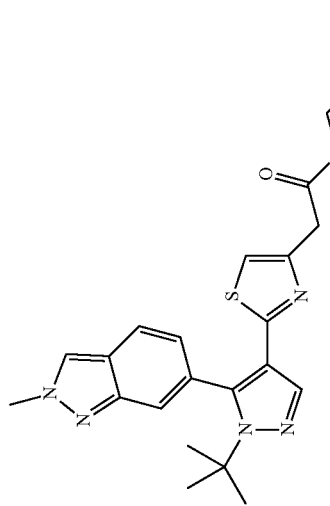 |

TABLE 1-continued

| Example No. | 160 | 161 | 162 |
|---|---|---|---|
| salt | free | free | free |
| structural formula | (structure) | (structure) | (structure) |

| Example No. | 163 | 164 | 165 |
|---|---|---|---|
| salt | free | free | free |
| structural formula | (structure) | (structure) | (structure) |

TABLE 1-continued

| salt | free | free | free |
|---|---|---|---|
| Example No. | 166 | 167 | 168 |
| structural formula | | | |

| salt | free | free | free |
|---|---|---|---|
| Example No. | 169 | 170 | 171 |
| structural formula | | | |

| salt | Example No. | structural formula | salt |
|---|---|---|---|
| free | 172 | (structure) | free |
| free | 173 | (structure) | free |

Experimental Example 1

RORγt Binding Test

The binding activity of the test compound to RORγt was measured by a time resolved fluorescence resonance energy transfer method (TR-FRET) utilizing histidine-tagged RORγt, fluorescent-labeled cholesterol (BODIPY-cholesterol, AVIVA), and terbium-labeled anti-histidine tag antibody (Invitrogen). First, a test compound diluted with an assay buffer (20 mM Tris-HCl (pH 7.5), 100 mM NaCl, 1 mM DTT, 0.1% BSA) was added to a 384 well plate by 3 μL. Then, RORγt diluted with an assay buffer to 240 nM was added by 3 μL, after which fluorescent-labeled cholesterol diluted with the assay buffer to 12 μM was added by 3 μL, and the mixture was stood at room temperature for 20 min. Thereafter, a terbium-labeled anti-histidine tag antibody diluted with the assay buffer to 8 nM was added by 3 μL. The mixture was stood at room temperature for 20 min, and fluorescence intensity (excitation wavelength 320 nm, fluorescence wavelength 520 nm, delay time 100 microseconds) was measured by Envision (PerkinElmer).

The results (binding inhibitory rate of fluorescent-labeled cholesterol to RORγt at test compound 1 μM) measured by the above-mentioned method are shown in Table 2.

TABLE 2

| test compound (Example No) | inhibitory rate (%) |
|---|---|
| 14 | 92.0 |
| 18 | 96.1 |
| 39 | 98.7 |
| 41 | 94.6 |
| 43 | 98.3 |
| 51 | 95.3 |
| 79 | 95.4 |
| 97 | 87.3 |
| 128 | 97.8 |
| 150 | 98.7 |
| 152 | 95.9 |
| 170 | 86.5 |

Experimental Example 2

Cofactor Recruitment Test

Cofactor recruitment test was performed by Alpha Screen (Histidine Detection Kit, PerkinElmer) method. First, a test compound was diluted with an assay buffer (50 mM Tris-HCl (pH 7.5), 50 mM KCl, 1 mM DTT, 0.1% BSA) and added to a 384 well plate by 5 μL. Then, RORγt diluted with an assay buffer to 125 nM was added by 10 μL each, after which solutions of 25 nM biotinylated SRC-1 peptide (biotin-CLTARHKILHRLLQEGSPSD), 12.5 μg/mL acceptor beads and 12.5 μg/mL donor beads prepared with the assay buffer were added by 10 μL each. The mixture was stood in a dark place for 1 hr, and the signal value was measured by Envision (PerkinElmer).

The results (signal value inhibitory rate at test compound 1 μM) measured by the above-mentioned method are shown in Table 3.

TABLE 3

| test compound (Example No) | inhibitory rate (%) |
|---|---|
| 14 | 109.0 |
| 18 | 102.0 |
| 39 | 101.0 |
| 41 | 101.0 |
| 43 | 101.0 |
| 51 | 78.6 |
| 79 | 99.8 |
| 97 | 98.8 |
| 128 | 101.0 |
| 150 | 99.3 |
| 152 | 95.4 |
| 170 | 100.0 |

Experimental Example 3

Jurkat Reporter Test

The Jurkat cells used for the reporter test were cultured in a culture medium (RPMI (Invitrogen), 10% FCS (AusGeneX), 100 U/mL penicillin, 100 μg/mL streptomycin). On the day of the test, $4 \times 10^7$ cells were recovered by a centrifugal operation (1000 rpm, 5 min.) and suspended in PBS (phosphate buffered saline) (Invitrogen). Thereafter, the cells were recovered again by a centrifugal operation, and suspended in 2 mL of R buffer (NEON transfection kit, Invitrogen). Then, a reporter vector 53 μg wherein a human IL-17 ROR response element was inserted into the upstream of luciferase of pGL 4.28 (Promega), and a vector (27 μg) wherein RORγt sequence was inserted into the downstream of CMV promoter were added to the cell suspension. Gene transfer was performed by Electroporation apparatus (NEON, Invitrogen) under the conditions of pulse voltage 1350 V, interval 10 milliseconds, number of times 3. The cells after gene transfer were suspended in 40 mL of a reaction medium (RPMI, 10% Lipid reduced FCS (HyClone), 10 mM HEPES (pH 7.5), 100 U/mL penicillin, 100 μg/mL streptomycin, 5 μM lovastatin), and plated in a 96 well plate by 90 μL. A test compound diluted with the reaction medium was added by 10 μL, and the cells were cultured overnight in an incubator. Bright-Glo (Promega) was added by 100 μL, and the mixture was stirred at room temperature for 10 min, and the luminescence level was measured by Envision (PerkinElmer).

The results (luminescence level inhibitory rate at test compound 3 μM) measured by the above-mentioned method are shown in Table 4.

TABLE 4

| test compound (Example No) | inhibitory rate (%) |
|---|---|
| 14 | 81.0 |
| 18 | 87.1 |
| 39 | 101.0 |
| 41 | 82.1 |
| 43 | 94.2 |
| 51 | 94.9 |
| 79 | 85.7 |
| 97 | 84.1 |
| 128 | 97.1 |
| 150 | 98.4 |
| 152 | 96.0 |
| 170 | 94.4 |

Experimental Example 4

Mouse Th17 Cell Differentiation Induction Test

CD4 positive naive T cells were collected from the spleen cells of BALB/c mice (female, 8-11w) using CD4+CD62L+

T Cell Isolation kit II (Miltenyi Biotec). The CD4 positive naive T cells were plated in a 96 well plate ($3 \times 10^5$ cells/well), stimulated (37° C. for culture) with anti-mouse CD3ε antibody (10 μg/mL, solid phase) and anti-CD28 antibody (5 μg/mL) for 4 days in the presence of anti-IFN-γ antibody, anti-IL-4 antibody, anti-IL-2 antibody, IL-6, TGF-β and IL-23 to allow for differentiation into Th17 cells. The compound was dissolved in DMSO and then added. The cells were cultured under these conditions for 4 days, the concentration of IL-17A in the culture supernatant obtained by centrifugation was measured by ELISA, and differentiation of the Th17 cells was evaluated.

The results (inhibitory rate at test compound 10 μM) measured by the above-mentioned method are shown in Table 5.

TABLE 5

| test compound (Example No) | inhibitory rate (%) |
|---|---|
| 14 | 77.0 |
| 18 | 96.3 |
| 39 | 95.0 |
| 41 | 92.6 |
| 43 | 78.6 |
| 51 | 86.0 |
| 79 | 69.0 |
| 97 | 95.0 |
| 128 | 97.7 |
| 150 | 97.7 |
| 152 | 91.2 |

Experimental Example 5

Human Th17 Cell Differentiation Induction Test

Using peripheral blood mononuclear cells (PBMC) collected from human peripheral blood by a density gradient centrifugation method, CD4 positive naive T cells were collected. The CD4 positive naive T cells were plated in a 96 well plate ($2 \times 10^4$ cells/well), and stimulated (37° C. for culture) with anti-CD3/28Ab Dynabeads for 6 days in the presence of IL-1β, IL-6, IL-23, TGFβ, anti-IFNγ Ab, anti-IL-4 Ab to allow for differentiation into Th17 cells. The compound was dissolved in DMSO and then added. After culture for 6 days, the concentration of IL-17A in the culture supernatant obtained by centrifugation was measured by ELISA, and differentiation of the Th17 cells was evaluated.

The results (inhibitory rate at test compound 10 μM) measured by the above-mentioned method are shown in Table 6.

TABLE 6

| test compound (Example No) | inhibitory rate (%) |
|---|---|
| 39 | 100.0 |

Experimental Example 6

Human PBMC IL17 Production Test

Peripheral blood mononuclear cells (PBMC) collected from human peripheral blood by a density gradient centrifugation method were stimulated by Dynabeads (registered trade mark; anti-CD3/CD28 antibody) and cultured at 37° C. for 3 days. The compound was dissolved in DMSO and then added. After culture for 3 days under such conditions, the concentration of IL-17A in the culture supernatant obtained by centrifugation was measured by ELISA, and the activity of the compound on IL-17 production was evaluated.

The results (inhibitory rate at test compound 10 μM) measured by the above-mentioned method are shown in Table 7.

TABLE 7

| test compound (Example No) | inhibitory rate (%) |
|---|---|
| 39 | 91.3 |
| 150 | 92.0 |
| 152 | 92.0 |

INDUSTRIAL APPLICABILITY

The compound of the present invention has an RORγt receptor inhibitory activity, and is useful as an agent for the prophylaxis or treatment of inflammatory bowel disease (IBD), ulcerative colitis (UC), Crohn's disease (CD), rheumatoid arthritis, multiple sclerosis, psoriasis and the like.

This application is based on a patent application No. 2011-167693 filed in Japan, the contents of which are incorporated in full herein.

The invention claimed is:
1. A compound represented by the formula (I):

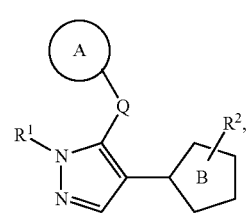

wherein:
ring A is
(1) a $C_{3-7}$ cycloalkyl group,
(2) a $C_{3-8}$ cycloalkenyl group,
(3) a $C_{6-14}$ aryl group optionally substituted by 1 to 3 substituents, which are same or different, selected from the group consisting of
    (i) a halogen atom,
    (ii) $C_{1-6}$ alkyl optionally substituted by 1 to 3 substituents, which are same or different, selected from the group consisting of
        (a) a halogen atom,
        (b) hydroxyl, and
        (c) cyano,
    (iii) $C_{1-6}$ alkoxy optionally substituted by 1 to 3 halogen atoms, which is same or different,
    (iv) $C_{6-14}$ aryloxy,
    (v) cyano,
    (vi) $C_{1-10}$ alkylsulfonyl,
    (vii) mono- or bis($C_{1-6}$ alkyl-carbonyl)amino, and
    (viii) a heterocyclic group, or
(4) a heterocyclic group optionally substituted by 1 to 3 substituents, which are same or different, selected from the group consisting of
    (i) a halogen atom,
    (ii) $C_{1-6}$ alkyl optionally substituted by 1 to 3 halogen atoms, which are same or different, and
    (iii) $C_{1-6}$ alkoxy, Q is a bond, —CH$_2$—, —(CH$_2$)$_2$—, or —CH=CH—, R$^1$ is
(1) a C$_{1-10}$ alkyl group optionally substituted 1 to 3 substituents, which are same or different, selected from the group consisting of
   (i) a halogen atom,
   (ii) a hydroxy group,
   (iii) a C$_{3-7}$ cycloalkyl group optionally substituted by 1 or 2 halogen atoms, which are same or different,
   (iv) C$_{1-6}$ alkoxy optionally substituted by 1 to 3 halogen atoms, which are same or different, and
   (v) a non-aromatic heterocyclic group,
(2) a C$_{3-7}$ cycloalkyl group,
(3) a phenyl group, or
(4) a heterocyclic group bonded to the pyrazole ring via a carbon atom, ring B is a thiazole ring which is substituted by R$^2$ and optionally further substituted by C$_{1-6}$ alkyl, and R$^2$ is
(1) an non-aromatic heterocyclic group-carbonyl-C$_{1-6}$ alkyl group optionally substituted by at least one substituent selected from the group consisting of
   (i) oxo,
   (ii) hydroxy,
   (iii) C$_{1-6}$ alkyl,
   (iv) carboxy,
   (v) C$_{1-10}$ alkoxy-carbonyl, and
   (vi) C$_{6-14}$ aryl,
(2) an aminocarbonyl-C$_{1-6}$ alkyl group substituted by 1 or 2 substituents selected from the group consisting of
   (i) C$_{1-6}$ alkyl optionally substituted by at least one substituent selected from the group consisting of
      (a) a halogen atom,
      (b) hydroxy,
      (c) C$_{1-6}$ alkoxy,
      (d) cyano,
      (e) C$_{1-10}$ alkoxy-carbonyl,
      (f) a non-aromatic heterocyclic group optionally substituted by one C$_{1-6}$ alkyl optionally substituted by
         (a) hydroxy,
         (b) C$_{6-14}$ aryl optionally substituted by 1 to 3 substituents, which are same or different, selected from the group consisting of
            (a') a halogen atom,
            (b') C$_{1-6}$ alkyl substituted by 1 to 3 halogen atoms, which are same or different,
            (c') C$_{1-6}$ alkoxy optionally substituted 1 to 3 halogen atoms which are same or different,
            (d') cyano,
            (e') amino substituted by C$_{1-6}$ alkyl,
            (f') C$_{1-10}$ alkylsulfonyl,
            (g') C$_{6-14}$ aryl, and
            (h') an aromatic heterocyclic group, and
         (c) an aromatic heterocyclic group optionally substituted by 1 or 2 C$_{1-6}$ alkyl, which are same or different,
      (ii) C$_{6-14}$ aryl optionally substituted by at least one substituent selected from the group consisting of
         (a) C$_{1-6}$ alkoxy,
         (b) an aromatic heterocyclic group, and
         (c) mono- or bis(C$_{1-6}$ alkyl-carbonyl)amino, and
      (iii) a non-aromatic heterocyclic group,
(3) a non-aromatic heterocyclic group-C$_{1-6}$ alkyl group,
(4) a non-aromatic heterocyclic group-C$_{1-6}$ alkylaminocarbonyl group,
(5) an aminocarbonyl-C$_{2-6}$ alkenyl group optionally substituted by C$_{1-6}$ alkyl optionally substituted by a non-aromatic heterocyclic group,
(6) a C$_{1-6}$ alkylcarbonylamino-C$_{1-6}$ alkyl group optionally substituted by a non-aromatic heterocyclic group,
(7) a non-aromatic heterocyclic group-aminocarbonyl group,
(8) a non-aromatic heterocyclic group-carbonyl group optionally substituted by oxo, or
(9) a non-aromatic heterocyclic group optionally substituted by 1 to 5 substituents selected from the group consisting of
   (a) C$_{1-10}$ alkoxy-carbonyl optionally substituted by hydroxy or 1 to 6 halogen atoms, which are same or different, and
   (b) C$_{6-14}$ arylcarbonyl optionally substituted by cyano,
or a salt thereof.

2. The compound or the salt thereof according to claim 1, wherein R$^1$ is
(1) the C$_{3-7}$ cycloalkyl group, or
(2) a tert-butyl group optionally substituted by the 1 to 3 substituents, which are same or different, selected from the group consisting of
   (a) a halogen atom, and
   (b) C$_{3-7}$ cycloalkyl group optionally substituted by 1 or 2 halogen atoms, which are same or different.

3. The compound or the salt thereof according to claim 1, wherein a partial structure:

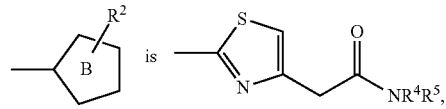

wherein one of R$^4$ and R$^5$ is a hydrogen atom or a C$_{1-3}$ alkyl group, and the other is the C$_{1-6}$ alkyl group substituted by at least one substituent selected from the group consisting of
(1) a non-aromatic heterocyclic group optionally substituted by one C$_{1-6}$ alkyl optionally substituted by hydroxy,
(2) C$_{6-14}$ aryl optionally substituted by 1 to 3 substituents, which are same or different, selected from the group consisting of
   (i) a halogen atom,
   (ii) C$_{1-6}$ alkyl substituted by 1 to 3 halogen atoms, which are same or different,
   (iii) C$_{1-6}$ alkoxy optionally substituted by 1 to 3 halogen atoms, which are same or different,
   (iv) cyano,
   (v) amino substituted by C$_{1-6}$ alkyl,
   (vi) C$_{1-10}$ alkylsulfonyl,
   (vii) C$_{6-14}$ aryl, and
   (viii) an aromatic heterocyclic group, and an aromatic heterocyclic group optionally substituted by 1 or 2 C$_{1-6}$ alkyl, which are same or different.

4. 2-{2-[1-tert-Butyl-5-(4-methoxyphenyl)-1H-pyrazol-4-yl]-1,3-thiazol-4-yl}-N-(tetrahydro-2H-pyran-4-ylmethyl)acetamide or a salt thereof.

5. 2-{2-[1-Cyclohexyl-5-(4-fluorophenyl)-1H-pyrazol-4-yl]-1,3-thiazol-4-yl}-N-(tetrahydro-2H-pyran-4-ylmethyl)acetamide or a salt thereof.

6. 2-{2-[1-tert-Butyl-5-(4-fluorophenyl)-1H-pyrazol-4-yl]-1,3-thiazol-4-yl}-N-[4-(1H-imidazol-1-yl)benzyl]acetamide or a salt thereof.

7. A pharmaceutical composition comprising the compound or the salt thereof according to claim 1; and at least one pharmaceutically acceptable carrier.

8. The pharmaceutical composition according to claim 7, which is an RORγt inhibitor.

9. The pharmaceutical composition according to claim 8, which is a therapeutic drug for inflammatory bowel disease (IBD), ulcerative colitis (UC), Crohn's disease (CD), rheumatoid arthritis, multiple sclerosis, or psoriasis.

10. A method of inhibiting RORγt, comprising administering an effective amount of the compound or the salt thereof according to claim 1 to a mammal in need thereof.

11. A therapeutic method for inflammatory bowel disease (IBD), ulcerative colitis (UC), Crohn's disease (CD), rheumatoid arthritis, multiple sclerosis, or psoriasis, comprising administering an effective amount of the compound or the salt thereof according to claim 1 to a mammal in need thereof.

12. The compound or the salt thereof according to claim 1 that treats inflammatory bowel disease (IBD), ulcerative colitis (UC), Crohn's disease (CD), rheumatoid arthritis, multiple sclerosis, or psoriasis.

* * * * *